US012806021B2

(12) United States Patent
Eigler et al.

(10) Patent No.: US 12,806,021 B2
(45) Date of Patent: Nov. 24, 2026

(54) INTERATRIAL SHUNT HAVING PHYSIOLOGIC SENSOR

(71) Applicant: V-Wave Ltd., Caesarea (IL)

(72) Inventors: Neal Eigler, Agoura Hills, CA (US); Erez Rozenfeld, Shoham (IL); Nir Nae, Binyamina (IL); Lior Rosen, Zikhron Ya'akov (IL); James S. Whiting, Los Angeles, CA (US); John Wardle, San Clemente, CA (US); Werner Hafelfinger, Thousand Oaks, CA (US); James D. Loudin, Morada, CA (US); Brian M. Mann, Edgartown, MA (US)

(73) Assignee: V-Wave Ltd., Caesarea (IL)

( * ) Notice: Subject to any disclaimer, the term of this patent is extended or adjusted under 35 U.S.C. 154(b) by 1216 days.

(21) Appl. No.: 17/649,331

(22) Filed: Jan. 28, 2022

(65) Prior Publication Data

US 2022/0151784 A1 May 19, 2022

Related U.S. Application Data

(63) Continuation-in-part of application No. 17/098,251, filed on Nov. 13, 2020, now Pat. No. 11,234,702.

(51) Int. Cl.
*A61F 2/24* (2006.01)

(52) U.S. Cl.
CPC .... *A61F 2/2487* (2013.01); *A61F 2220/0008* (2013.01); *A61F 2250/0002* (2013.01)

(58) Field of Classification Search
CPC ......... A61B 2017/1103; A61B 17/1114; A61B 2017/1132; A61B 2017/1139;
(Continued)

(56) References Cited

U.S. PATENT DOCUMENTS 744,589 A 11/1903 Moore
3,852,334 A 12/1974 Dusza et al.
(Continued)

FOREIGN PATENT DOCUMENTS

AU 2003291117 B2 4/2009
CA 2378920 A1 2/2001
(Continued)

OTHER PUBLICATIONS

International Search Report & Written Opinion dated Feb. 9, 2022 in Int'l PCT Patent Appl. Serial No. PCT/IB2021/060473 (2010).
(Continued)

*Primary Examiner* — Thomas McEvoy
(74) *Attorney, Agent, or Firm* — Greenberg Traurig, LLP; Christopher C. Bolten; Albert K. Heng

(57) ABSTRACT

Interatrial shunts having incorporated physiologic sensors are provided for monitoring and treating cardiovascular syndromes, including heart failure and pulmonary hypertension, in which the one or more sensors are affixed to the shunt to measure a physiologic parameter within the interatrial shunt. The shunt may include an anchor having a first flared region, a second flared region, and a neck region disposed between the first flared region and the second flared region, and a biocompatible covering disposed on the anchor to form a lumen. The one or more sensors may be pivotally coupled to the first flared region such that the one or more sensors may transition between a delivery configuration and a deployed configuration where the sensing surface of the one or more sensors is in fluid communication with the lumen.

22 Claims, 44 Drawing Sheets

(58) Field of Classification Search
CPC . A61B 2017/1135; A61B 5/026; A61B 5/024; A61B 5/02444; A61B 5/021; A61B 5/0215; A61B 2017/00575; A61B 2017/00579; A61B 2017/00584; A61B 2017/00597; A61B 2017/00606
See application file for complete search history.

(56) References Cited

U.S. PATENT DOCUMENTS 3,874,388 A 4/1975 King et al.
3,952,334 A 4/1976 Bokros et al.
4,326,304 A * 4/1982 Klawitter .............. A61F 2/2403 137/527.8
4,364,395 A 12/1982 Redmond et al.
4,484,955 A 11/1984 Hochstein
4,601,309 A 7/1986 Chang
4,617,932 A 10/1986 Kornberg
4,662,355 A 5/1987 Pieronne et al.
4,665,906 A 5/1987 Jervis
4,705,507 A 11/1987 Boyles
4,836,204 A 6/1989 Landymore
4,979,955 A 12/1990 Smith
4,988,339 A 1/1991 Vadher
4,995,857 A 2/1991 Arnold
5,035,702 A 7/1991 Taheri
5,035,706 A 7/1991 Giantureo et al.
5,037,427 A 8/1991 Harada et al.
5,089,005 A 2/1992 Harada
5,108,420 A 4/1992 Marks
5,186,431 A 2/1993 Tamari
5,197,978 A 3/1993 Hess
5,234,447 A 8/1993 Kaster et al.
5,267,940 A 12/1993 Moulder
5,290,227 A 3/1994 Pasque
5,312,341 A 5/1994 Turi
5,326,374 A 7/1994 Ilbawi et al.
5,332,402 A 7/1994 Teitelbaum
5,334,217 A 8/1994 Das
5,378,239 A 1/1995 Termin et al.
5,409,019 A 4/1995 Wilk
5,429,144 A 7/1995 Wilk
5,479,945 A 1/1996 Simon
5,500,015 A 3/1996 Deac
5,531,759 A 7/1996 Kensey et al.
5,545,210 A 8/1996 Hess et al.
5,556,386 A 9/1996 Todd
5,562,641 A 10/1996 Flomenblit et al.
5,578,008 A 11/1996 Hara
5,584,803 A 12/1996 Stevens et al.
5,597,377 A 1/1997 Aldea
5,645,559 A 7/1997 Hachtman et al.
5,655,548 A 8/1997 Nelson et al.
5,662,711 A 9/1997 Douglas
5,702,412 A 12/1997 Popov et al.
5,725,552 A 3/1998 Kotula et al.
5,741,324 A 4/1998 Glastra
5,749,880 A 5/1998 Banas et al.
5,779,716 A 7/1998 Cano et al.
5,795,307 A 8/1998 Krueger
5,810,836 A 9/1998 Hussein et al.
5,824,062 A 10/1998 Patke et al.
5,824,071 A 10/1998 Nelson et al.
5,846,261 A 12/1998 Kotula et al.
5,876,434 A 3/1999 Flomenblit et al.
5,910,144 A 6/1999 Hayashi
5,916,193 A 6/1999 Stevens et al.
5,938,695 A 8/1999 Borghi
5,941,850 A 8/1999 Shah et al.
5,951,583 A 9/1999 Jensen et al.
5,957,949 A 9/1999 Leonhardt et al.
5,990,379 A 11/1999 Gregory
6,007,544 A 12/1999 Kim
6,010,529 A 1/2000 Herweck et al.
6,027,518 A 2/2000 Gaber
6,039,755 A 3/2000 Edwin et al.
6,039,759 A 3/2000 Carpentier et al.
6,059,810 A 5/2000 Brown et al.
6,086,610 A 7/2000 Duerig et al.
6,111,520 A 8/2000 Allen et al.
6,117,159 A 9/2000 Huebsch et al.
6,120,534 A 9/2000 Ruiz
6,124,523 A 9/2000 Banas et al.
6,126,686 A 10/2000 Badylak et al.
6,165,188 A 12/2000 Saadat et al.
6,210,318 B1 4/2001 Lederman
6,214,029 B1 4/2001 Thill et al.
6,214,039 B1 4/2001 Banas et al.
6,216,029 B1 4/2001 Paltieli
6,217,541 B1 4/2001 Yu
6,221,096 B1 4/2001 Aiba et al.
6,231,587 B1 5/2001 Makower
6,242,762 B1 6/2001 Brown et al.
6,245,099 B1 6/2001 Edwin et al.
6,254,564 B1 7/2001 Wilk et al.
6,260,552 B1 7/2001 Mortier et al.
6,264,684 B1 7/2001 Banas et al.
6,270,515 B1 8/2001 Linden et al.
6,270,526 B1 8/2001 Cox
6,277,078 B1 8/2001 Porat et al.
6,278,379 B1 8/2001 Allen et al.
6,290,728 B1 9/2001 Phelps et al.
6,302,892 B1 10/2001 Wilk
6,306,141 B1 10/2001 Jervis
6,328,699 B1 12/2001 Eigler et al.
6,344,022 B1 2/2002 Jarvik
6,358,277 B1 3/2002 Duran
6,391,036 B1 5/2002 Berg et al.
6,398,803 B1 6/2002 Layne et al.
6,406,422 B1 6/2002 Landesberg
6,447,539 B1 9/2002 Nelson et al.
6,451,051 B2 9/2002 Drasler et al.
6,458,153 B1 10/2002 Bailey et al.
6,468,303 B1 10/2002 Amplatz et al.
6,475,136 B1 11/2002 Forsell
6,478,776 B1 11/2002 Rosenman et al.
6,485,507 B1 11/2002 Walak et al.
6,488,702 B1 12/2002 Besselink
6,491,705 B2 12/2002 Gifford, III et al.
6,527,698 B1 3/2003 Kung et al.
6,544,208 B2 4/2003 Ethier et al.
6,547,814 B2 4/2003 Edwin et al.
6,562,066 B1 5/2003 Martin
6,572,652 B2 6/2003 Shaknovich
6,579,314 B1 6/2003 Lombardi et al.
6,589,198 B1 7/2003 Soltanpour et al.
6,616,675 B1 9/2003 Evard et al.
6,632,169 B2 10/2003 Korakianitis et al.
6,638,303 B1 10/2003 Campbell
6,641,610 B2 11/2003 Wolf et al.
6,645,220 B1 11/2003 Huter et al.
6,652,578 B2 11/2003 Bailey et al.
6,685,664 B2 2/2004 Levin et al.
6,712,836 B1 3/2004 Berg et al.
6,740,115 B2 5/2004 Lombardi et al.
6,758,858 B2 7/2004 McCrea et al.
6,764,507 B2 7/2004 Shanley et al.
6,770,087 B2 8/2004 Layne et al.
6,797,217 B2 9/2004 McCrea et al.
6,805,711 B2 10/2004 Quijano et al.
6,890,350 B1 5/2005 Walak
6,923,829 B2 8/2005 Boyle et al.
6,970,742 B2 11/2005 Mann et al.
7,001,409 B2 2/2006 Amplatz
7,004,966 B2 2/2006 Edwin et al.
7,025,777 B2 4/2006 Moore
7,060,150 B2 6/2006 Banas et al.
7,083,640 B2 8/2006 Lombardi et al.
7,115,095 B2 10/2006 Eigler et al.
7,118,600 B2 10/2006 Dua et al.
7,128,758 B2 10/2006 Cox
7,137,953 B2 11/2006 Eigler et al.
7,147,604 B1 12/2006 Allen et al.
7,149,587 B2 12/2006 Wardle et al.
7,169,160 B1 1/2007 Middleman et al.

(56) References Cited

U.S. PATENT DOCUMENTS 7,169,172 B2 1/2007 Levine et al.
7,195,594 B2 3/2007 Eigler et al.
7,208,010 B2 4/2007 Shanley et al.
7,226,558 B2 6/2007 Nieman et al.
7,245,117 B1 7/2007 Joy et al.
7,294,115 B1 11/2007 Wilk
7,306,756 B2 12/2007 Edwin et al.
7,402,899 B1 7/2008 Whiting et al.
7,439,723 B2 10/2008 Allen et al.
7,468,071 B2 12/2008 Edwin et al.
7,483,743 B2 1/2009 Mann et al.
7,498,799 B2 3/2009 Allen et al.
7,509,169 B2 3/2009 Eigler et al.
7,550,978 B2 6/2009 Joy et al.
7,575,586 B2 8/2009 Berg et al.
7,578,899 B2 8/2009 Edwin et al.
7,590,449 B2 9/2009 Mann et al.
7,615,010 B1 11/2009 Najafi et al.
7,621,879 B2 11/2009 Eigler et al.
7,632,303 B1 12/2009 Stalker et al.
7,679,355 B2 3/2010 Allen et al.
7,717,854 B2 5/2010 Mann et al.
7,789,975 B2 9/2010 Cheung et al.
7,794,473 B2 9/2010 Tessmer et al.
7,839,153 B2 11/2010 Joy et al.
7,842,083 B2 11/2010 Shanley et al.
7,854,172 B2 12/2010 O'Brien et al.
7,862,513 B2 1/2011 Eigler et al.
7,914,639 B2 3/2011 Layne et al.
7,939,000 B2 5/2011 Edwin et al.
7,988,724 B2 8/2011 Salahieh et al.
7,993,383 B2 8/2011 Hartley et al.
8,012,194 B2 9/2011 Edwin et al.
8,016,877 B2 9/2011 Seguin et al.
8,021,420 B2 9/2011 Dolan
8,025,625 B2 9/2011 Allen
8,025,668 B2 9/2011 McCartney
8,043,360 B2 10/2011 McNamara et al.
8,070,708 B2 12/2011 Rottenberg et al.
8,091,556 B2 1/2012 Keren et al.
8,096,959 B2 1/2012 Stewart et al.
8,137,605 B2 3/2012 McCrea et al.
8,142,363 B1 3/2012 Eigler et al.
8,147,545 B2 4/2012 Avior
8,157,852 B2 4/2012 Bloom et al.
8,157,860 B2 4/2012 McNamara et al.
8,157,940 B2 4/2012 Edwin et al.
8,158,041 B2 4/2012 Colone
8,187,321 B2 5/2012 Shanley et al.
8,202,313 B2 6/2012 Shanley et al.
8,206,435 B2 6/2012 Shanley et al.
8,216,398 B2 7/2012 Bledsoe et al.
8,221,491 B1 7/2012 Burmeister et al.
8,235,916 B2 8/2012 Whiting et al.
8,235,933 B2 8/2012 Keren et al.
8,246,677 B2 8/2012 Ryan
8,287,589 B2 10/2012 Otto et al.
8,298,150 B2 10/2012 Mann et al.
8,298,244 B2 10/2012 Garcia et al.
8,303,511 B2 11/2012 Eigler et al.
8,313,524 B2 11/2012 Edwin et al.
8,328,751 B2 12/2012 Keren et al.
8,337,650 B2 12/2012 Edwin et al.
8,348,996 B2 1/2013 Tuval et al.
8,357,193 B2 1/2013 Phan et al.
8,398,708 B2 3/2013 Meiri et al.
8,460,366 B2 6/2013 Rowe
8,468,667 B2 6/2013 Straubinger et al.
8,480,594 B2 7/2013 Eigler et al.
8,579,966 B2 11/2013 Seguin et al.
8,597,225 B2 12/2013 Kapadia
8,617,337 B2 12/2013 Layne et al.
8,617,441 B2 12/2013 Edwin et al.
8,652,284 B2 2/2014 Bogert et al.
8,660,667 B1 2/2014 Kusumoto
8,665,086 B2 3/2014 Miller et al.
8,696,611 B2 4/2014 Nitzan et al.
8,715,314 B1 5/2014 Janardhan et al.
8,790,241 B2 7/2014 Edwin et al.
8,808,294 B2 8/2014 Fox et al.
8,882,697 B2 11/2014 Celermajer et al.
8,882,798 B2 11/2014 Schwab et al.
8,911,489 B2 12/2014 Ben-Muvhar
9,005,155 B2 4/2015 Sugimoto
9,034,034 B2 5/2015 Nitzan et al.
9,055,917 B2 6/2015 Mann et al.
9,060,696 B2 6/2015 Eigler et al.
9,067,050 B2 6/2015 Gallagher et al.
9,205,236 B2 12/2015 McNamara et al.
9,220,429 B2 12/2015 Nabutovsky et al.
9,232,997 B2 1/2016 Sugimoto et al.
9,358,371 B2 6/2016 McNamara et al.
9,393,115 B2 7/2016 Tabor et al.
9,456,812 B2 10/2016 Finch et al.
9,622,895 B2 4/2017 Cohen et al.
9,629,715 B2 4/2017 Nitzan et al.
9,681,948 B2 6/2017 Levi et al.
9,707,382 B2 7/2017 Nitzan et al.
9,713,696 B2 7/2017 Yacoby et al.
9,724,499 B2 8/2017 Rottenberg et al.
9,757,107 B2 9/2017 McNamara et al.
9,789,294 B2 10/2017 Taft et al.
9,918,677 B2 3/2018 Eigler et al.
9,943,670 B2 4/2018 Keren et al.
9,980,815 B2 5/2018 Nitzan et al.
10,045,766 B2 8/2018 McNamara et al.
10,047,421 B2 8/2018 Khan et al.
10,076,403 B1 9/2018 Eigler et al.
10,105,103 B2 10/2018 Goldshtein et al.
10,111,741 B2 10/2018 Michalak
10,136,897 B2 11/2018 Watson et al.
10,207,087 B2 2/2019 Keren et al.
10,207,807 B2 2/2019 Moran et al.
10,251,740 B2 4/2019 Eigler et al.
10,251,750 B2 4/2019 Alexander et al.
10,265,169 B2 4/2019 Desrosiers et al.
10,299,687 B2 5/2019 Nabutovsky et al.
10,357,320 B2 7/2019 Beira
10,357,357 B2 7/2019 Levi et al.
10,368,981 B2 8/2019 Nitzan et al.
10,463,490 B2 11/2019 Rottenberg et al.
10,478,594 B2 11/2019 Yacoby et al.
10,542,994 B2 1/2020 Ben-Muvhar et al.
10,548,725 B2 2/2020 Alkhatib et al.
10,561,423 B2 2/2020 Sharma
10,583,002 B2 3/2020 Lane et al.
10,639,459 B2 5/2020 Nitzan et al.
10,828,151 B2 11/2020 Nitzan et al.
10,835,394 B2 11/2020 Nae et al.
10,898,698 B1 1/2021 Eigler et al.
10,912,645 B2 2/2021 Rottenberg et al.
10,925,706 B2 2/2021 Eigler et al.
10,940,296 B2 3/2021 Keren
11,045,338 B2 6/2021 Boyle et al.
11,109,988 B2 9/2021 Rosen et al.
11,135,054 B2 10/2021 Nitzan et al.
11,234,702 B1 2/2022 Eigler et al.
11,253,353 B2 2/2022 Levi et al.
11,255,379 B2 2/2022 Baskin et al.
11,266,501 B2 3/2022 Rottenberg et al.
11,291,807 B2 4/2022 Eigler et al.
11,304,831 B2 4/2022 Nae et al.
11,382,747 B2 7/2022 Rottenberg et al.
11,458,287 B2 10/2022 Eigler et al.
11,497,631 B2 11/2022 Rosen et al.
11,607,327 B2 3/2023 Nae et al.
11,612,385 B2 3/2023 Nae et al.
11,690,976 B2 7/2023 Yacoby et al.
11,744,589 B2 9/2023 Ben-David et al.
11,813,386 B2 11/2023 Nae et al.
11,850,138 B2 12/2023 Eigler et al.
11,865,282 B2 1/2024 Nae et al.
12,005,214 B2 6/2024 Nitzan et al.
12,115,328 B2 10/2024 Nae et al.

(56) References Cited

U.S. PATENT DOCUMENTS

| | | | |
|---|---|---|---|
| 12,186,176 | B2 | 1/2025 | Eigler et al. |
| 12,186,510 | B2 | 1/2025 | Keren |
| 12,226,602 | B2 | 2/2025 | Nae et al. |
| 12,251,529 | B2 | 3/2025 | Nae et al. |
| 12,296,122 | B2 | 5/2025 | Nae et al. |
| 12,303,390 | B2 | 5/2025 | Rottenberg et al. |
| 12,311,134 | B2 | 5/2025 | Eigler et al. |
| 12,349,912 | B2 | 7/2025 | Ben-David et al. |
| 12,369,918 | B2 | 7/2025 | Eigler et al. |
| 12,453,626 | B2 | 10/2025 | Eigler et al. |
| 12,465,485 | B2 | 11/2025 | Nitzan et al. |
| 12,465,488 | B2 | 11/2025 | Rottenberg et al. |
| 12,502,272 | B2 | 12/2025 | Nitzan et al. |
| 2001/0007956 | A1 | 7/2001 | Letac et al. |
| 2001/0020154 | A1 | 9/2001 | Bigus et al. |
| 2001/0021872 | A1 | 9/2001 | Bailey et al. |
| 2002/0042565 | A1 | 4/2002 | Cooper et al. |
| 2002/0051730 | A1 | 5/2002 | Bodnar et al. |
| 2002/0099431 | A1 | 7/2002 | Armstrong et al. |
| 2002/0120277 | A1 | 8/2002 | Hauschild et al. |
| 2002/0165479 | A1 | 11/2002 | Wilk |
| 2002/0165606 | A1 | 11/2002 | Wolf et al. |
| 2002/0169371 | A1 | 11/2002 | Gilderdale |
| 2002/0169377 | A1 | 11/2002 | Khairkhahan et al. |
| 2002/0173742 | A1 | 11/2002 | Keren et al. |
| 2002/0183628 | A1 | 12/2002 | Reich et al. |
| 2003/0028213 | A1 | 2/2003 | Thill et al. |
| 2003/0045902 | A1 | 3/2003 | Weadock |
| 2003/0097172 | A1 | 5/2003 | Shalev et al. |
| 2003/0100920 | A1 | 5/2003 | Akin et al. |
| 2003/0125798 | A1 | 7/2003 | Martin |
| 2003/0136417 | A1 | 7/2003 | Fonseca et al. |
| 2003/0139819 | A1 | 7/2003 | Beer et al. |
| 2003/0176914 | A1 | 9/2003 | Rabkin et al. |
| 2003/0208263 | A1 | 11/2003 | Burmeister et al. |
| 2003/0209835 | A1 | 11/2003 | Chun et al. |
| 2003/0216679 | A1 | 11/2003 | Wolf et al. |
| 2003/0216803 | A1 | 11/2003 | Ledergerber |
| 2004/0010219 | A1 | 1/2004 | McCusker et al. |
| 2004/0016514 | A1 | 1/2004 | Nien |
| 2004/0073242 | A1 | 4/2004 | Chanduszko |
| 2004/0077988 | A1 | 4/2004 | Tweden et al. |
| 2004/0087984 | A1 | 5/2004 | Kupiecki et al. |
| 2004/0088045 | A1 | 5/2004 | Cox |
| 2004/0093075 | A1 | 5/2004 | Kuehne |
| 2004/0102797 | A1 | 5/2004 | Golden et al. |
| 2004/0116999 | A1 | 6/2004 | Ledergerber |
| 2004/0138743 | A1 | 7/2004 | Myers et al. |
| 2004/0147869 | A1 | 7/2004 | Wolf et al. |
| 2004/0147871 | A1 | 7/2004 | Burnett |
| 2004/0147886 | A1 | 7/2004 | Bonni |
| 2004/0147969 | A1 | 7/2004 | Mann et al. |
| 2004/0162514 | A1 | 8/2004 | Alferness et al. |
| 2004/0193261 | A1 | 9/2004 | Berreklouw |
| 2004/0210190 | A1 | 10/2004 | Kohler et al. |
| 2004/0210307 | A1 | 10/2004 | Khairkhahan |
| 2004/0225352 | A1 | 11/2004 | Osborne et al. |
| 2004/0249335 | A1 | 12/2004 | Faul et al. |
| 2005/0003327 | A1 | 1/2005 | Elian et al. |
| 2005/0033327 | A1 | 2/2005 | Gainor et al. |
| 2005/0033351 | A1 | 2/2005 | Newton |
| 2005/0065589 | A1 | 3/2005 | Schneider et al. |
| 2005/0125032 | A1 | 6/2005 | Whisenant et al. |
| 2005/0137682 | A1 | 6/2005 | Justino |
| 2005/0148925 | A1 | 7/2005 | Rottenberg et al. |
| 2005/0149097 | A1 | 7/2005 | Regnell et al. |
| 2005/0149166 | A1 | 7/2005 | Schaeffer et al. |
| 2005/0165344 | A1 | 7/2005 | Dobak, III |
| 2005/0182486 | A1 | 8/2005 | Gabbay |
| 2005/0228480 | A1 | 10/2005 | Douglas et al. |
| 2005/0267524 | A1 | 12/2005 | Chanduszko |
| 2005/0283231 | A1 | 12/2005 | Haug et al. |
| 2005/0288596 | A1 | 12/2005 | Eigler et al. |
| 2005/0288706 | A1 | 12/2005 | Widomski et al. |
| 2005/0288786 | A1 | 12/2005 | Chanduszko |
| 2006/0009800 | A1 | 1/2006 | Christianson et al. |
| 2006/0015002 | A1 | 1/2006 | Moaddeb et al. |
| 2006/0015178 | A1 | 1/2006 | Moaddeb et al. |
| 2006/0025857 | A1 | 2/2006 | Bergheim et al. |
| 2006/0052821 | A1 | 3/2006 | Abbott et al. |
| 2006/0064055 | A1 | 3/2006 | Pile-Spellman et al. |
| 2006/0106449 | A1 | 5/2006 | Ben Muvhar |
| 2006/0111660 | A1 | 5/2006 | Wolf et al. |
| 2006/0111704 | A1 | 5/2006 | Brenneman et al. |
| 2006/0116710 | A1 | 6/2006 | Corcoran et al. |
| 2006/0122522 | A1 | 6/2006 | Chavan et al. |
| 2006/0122647 | A1 | 6/2006 | Callaghan et al. |
| 2006/0167541 | A1 | 7/2006 | Lattouf |
| 2006/0184231 | A1 | 8/2006 | Rucker |
| 2006/0212110 | A1 | 9/2006 | Osborne et al. |
| 2006/0241745 | A1 | 10/2006 | Solem |
| 2006/0256611 | A1 | 11/2006 | Bednorz et al. |
| 2006/0282157 | A1 | 12/2006 | Hill et al. |
| 2007/0010852 | A1 | 1/2007 | Blaeser et al. |
| 2007/0021739 | A1 | 1/2007 | Weber |
| 2007/0043391 | A1 | 2/2007 | Moszner et al. |
| 2007/0043435 | A1 | 2/2007 | Seguin et al. |
| 2007/0073337 | A1 | 3/2007 | Abbott et al. |
| 2007/0093048 | A1 | 4/2007 | Shim |
| 2007/0118207 | A1 | 5/2007 | Amplatz et al. |
| 2007/0129756 | A1 | 6/2007 | Abbott et al. |
| 2007/0129784 | A1 | 6/2007 | Lendlein et al. |
| 2007/0191863 | A1 | 8/2007 | De Juan, Jr. et al. |
| 2007/0193632 | A1 * | 8/2007 | Shu ........................ F16K 1/165 623/2.26 |
| 2007/0213813 | A1 | 9/2007 | Von Segesser et al. |
| 2007/0249985 | A1 | 10/2007 | Brenneman et al. |
| 2007/0276413 | A1 | 11/2007 | Nobles |
| 2007/0276414 | A1 | 11/2007 | Nobles |
| 2007/0282157 | A1 | 12/2007 | Rottenberg et al. |
| 2007/0293939 | A1 | 12/2007 | Shrivastava et al. |
| 2007/0299384 | A1 | 12/2007 | Faul et al. |
| 2008/0034836 | A1 | 2/2008 | Eigler et al. |
| 2008/0051829 | A1 | 2/2008 | Eidenschink et al. |
| 2008/0086205 | A1 | 4/2008 | Gordy et al. |
| 2008/0125861 | A1 | 5/2008 | Webler et al. |
| 2008/0171944 | A1 | 7/2008 | Brenneman et al. |
| 2008/0177300 | A1 | 7/2008 | Mas et al. |
| 2008/0221609 | A1 | 9/2008 | McGuckin et al. |
| 2008/0243081 | A1 | 10/2008 | Nance et al. |
| 2008/0262602 | A1 | 10/2008 | Wilk et al. |
| 2008/0264102 | A1 | 10/2008 | Berra |
| 2008/0274011 | A1 | 11/2008 | Flomenblit et al. |
| 2008/0319525 | A1 | 12/2008 | Tieu et al. |
| 2009/0030499 | A1 | 1/2009 | Bebb et al. |
| 2009/0054976 | A1 | 2/2009 | Tuval et al. |
| 2009/0125104 | A1 | 5/2009 | Hoffman |
| 2009/0149947 | A1 | 6/2009 | Frohwitter |
| 2009/0198315 | A1 | 8/2009 | Boudjemline |
| 2009/0248133 | A1 | 10/2009 | Bloom et al. |
| 2009/0264859 | A1 | 10/2009 | Mas |
| 2009/0276040 | A1 | 11/2009 | Rowe et al. |
| 2009/0319037 | A1 | 12/2009 | Rowe et al. |
| 2010/0004740 | A1 | 1/2010 | Seguin et al. |
| 2010/0022940 | A1 | 1/2010 | Thompson |
| 2010/0023046 | A1 | 1/2010 | Heidner et al. |
| 2010/0023047 | A1 | 1/2010 | Simpson |
| 2010/0057192 | A1 | 3/2010 | Celermajer |
| 2010/0069836 | A1 | 3/2010 | Satake |
| 2010/0070022 | A1 | 3/2010 | Kuehling |
| 2010/0081867 | A1 | 4/2010 | Fishler et al. |
| 2010/0100167 | A1 | 4/2010 | Bortlein et al. |
| 2010/0121434 | A1 | 5/2010 | Paul et al. |
| 2010/0125288 | A1 | 5/2010 | Gelfand et al. |
| 2010/0179590 | A1 | 7/2010 | Fortson et al. |
| 2010/0191326 | A1 | 7/2010 | Alkhatib |
| 2010/0249490 | A1 | 9/2010 | Farnan |
| 2010/0249491 | A1 | 9/2010 | Farnan et al. |
| 2010/0249909 | A1 | 9/2010 | McNamara et al. |
| 2010/0249910 | A1 | 9/2010 | McNamara et al. |
| 2010/0249915 | A1 | 9/2010 | Zhang |
| 2010/0256548 | A1 | 10/2010 | McNamara et al. |
| 2010/0256753 | A1 | 10/2010 | McNamara et al. |
| 2010/0298632 | A1 | 11/2010 | Levine et al. |

(56) References Cited

U.S. PATENT DOCUMENTS

| | | | |
|---|---|---|---|
| 2010/0298755 | A1 | 11/2010 | McNamara et al. |
| 2010/0324652 | A1 | 12/2010 | Aurilia et al. |
| 2011/0022057 | A1 | 1/2011 | Eigler et al. |
| 2011/0022157 | A1 | 1/2011 | Essinger et al. |
| 2011/0054515 | A1 | 3/2011 | Bridgeman et al. |
| 2011/0071623 | A1 | 3/2011 | Finch et al. |
| 2011/0071624 | A1 | 3/2011 | Finch et al. |
| 2011/0093059 | A1 | 4/2011 | Fischell et al. |
| 2011/0106149 | A1 | 5/2011 | Ryan et al. |
| 2011/0137398 | A1 | 6/2011 | Magnuson et al. |
| 2011/0152923 | A1 | 6/2011 | Fox |
| 2011/0152994 | A1 | 6/2011 | Hendriksen et al. |
| 2011/0190874 | A1 | 8/2011 | Celermajer et al. |
| 2011/0213449 | A1 | 9/2011 | Ginn et al. |
| 2011/0218477 | A1 | 9/2011 | Keren et al. |
| 2011/0218478 | A1 | 9/2011 | Keren et al. |
| 2011/0218479 | A1 | 9/2011 | Rottenberg et al. |
| 2011/0218480 | A1 | 9/2011 | Rottenberg et al. |
| 2011/0218481 | A1 | 9/2011 | Rottenberg et al. |
| 2011/0218613 | A1 | 9/2011 | Leopold et al. |
| 2011/0251675 | A1 | 10/2011 | Dwork |
| 2011/0257723 | A1 | 10/2011 | McNamara |
| 2011/0264191 | A1 | 10/2011 | Rothstein |
| 2011/0264203 | A1 | 10/2011 | Dwork et al. |
| 2011/0265908 | A1 | 11/2011 | Clerc et al. |
| 2011/0276086 | A1 | 11/2011 | Al-Qbandi et al. |
| 2011/0295182 | A1 | 12/2011 | Finch et al. |
| 2011/0295183 | A1 | 12/2011 | Finch et al. |
| 2011/0295362 | A1 | 12/2011 | Finch et al. |
| 2011/0295366 | A1 | 12/2011 | Finch et al. |
| 2011/0306916 | A1 | 12/2011 | Nitzan et al. |
| 2011/0319806 | A1 | 12/2011 | Wardle |
| 2012/0022507 | A1 | 1/2012 | Najafi et al. |
| 2012/0022633 | A1 | 1/2012 | Olson et al. |
| 2012/0035590 | A1 | 2/2012 | Whiting et al. |
| 2012/0041422 | A1 | 2/2012 | Whiting et al. |
| 2012/0046528 | A1 | 2/2012 | Eigler et al. |
| 2012/0046739 | A1 | 2/2012 | Von Oepen et al. |
| 2012/0053686 | A1 | 3/2012 | McNamara et al. |
| 2012/0071918 | A1 | 3/2012 | Amin et al. |
| 2012/0109056 | A1 | 5/2012 | Rasmussen |
| 2012/0130301 | A1 | 5/2012 | McNamara et al. |
| 2012/0165928 | A1 | 6/2012 | Nitzan et al. |
| 2012/0179172 | A1 | 7/2012 | Paul, Jr. et al. |
| 2012/0190991 | A1 | 7/2012 | Bornzin et al. |
| 2012/0265296 | A1 | 10/2012 | McNamara et al. |
| 2012/0271277 | A1 | 10/2012 | Fischell et al. |
| 2012/0271398 | A1 | 10/2012 | Essinger et al. |
| 2012/0289815 | A1 | 11/2012 | Keast et al. |
| 2012/0289882 | A1 | 11/2012 | McNamara et al. |
| 2012/0290062 | A1 | 11/2012 | McNamara et al. |
| 2013/0030521 | A1 | 1/2013 | Nitzan et al. |
| 2013/0046373 | A1 | 2/2013 | Cartledge et al. |
| 2013/0096965 | A1 | 4/2013 | Pappas et al. |
| 2013/0138145 | A1 | 5/2013 | Von Oepen |
| 2013/0166021 | A1 | 6/2013 | Bruchman et al. |
| 2013/0178783 | A1 | 7/2013 | McNamara et al. |
| 2013/0178784 | A1 | 7/2013 | McNamara et al. |
| 2013/0184633 | A1 | 7/2013 | McNamara et al. |
| 2013/0184634 | A1 | 7/2013 | McNamara et al. |
| 2013/0197423 | A1 | 8/2013 | Keren et al. |
| 2013/0197547 | A1 | 8/2013 | Fukuoka et al. |
| 2013/0197629 | A1 | 8/2013 | Gainor et al. |
| 2013/0204175 | A1 | 8/2013 | Sugimoto |
| 2013/0231737 | A1 | 9/2013 | McNamara et al. |
| 2013/0253342 | A1 | 9/2013 | Griswold et al. |
| 2013/0261531 | A1 | 10/2013 | Gallagher et al. |
| 2013/0281988 | A1 | 10/2013 | Magnin et al. |
| 2013/0304192 | A1 | 11/2013 | Chanduszko |
| 2013/0331864 | A1 | 12/2013 | Jelich et al. |
| 2014/0012181 | A1 | 1/2014 | Sugimoto et al. |
| 2014/0012303 | A1 | 1/2014 | Heipl |
| 2014/0012368 | A1 | 1/2014 | Sugimoto et al. |
| 2014/0012369 | A1 | 1/2014 | Murry, III et al. |
| 2014/0039599 | A1 | 2/2014 | Berreklouw |
| 2014/0067037 | A1 | 3/2014 | Fargahi |
| 2014/0094904 | A1 | 4/2014 | Salahieh et al. |
| 2014/0128795 | A1 | 5/2014 | Keren et al. |
| 2014/0128796 | A1 | 5/2014 | Keren et al. |
| 2014/0163449 | A1 | 6/2014 | Rottenberg et al. |
| 2014/0194971 | A1 | 7/2014 | McNamara |
| 2014/0213959 | A1 | 7/2014 | Nitzan et al. |
| 2014/0222144 | A1 | 8/2014 | Eberhardt et al. |
| 2014/0249621 | A1 | 9/2014 | Eidenschink |
| 2014/0257167 | A1 | 9/2014 | Celermajer |
| 2014/0275916 | A1 | 9/2014 | Nabutovsky et al. |
| 2014/0277045 | A1 | 9/2014 | Fazio et al. |
| 2014/0277054 | A1 | 9/2014 | McNamara et al. |
| 2014/0303710 | A1 | 10/2014 | Zhang et al. |
| 2014/0350565 | A1 | 11/2014 | Yacoby et al. |
| 2014/0350658 | A1 | 11/2014 | Benary et al. |
| 2014/0350661 | A1 | 11/2014 | Schaeffer |
| 2014/0350669 | A1 | 11/2014 | Gillespie et al. |
| 2014/0357946 | A1 | 12/2014 | Golden et al. |
| 2014/0358222 | A1 | 12/2014 | Gorman, III et al. |
| 2014/0364941 | A1 | 12/2014 | Edmiston et al. |
| 2015/0005810 | A1 | 1/2015 | Center et al. |
| 2015/0034217 | A1 | 2/2015 | Vad |
| 2015/0039084 | A1 | 2/2015 | Levi et al. |
| 2015/0066140 | A1 | 3/2015 | Quadri et al. |
| 2015/0073539 | A1 | 3/2015 | Geiger et al. |
| 2015/0112383 | A1 | 4/2015 | Sherman et al. |
| 2015/0119796 | A1 | 4/2015 | Finch |
| 2015/0127093 | A1 | 5/2015 | Hosmer et al. |
| 2015/0142049 | A1 | 5/2015 | Delgado et al. |
| 2015/0148731 | A1 | 5/2015 | McNamara et al. |
| 2015/0148896 | A1 | 5/2015 | Karapetian et al. |
| 2015/0157455 | A1 | 6/2015 | Hoang et al. |
| 2015/0173897 | A1 | 6/2015 | Raanani et al. |
| 2015/0182334 | A1 | 7/2015 | Bourang et al. |
| 2015/0190229 | A1 | 7/2015 | Seguin |
| 2015/0196383 | A1 | 7/2015 | Johnson |
| 2015/0201998 | A1 | 7/2015 | Roy et al. |
| 2015/0209143 | A1 | 7/2015 | Duffy et al. |
| 2015/0230924 | A1 | 8/2015 | Miller et al. |
| 2015/0238314 | A1 | 8/2015 | Bortlein et al. |
| 2015/0245908 | A1 | 9/2015 | Nitzan et al. |
| 2015/0272731 | A1 | 10/2015 | Racchini et al. |
| 2015/0282790 | A1 | 10/2015 | Quinn et al. |
| 2015/0282931 | A1 | 10/2015 | Brunnett et al. |
| 2015/0294313 | A1 | 10/2015 | Kamal et al. |
| 2015/0297346 | A1 | 10/2015 | Duffy et al. |
| 2015/0313599 | A1 | 11/2015 | Johnson et al. |
| 2015/0335801 | A1 | 11/2015 | Farnan et al. |
| 2015/0359556 | A1 | 12/2015 | Vardi |
| 2016/0007924 | A1 | 1/2016 | Eigler et al. |
| 2016/0022423 | A1 | 1/2016 | McNamara et al. |
| 2016/0022970 | A1 | 1/2016 | Forcucci et al. |
| 2016/0045165 | A1 | 2/2016 | Braido et al. |
| 2016/0045311 | A1 | 2/2016 | McCann et al. |
| 2016/0073907 | A1 | 3/2016 | Nabutovsky et al. |
| 2016/0120550 | A1 | 5/2016 | McNamara et al. |
| 2016/0129260 | A1 | 5/2016 | Mann et al. |
| 2016/0157862 | A1 | 6/2016 | Hernandez et al. |
| 2016/0166381 | A1 | 6/2016 | Sugimoto et al. |
| 2016/0184561 | A9 | 6/2016 | McNamara et al. |
| 2016/0206423 | A1 | 7/2016 | O'Connor et al. |
| 2016/0213467 | A1 | 7/2016 | Backus et al. |
| 2016/0220360 | A1 | 8/2016 | Lin et al. |
| 2016/0220365 | A1 | 8/2016 | Backus et al. |
| 2016/0262878 | A1 | 9/2016 | Backus et al. |
| 2016/0262879 | A1 | 9/2016 | Meiri et al. |
| 2016/0287386 | A1 | 10/2016 | Alon et al. |
| 2016/0296325 | A1 | 10/2016 | Edelman et al. |
| 2016/0361167 | A1 | 12/2016 | Tuval et al. |
| 2016/0361184 | A1 | 12/2016 | Tabor et al. |
| 2017/0028176 | A1 | 2/2017 | Van Dam et al. |
| 2017/0035435 | A1 | 2/2017 | Amin et al. |
| 2017/0056171 | A1 | 3/2017 | Cooper et al. |
| 2017/0072173 | A1 | 3/2017 | Van Dam et al. |
| 2017/0106176 | A1 | 4/2017 | Taft et al. |
| 2017/0112624 | A1 | 4/2017 | Patel |
| 2017/0113026 | A1 | 4/2017 | Finch |
| 2017/0128705 | A1 | 5/2017 | Forcucci et al. |

(56) References Cited

U.S. PATENT DOCUMENTS

| | | | |
|---|---|---|---|
| 2017/0135685 | A9 | 5/2017 | McNamara et al. |
| 2017/0165062 | A1 | 6/2017 | Rothstein |
| 2017/0165532 | A1 | 6/2017 | Khan et al. |
| 2017/0196509 | A1 * | 7/2017 | Hunter .................. A61F 2/2472 |
| 2017/0216025 | A1 | 8/2017 | Nitzan et al. |
| 2017/0224323 | A1 | 8/2017 | Rowe et al. |
| 2017/0224444 | A1 | 8/2017 | Viecilli et al. |
| 2017/0231766 | A1 | 8/2017 | Hariton et al. |
| 2017/0273790 | A1 | 9/2017 | Vettukattil et al. |
| 2017/0281339 | A1 | 10/2017 | Levi et al. |
| 2017/0312486 | A1 | 11/2017 | Nitzan et al. |
| 2017/0319823 | A1 | 11/2017 | Yacoby et al. |
| 2017/0325956 | A1 | 11/2017 | Rottenberg et al. |
| 2017/0340460 | A1 | 11/2017 | Rosen et al. |
| 2017/0348100 | A1 | 12/2017 | Lane et al. |
| 2018/0028314 | A1 | 2/2018 | Ekvall et al. |
| 2018/0085128 | A1 | 3/2018 | Bellomo et al. |
| 2018/0099128 | A9 | 4/2018 | McNamara et al. |
| 2018/0104053 | A1 | 4/2018 | Alkhatib et al. |
| 2018/0110609 | A1 | 4/2018 | Ehnes et al. |
| 2018/0116843 | A1 | 5/2018 | Schreck et al. |
| 2018/0125630 | A1 | 5/2018 | Hynes et al. |
| 2018/0130988 | A1 | 5/2018 | Nishikawa et al. |
| 2018/0153691 | A1 | 6/2018 | Anderson et al. |
| 2018/0200496 | A1 | 7/2018 | Kratzberg et al. |
| 2018/0235791 | A1 | 8/2018 | Kang et al. |
| 2018/0243071 | A1 | 8/2018 | Eigler et al. |
| 2018/0256865 | A1 | 9/2018 | Finch et al. |
| 2018/0263766 | A1 | 9/2018 | Nitzan et al. |
| 2018/0280667 | A1 | 10/2018 | Keren |
| 2018/0280668 | A1 | 10/2018 | Alaswad |
| 2018/0344994 | A1 | 12/2018 | Karavany et al. |
| 2018/0360632 | A1 | 12/2018 | Kim |
| 2019/0000327 | A1 | 1/2019 | Doan et al. |
| 2019/0008628 | A1 | 1/2019 | Eigler et al. |
| 2019/0015103 | A1 | 1/2019 | Sharma |
| 2019/0015188 | A1 | 1/2019 | Eigler et al. |
| 2019/0021861 | A1 | 1/2019 | Finch |
| 2019/0076275 | A1 | 3/2019 | Kim |
| 2019/0076583 | A1 | 3/2019 | Kim |
| 2019/0083076 | A1 | 3/2019 | Alanbaei |
| 2019/0091047 | A1 | 3/2019 | Walsh |
| 2019/0091438 | A1 | 3/2019 | Higgins et al. |
| 2019/0110911 | A1 | 4/2019 | Nae et al. |
| 2019/0151122 | A1 | 5/2019 | Kim |
| 2019/0239754 | A1 | 8/2019 | Nabutovsky et al. |
| 2019/0254814 | A1 | 8/2019 | Nitzan et al. |
| 2019/0262118 | A1 | 8/2019 | Eigler et al. |
| 2019/0328513 | A1 | 10/2019 | Levi et al. |
| 2019/0336163 | A1 | 11/2019 | McNamara et al. |
| 2020/0060825 | A1 | 2/2020 | Rottenberg et al. |
| 2020/0078196 | A1 | 3/2020 | Rosen et al. |
| 2020/0078558 | A1 | 3/2020 | Yacoby et al. |
| 2020/0085600 | A1 | 3/2020 | Schwartz et al. |
| 2020/0138612 | A1 | 5/2020 | Higashi et al. |
| 2020/0188091 | A1 | 6/2020 | Lane et al. |
| 2020/0197178 | A1 | 6/2020 | Vecchio |
| 2020/0238059 | A1 | 7/2020 | Wang et al. |
| 2020/0261224 | A1 | 8/2020 | Gross |
| 2020/0261705 | A1 | 8/2020 | Nitzan et al. |
| 2020/0268537 | A1 | 8/2020 | Reisin et al. |
| 2020/0281611 | A1 | 9/2020 | Kelly et al. |
| 2020/0315599 | A1 | 10/2020 | Nae et al. |
| 2020/0368505 | A1 | 11/2020 | Nae et al. |
| 2021/0022507 | A1 | 1/2021 | Williams |
| 2021/0052378 | A1 | 2/2021 | Nitzan et al. |
| 2021/0100665 | A1 | 4/2021 | Nae et al. |
| 2021/0121179 | A1 | 4/2021 | Ben-David et al. |
| 2021/0161637 | A1 | 6/2021 | Eigler et al. |
| 2021/0205590 | A1 | 7/2021 | Fahey et al. |
| 2021/0338990 | A1 | 11/2021 | Eigler et al. |
| 2022/0008014 | A1 | 1/2022 | Rowe et al. |
| 2022/0125571 | A1 | 4/2022 | El Azouzi et al. |
| 2022/0211361 | A1 | 7/2022 | Rolando et al. |
| 2022/0290275 | A1 | 9/2022 | Born et al. |
| 2022/0304803 | A1 | 9/2022 | Guyenot et al. |
| 2022/0313426 | A1 | 10/2022 | Gifford, III et al. |
| 2022/0346935 | A1 | 11/2022 | Shermer et al. |
| 2024/0139478 | A1 | 5/2024 | Robertson et al. |
| 2024/0252791 | A1 | 8/2024 | Ortiz Garcia et al. |
| 2025/0262418 | A1 | 8/2025 | Nae et al. |
| 2025/0281726 | A1 | 9/2025 | Eigler et al. |
| 2025/0331858 | A1 | 10/2025 | Ben-David et al. |
| 2025/0352210 | A1 | 11/2025 | Eigler et al. |

FOREIGN PATENT DOCUMENTS

| | | | |
|---|---|---|---|
| CN | 101505680 | A | 8/2009 |
| CN | 105555204 | A | 5/2016 |
| CN | 108451569 | A | 8/2018 |
| CN | 113397762 | A | 9/2021 |
| DE | 10142998 | B4 | 2/2005 |
| DE | 102015122113 | A1 | 6/2017 |
| EP | 1808135 | A1 | 7/2007 |
| EP | 1987777 | A2 | 11/2008 |
| EP | 2238933 | A1 | 10/2010 |
| EP | 2305321 | A1 | 4/2011 |
| EP | 1965842 | B1 | 11/2011 |
| EP | 2702965 | A1 | 3/2014 |
| EP | 3400907 | A1 | 11/2018 |
| EP | 4458323 | A1 | 11/2024 |
| FR | 2827153 | A1 | 1/2003 |
| GB | 2468861 | A | 9/2010 |
| JP | 2020509812 | A | 4/2020 |
| WO | WO-9531945 | A1 | 11/1995 |
| WO | WO-9702850 | A1 | 1/1997 |
| WO | WO-9727898 | A1 | 8/1997 |
| WO | WO-9960941 | A1 | 12/1999 |
| WO | WO-0044311 | A2 | 8/2000 |
| WO | WO-0050100 | A1 | 8/2000 |
| WO | WO-0110314 | A2 | 2/2001 |
| WO | WO-0126585 | A1 | 4/2001 |
| WO | WO-0191828 | A2 | 12/2001 |
| WO | WO-0226281 | A1 | 4/2002 |
| WO | WO-02071974 | A2 | 9/2002 |
| WO | WO-02087473 | A1 | 11/2002 |
| WO | WO-03050320 | A1 | 6/2003 |
| WO | WO-03053495 | A2 | 7/2003 |
| WO | WO-2005027752 | A1 | 3/2005 |
| WO | WO-2005074367 | A2 | 8/2005 |
| WO | WO-2006127765 | A1 | 11/2006 |
| WO | WO-2007083288 | A2 | 7/2007 |
| WO | WO-2008055301 | A1 | 5/2008 |
| WO | WO-2008070797 | A2 | 6/2008 |
| WO | WO-2009029261 | A1 | 3/2009 |
| WO | WO-2010128501 | A1 | 11/2010 |
| WO | WO-2010129089 | A2 | 11/2010 |
| WO | WO-2010139771 | A2 | 12/2010 |
| WO | WO-2010139771 | A3 | 1/2011 |
| WO | WO-2011062858 | A1 | 5/2011 |
| WO | WO-2011062970 | A1 | 5/2011 |
| WO | WO-2013028837 | A1 | 2/2013 |
| WO | WO-2013096965 | A1 | 6/2013 |
| WO | WO-2013172474 | A1 | 11/2013 |
| WO | WO-2016178171 | A1 | 11/2016 |
| WO | WO-2017031235 | A1 | 2/2017 |
| WO | WO-2017118920 | A1 | 7/2017 |
| WO | WO-2018158747 | A1 | 9/2018 |
| WO | WO-2019015617 | A1 | 1/2019 |
| WO | WO-2019085841 | A1 | 5/2019 |
| WO | WO-2019109013 | A1 | 6/2019 |
| WO | WO-2019142152 | A1 | 7/2019 |
| WO | WO-2019179447 | A1 | 9/2019 |
| WO | WO-2019212812 | A1 | 11/2019 |
| WO | WO-2019218072 | A1 | 11/2019 |
| WO | WO-2020163112 | A1 | 8/2020 |
| WO | WO-2020206062 | A1 | 10/2020 |
| WO | WO-2020257530 | A1 | 12/2020 |
| WO | WO-2021050589 | A1 | 3/2021 |
| WO | WO-2021113670 | A1 | 6/2021 |
| WO | WO-2021212011 | A2 | 10/2021 |
| WO | WO-2021224736 | A1 | 11/2021 |
| WO | WO-2022046921 | A1 | 3/2022 |
| WO | WO-2022076601 | A1 | 4/2022 |

(56) References Cited

FOREIGN PATENT DOCUMENTS

| | | | |
|---|---|---|---|
| WO | WO-2022091018 | A1 | 5/2022 |
| WO | WO-2022091019 | A1 | 5/2022 |
| WO | WO-2022103973 | A1 | 5/2022 |
| WO | WO-2023079498 | A1 | 5/2023 |
| WO | WO-2024088350 | A1 | 5/2024 |
| WO | WO-2024249425 | A1 | 12/2024 |
| WO | WO-2025021050 | A1 | 1/2025 |
| WO | WO-2025021068 | A1 | 1/2025 |
| WO | WO-2025039936 | A1 | 2/2025 |
| WO | WO-2025039940 | A1 | 2/2025 |

OTHER PUBLICATIONS

U.S. Appl. No. 09/839,643 / U.S. Pat. No. 8,091,556, filed Apr. 20, 2001 / Jan. 10, 2012.
U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Jul. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,807, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.
U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852 / U.S. Pat. No. 10,368,981, filed Apr. 20, 2017 / Aug. 6, 2019.
U.S. Appl. No. 15/570,752 / U.S. Pat. No. 10,940,296, filed Oct. 31, 2017 / Mar. 9, 2021.
U.S. Appl. No. 15/608,948, filed May 30, 2017.
U.S. Appl. No. 15/624,314 / U.S. Pat. No. 10,357,357, filed Jun. 15, 2017 / Jul. 23, 2019.
U.S. Appl. No. 15/650,783 / U.S. Pat. No. 10,639,459, filed Jul. 14, 2017 / May 5, 2020.
U.S. Appl. No. 15/656,936 / U.S. Pat. No. 10,478,594, filed Jul. 21, 2017 / Nov. 19, 2019.
U.S. Appl. No. 15/668,622 / U.S. Pat. No. 10,463,490, filed Aug. 3, 2017 / Nov. 5, 2019.
U.S. Appl. No. 15/798,250 / U.S. Pat. No. 11,109,988, filed Oct. 30, 2017 / Sep. 7, 2021.
U.S. Appl. No. 15/988,888 / U.S. Pat. No. 10,828,151, filed May 24, 2018 / Nov. 10, 2020.
U.S. Appl. No. 16/130,978 / U.S. Pat. No. 10,251,740, filed Sep. 13, 2018 / Apr. 9, 2019.
U.S. Appl. No. 16/130,988 / U.S. Pat. No. 10,925,706, filed Sep. 13, 2018 / Feb. 23, 2021.
U.S. Appl. No. 16/205,213 / U.S. Pat. No. 10,835,394, filed Nov. 29, 2018 / Nov. 17, 2020.
U.S. Appl. No. 16/374,698, filed Apr. 3, 2019.
U.S. Appl. No. 16/395,209 / U.S. Pat. No. 11,135,054, filed Apr. 25, 2019 / Oct. 5, 2021.
U.S. Appl. No. 16/408,419, filed May 9, 2019.
U.S. Appl. No. 16/505,624, filed Jul. 8, 2019.
U.S. Appl. No. 16/672,420, filed Nov. 1, 2019.
U.S. Appl. No. 16/686,013, filed Nov. 15, 2019.
U.S. Appl. No. 16/866,377, filed May 4, 2020.
U.S. Appl. No. 16/875,652 / U.S. Pat. No. 10,898,698, filed May 15, 2020 / Jan. 26, 2021.
U.S. Appl. No. 16/876,640, filed May 18, 2020.
U.S. Appl. No. 16/878,228 / U.S. Pat. No. 10,912,645, filed May 19, 2020 / Feb. 9, 2021.
U.S. Appl. No. 16/963,139, filed Jul. 17, 2020.
U.S. Appl. No. 17/092,063, filed Nov. 6, 2020.
U.S. Appl. No. 17/092,081, filed Nov. 6, 2020.
U.S. Appl. No. 17/095,615, filed Nov. 11, 2020.
U.S. Appl. No. 17/098,251 / U.S. Pat. No. 11,234,702, filed Nov. 13, 2020 / Feb. 1, 2022.
U.S. Appl. No. 17/166,771, filed Feb. 3, 2021.
U.S. Appl. No. 17/175,549, filed Feb. 12, 2021.
U.S. Appl. No. 17/192,612, filed Mar. 4, 2021.
U.S. Appl. No. 17/465,791, filed Sep. 2, 2021.
U.S. Appl. No. 17/490,510, filed Sep. 30, 2021.
U.S. Appl. No. 17/600,079, filed Sep. 29, 2021.
U.S. Appl. No. 17/649,176, filed Jan. 27, 2022.
Borlaug, et al., Latent Pulmonary Vascular Disease May Alter the Response to Therapeutic Atrial Shunt Device in Heart Failure, Circulation (Mar. 2022).
Flachskampf, et al., Influence of Orifice Geometry and Flow Rate on Effective Valve Area: An In Vitro Study, Journal of the American College of Cardiology, 15(5):1173-1180 (Apr. 1990).
Greitz, et al., Pulsatile Brain Movement and Associated Hydrodynamics Studied by Magnetic Resonance Phase Imaging, Diagnostic Neuroradiology, 34(5): 370-380 (1992).
International Search Report & Written Opinion dated Feb. 3, 2023 in Int'l PCT Patent Appl. Serial No. PCT/IB2022/060621 (2210).
International Search Report & Written Opinion dated Mar. 29, 2023 in Int'l PCT Patent Appl. Serial No. PCT/IB2023/050743 (2410).
International Search Report & Written Opinion dated May 17, 2022 in Int'l PCT Patent Appl. Serial No. PCT/IB2022/051177 (2310).
Kaye, et al., One-Year Outcomes After Transcatheter Insertion of an Interatrial Shunt Device for the Management of Heart Failure with Preserved Ejection Fraction, Circulation: Heart Failure, 9(12):e003662 (Dec. 2016).
Shah, et al., Atrial Shunt Device for Heart Failure With Preserved and Mildly Reduced Ejection Fraction (Reduce Lap-HF II): A Randomised, Multicentre, Blinded, Sham-Controlled Trial, The Lancet, 399(10330):1130-1140 (Mar. 2022).
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).

(56) References Cited

OTHER PUBLICATIONS

Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Ando, et al., Left ventricular decompression through a patent foramen ovale in a patient with hypertrophic cardiomyopathy: A case report, Cardiovascular Ultrasound, 2: 1-7 (2004).
Article 34 Amendments dated May 28, 2013 in Int'l PCT Patent Appl. Serial No. PCT/IB2012/001859 (0810).
Article 34 Amendments dated Nov. 27, 2012 in Int'l PCT Patent Appl. Serial No. PCT/IL2011/000958 (0710).
Ataya et al., "A Review of Targeted Pulmonary Arterial Hypertension-Specific Pharmacotherapy," J. Clin. Med., 5(12):114 (2016).
"Atrium Advanta V12, Balloon Expandable Covered Stent, Improving Patient Outcomes with an Endovascular Approach," Brochure, 8 pages, Getinge (2017).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," Chest, 156(6):1176-1186 (2019).
Boehm, et al., "Balloon Atrial Septostomy: History and Technique," Images Paeditr. Cardiol., 8(1):8-14 (2006).
Braunwald, Heart Disease, Chapter 6, pp. 186.
Bridges, et al., "The Society of Thoracic Surgeons Practice Guideline Series: Transmyocardial Laser Revascularization," Ann Thorac Surg., 77:1494-1502 (2004).
Bristow, et al., "Improvement in cardiac myocite function by biological effects of medical therapy: a new concept in the treatment of heart failure," European Heart Journal, 16 (Suppl.F): 20-31 (1995).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Case, et al., "Relief of High Left-Atrial Pressure in Left-Ventricular Failure," Lancet, (pp. 841-842), Oct. 17, 1964.
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Coats, et al., "Controlled Trial of Physical Training in Chronic Heart Failure: Exercise Performance, Hemodynamics, Ventilation, and Autonomic Function," Circulation, 85: 2119-2131 (1992).
Davies et al., "Abnormal left heart function after operation for atrial septal defect," British Heart Journal, 32:747-753 (1970).
Davies, et al., "Reduced Contraction and Altered Frequency Response of Isolated Ventricular Myocytes From Patients With Heart Failure, Circulation," 92: 2540-2549 (1995).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Ennezat, et al., An unusual case of low-flow, low gradient severe aortic stenosis: Left-to-right shunt due to atrial septal defect, Cardiology, 113(2):146-148, (2009).
Eshaghian et al., "Relation of Loop Diuretic Dose to Mortality in Advanced Heart Failure," Am J Cardiol., 97:1759-1764 (2006).
Ewert, et al., Acute Left Heart Failure After Interventional Occlusion of an Artial Septal Defect, Z Kardiol, 90(5): 362-366 (May 2001).
Ewert, et al., Masked Left Ventricular Restriction in Elderly Patients With Atrial Septal Defects: A Contraindication for Closure?, Catheterization and Cardiovascular Intervention, 52:177-180 (2001).
Extended European Search Report dated Jan. 8, 2015 in EP Patent Appl No. 10772089.8. (0530).
Extended European Search Report dated Mar. 29, 2019 in EP Patent Appl. Serial No. EP16789391 (1830).
Extended European Search Report dated Sep. 19, 2016 in EP Patent Appl. No. 16170281.6 (0731).

(56) References Cited

OTHER PUBLICATIONS

Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geiran, et al., Changes in cardiac dynamics by opening an interventricular shunt in dogs, J. Surg. Res. 48(1):6-12 (1990).
Gelernter-Yaniv, et al., Transcatheter Closureof Left-To-Right Interatrial Shunts to Resolve Hypoxemia, Congenit. Heart Dis. 31(1): 47-53 (Jan. 2008).
Geva et al., "Atrial septal defects," Lancet, 383:1921-32 (2014).
Gewillig, et al., Creation with a stent of an unrestrictive lasting atrial communication, Cardio. Young 12(4): 404-407 (2002).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure a Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 6, 2013 in Int'l PCT Patent Appl. No. PCT/IB2012/001859, 12 pages (0810).
International Search Report & Written Opinion dated Feb. 7, 2020 in Int'l PCT Patent Appl. Serial No. PCT/IB2019/060257 (1410).
International Search Report & Written Opinion dated May 13, 2019 in Int'l PCT Patent Appl. No. PCT/IB2019/050452 (1610).
International Search Report & Written Opinion dated May 29, 2018 in Int'l PCT Patent Appl. Serial No. PCTIB2018/051355 (1310).
International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710).
International Search Report & Written Opinion dated Jul. 23, 2021 in Int'l PCT Patent Appl. Serial No. PCT/IB2021/053594 (1910).
International Search Report & Written Opinion dated Aug. 12, 2020 in Int'l PCT Patent Appl. Serial No. PCT/IB2020/053118 (1010).
International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 11, 2017 in Int'l PCT Patent Appl. Serial No. PCT/IB2017/053188 (1110).
International Search Report & Written Opinion dated Oct. 26, 2007 in Int'l PCT Patent Appl. Serial No. PCT/IB07/50234 (0610).
International Search Report dated Apr. 7, 2008 in Int'l PCT Patent Appl. Serial No. PCT/IL05/00131 (0410).
International Search Report dated Aug. 25, 2010 in Intl PCT Patent Appl. Serial No. PCT/IL2010/000354 (0510).
ISR & Written Opinion dated Feb. 16, 2015 in Int'l PCT Patent Appl. Serial No. PCT/IB2014/001771 (0910).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalities of Treatment in Pulmonary Hypertension," J Am Coll Cardiol., 54:S67-77 (2009).
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer, et al., Controlled Trial of Captopril in Chronic Heart Failure: A Rest and Exercise Hemodynamic Study, Circulation, 67(4): 807-816, 1983.
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).

(56) References Cited

OTHER PUBLICATIONS

Kurzyna et al., "Atrial Septostomy in Treatment of End-Stage Right Heart Failure in Patients With Pulmonary Hypertension," Chest, 131:977-983 (2007).
Lai et al., Bidirectional Shunt Through a Residual Atrial Septal Defect After Percutaneous Transvenous Mitral Commissurotomy, Cadiology, 83(3): 205-207 (1993).
Lammers et al., "Efficacy and Long-Term Patency of Fenerstrated Amplatzer Devices in Children," Catheter Cardiovasc Interv., 70:578-584 (2007).
Lemmer, et al., Surgical Implications of Atrial Septal Defect Complicating Aortic Balloon Valvuloplasty, Ann. thorac. Surg, 48(2):295-297 (Aug. 1989).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of the Requirements for the Degree of Master of Applied Science in the Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Merriam-Webster OnLine Dictionary, Definition of "chamber", printed Dec. 20, 2004.
Mu et al., "Dual mode acoustic wave sensor for precise pressure reading," Applied Physics Letters, 105:113507-1-113507-5 (2014).
Nagaraju et al., "A 400μW Differential FBAR Sensor Interface IC with digital readout," IEEE., pp. 218-221 (2015).
Non-Final Office Action dated Oct. 28, 2021 in U.S. Appl. No. 16/672,420 (0407).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Partial Supplemental European Search Report dated Dec. 11, 2018 in EP Patent Appl. Serial No. 16789391.6 (1830).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," Pace, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin.2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Roven, Effect of Compromising Right Ventricular Function in Left Ventricular Failure by Means of Interatrial and Other Shunts 24:209-219 (Aug. 1969).
Salehian, et al., Improvements in Cardiac Form and Function After Transcatheter Closure of Secundum Atrial Septal Defects, Journal of the American College of Cardiology, 45(4):499-504 (2005).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schmitto, et al., Chronic Heart Failure Induced by Multiple Sequential Coronary Microembolization in sheep, The International Journal of Artificial Organs, 31(4):348-353 (2008).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert, et al., Left ventricular Conditioning in the Elderly Patient to Prevent Congestive Heart Failure After Transcatheter Closure of the Atrial Septal Defect, Catheterization and Cardiovascular Interventions, 64(3): 333-337 (2005).

(56) References Cited

OTHER PUBLICATIONS

Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Stormer, et al., Comparative Study of in Vitro Flow Characteristics Between a Human Aortic Valve and a Designed Aortic Valve and Six Corresponding Types of Prosthetic Heart Valves, European Surgical Research 8(2):117-131 (1976).
Stumper, et al., Modified Technique of Stent Fenestration of the Atrial Septum, Heart, 89:1227-1230, (2003).
Su et al., "A film bulk acoustic resonator pressure sensor based on lateral field excitation," International Journal of Distributed Sensor Networks, 14(11):1-8 (2018).
Supplementary European Search Report dated Nov. 13, 2009 in EP Patent Appl. Serial No. 05703174.2 (0430).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor, et al., Comparative Pathology of an Implantable Left Atrial Pressure Sensor, ASAIO Journal, Clinical Cardiovascular/Cardiopulmonary Bypass, 59(5):486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131 (0410).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Zhou, et al., Unidirectional Valve Patch for Repair of Cardiac Septal Defects with Pulmonary Hypertension, Annals of Thoracic Surgeons, 60:1245-1249, (1995).
Clowes, et al., Mechanisms of Arterial Graft Healing—Rapid Transmural Capillary Ingrowth Provides a Source of Intimal Endothelium and Smooth Muscle in Porous PTFE Prostheses, Am. J. Pathol., 123(2):220-230 (May 1986).
Extended EP Search Report dated Jan. 24, 2025 in EP Patent Appl. Serial No. 24202131.9 (103002).
Hibbert, Benjamin et al., Left Atrial to Coronary Sinus Shunting for Treatment of Symptomatic Heart Failure, JACC: Cardiovascular Interventions, vol. 16, No. 11 (Jun. 12, 2023).
International Preliminary Report on Patentability_PCT/IB2022/060621 Dated May 2, 2024.
International Search Report & Written Opinion dated Jan. 15, 2025 in Int'l PCT Patent Appl. Serial No. PCT/IB2024/060159 (271001).
O'Riordan, Michael, The Hole Story: Interatrial Shunt Companies Are-Mostly-Pushing Ahead, tctmd.com, available at https://www.tctmd.com/news/hole-story-interatrial-shunt-companies-are-mostly-pushing-ahead (Jun. 20, 2024).
Patel et al., Atrial Shunt Device Effects on Cardiac Structure and Function in Heart Failure With Preserved Ejection Fraction, JAMA Cardiology (Apr. 17, 2024).
Pfeiffer, In vivo fluid dynamics of the Ventura interatrial shunt device in patients with heart failure, ESC Heart Failure, DOI: 10.1002/ehf2.14859 (May 22, 2024).
RELIEVE-HF: Does Impact of Interatrial Shunting Differ by HF Type? American College of Cardiology (ACC), available at: https://www.acc.org/Latest-in-Cardiology/Articles/2024/04/02/17/02/sat-930am-relieve-hf-acc-2024 (Apr. 6, 2024).
Rodes-Cabau, et al., Interatrial shunt therapy in advanced heart failure: Outcomes from the open-label cohort of the RELIEVE-HF trial, Eur. J. Heart. Fail., 26(4):1078-1089 (Apr. 2024).
Shah, Sanjiv et al.: Supplemental Materials to Atrial shunt device for heart failure with preserved and mildly reduced ejection fraction (Reduce LAP-HF II): a randomised, multicentre, blinded, sham-controlled trial, The Lancet, vol. 399, Issue 10330 p. 1130-1140, available at: https://www.thelancet.com/journals/lancet/article/PIIS0140-6736(22)00016-2/abstract (Mar. 19, 2022).
Shah, Sanjiv J., RELIEVE-HF Trial: Discussant, ACC.24 (Apr. 6, 2024).
Simard, Trevor et al., Percutaneous Atriotomy for Levoatrial-to-Coronary Sinus Shunting in Symptomatic Heart Failure, JACC: Cardiovascular Interventions, vol. 13, No. 10 (May 25, 2020).
Stone, et al., Supplemental Material-3 to Interatrial Shunt Treatment for Heart Failure: The Randomized RELIEVE-HF Trial, Circulation, 150(24):1931-1943 (Dec. 2024).
Stone, Gregg, A Double-blind, Randomized Placebo-Procedure-Controlled Trial of an Interatrial Shunt in Patients with HFrEF and HFpEF: Principal Results from the RELIEVE-HF Trial, American College of Cardiology (ACC) (Apr. 6, 2024).
Stone, Gregg et al.: Supplemental Material 1—Interatrial Shunt Treatment for Heart Failure: The Randomized RELIEVE-HF Trial, available at: https://www.ahajournals.org/doi/suppl/10.1161/CIRCULATIONAHA.124.070870 (Dec. 10, 2024).

(56) References Cited

OTHER PUBLICATIONS

Stone, Gregg et al.: Supplemental Materials 2 to Interatrial Shunt Treatment for Heart Failure: The Randomized RELIEVE-HF Trial, available at: https://www.ahajournals.org/doi/suppl/10.1161/CIRCULATIONAHA.124.070870 (Dec. 10, 2024).
Stone, Gregg W., Predictors of Outcomes After Inter-Atrial Shunt Treatment in HFrEF and HFpEF: The RELIEVE-HF trial, THT 2025 (Feb. 11, 2025).
Stone, Interatrial Shunt Treatment for Heart Failure: The Randomized RELIEVE-HF Trial, Circulation. 2024; 150:1931-1943. DOI: 10.1161/CIRCULATIONAHA.124.070870 (Dec. 10, 2024).
Sullivan, et al., Tutorial in Biostatistics, Presentation of multivariate data for clinical use: The Framingham Study risk score functions, Statistics In Medicine, Statist. Med., 23:1631-1660 (2004).
Ge, et al., Feasability of a novel implantable device to provide heart failure therapy and left atrial pressure monitoring in a chronic animal study, *ESC Congress 2025*, (Aug. 29, 2025), available at https://esc365.escardio.org/presentation/306434.
Pocock, et al., Prognostic Modeling of Individual Patient Risk and Mortality Impact of Ischemic and Hemorrhagic Complications, Assessment From the Acute Catheterization and Urgent Intervention Triage Strategy Trial, *Circulation*, 121(1):43-51 (Jan. 2010).

* cited by examiner

| | |
|---|---|
| Peak Velocity (M/s) | 1.19 |
| Peak Gradient (mmHg) | 5.6 |
| Mean Velocity (M/s) | 0.90 |
| Mean Gradient (mmHg) | 3.2 |

| | |
|---|---|
| Peak Velocity (M/s) | 2.5 |
| Peak Gradient (mmHg) | 25 |
| Mean Velocity (M/s) | 1.7 |
| Mean Gradient (mmHg) | 12 |

INTERATRIAL SHUNT HAVING PHYSIOLOGIC SENSOR

CROSS-REFERENCE TO RELATED APPLICATIONS

This application is a continuation-in-part application of U.S. patent application Ser. No. 17/098,251, filed Nov. 13, 2020, now U.S. Pat. No. 11,234,702, the entire contents of which are incorporated herein by reference.

FIELD OF THE INVENTION

The present invention related to devices and methods for regulating pressure within a circulatory system and in particular to regulate blood pressure in a heart using an interatrial shunt having a physiologic sensor.

BACKGROUND OF THE INVENTION

There remain multiple cardiovascular and cardiopulmonary disorders comprising scores of millions of patients that have largely unmet clinical therapeutic needs. These disorders include but are not limited to, the syndromes known as heart failure (HF) and pulmonary arterial hypertension (PAH). Despite decades of advances in therapy, a large segment of these patients have a severely limited quality of life that includes disabling symptoms, poor exercise tolerance, inability to perform work, recurrent hospitalizations for acute worsening, and an unacceptably high rate of death. This remains true even when patients are treated with the most beneficial therapeutic regimens known as Guideline Directed Medical Therapy (GDMT). This disclosure describes apparatus and methods for treating this broad group of disorders with interatrial shunt devices that are combined with implantable physiological sensors.

Heart Failure and Pulmonary Arterial Hypertension.

Heart Failure (HF) is defined as the pathophysiologic state where the heart is unable to pump enough blood to meet the body's demands or where it requires higher internal filling pressures to do so. Most patients with HF suffer predominantly from left ventricular (LV) failure, although right ventricular (RV) failure may be present as well but usually to lesser degrees. The syndrome of HF results from the progression of underlying heart disease, most commonly: ischemic heart disease, systemic hypertension, diabetes mellitus, idiopathic cardiomyopathy, valvular heart disease, myocarditis, followed by a multitude of other less common causes.

HF affects 6 million Americans and more than 26 million people worldwide. The prevalence of HF within the U.S. population approximately doubles with each decade of life. In the U.S., there are now 870,000 newly diagnosed cases and 308,000 deaths per year. There are more than 1 million hospitalizations annually where the primary cause of admission is Acute Decompensated Heart Failure (ADHF). Additionally, there are almost 700,000 Emergency Room visits and at least 6 million office/clinic visits that add societal, logistical, and economic burdens to the system. In the coming decades, HF is expected to become an increasingly larger healthcare problem as the population ages. HF is most often an incurable disorder.

While traditionally associated with reduced LV systolic function (a poorly contracting LV), it is now recognized that HF also commonly occurs with normal or only mildly reduced contraction where the problem is an overly stiff ventricle that has difficulty filling in diastole. LV systolic function is assessed by the ejection fraction (LVEF), which is the volume of blood ejected with systole divided by the end diastolic volume. LVEF normally averages around 60%. HF is thus divided into two clinical syndromes: heart failure with reduced ejection fraction (HFrEF) where LVEF is <40% and heart failure with preserved ejection fraction (HFpEF), where LVEF is by some definitions, at least 40%. HFpEF patients tend to be older, more frequently female, hypertensive, and diabetic than those with HFrEF. The prevalence of ADHF hospital admissions is approximately equally split between HFpEF and HFrEF.

Irrespective of LVEF and evidenced based treatment with Guideline Directed Medical Therapy (GDMT), most patients have a progressive course characterized by worsening symptoms, ADHF hospitalizations, and death. Patients admitted with ADHF have an in-hospital mortality of 4%, a 90-day mortality of 10%, and according to the large registry studies, a one-year mortality of 30%. Shah et al. analyzed 39,982 patients ≥65 years old admitted to hospital with HF. Irrespective of LVEF, 5-year mortality averaged 75% and over 96% either died or were readmitted to a hospital during follow-up. Hospitalization for ADHF are associated with high readmission rates and increasing mortality. Readmission rates are 25% at 30-days and 50% by 6 months. There is an increased mortality risk with recurrent HF hospitalizations. The median survival after the first, second, third, and fourth HF-hospitalizations is 2.4, 1.4, 1.0, and 0.6 years, respectively. It is generally appreciated that therapy that successfully prevents ADHF related hospitalizations likely will prolong life expectancy.

Outpatient GDMT for HFrEF focuses on giving maximally tolerated doses of medication categories that reduce morbidity and mortality in large randomized clinical trials. These drugs include angiotensin converting enzyme inhibitors, angiotensin receptor blockers, neprilysin inhibitors, beta blockers, mineralocorticoid inhibitors, ivabradine and soon expected for sodium-glucose cotransporter-2 inhibitors. Most often however, benefit has been confined to less symptomatic patients (New York Heart Association Class II). To achieve the best outcomes, drugs must be frequently titrated up or down to tolerance. These drugs are less effective at controlling symptoms, especially dyspnea (shortness of breath) on exertion or at rest. Chronic symptoms are best managed with oral diuretics, usually potent loop diuretics such as furosemide and with the addition of long acting nitrates in some cases. ADHF may be treated with fluid removal with intravenous loop diuretics. Dosing of diuretics, whether oral or parenteral, is largely empirical and often difficult to manage. Over-use of is associated with dehydration, renal impairment, electrolyte imbalance, and death.

Several devices have evidence-based indications in HFrEF, including Cardiac Resynchronization Therapy (CRT or biventricular pacing) with or without an Implantable Cardioverter/Defibrillator (ICD), percutaneous mitral valve repair with the MitraClip device in patients with severe functional mitral regurgitation and moderate LV dysfunction, and Ventricular Assist Devices for patients with end-stage disease.

HFpEF is different. No randomized trials of medications or the above-mentioned devices have achieved their primary endpoints. GDMT for HFpEF is limited to management of underlying predisposing conditions such as hypertension, atrial fibrillation, and treating symptoms and acute exacerbations with diuretics.

The precipitating factors associated with ADHF are non-compliance with diet and medications, failure to seek medical care, inappropriate therapies and acute exacerbation of underlying cardiovascular disorders such as acute ischemic syndromes or hypertensive crises. These factors either increase total body fluid volume by causing sodium and water retention by the kidneys or they redistribute body fluid from the splanchnic to the pulmonary venous capacitance vascular beds, or both. Excess volume elevates left-sided hydrostatic pressures including left atrial pressure (LAP) and left ventricular end diastolic pressure (LVEDP). Elevated hydrostatic pressure becomes the primary driving force for fluid transudation from the pulmonary capillaries and veins into the pulmonary interstitium and eventually alveolar air spaces known as pulmonary edema. About 90% of ADHF hospitalizations present with symptoms, signs, or laboratory evidence of pulmonary congestion. When ADHF develops, respiratory symptoms, such as tachypnea and dyspnea predominate. Ultimately, if this process is not reversed, severe pulmonary edema ensues and there is increased likelihood of death.

Normal LAP ranges from 6-12 mmHg. Since the early 1970's, Swan-Ganz catheter measurements of Pulmonary Capillary Wedge Pressure (PCWP) have served at a close approximation of LAP. When PCWP elevations are sustained above 25 mmHg in patients without a history of prior HF, pulmonary edema develops within several hours. Patients with chronic heart failure may tolerate higher filling pressures (30-35 mmHg) due to increased lymphatic drainage of the lungs. HF patients with elevated cardiac filling pressures are at increased risk for hospitalization and death, whereas other hemodynamic parameters, such as right atrial pressure, pulmonary arterial pressure, systemic arterial pressure, cardiac index, and systemic vascular resistance are not as predictive.

Turning now to PAH: WHO Clinical Group I Pulmonary Hypertension, better known as Pulmonary Arterial Hypertension (PAH), is a rare but serious and complex set of clinical disorders. The prevalence in the U.S. ranges from 0.4-1.2 cases per 10,000 population, affecting approximately 13,000 to 40,000 patients. The mean age at diagnosis is between 50 and 65 years with a predominance of female patients. One-half of patients have idiopathic (IPAH) including a minority with heritable forms of PAH. The remainder have associated conditions (APAH), where the underlying etiologies are most commonly connective tissue disorders, chief among these systemic sclerosis (scleroderma). A small percentage of cases have other associated causes including drug-induced PAH, congenital heart disease (corrected and uncorrected), portal hypertension, and HIV as their etiologies. PAH is characterized by pre-capillary pulmonary hypertension where the mean pulmonary artery pressure (mPAP) is ≥25 mmHg; PCWP or LAP is ≤15 mmHg; and pulmonary vascular resistance (PVR) is usually ≥3 Wood units. The early pathological basis of PAH are lesions of the distal pulmonary arteries (<500 μm diameter) including medial hypertrophy, intimal proliferative fibrotic changes, adventitial thickening with perivascular inflammatory infiltrates. Late findings are more complex lesions (plexiform, dilated lesions), and thrombotic lesions.

The symptoms of PAH are non-specific including shortness of breath, fatigue, weakness, chest pain and syncope and are initially associated with exertion. With progression, symptoms of severe RV failure and low cardiac output predominate and often occur at rest. This includes abdominal distention and lower extremity swelling, profound fatigue and marked intolerance to activity. PAH has a profound psychosocial and economic impact on patients and their caregivers. Risk factors for a poor prognosis are: evidence of RV failure, rapid progression of symptoms, recurrent syncope, worsening WHO functional class, reduced 6-minute walk distance (6MWD), reduced peak $VO_2$ or $VE/CO_2$ on cardiopulmonary exercise testing, elevated natriuretic hormone levels, imaging findings of right RV failure (reduced RV function, increased RA or RV size, RV eccentricity, pericardial effusion), and abnormal invasive hemodynamic measurements including elevated right atrial pressure (RAP), low cardiac index (CI) and reduced mixed venous oxygen saturation ($SvO_2$). Many of these parameters reflect the degree of RV failure, which is the most common cause of death.

Although the last two decades have seen important advances in palliative medical therapy, PAH remains a universally fatal disorder with median survival of 5 years. There is one exception that is potentially important when considering the use of interatrial shunts. The few patients with uncorrected congenital heart disease often have a prior left to right shunt due to atrial septal defects (ASD), ventricular septal defects (VSD), or patent ductus arteriosus, and the like. As PAH progresses these shunts reverse direction and become predominantly right to left. This is known as Eisenmenger's physiology where cyanosis of the extremities due to arterial oxygen desaturation becomes a frequent clinical finding. Parenthetically, Eisenmenger's patients with PAH appear to have a survival advantage over those with IPAH or APAH from other causes.

There are now multiple approved drug classes, including prostanoids, prostaglandin receptor agonists, endothelin receptor antagonists, phosphodiesterase type-5 inhibitors, soluble guanylate cyclase stimulators, and calcium channel blockers. Drug therapy results in significant symptomatic improvement and a slower rate of clinical deterioration. Sequential oral drug combination therapy is the most widely used strategy in clinical practice. Randomized trials that add newer agents to patients who are already on GDMT have shown an improvement in the combined endpoint of morbidity and mortality. When symptoms are no longer controlled on oral meds, patients are placed on parenteral prostanoids, ultimately requiring indwelling catheters and infusion pumps. Continuous intravenous epoprostenol is the only drug that has been shown to increase survival. Parenteral prostanoids, however, are often associated with frequent and disabling adverse effects such as vomiting, headache, hypotension, flushing, jaw and leg pain and diarrhea. Serious adverse events related to intravenous delivery systems include pump malfunction, local site infection, catheter obstruction and sepsis. Abrupt interruption of therapy has precipitated rebound worsening pulmonary hypertension, acute RV decompensation and death. Patients refuse parenteral therapy, or it must be discontinued in about 30% of cases. Lung transplantation is an essential treatment option for PAH patients, but due to scarcity of donor lungs and survival rates lower than for other pulmonary disorders, less than 200 U.S. PAH patients are transplanted each year.

It is understood that beyond HF and PAH, there are other cardiovascular or cardiopulmonary disorders familiar to those with ordinary skill in the art, including but not limited to mitral annular calcification causing mitral stenosis, intractable pulmonary edema with or without cardiogenic shock due to acute myocardial infarction, acute myocarditis, chronic thromboembolic pulmonary hypertension, weening from extracorporeal membrane oxygenation (ECMO) therapy etc., that are associated with left or right ventricular dysfunction. As with HF and PAH, there are resulting elevations of cardiac filling pressures that may be targets of specifically directed therapies that include the use of implantable sensors, the use of interatrial shunt devices, or both. Moreover, there are other interventions performed on patients with cardiovascular or cardiopulmonary disorders that involve transseptal catheterization, including mitral valve repair, left atrial appendage occlusion, pulmonary vein ablation of atrial fibrillation, and the like, where at the completion of the intervention, the patients may also benefit from the transseptal placement of implantable sensors or interatrial shunts, or both in combination.

Experience with Implantable Pressure Sensors in HF and PAH:

Implantable pressure sensors include circuitry to measure absolute pressure, which is compared to an external reference pressure to calculate gauge pressure. Alternatively, designs have been described that measure differential pressure between two cardiac chambers or blood vessels. Two main types of pressure sensors have been used for implantable cardiovascular applications, piezoresistive and capacitive. Piezoresistive strain gauges may be bonded to a force collector such as a diaphragm to measure strain or deflection (force) applied over an area (pressure). Strain gauge transducers are usually connected to form a Wheatstone bridge circuit to maximize output. Capacitive sensors use a diaphragm and a pressure cavity to create a variable capacitor. Both sensor types are now fabricated with micro-electromechanical (MEMs) technology resulting in very small packages about 1.0×1.0×0.1-mm. Piezoresistive devices are better suited for periodic rather than continuous measurements due to higher power consumption.

In some applications, capacitive sensors have been a better choice due to higher sensitivity to pressure changes, lower noise, and lower temperature sensitivity. The major challenges for achieving accurate, durable and practical implantable sensor performance are having: hermetic biocompatible packaging that resists ingress of corrosive body fluids and their well-known effects on delicate electronic components; packaging that minimize residual internal stress on the sensing elements; having robust offset drift compensation; sufficiently low power requirements to permit leadless designs for remote powering/telemetry with sufficient range and bandwidth; defibrillation protection, and compatibility with magnetic resonance scanning. It is understood by those with ordinary skill in the art that other sensor technologies that measure pressure, flow, velocity, temperature, pH, or the concentration of certain chemical species could be similarly applied to the implanted cardiovascular environment when they are shown able to perform advantageously.

Implantable sensors that measure intracardiac or pulmonary artery pressures are successfully used to inform clinicians of impending decompensation and guide medication adjustments. This approach shows benefits in comparison with standard GDMT for improving symptoms and preventing ADHF episodes in broad populations of HF patients, whether HFrEF or HFpEF. More recently, sensors have also been used in the management of patients with severe PAH.

Implantable hemodynamic monitoring systems have been developed for outpatient HF evaluation and management with the goal of reducing episodes of clinical decompensation. By example, investigational implantable pressure sensors placed by transseptal catheterization procedures in the left atrium have included devices developed by Savacor-St Jude Medical now Abbott Laboratories, Abbott Park IL, and by Vectorius Medical Technologies, Tel Aviv, Israel. By another example, devices placed in the pulmonary artery that measure pulmonary artery pressure (PAP), a surrogate/estimate for LAP, include products by CardioMEMs now Abbott Laboratories, Abbott Park IL and Endotronix, Inc., Lisle, IL There are also other examples of implantable pressure sensors from multiple manufacturers that are familiar to those with ordinary skill in the art.

By way of example, the Savacor HeartPOD™ system includes an implantable sensor lead connected to a subcutaneously positioned antenna coil, or to a specially designed CRT/ICD system, where the antenna coil is built into the generator header, as described in Ritzema J, et al., "Direct left atrial pressure monitoring in ambulatory heart failure patients: Initial experience with a new permanent implantable device," Circulation 2007; 116; 2952-2959, and Maurer M S, et al., "Rationale and design of the left atrial pressure monitoring to optimize heart failure therapy study (LAPTOP-HF)," J Cardiac Failure 2015; 21:479-488. Additional components include a handheld Patient Advisory Module (PAM) for communication with the implant and for uploading patient data and downloading prescriptions from secure web-based software used by clinicians. The sensor lead had a 3-mm diameter by 7-mm long cylindrical hermetically sealed sensor module with a titanium pressure sensing diaphragm at its distal end that contains internal piezoresistive strain gauges and application specific circuitry for measuring and communicating LAP, temperature, and intracardiac electrograms. Folding nitinol anchors affixed the sensor module in the interatrial septum, accommodating any septal thickness. The anchors were designed to fold forward when constrained for deployment and facilitate late percutaneous extraction of sensor lead using standard pacing lead removal techniques if required, as described in Pretorious V, et al., "An implantable left atrial pressure sensor lead designed for percutaneous extraction using standard techniques," Pacing Clin Electrophysiol 2013 May; 36(5):570-7.

The implanted LAP sensor is powered and interrogated through the skin by 125-kHz radiofrequency wireless telemetry from the PAM. When held in the correct location over the subcutaneous antenna coil, the PAM vibrates momentarily indicating to the patient that information acquisition was taking place and vibrates again when the acquisition was completed (usually 15 seconds). During interrogation, high-fidelity physiological pressure and electrocardiographic waveforms are collected and stored on the PAM. LAP is calculated by subtracting absolute pressure obtained by the implant from an atmospheric reference measured by a second pressure sensor located in the PAM.

Patient sensor readings are uploaded via the Internet daily to the centralized secure database. The waveforms and trend data were evaluated by the patient's HF physician, either periodically or based on alerts generated when parameters were out of bounds. Physician then download updated prescriptions and instructions to the PAM for patient viewing. The PAM's reminder function alerted patients to measure resting LAP within scheduled morning and evening time windows before they took their heart failure medications.

The PAM could be set to display LAP values and to inform patients when medications are due including dosages. This occurs in two ways. First, prescriptions are adjusted according to overall LAP trends. This type of dosing was called "Static Rx." If further enabled, the PAM displays physician-directed patient self-management instructions called "DynamicRx™," which allows treatments to be adjusted by the current LAP value. DynamicRx was based on 5 LAP ranges (very low, low, optimal, high, and very high). Each range is associated with a prescription for medication dosing, activity level, sodium and fluid intake, and physician contact instructions. Local investigators adjust these ranges for each patient. Although DynamicRx prescribing is at the discretion of the local investigator, the general aim is to reduce or eliminate diuretic doses for low or very low LAP and increase diuretic or long-acting nitrate vasodilator doses for high or very high LAP.

Sensor drift compensation included internal automatic adjustment for changes in temperature and atmospheric pressure. Longer term changes in sensor offset could be due to intrinsic drift in the internal gauges and electronics or to extrinsic changes from neoendocardial tissue growth over the sensor membrane. As described in by McClean et al., "Noninvasive calibration of cardiac pressure transducers in patients with heart failure: An aid to implantable hemodynamic monitoring and therapeutic guidance," J Card Fail 2006; 12:568-576, the accuracy of implanted sensors could be assessed by measuring intracardiac pressures and airway pressure simultaneously during Valsalva maneuver. Within 2-3 seconds after increasing intrathoracic pressure above 20 mmHg, intracardiac pressures during diastole equalize with airway pressure. In practice, the implanted LAP sensor is checked periodically during clinic visits by having the patient perform a Valsalva maneuver while exhaling into a mouthpiece that was connected to the PAM's atmospheric reference pressure sensor. This results in quantification and corrections of offset drift, irrespective of the cause. Additionally, it was discovered that specific features within the LAP waveform could be used to detect and automatically compensate for offset drift between clinic visits.

Ritzema et al. in "Physician-directed patient self-management of left atrial pressure in advanced chronic heart failure," Circulation 2010; 121:1086-1095 reported a prospective, observational, first-in-human study using the Savacor HeartPOD™ system in 40 consecutive patients with HFrEF or HFpEF and a history of NYHA class III or IV HF with prior ADHF hospitalizations. Patients were implanted and readings acquired twice daily. For the first 3 months, patients and clinicians were blinded to sensor readings and treatment continued per usual clinical assessment. Thereafter, physician-directed patient self-management prescriptions (DynamicRx) were applied. Freedom from HF events (ADHF hospitalization or all-cause death) was 61% at 3 years and were significantly less frequent after the first 3 months. LAP fell from a mean 17.6 mm Hg in the first 3 months to 14.8 mm Hg; P=0.003) during pressure-guided therapy. The frequency of elevated readings (>25 mm Hg) was reduced by 67% (P<0.001). LAP control was empirically defined if the frequency of pressures >25 mm Hg was <10% for 6 consecutive months. LAP control was achieved in 77% of patients. HF events were 98% less frequent during periods of LAP control than during periods without LAP control (P<0.001). There were also significant improvements in symptoms and LVEF. Doses of renin-angiotensin system inhibitors and beta-blockers were up titrated by 37% (P<0.001) and 40% (P<0.001), respectively, whereas doses of loop diuretics fell by 27% (P=0.15). The authors showed unequivocally that LAP elevation always precedes clinical decompensation. Moreover, implantable LAP monitoring linked to a self-management therapeutic strategy could change the management of advanced heart failure by facilitating more optimal therapy and improved outcomes.

The original design of the HeartPOD LAP sensor had the sensing diaphragm protruding into the left atrium approximately 1-mm beyond its three anchoring legs that rested on the left atrial side of the septum. In a later, improved version, the anchor legs were placed more proximally on the sensor module body so that sensing diaphragm protruded into the LA by approximately 2.5 mm. In a comparative inter-species pathology study, Trainor and colleagues, in "Comparative pathology of an implantable left atrial pressure sensor," ASAIO journal 2013; 59:486-492 and "Integrated microscopy techniques for comprehensive pathology evaluation of an implantable left atrial pressure sensor," J Histotechnology 2013; 36:17-24, demonstrated in a comparative pathology study of 3 species, ovine, canine and humans, that significant neoendocardial tissue (pannus) formation was observed over the sensing diaphragm in 20 of 31 original sensors compared with only 3 of 40 specimens with the improved geometry sensor. Of the 20 original sensors with tissue coverage, 7 had demonstrable artifacts in the LA pressure waveform. In each case with artifacts, pannus formation over the sensing diaphragm had a thickness >0.3 mm. These data indicate that when tissue coverage exceeds this thickness, the tissue interferes with fluid pressure measurement. None of the improved sensors had waveform artifacts or tissue thickness >0.3 mm. It could be concluded that the improved sensor geometry eliminated waveform artifacts by preventing thick neoendocardial tissue overgrowth, promoting prolonged and artifact free sensor waveform fidelity.

Troughton et al., in "Direct left atrial pressure monitoring in severe heart failure: long-term sensor performance," J Cardiovasc Trans Res 2011; 4:3-13, showed that with the original design of the sensor, waveform artifacts were seen in about 15% of cases by 4 months and none thereafter. This indicates that waveform artifacts are the result of device healing, was likely caused by compressing or pulling of the diaphragm from mechanical coupling to the atrial wall by interconnecting tissue overgrowth. Once the improved geometry sensor was used, waveform artifacts were eliminated in the next 41 consecutive patients. Thus, the design change of advancing the pressure sensing diaphragm to 2.5 mm from septal wall into the left atrium minimizes tissue thickness over the sensor and decouples it from contraction and stretching movements of the atrial wall.

As reported in Maurer et al., "Rationale and design of the Left Atrial Pressure Monitoring to Optimize Heart Failure Therapy Study (LAPTOP-HF)," J Card Fail 2015; 21:479-88, a randomized controlled outcomes study was conducted, the LAPTOP-HF trial, that examined the safety and efficacy of the HeartPOD system in NYHA functional class III patients who either were hospitalized for HF during the previous 12 months or had an elevated B-type natriuretic peptide level, regardless of ejection fraction). Treatment patients measured LAP twice daily and used physician directed patient self-management to guide therapy while a control group receiving optimal medical therapy alone. Enrollment in the LAPTOP-HF trial was stopped early, due to a perceived excess of transseptal related complications. The trial was done at a time before widespread use of new catheterization techniques had greatly improved transseptal safety. Preliminary results were presented during a Late Breaking Clinical Trials Session at the 2016 Heart Failure Society of America meeting, as reported in Abraham W T, et al. "Hemodynamic monitoring in advanced heart failure: Results from the LAPTOP-HF trial," J Card Fail 2016; 22:940. When the results were analyzed using the CHAMPION trial endpoint of recurrent heart failure hospitalizations (see below), the results of the LAPTOP-HF trial were similar to those of CHAMPION, showing a 41% relative risk reduction (p=0.005).

Another example of intracardiac sensing is a next generation implantable LAP monitoring system called V-LAP was developed by Vectorious Medical Technologies (Tel Aviv, Israel). That sensor is wireless and leadless and has a cylindrical profile (14 mm in length and 2.5 mm in diameter). As described in PCT International Patent Publication WO 2014/170771, and in "A Novel Wireless Left Atrial Pressure Monitoring System for Patients with Heart Failure, First Ex-Vivo and Animal Experience," by Perl et al. in J Cardiovascular Translational Research 2019, 12:290-298, the sensor employs a MEMS variable capacitor sensing surface disposed at the left atrial extreme of the sensor module, and application-specific integrated circuit technology that features on board automatic drift compensation. The bulk of the sensor length comprises an inductor antenna coil wrapped around a small ferrite core. The sensor is anchored to the fossa ovalis with two woven superelastic nitinol disks like an Amplatzer ASD closure device occupying an 18 mm diameter region of the fossa ovalis. The system also includes an external wearable belt that remotely powers the implant, displays pressure readings to the patient, and transmits LAP waveform information to a web-based database. In animal studies, the device was safe, and was shown to communicate with the external belt at depths of up to 30 cm. The device is currently in early human clinical trial and appears to be working well in the first 21 patients implanted with short term follow-up.

Yet another example of an intracardiac pressure sensor is the CardioMEMS Champion™ HF Monitoring System, which measures PAP using a wireless pressure sensor designed to be implanted in a branch of the pulmonary artery during a right-heart catheterization procedure. The sensor is 15-mm in length, 3.4-mm in width and 2-mm thick and is disposed in a hermetically sealed fused silica body encapsulated with medical grade silicone. The housing contains an inductor coil and a pressure sensitive MEMS variable capacitor comprising a high-Q LC resonant circuit such that when pressure changes, the resonant frequency changes. An external electronics unit transmits RF pulses to the sensor, where the energy is re-radiated after excitation stops, and the pressure information is encoded in the frequency of the sensor transmit signal. Pressure readings are uploaded to a database where the physician views the patient's PAP waveforms including trend plots of systolic, diastolic, and mean pressures as well as heart rate. The patient is then contacted and given instructions how to adjust therapy.

Abraham et al. in "Wireless pulmonary artery haemodynamic monitoring in chronic heart failure: a randomized controlled trial," The Lancet DOI:10.1016/S0140-6736(11)60101-3, "Sustained efficacy of pulmonary artery pressure to guide adjustment of chronic heart failure therapy: complete follow-up results from the CHAMPION randomized trial," Lancet 2016; 387:453-461.doi.org/10.1016/S0140-6736(15)00723-0 and "Wireless pulmonary artery pressure monitoring guides management to reduce decompensation in heart failure with preserved ejection fraction," Circ Heart Fail 2014; 7:935-944, reported extensively on the results of the CHAMPION trial of the CardioMEMS system. This was a patient blinded randomized controlled trial of 550 NYHA Class III patients with a history of HF hospitalization during the prior 12 months, irrespective of systolic function (22% of patients had LVEF ≥40%), and patients were on GDMT. In the treatment group, PAP trends were used to adjust medications, which in most instances were loop diuretics and long acting nitrates. During follow-up (average 17.6 months), the treatment group had a 39% reduction in HF hospitalizations compared with the control group ($p<0.0001$). HF-hospitalization in HFpEF patients was 50% lower ($P<0.0001$) in the treatment group patients vs. the control group. The effect in patients with HFrEF was less striking but still highly statistically significant. In response to pulmonary artery pressure information, more changes in diuretic and venodilator therapies were made in the treatment group, regardless of EF. These data establish that volume management, whether by diuretics (elimination of salt and water) or long-acting nitrates (venodilation), given in response to elevated left-sided pressure, reduces episodes of ADHF in both HFrEF and HFpEF.

Benza et al. in "Monitoring pulmonary arterial hypertension using an implantable hemodynamic sensor," Chest 2019; 156(6):1176-1186, reported on the safety and utility of the CardioMEMS device in 27 patients with PAH with NYHA III (85%) or IV (15%) and with RV failure. All patients were on at least 2 drugs including 69% on parenteral prostacyclins. Patients were followed-up for 2.5±1.4 years. 26 patients were implanted successfully without major complications. Most patients (92%) were female, aged 51±18 with IPAH in 50% and associated connective tissue disease, APAH in 31%. There were 8 hospitalization for RV failure, 6 of these were in 2 patients. There were 5 deaths, 3 in the first year, with one death due to PA rupture during implant and 2 in the second. There were significant reductions in mean PAP (42±13 to 34±14) and elevations in CO (5.8±1.5 to 6.8±1.8) at 1-year. Improvements in RV stroke volume, vascular compliance, and RV efficiency were also observed, as well as reductions in RV stroke work and total pulmonary resistance. NYHA functional class ($P<0.001$), natriuretic peptides ($P<0.01$), and Minnesota Living with Heart Failure Questionnaire Quality of Life score ($P<0.001$) also improved from baseline and mirrored the hemodynamic changes. The authors concluded that implantable monitoring in PAH patients appears safe, may reduce hospitalization, and allows rapid optimization of hemodynamics and functional outcomes.

In comparison to PAP, the LAP waveform contains more specific information about filling, compliance and function of the LA, LV and the role of functional mitral valve regurgitation in ADHF. As an example, consider the meaning and specificity of an elevation in mean LAP vs. PAP, whether systolic, mean, or diastolic pressure. Both will rise due to intravascular volume overload, LV failure, or LA outflow obstruction. Additionally, PA pressures are also be elevated in pre-capillary (PAH) or post capillary (secondary) pulmonary hypertension. Secondary pulmonary hypertension is a common condition associated with left-sided HF. At first, there are reactive changes that cause pulmonary arterial constriction that will respond to improving HF. Later, in response to prolonged elevations in pulmonary venous pressure from HF, the pulmonary arterial vasculature develops fixed lesions that are identical to PAH. In this setting, PA diastolic pressure, which is normally very similar to LAP, will be elevated substantially higher than LAP. If PAP is being used to guide diuretic therapy for HF and there is substantial secondary PAH, over-diuresis resulting in a very low LAP with dehydration, worsening renal function, electrolyte imbalance necessitating hospitalization will be more frequent, because PA diastolic pressure substantially overestimates LAP. For example, in the CHAMPION trial the incidence of dehydration resulting in hospitalization in the PAP guided therapy arm was twice that in the control arm using standard clinically based diuretic dosing.

There are several other diagnostic features in the LAP waveform known to those familiar with cardiac hemodynamic physiology, that involve the configuration of the waveform's components (a- and v-waves, x- and y-descents, etc.). Also, individual pressure measurements in ambulatory patients are not by themselves sufficient to predict how or if a patient will respond to a given therapy. Many patients have highly variable pressures, subject to rapid physiological changes from acute myocardial ischemia, or afterload changes resulting from severe functional mitral regurgitation. Their LAP excursions can be volatile, ranging from normal values to mean pressures as high a 50-mmHg with giant v-waves as high as 80-100 mmHg. These changes can occur over just a few hours and, in some cases, over just a few minutes. Even so, these rapid fluctuations rarely result in serious adverse HF events such as ADHF hospitalization or death. Instead, when detected, these changes can be highly diagnostic and can aid in individual patient management. Also, single observation hemodynamics should be understood to be just a "snapshot" but not the whole physiological picture. Pressure trends over time are more useful for predicting clinical outcomes.

To be successful, implantable hemodynamic monitoring may utilize: frequent caregiver data review, approximately weekly, and responding to automated alerts; developing effective prescriptive changes to the data; transmission of prescriptive changes to the patient; diligent patient adherence to their prescription; and time for the patient to manifest response or non-response to the changes. It also takes time to recognize when filling pressures are deteriorating and to determine, often through trial and error, which medications and dosages the patient will respond to. Although better than standard medical therapy, pressure guided therapy has similar built-in delays and multiple points for failure. Physician-directed patient self-management overcomes many of these limitations. These drawbacks notwithstanding, there is accumulating clinical evidence that implantable hemodynamic monitoring is revolutionizing the care of HF patients and thus far is the only intervention to demonstrate significant outcomes benefits for HFpEF patients in randomized controlled clinical trials. There is for the first time also evidence that pressure guided therapy may have a role in the management of PAH.

Finally, with respect to implantable sensors, the types described thus far have been limited to devices that directly measure pressure. This is only because they are the most studied and are of proven durability as chronic implants. In addition, our understanding of physiology allows physicians to glean meaning from pressure values, as they have been long established from cardiac catheterization experience. In short, pressure data are actionable—they are proven successfully to guide therapeutic decision making.

The limitations of standard and hemodynamic guided therapy establish a clear need for a means to automatically regulate left and right atrial pressures in HF and PAH, respectively. That such a means should be effective without delays; prevent over-treatment of the patient or cause other cardiac, vascular, or end-organ dysfunction; be compatible or complimentary with other therapies; and not require "hands-on" management by the caregiver; would be recognized as a medical breakthrough.

Experience with Interatrial Shunting in HF and PAH:

As context for the potential benefits of interatrial shunts, it is important to understand the implications of having a naturally occurring congenital atrial septal defects (ASD) involving the mid portion of the interatrial septum, known as ostium secundum ASD. ASDs are one of the most common types of congenital heart defects. When sufficiently large, the ASD presents during childhood or early adulthood with biatrial and RV enlargement due to left to right atrial shunting with volume overload of the right heart. The flow in the pulmonary artery vs. the aorta (Qp:Qs) is often >2:1. These defects must be closed to prevent the development of PAH causing RV failure and death.

Not infrequently, however, ASDs are well tolerated and present only in adulthood, often as incidental findings on an echocardiogram. Patients with small ASDs that are <10 mm in diameter, or where Qp:Qs is <1.5, generally do not develop volume overload, pulmonary hypertension and subsequent RV failure. Guideline recommendations are not to close these defects unless there is progressive RV dilatation or evidence of systemic thromboembolism originating from the venous system (paradoxical embolism), as discussed, for example, in Webb G and Gatzoulis M A, "Atrial septal Defects in the Adult: Recent progress and overview," Circulation 2006; 114:1645:1653 and Baumgartner H, et al., "ESC guidelines for the management of grown-up congenital heart disease (new version 2010)," Eur Heart J 2010; 31:2915-2957. It is recommended that these patients be followed every few years by echocardiography. Nonetheless, their risk of developing right heart volume overload is very small.

As discussed in Wiedemann H R, "Earliest description by Johann Friedrich Meckel, Senior (1750) of what is known today as Lutembacher syndrome (1916)," Am J Med Genet. 1994 Oct. 15. 53(1):59-64 and Aminde L N, et al., "Current diagnostic and treatment strategies for Lutembacher syndrome: the pivotal role of echocardiography," Cardiovasc Diagn Ther 2015; 5:122-132, Lutembacher syndrome is defined as the coexistence of mitral stenosis (MS), usually of rheumatic origin, and a left-to-right shunt at the atrial level, most often ostium secundum ASD. The ASD may also be iatrogenic or secondary to complications of transseptal crossing. The classical teaching is that each of these two lesions modifies the hemodynamics and clinical expression of the other: the frequent pulmonary edema and hemoptysis characteristics of MS are reduced by the decompressing effect of the ASD. Specifically, the elevated LAP caused by MS drives offloading of blood into the right atrium through the ASD, relieving the build-up of back pressure in the pulmonary veins, thus avoiding pulmonary congestion. Pulmonary vascular resistance, RV compliance, severity of MS and the size of the ASD are important factors determining the hemodynamics and clinical outcomes in these patients.

Accordingly, it has been observed that HF patients with coexisting congenital ASDs may have better outcomes and closure of ASD may unmask subclinical LV dysfunction by provoking immediate ADHF with resulting pulmonary edema. This fact is conspicuously noted as a warning in the ESC, AHA/ACC, and Canadian Guidelines for treating adults with congenital heart disease, as discussed, for example, in Viaene D, et. al., "Pulmonary oedema after percutaneous ASD-closure," Acta Cardiol. 2010 April; 65(2):257-60, Schubert S, et al., "Left ventricular conditioning in the elderly patient to prevent congestive heart failure after transcatheter closure of atrial septal defect," Catheter Cardiovasc Interv 2005; 64:333-337, and Davies H, et al., "Abnormal left heart function after operation for atrial septal defect. Br Heart J 1970; 32:747-753." When ASD closure is being considered in adults with suspected left ventricular dysfunction, it is recommended to first occlude the defect with a balloon and measure the rise in LAP to unmask the potential to develop overt clinical HF. This is because if LV dysfunction is present, the ASD is functioning as a "pop-off" valve for the systemic (left) ventricle, preventing pulmonary venous hypertension. As already described, patients with ASD and Eisenmenger's physiology have improved survival with PAH. Thus, there is now a body of evidence showing that ASDs prevent ADHF in the presence of LV dysfunction and acute RV failure in PAH.

Further support for the utility of having a right to left interatrial shunt in PAH comes from the experience with balloon atrial septostomy (BAS) where progressively larger balloons are inflated until the systemic oxygen saturation just begins to decline. Balloon sizes typically range from 4 to 12 mm in diameter, averaging around 8 mm.

Irrespective of whether shunting is accomplished by BAS or implantation of a permanent shunt device, left atrial access must first be accomplished by transseptal catheterization, a procedure well known to those with ordinary skill in the art of cardiac catheterization. In brief, the transseptal catheterization system is placed from an entrance site usually in the right femoral vein, across the interatrial septum in the region of fossa ovalis (FO), which is the central and thinnest region of the interatrial septum. This is the same general location where a congenital ostium secundum ASD would be located. The FO in adults is typically 15-20 mm in its major axis dimension and ≤3 mm in thickness, but in certain circumstances may be up to 10 mm thick. LA chamber access may be achieved using a variety of different techniques including needle puncture, stylet puncture, screw needle puncture, and radiofrequency ablation. In BAS, the passageway between the two atria is dilated to create an iatrogenic ASD. The passageway is similarly dilated to facilitate passage of a shunt device of a desired orifice size. Dilation is accomplished by advancing a tapered sheath/dilator catheter system or inflation of angioplasty balloons across the FO.

In PAH, successful BAS decompresses the RV, increases LV preload, systemic cardiac output, and oxygen transport, causing only moderate degrees of arterial $O_2$ desaturation. Studies such as Sandoval J, et al., "Graded balloon dilation atrial septostomy in severe primary pulmonary hypertension. A therapeutic alternative for patients nonresponsive to vasodilator treatment," J Am Coll Cardiol 1998; 32:297-304, Kurzyna M, et al., "Atrial septostomy in treatment of end-stage right heart failure in Patients with pulmonary hypertension," Chest 2007; 131:977-983 and Ciarka A, et al., "Atrial septostomy decreases sympathetic overactivity in pulmonary arterial hypertension," Chest 2007; 131:1831-1837, show improvements in WHO/NYHA symptom class, exercise capacity, RAP, decreases in sympathetic activation and B type natriuretic peptide levels. Factors associated with procedure-related mortality have been evaluated in 320 literature septostomy cases, as reported in Sandoval J, et al. eds, Right Ventricle in Health and Disease, New York: Humana Press, Springer Science Business Media; 2015. These are RAP>20-mmHg, CI<1.5 L/min/2, pre-existing LV dysfunction. One-month periprocedural mortality as low as 2% have been reported in Maluli H, et al., "Atrial Septostomy: A contemporary review," Clinical Cardiology. 2015; 38:393. These benefits notwithstanding, BAS has important limitations. It is difficult to predict what size balloon to use. In some cases, the FO is more elastic and will recoil after balloon deflation and in others, it is more fibrotic and may be torn. Increased mortality has been associated when septostomy creates too large a shunt, resulting in severe systemic oxygen desaturation (<80%). See, e.g., Rich S, et al., "Atrial septostomy as palliative therapy for refractory primary pulmonary hypertension," Am J Cardiol 1983; 51:1560-1561. Maintenance of shunt patency is another limitation affecting about one-third of patients, often requiring multiple procedures over a period of a few months, as discussed in Sandoval J, et al., "Effect of atrial septostomy on the survival of patients with severe pulmonary arterial hypertension," Eur Respir J 2011:1343-1348. BAS is now rarely used and is considered a palliative therapy or bridge to lung transplantation at a few experienced centers.

The foregoing observations have led to the development of percutaneously implanted interatrial shunt prostheses, that are now being tested in human clinical trials in HF and PAH. In HF, by shunting blood from the left to the right atrium, the pressure in the LA is lowered or prevented from elevating as high as it would otherwise (LA decompression). Such an accomplishment prevents, relieves, or limits the symptoms, signs, and syndromes associated of pulmonary congestion. These include severe shortness of breath, pulmonary edema, hypoxia, the need for acute hospitalization, mechanical ventilation, and in some cases, death. In PAH, a shunt device will divert flow from the right to the left atrium due to reversal of the normal interatrial pressure gradient. The aim is to reduce RV preload and increase left-sided cardiac output and tissue oxygen delivery without causing severe arterial oxygen desaturation. The anticipated outcomes are a reduction in symptoms, increased exercise capacity, prevention of acute RV decompensation, and improved life expectancy.

Specifically, in HF, the major physiological mechanism of interatrial shunting is to relieve the LV of excess volume and pressure by diverting blood from the left to the right atrium as regulated by the interatrial pressure gradient. In doing so, the amplitude and duration of LAP and LVEDP excursions is limited. LAP exceeds RAP in the overwhelming majority of HF patients. In the absence of severe RV dysfunction, the quantity LAP-RAP, increases as left ventricular failure worsens and LAP rises. Thus, the amount of blood shunted to the right heart increases with worsening left-sided heart failure. When LAP and LVEDP are elevated, the LV is operating on the steeper portion of its diastolic compliance curve, irrespective of the patient having HFrEF or HFpEF. The reduction in LV end-diastolic volume results in an obligate and substantial fall in LV end-diastolic pressure. There will be a commensurate fall in upstream filling pressures including LAP, pulmonary venous pressure, and pulmonary artery pressure. This change in LV volume and pressure is like the action of diuretics that remove excess volume, except that a shunt works automatically, instantaneously, and continuously. Moreover, the effect is automatically appropriate for the level of LAP or LVEDP. The higher the left sided filling pressure, the more shunting and thus unloading. At smaller interatrial gradients, there is less shunting so that the effect on LV volume and filling pressures becomes progressively smaller until it is negligible. Thus, unlike diuretic therapy, over-treatment causing volume depletion and significant lowering of cardiac output is prevented. Lastly, interatrial shunting requires no adjustments by the physician or patient and the therapy is complimentary with all known medications and device therapies, including implantable hemodynamic monitoring with pressure guided drug dosing. The anticipated clinical result will be mitigation of, or even prevention of pulmonary congestive symptoms.

Shunt flow is generally governed by the pressure gradient between the atria and the fluid mechanical properties of the shunt device. The latter are typically affected by the shunt geometry and biomaterial composition. For example, the general flow properties of similar shunt designs have been shown to be related to the mean interatrial pressure gradient and the effective orifice diameter. One concern about interatrial shunt devices for HF, like that seen with uncorrected congenital ASDs, is that if the shunt is too large, RV volume overload will develop eventually causing precapillary PAH with RV failure. Patients could then develop Eisenmenger's physiology with reversal of the direction of shunt flow from the right to the left atrium. As already mentioned, with a small shunt the extra volume is well tolerated due to the large vascular compliance of the right heart and systemic veins. Thus, the critical dimensional consideration for interatrial shunt devices is that the shunt be sufficiently large to unload the left heart yet sufficiently small not to overload the right heart.

Two types of percutaneously implantable shunts have been described in the medical and patent literature. In small-size clinical trials, both types have been shown to be associated with improvements in symptoms, quality of life measurements, and exercise capacity. The first type of shunt is henceforth referred to as an orifice-plate mesh shunt. Orifice-plate mesh shunts comprise a metallic mesh that wraps around both sides of the septum with a hole in the center and anatomically mimics the location and geometrical characteristics of a small congenital ostium secundum ASD. The shunt geometry generally resembles a thin plate with a hole in it. In most embodiments, the "plate" comprises both mesh material and atrial septal tissue encased by the mesh.

Modified Amplatzer septal occluders with custom fenestrations were the first device approach tried, as discussed in a study performed by Schubert et al., "Left ventricular conditioning in the elderly patient to prevent congestive heart failure after transcatheter closure of atrial septal defect," Catheter Cardiovasc Interv 2005; 64:333-337. In that study, patients with an ASD and who experienced elevated LAP when the defect was occluded were implanted with fenestrated Amplatzer occluders. As reported in "Fenestrated occluders for treatment of ASD in elderly patients with pulmonary hypertension and/or right heart failure," 2008; 21:44-49, DOI: 10.1111/j.1540-8183.2007.00324.x, Bruch and colleagues implanted 5 to 8 mm diameter fenestrated Amplatzer septal occluders in 15 ASD patients of advanced age having large left-to-right shunts, pulmonary hypertension, and/or right heart failure, who were at high risk for LV failure. Symptomatic patients showed an improvement in the NYHA class, and no HF decompensation occurred. RV end diastolic dimension and pulmonary artery pressure decreased significantly. Long term follow-up, however, as reported in Lammers A E, et al., "Efficacy and long-term patency of fenestrated Amplatzer devices in children," Catheter Cardiovasc Interv 2007; 70:578-584 and Sandoval J, et al. "Effect of atrial septostomy on the survival of patients with severe pulmonary arterial hypertension," European Respiratory Journal. 2011; 38:1343-1348, has shown that this device is associated with a high closure rate possibly related to the lack of controlled endothelialization in the passageway between the atria. Fenestrated Amplatzer devices have largely been abandoned as they require making a rather large passageway through the septum and leave much foreign material in the septum with the risk of thrombus formation.

Placing a stent that is in-situ expanded to a diabolo or hourglass shape has shown improved patency over the modified fenestrated Amplatzer device. Diabolo stents have been used mostly in PAH, but early designs posed a risk of acute stent embolization, as described in Troost E, et al., "Modified technique of stent fenestration of the interatrial septum improves patients with pulmonary hypertension," Catheter Cardiovasc Interv 2009; 73:173-179. Although both fenestrated Amplatzer and diabolo stents achieved outcomes similar to BAS, the long-term risk of closure/stenosis could result in ineffective shunting.

A second example of an orifice-plate mesh shunt currently in clinical trials is the Inter-Atrial Shunt Device IASD II developed Corvia Medical, Inc., Tewksbury Massachusetts. The IASD II consists of a self-expanding superelastic nitinol mesh that forms a pair of disc-like flanges with an open orifice structure in the center. The maximal diameter of the discs is 19.4 mm and the orifice diameter is 8 mm. Each disc flange has multiple truss-like legs that deploy into a preset configuration that wraps around the LA and RA sides of the interatrial septum. The device is secured by its applying a clamping force compressing the septal tissue between the flanges. The bare metallic frame is not encapsulated.

In the REDUCE LAP-HF feasibility study, described in Hasenfuss G, et al, on behalf of the REDUCE LAP-HF Trial Investigators, "Rationale and design of the reduce elevated left atrial pressure in patients with heart failure (Reduce LAP-HF) trial," J Cardiac Fail 2015; 21:594-600 and Hasenfuss, G., et al, on behalf of the REDUCE LAP-HF study investigators, "A transcatheter intracardiac shunt device for heart failure with preserved ejection fraction (REDUCE LAP-HF): a multicentre, open-label, single-arm, phase 1 trial," Lancet 2016; 387:1298-304, shunt placement was successful in 64 of 68 patients. The study population was exclusively HFpEF including a mix of NYHA class II and III patients with baseline elevated LAP, borderline pulmonary hypertension and normal RV function. No patient had a periprocedural or major adverse cardiac or cerebrovascular event or need for cardiac surgical intervention for device-related complications during the first 6-months. There were sustained improvements in NYHA class, quality-of-life scores, and 6-minute walk distance ("6MWD") extending out to one year. Transthoracic echo imaging confirmed the presence of left to right shunt at 12-months in 48 of 64 (75%) of patients but did not assess the degree of shunt narrowing. There were modest but stable reductions in LV end-diastolic volume index with a concomitant rise in the RV end-diastolic index. Tricuspid annular plane systolic excursion (TAPSE) was significantly improved at 12 months with the increase in RVEF suggesting that the RV tolerated the additional volume generated by the shunt. The Qp:Qs ratio at 12-months averaged 1.25. Shunted patients benefited with improvements in exercise capacity accompanied by a reduction in LAP during exercise. Symptoms and quality of life metrics were also improved in ≥40% of patients out to 1 year.

Feldman et. al., and then Shah et. al., reported on the REDUCE LAP-HF I trial in Feldman T, et al., "A transcatheter interatrial shunt device for the treatment of heart failure with preserved ejection fraction (REDUCE LAP-HF I): A phase 2, randomized, sham-controlled trial," 10.1161/CIRCULATIONAHA.117.032094 and Shah S J, et al., "One-year safety and clinical outcomes of a transcatheter interatrial shunt device for the treatment of heart failure with preserved ejection fraction in the Reduce Elevated Left Atrial Pressure in Patients with Heart Failure (REDUCE LAP-HF I) Trial. A Randomized Clinical Trial," JAMA Cardiol. doi:10.1001/jamacardio.2018.2936. This was a phase 2, randomized, parallel-group, blinded multicenter trial in patients with NYHA class III or ambulatory class IV HF, LVEF ≥40%, exercise PCWP ≥25 mmHg, and PCWP-RAP gradient 5 mmHg. Participants were randomized to the IASD II device vs. a sham control procedure. The patients and investigators assessing the patients during follow-up were blinded to treatment assignment. The primary effectiveness endpoint was exercise PCWP at 1 month. The primary safety endpoint was major adverse cardiac, cerebrovascular, and renal events (MACCRE) at 1 month. A total of 44 patients were randomized to the IASD (n=22) and control (n=22) groups. Mean age was 70±9 years and 50% were female. At 1 month, shunt treatment had a greater reduction in PCWP compared to sham-control (P=0.028 accounting for all stages of exercise). In addition, PCWP during passive leg raise and during 20 W of exercise decreased to a greater degree in shunted patients. At one-year, there were trends for a reduction in MACCRE and in HF events requiring intravenous treatment. The IASD II device is currently being evaluated in a larger scale pivotal randomized blinded controlled trial called REDUCE-LAP HF II (NCT030880330).

Another example of such a mesh type shunt is the Atrial Flow Regulator (AFR) device, developed by Occlutech International AB, Helsingborg, Sweden. The AFR resembles an Amplatzer type dual disc occluder used for closing congenital secundum ASDs, which additionally includes a short open barrel orifice in the center that connects the two discs. This shunt is available with orifice sizes from 4 to 10 mm in 2 mm increments and with different barrel lengths to accommodate FOs of different thicknesses. The diameter of the disks ranges from 22-26 mm depending on the orifice size.

In a feasibility study for the Occlutech device, the AFR-PRELIEVE trial (NCT03030274), reported in Paitazoglou C, et al., "The AFR-PRELIEVE TRIAL: A prospective, non-randomized, pilot study to assess the Atrial Flow Regulator (AFR) in Heart Failure Patients with either preserved or reduced ejection fraction," EuroIntervention 2019; Jaa-588 2019, doi: 10.4244/EIJ-D-19-00342, 36 patients with NYHA class II or IV HF and PCWP >15 mmHg at rest or ≥25 mmHg at exercise, were enrolled irrespective of LVEF (44.5% HFrEF, 55.5% HFpEF). Implantation success and patency at 3-months were 100%. Qp:Qs averaged 1.2. There were significant improvements over baseline in NYHA class, exercise capacity and quality of life scores. Longer-term data have yet to be published.

A single-center open-labeled study using the AFR device, Rajeshkumar R, et al., "Atrial septostomy with a predefined diameter using a novel Occlutech atrial flow regulator improves symptoms and cardiac index in patients with severe pulmonary arterial hypertension," Cathet Cardiovasc Inerv 2017; 1-9, reported good intermediate term in patients with severe PAH presenting with syncope and RV failure. Twelve (12) patients age 28±8 years with NYHA III (n=9) or IV (n=4) symptoms were successfully implanted without major complications. Patients received 8- or 10-mm devices. RAP immediately fell by 4.1±3.2 mmHg after shunt implantation. All patients had elimination of syncope with NYHA improving to class II (n=7) and class III (n=5) at the duration of follow-up. 6MWD improved from 377±33 to 423±31 m. Cardiac index and systemic oxygen transport were also significantly improved. The shunt was patent in all patients at a median follow-up of 6-months. $SaO_2$ decreased from 98±0.2 to 92±3 at rest and 85±3% after exercise. The AFR device is now being evaluated in the PROPHET trial (NCT03022851), a prospective, non-randomized, study to assess the safety and efficacy of the AFR in 30 patients with PAH.

The major benefit of the foregoing orifice-plate mesh shunts over other shunt designs is simplicity of manufacture. Although relatively simple in theory and construction, orifice-plate mesh type shunts have several important drawbacks that are expected to reduce their overall potential for clinical safety and effectiveness.

A first drawback of orifice-plate devices is the susceptibility to narrow or close during the post-implantation healing period. For example, neoendocardial tissue ingrowth, referred to as pannus, grows from the underlining tissue to cover the mesh and narrow or partially occlude the shunt orifice. During the period following implantation, local trauma caused by crossing and dilating the FO, plus the chronic effects of continuous pressure applied by the mesh material on the septal tissue, provoke a localized healing response. This response entails activation of an inflammatory process, attracting lymphocytes and macrophages to the area of tissue injury. These inflammatory cells in turn release a variety of cytokines that signal fibroblasts and smooth-muscle cells from the wound margins to dedifferentiate, migrate, proliferate and encapsulate affected portions of the implanted device. The fibroblasts and smooth muscle cells then secrete extracellular matrix material composed of collagen and proteoglycans. Extracellular matrix forms the bulk of the pannus. The duration of this healing phase in humans is typically up to 6-9 months but may be longer if there is a chronic source for tissue injury such as device compression or erosion of adjacent tissue. Eventually this pannus is covered with neoendothelial cells, causing the pannus growth to stop or stabilize. In the long term, the collagen of the pannus remodels, but generally retains its space occupying properties. Such tissue ingrowth typically spreads over the surfaces of the implant's struts, mesh, or discs, and may substantially narrow the orifice lumen or even entirely occlude the shunt. Narrowing or occlusion of the shunt inhibits or prevents LA decompression and limits any positive effect for the patient.

The degree of luminal narrowing may be quite variable between patients due to differences in the severity of local injury—the more injury, the more exaggerated the pannus formation. In addition, variability results from differences in host wound healing responses. For example, the amount and character of extracellular matrix may affect the duration of healing and amount of material deposited. Thus, for an orifice-plate mesh shunt, the eventual orifice lumen size will be highly variable. These processes will be familiar to one with ordinary skill in the art as it is generally analogous to the type of late lumen loss that occurs in arteries when bare metal stents are used to treat atherosclerotic stenosis.

A second drawback of orifice-plate mesh shunts is the potential for paradoxical embolization. Paradoxical embolization refers to thromboembolism originating in the venous vasculature (venous thromboembolism or VTE), such that an embolus traverses right-to-left through a cardiac shunt into the systemic arterial circulation. The most severe complication of paradoxical embolization occurs when an embolus lodges in the cerebral circulation with resulting cerebral infarction (stroke). Most frequently, VTE is the consequence of in situ thrombosis in the deep veins (deep venous thrombosis or DVT) of the lower extremities or pelvis.

HF is a well-recognized risk factor for DVT and VTE, especially in patients with reduced left ventricular systolic function, as reported in Howell M D, et al., "Congestive heart failure and outpatient risk of venous thromboembolism: a retrospective, case-control study," J Clin Epidemiol. 2001; 54:810-816. About 3% of deaths in heart failure patients are due to VTE, usually associated with pulmonary embolism, as reported in Beemath A, et al., "Pulmonary embolism as a cause of death in adults who died with heart failure," Am J Cardiol. 2006; 98:1073-1075. There is evidence that the risk of paradoxical embolism is directly related to the orifice size of naturally occurring atrial level shunts such as ASDs. In patients with clinically significant (typically 20 mm in diameter or greater) ASD referred for closure, the incidence of paradoxical embolus has been reported to be up to 14%. See, e.g., Chiche O, et al.

"Prevalence of patent foramen ovale and stroke in pulmonary embolism patients," Eur Heart J. 2013; 34:1142 and Bannan A, et al., "Characteristics of adult patients with atrial septal defects presenting with paradoxical embolism," Catheter Cardiovasc Interv 2009; 74:1066-9.

Clinically relevant venous emboli tend to form in the popliteal veins or more proximally in larger veins of the upper thigh or pelvis. The diameter of the popliteal vein ranges from 6.2 to 20.1 mm. Often, emboli are described as having the form of a cast of the vein's lumen with a width equal to the diameter of the vein of origin. These thrombi tend also tend to be elongated, corresponding to the length of the occluded venous segment. Since ischemic damage from the lodging of an embolus is limited to the watershed organ territory supplied by the occluded vessel, larger emboli tend to cause more damage and have associated more dangerous consequences, especially when the occluding vessel perfuses the brain.

From these observations, it seems reasonable to expect that orifice-plate mesh shunts, by virtue of their anatomic similarities with congenital secundum ASDs, would have a theoretically similar risk of paradoxical embolization. It is easily understandable that a thin plate-orifice mesh type of artificial shunt might be more susceptible to paradoxical embolization than other types of shunts with longer orifice geometries, e.g., a nozzle. For any given quanta of RA volume (blood or thrombus), the statistical likelihood of traversing retrograde across the shunt and into the LA would be expected to be a complex function of the duration of pressure gradient reversal, flow patterns in the RA, shunt tunnel distance affecting the length of the flow velocity streamlines, flow velocity and orifice size.

A third drawback of orifice-plate mesh shunts is that percutaneous removal from the body is only possible at the time of implantation. Should the shunt become a nidus for infection, develop fatigue or corrosion fractures of its metallic framework, or erode or otherwise impinge on other vital cardiac structures, it cannot be removed by percutaneous retrieval/removal techniques. This is because the shunt, with its large "footprint" on the interatrial septum, is encased in pannus tissue. The shunt can only be safely removed by open-heart surgery. This entails that the heart be bypassed using an extracorporeal membrane pump oxygenator (cardiopulmonary bypass), so the heart can be opened, the shunt removed by surgical incision of the extensive pannus and the septum repaired. Performing such surgical procedures in patients with already established severe HF or PAH would likely be contraindicated due to unacceptable morbidity and mortality risks.

A fourth drawback of orifice-plate mesh type of shunts is that their geometric design renders them relatively inefficient in supporting high flow. For any given pressure gradient across the shunt, the geometry of an orifice plate requires a larger orifice because it has a reduced effective orifice size compared with other geometries, such as a Venturi-shaped lumen, or a conical shaped nozzle. This is because with an orifice-plate, there are more energy losses associated with eddy currents at the edges of the orifice. Orifice-plate geometries may be categorized as having a relatively low discharge coefficient, which is a dimensionless fluid-mechanical parameter that relates flow to actual orifice size. For practical purposes, the discharge coefficient is the ratio of areas of the exiting jet *Vena contracta*, which is the narrowest portion of the jet, compared to the shunt orifice. For example, the coefficient of discharge for orifice plates placed in pipes tends to be approximately 0.6, but rarely exceeds 0.65. The discharge coefficient is affected by the orifice and chamber dimensions, the pressure gradient, and the viscosity of blood and/or the Reynolds number of the specific flow condition. This differs from the more efficient passage of flow through a constricted nozzle or a classic Venturi type of narrowing, where the discharge coefficient usually exceeds 0.9 and is typically in the range of 0.94 to 0.98. The result is that, in comparison with more efficient shunt lumen geometries, an orifice-plate mesh shunt requires a larger orifice diameter to accommodate the same amount of flow for any given pressure differential across the shunt.

The sizing for orifice-plate mesh type shunts comes from the work of Kaye et al., "Effects of an interatrial shunt on test and exercise hemodynamics: results of a computer simulation in heart failure," J Cardiac Fail 2014; 20:212-221, who simulated the hemodynamic effects of ASDs using a validated computer model based on HFpEF patient hemodynamic data. They speculated that the optimal size for a plate orifice type of shunt resembling an ASD is 8 mm in diameter by showing that LAP would be reduced during exercise from 28 to 17 mmHg. The tradeoffs were a 12% reduction in peak cardiac output and a ratio of pulmonary to systemic blood flow (Qp:Qs) of 1.3-1.4, and a small rise in RA pressure. With a smaller shunt orifice size, for example 6.4 mm, exercise LAP was still reduced to about 20 mmHg with a smaller reduction in systemic cardiac output, a smaller Qp:Qs and no appreciable rise in right atrial pressure. It might be anticipated that after healing, orifice-plate mesh type shunts may have a reduction in average orifice diameter in the 6 mm range. A nozzle or Venturi configuration however, with orifice diameters that range from 5 to 6-mm would be equivalent to orifice plate ASD diameters of approximately 6.3 to 7.4-mm.

A fifth drawback of orifice-plate mesh shunts is that they tend to occupy a large area or footprint on the interatrial septum. The flanges of the device that anchor the shunt typically occupy the entire area of the fossa ovalis and may overlap adjoining muscular portions of the interatrial septum. These flanges exert persistent pressure on the septum, causing injuring and stimulating an exaggerated healing response as described above. Also, the rigidity of the mesh may interfere with the normal motion of the muscular septum. The flanges additionally may impinge on adjacent cardiac structures such as the roof of the left atrium, the ostia of the right pulmonary veins, and the aortic root and sinuses of Valsalva, where due to chronic rubbing contact or sandwiching compressive forces, they may erode into these vital structures. Such erosion has been associated with severe complications including cardiac tamponade and death. For example, the similarly sized Amplatzer ASD disc occlusion device described above has been occasionally associated with erosion into adjoining tissues with resulting catastrophic outcomes.

A sixth drawback of orifice-plate mesh shunts are potential difficulties associated with placing relatively large devices with complex three-dimensional geometries, difficulties such as positioning the shunts accurately in the FO, obtaining sufficient tissue anchoring to prevent migration, and having devices conform to irregularities of the cardiac anatomy. For example, in a report of attempted implantation of orifice-plate mesh shunts in 66 patients in the above-cited Lancet publication authored by Hasenfuss, et al., device placement of the IASD II was not possible in two patients. And of the 64 implanted patients, the device had to be removed and re-implanted in another 3 patients due to misplacement, migration, or embolization of the first attempted implant.

A final and seventh drawback of orifice-plate mesh shunts is that the large footprint on the atrial septum may hinder or render impossible performing other interventional procedures that require transseptal access. The large flange diameter and small mesh pore sizes generally make catheter crossing of the atrial septum possible only through the central shunt orifice itself. Transseptal procedures using small diameter catheters, such as atrial fibrillation RF ablation, may be conducted through the orifice-plate lumen only if it is not obstructed by pannus and the orifice location permits entry into all four pulmonary veins. Other structural heart disease procedures that have large diameter delivery systems and/or require crossing the FO in specific locations may encounter difficulties or simply not be possible. These procedures include left atrial appendage occlusion, mitral valve edge-to-edge ("MitraClip") repair, and transvascular mitral valve replacement. For example, placing of a MitraClip optimally requires crossing the FO in its superior-posterior quadrant. The guiding catheter has a tip outer diameter of 7.3 mm (22 Fr). Similar transseptal access may be needed to perform reconstructive mitral annuloplasty with the Cardioband device marketed by Valtech. In these cases, the only alternatives might be higher risk therapeutic approaches involving trans-left ventricular apical access or open-heart surgery.

The second type of shunt is referred to as a valved unidirectional shunt. These shunts attempt to overcome some of the drawbacks of orifice-plate devices. For example, valved unidirectional shunts have embodiments containing a one-way or check-valve to limit reverse shunting and paradoxical embolization. Some of the valve configurations are designed to open when the LA-RA pressure gradient exceeds a predefined threshold. Other valve configurations close only when the RA pressure exceeds LA pressure (reversed gradient).

U.S. Pat. No. 9,034,034 to Nitzan, the entire contents of which are incorporated by reference herein, solves many of the drawbacks of plate-like orifice mesh shunts described above. One embodiment of the Nitzan-type shunt comprises an hourglass or diabolo outer shape, having a small FO footprint minimizing septal injury, which is expected to minimize pannus growth and obliteration of the shunt lumen. Its one-way valve also is designed to reduce the potential for reverse shunting and paradoxical embolization. The relatively small footprint of the shunt in contact with the septum and encapsulated collapsible nitinol frame is designed to facilitate percutaneous extraction from the septum and retrieval from the body using a standard goose-neck snare and large-bore sheath, thus making the device more easily retrieved. The Venturi tube-like inner lumen of the diabolo shape provides better bulk flow characteristics, permitting a smaller orifice for the same amount of flow compared to orifice plate shunts. And finally, the small footprint on the FO and the hourglass shape are designed to facilitate accurate placement and retention during implantation. This geometry also minimizes interference with normal motion of the interatrial septum, and the small footprint provides space surrounding the shunt for other potential interventional procedures that require transseptal catheterization.

One embodiment of the Nitzan design was implemented as the first generation "valved" shunt manufactured by V-Wave, Ltd (Caesarea, Israel). That shunt, designed to support unidirectional left-to-right flow, comprises a self-expanding frame constructed from a laser-cut nitinol tube. The frame includes five sinusoidal circumferential struts interconnected by six longitudinal bars. The frame is heat-set so that it has an asymmetrical hourglass shape or a diabolo shape. The shunt is deployed so that the neck (5.3 mm outer diameter) is placed across the FO and secured in place by its external surface geometry. The shunt's widest portion has a conical shape with an approximately 14.3 mm outer diameter at the LA end of the shunt, which in HF serves as an "entry" port on the distal end of the entry funnel. The entry funnel is deployed in the left atrium and registers the neck of the shunt to the region of the FO. A second, slightly narrower bell-shaped portion forms the exit portion of the shunt, which expands to a maximum outer diameter of 11.4 mm at the RA end of the shunt. The shunt does not require flanges, discs, or tissue anchors to secure it in place. Septal retention is achieved without applying persistent pressure, tension or rubbing contact on the tissue adjoining the device neck.

The foregoing valved shunt has a single inner lumen where flow is entrained into the entry funnel in the LA and passes through the constricted neck having a 5.1 mm inner diameter, which resembles a Venturi-type orifice, and then exits through a bioprosthetic valve positioned near the RA end of the shunt. The entry funnel and the central neck region are encapsulated with expanded polytetrafluoroethylene (ePTFE) to form a skirt or cover over the frame. The skirt is designed to facilitate laminar flow and limit pannus ingrowth during device healing. The exit bell-shaped portion contains three, glutaraldehyde-fixed, porcine pericardial leaflets sutured to a series of holes in the nitinol frame at the right atrial extent of the ePTFE encapsulation. The leaflets are designed to create a smooth exit channel and remain in the open position, closing only when the RA pressure exceeds LA pressure by 1-2 mmHg, thus preventing reverse right-to-left shunting.

For deployment, the V-Wave shunt is compressed in a loading tube where it is attached to a triple-latch cable delivery catheter. The loading tube is inserted into a 14F delivery introducer sheath that has been previously placed after a transseptal catheterization from the right femoral vein across the FO. The shunt then is advanced through the sheath until the entry funnel has been deployed in the LA. The entire system is withdrawn as a unit until the LA funnel is in contact with the left side of the FO. The delivery catheter latches are unhooked from the shunt and the delivery catheter withdrawn, so that the right atrial side of the shunt is held only by its radial force against the delivery sheath. The delivery sheath then is withdrawn, thereby deploying the exit bell-shaped portion of the shunt on the RA side of the FO. Device placement may be guided and confirmed by fluoroscopy and echocardiography, e.g., intracardiac echo or transesophageal echo.

Pre-clinical testing on the V-Wave shunt was performed in an established juvenile ovine (sheep) model that created an ischemic cardiomyopathy form of heart failure as established a the peer-reviewed publication by Eigler et al, "Cardiac Unloading with an Implantable Interatrial Shunt in Heart Failure: Serial Observations in an Ovine Model of Ischemic Cardiomyopathy," Structural Heart 2017; 1:40-48. The sheep were pre-treated with sequential coronary artery microembolization as described in the publication, "A stable ovine congestive heart failure model" by Huang et al, "Remodeling of the chronic severely failing ischemic sheep heart after coronary microembolization: functional, energetic, structural, and cellular response," Am J Physiol Heart Circ Physiol. 2004; 286:H2141-H2150. After several weeks, the sheep manifested severe LV systolic dysfunction and develop elevated LV, LA, and pulmonary artery pressures. Once HF was established, the sheep were enrolled in a 12-week survival study. The V-Wave valved shunt was associated with significant improvements in LA pressure and LVEF. All manifestations of worsening heart failure were improved and, in some cases, reversed with interatrial shunting. Concurrent control animals with established heart failure but were not implanted with the V-Wave shunt, demonstrated progressive worsening of LVEF, and intracardiac/pulmonary pressure during follow-up. The physiological improvements in shunted animals were substantial even though the shunt volume was assessed to be small. The pulmonary blood flow/systemic blood flow ratio (Qp:Qs) was between 1.1 to 1.2, as measured by oximetry, which is consistent with a very small shunt and was well tolerated. The 5-mm diameter shunt selectively unloaded the left-heart leading to sustained reductions in LAP, improved LV performance, preserved inotropic and lusitropic function, and with blunted remodeling. Secondary pulmonary hypertension was prevented, and right-sided cardiac pressures and function were preserved.

In another peer reviewed published manuscript by Rodes-Cabau et al., "Interatrial shunting for heart failure: early and late results from the first-in-human experience with the V-Wave System," J Am Coll Cardiol Intv 2018; 11:2300-2310, doi: 10.1016/j.jcin.2018.07.001, n=38 patients were implanted with the V-Wave valved shunt human feasibility studies. Patients were 66±9 years old with NYHA Class III or ambulatory Class IV HF and had either HFrEF (n=30) or HFpEF (n=8). There was a high frequency of co-morbidities known to be associated with a poorer prognosis including coronary artery disease, diabetes mellitus, atrial fibrillation, and chronic kidney dysfunction. Other risk factors included elevated levels of natriuretic peptides, reduced exercise capacity, elevated intracardiac and pulmonary artery pressures, increased pulmonary vascular resistance, and reduced cardiac output. All patients were on GDMT prior to study enrollment. Shunt implantation was successful in all 38 patients without periprocedural mortality and no device replacements were performed. The time for completion of all study-related procedures, including shunt placement, averaged just over 1 hour.

The rate of major device- or procedure-related complications during the first 12 months was 2.6% (periprocedural cardiac tamponade resulting from transseptal catheterization was observed in 1 patient). During a median follow-up of 28 months, there were no device-related deaths, strokes, or thromboembolic events. There were no instances of device dislodgement, migration, embolization, thrombosis, or erosion on follow-up echocardiography. No shunts required removal or replacement for infection or strut fracture. Follow-up imaging studies show that there remained adjacent locations on the FO, potentially available for performing transseptal procedures to treat other cardiac conditions, including, for example, atrial fibrillation ablation, left atrial appendage occlusion, or mitral valve repair.

The pulmonary to systemic flow ratio (Qp:Qs), as measured by echocardiography, increased from 1.0±0.1 at baseline to 1.2±0.1 at 3 months after implantation ($p<0.01$). At 3- and 12-month follow-up, there were improvements in NYHA class (classes I and II in 78% and 60% of patients, respectively), quality of life (improvements ≥5 points in 74% and 73% of patients, respectively), and 6MWD (mean increases of 41±63 and 28±83 m, respectively; $p<0.02$ for all), without changes in objective measures systolic, diastolic, or global RV function. The rates of HF hospitalization and all-cause death were considerably and significantly lower than expected in comparison with the well-matched CHAMPION Control and Treatment arms, described above.

Shunt patency was defined as LA to RA flow through the shunt on transesophageal echo/Doppler study. All shunts were patent at 3 months, but by 12 months, 5 of 36 (14%) had occluded, and another 13 of 36 (36%) were stenotic (narrowed) at the valve. The root cause of valve stenosis was definitively determined. Explanted V-Wave shunts from 3 patients were retrieved and underwent histopathological analysis at 30, 34- and 27-months post implantation. Two of the patients required cardiac transplantation while the third patient died due to gradual progression of HF. The implant sites were fully healed as evidenced of coverage of implant surfaces by fully mature and endothelialized (CD31 positive) fibro-cellular neo-endocardium. Complete endothelial coverage was demonstrated microscopically and via SEM. Local biocompatibility was optimal in all explants, as demonstrated by a total lack of inflammatory response to the collagenous cusp bioprosthetic leaflets, the polytetrafluoroethylene (ePTFE) encapsulation or the metallic frame. No thrombosis was recorded. The bioprosthetic valve leaflets lost motility due to fusion of their commissural edges by fibro-cellular pannus. The inter-atrial channels remained patent and there was not pathologically or functionally meaningful calcification in the conduits or cusps. Thus, the bioprosthetic leaflets were thickened and stenotic with neoendocardial hyperplasia (pannus).

At a median follow-up of 28 months, patients with widely patent shunts had lower long-term rates of death, left ventricular assist device placement or heart transplantation ($p<0.001$), and HF hospitalization ($p<0.008$), along with a reduction of pulmonary capillary wedge pressure (from 23.3±5.4 mm Hg at baseline to 18.0±4.0 mm Hg at 12 months, $p<0.011$). Patients that maintained widely patent shunts tended to be older, had more severe underlying heart disease and co-morbidities, especially reduced renal function, lower exercise capacity, worse resting hemodynamics and lower LVEF in HFrEF patients. Patients with widely patent shunts also had significantly higher shunt flows during the early months after implantation. These "sicker" patients maintained their bioprosthetic leaflets in a more open configuration due to higher shunt flow. Patients with stenotic shunts behaved as a crossover-control, returning to the natural rate of disease progression after 1 year. Subjects with patent shunts had improvements in PCWP, PAP, pulmonary vascular resistance, LVEF, and exercise capacity. They also had fewer long-term heart failure events, including death, HF-hospitalizations, the combinations of death with hospitalization for HF or hospitalization for any cause. Patent shunt patients did not have deterioration of right heart function. Thus, it was concluded that having a long-term patent shunt was highly clinically advantageous. These observations established proof of concept that interatrial shunting has the intended device effects.

V-Wave subsequently developed a second generation of the Nitzan type shunt called the Ventura® Interatrial Shunt, in which the bioprosthetic tissue valve was removed and the ePTFE encapsulated skirt extended from the left atrial entrance port to the right atrial exit port. Data from GLP and the non-GLP chronic preclinical studies of normal physiology animal models showed that 31 consecutive 5.1-mm valveless shunts were successfully implanted. All shunts were widely patent at follow-up ranging from 45-180 days. The valveless shunt heals with neointimal hyperplasia (pannus) forming on the outer surface sealing where the neck crosses the fossa ovalis. Even if one of the atrial cones of the shunt contacts an atrial structure, the pannus tends to leave the lumen in the neck region widely patent entirely preserving the shunting function. Endothelialization developed gradually over the luminal surface of the ePTFE encapsulation. The normal physiology model had a trans-atrial left-to-right gradient of 2-3 mmHg, much smaller than expected in HF. Nonetheless, shunt remained widely patent whether treated with anticoagulation or dual antiplatelet therapy without evidence of device thrombosis. There were no thromboemboli or infarction of any downstream organ.

The second generation Ventura® Shunt has now been implanted in a small (n=14) patient feasibility study and in 82 of the scheduled 100 patients in an open labeled Roll-in registry arm of the RELIEVE-HF pivotal trial (NCT NCT03499236). All patients were successfully implanted with the shunt. On transesophageal echocardiographic follow-up at 6 months, 47 of 47 shunts that have reached the 6-month follow-up in the RELIEVE-HF roll-in registry are widely patent.

In summary, these implantable shunt devices, irrespective of specific design features, have consistently demonstrated beneficial therapeutic effects in patients with HF, where left to right interatrial shunting decompresses left heart preload and results in improved symptoms, exercise capacity, quality of life, and reduction in episodes of worsening HF requiring acute hospitalization. Similar outcome results have been reported for all shunt devices in differing patient groups encompassing nearly all etiologies of HF, irrespective of LV ejection fraction. There is thus a strong class-effect related to the improved physiology from having and maintaining a patent left to right interatrial shunt over a range of optimal shunt orifice sizes. Similarly, the results of interatrial shunting in PAH show that right to left shunting lowers RV preload with associated improvements in symptoms, exercise capacity, quality of life, and likely a reduction in episodes of acute worsening right-side HF, requiring hospitalization. A class effect, whether by BAS or shunt, has been demonstrated in that the beneficial mechanism is the improved physiology of having and maintaining a patent right to left interatrial shunt over a range of optimal shunt orifice sizes. Nonetheless, as discussed, the orifice-plate mesh type shunts appear to have multiple significant drawbacks that may limit their adoption by practitioners. The second-generation Ventura® Shunt device and others similar designs overcome all of the drawbacks of orifice-plate mesh shunt designs.

Specifically, the dimensions and materials of the Ventura® Shunt make it highly resistant to narrowing due to pannus or thrombus formation. Pannus formation is arrested some distance before its translational growth along the shunt surface can reach the orifice lumen. The length of the shunt, its orifice size, and the protrusion of the protective hood into the right atrial chamber reduce the likelihood and the severity of paradoxical embolization. That these shunts have been successfully percutaneously removed after up to 6 months in an animal model, leaving a residual 5 mm round defect in the septum, is another differentiating feature. The nozzle or Venturi effect with a high coefficient of discharge make these shunts highly efficient relative to orifice-plate mesh shunts, allowing a smaller size and in conjunction with their external hourglass shape, they occupy the smallest available footprint on the fossa ovalis. The external shape by itself secures the shunt in place without pinching of septal tissue. The external hourglass shape also reduces contact with adjoining areas greatly limiting the chances of device erosion into vital cardiac structures. This geometry makes shunt delivery in complex 3-dimensional anatomy relatively straightforward with a near 100% success rate. Finally, the small footprint leaves ample space for accessing the LA from other locations on the fossa ovalis adjacent to the shunt, permitting a wide range of structural heart disease and electrophysiological ablation procedures to be performed after shunt placement and healing.

Previous Known Efforts to Incorporate Sensors with Shunts:

Shunts that incorporate sensors are described, for example, for example, in U.S. Pat. No. 8,091,556 B2 to Keren et al., U.S. Pat. No. 8,070,708 B2 to Rottenberg et al., U.S. Pat. No. 9,681,948 B2 to Levi et al., and U.S. Pat. Nos. 8,696,611 B2 and 9,707,382 B2 to Nitzan et al., all of which patents are assigned to the assignee of the present disclosure and the entire contents of each of which are incorporated by reference herein. U.S. Pat. No. 10,413,284 B2 McNamara, the entire contents of which are incorporated by reference herein, also describes a shunt having a sensor, as described below. These patents generally describe that sensors may be incorporated into interatrial shunts to regulate the orifice area of a valve or gate via mechanical means, e.g. with a motor, and that sensor information may be useful for other purposes, such as making diagnoses and guiding drug therapy.

By way of example, U.S. Pat. No. 8,091,556 to Keren et al. describes a method of reducing LAP with a shunt that comprises a flow regulating apparatus such as a valve that is controlled by a sensor, a programmable signal processor, and a power source. The processor collects data and may communicate externally, even with the patient, who can then notify the physician in the event the device is activated by an exacerbated state of HF. The physician then establishes medical treatment to reduce the severity of the patient's condition.

U.S. Pat. No. 8,070,708 B2 to Rottenberg et al. describes an interatrial shunt with a flow regulation mechanism that responds to the changes in differential pressure between the atria. The flow regulating mechanism may include a valve that changes in a controlled way by differential pressure thresholds. In some embodiments, the differential pressure-regulating device may be actively controlled, for example, by a patient or medical service provider. In another embodiment, a pressure-dependent closed loop is described that employs one or more pressure transducers. The pressure transducers may measure an absolute pressure in one or more heart chambers, LAP, RAP, or a differential pressure between these two or any two heart chambers. The implant may be controlled wirelessly from an external transmitting unit. Blood flow changes in response to valve positioning may be monitored remotely.

U.S. Pat. No. 9,681,948 B2 to Levi, et al. describes a medical implant with an opening for blood flow through the atrial septum that may have a sensor mounted on the anchor portion of an interatrial shunt device. The anchoring device may include a flap or other unit that is adapted to close the orifice, wherein the opening and closing of the flap could be controlled responsive to a sensor output. The sensors may be located adjacent to the device or may be remote from the device. Operational energy may be provided to the controller by an embedded battery and/or by an external source. In some embodiments, an anchor device is coupled to a pacemaker or ICD and shares its power source. For example, the opening of the flap may depend on the absolute pressure in one or more of the chambers of the heart, on the temperature in one or more chambers of the heart, on the patient's blood pressure and/or on the patient's blood oxygen content. The control also may depend on any of the parameters used by pacemakers, for example in synchronized pacing. The sensors could be mounted on a petal or petals of the anchor portion of the shunt, located on one side of the atrial septal wall, while a second sensor is mounted on a petal located on the other side of the wall. Thus, readings from both of sensors may be read and compared to determine the relative conditions on opposite sides of the atrial septum. The patent describes that any type of sensor could be used and more or fewer sensors may be mounted on an anchor portion of the shunt device. For example, the sensors may include one or more pressure sensors, oxygen sensors, B Natriuretic Peptide (BNP) sensors, a sensor of toxic components, flow sensors and/or pH sensors.

U.S. Pat. Nos. 8,696,611 B2 and 9,707,382 B2, both to Nitzan et al., describe embodiments of diabolo-shaped shunts for regulating blood pressure between the two atrial chambers. Those patents include experimental evidence that the interatrial pressure difference could be measured by the valve leaflet-opening angle, and postulate that the angle could be determined by an imaging modality such as ultrasound. By quantifying the pressure, the physician then may adjust medications to help stabilize the patient and prevent (pulmonary) edema.

U.S. Pat. No. 10,413,284 B2 to McNamara et al. describes a system for treating a heart condition in a patient comprising: a cylindrical core segment defining a passage; a first annular flange adapted to engage a first surface of an atrial septum; a second annular flange adapted to engage a second surface of the atrial septum; and a motor mounted to the body element that is coupled to a movable flap to form an opening of the atrial septum, which allows blood to flow between left atrium and right atrium. The patent describes that the system further include a sensor for detecting data related to at least one of blood chemistry, blood pressure, temperature, electrical characteristics of the patient's heart, chemical characteristics of the blood and biomarkers in the blood. The patent further describes that the system may include a microprocessor in communication with the sensor. Sensors are described for detecting a plurality of physiological parameters associated with the heart. That system may be in communication with a remote monitoring facility that may include capabilities for displaying sensor data; for controlling devices for delivering therapy to the patient; and to present data to clinicians to recommend appropriate treatment such as administration of drugs based on the physiological data obtained by the sensors.

In view of the foregoing, it would be advantageous to provide an interatrial shunt that overcomes the drawback of previously known systems and devices, which provides long-term patency and in addition could provide actionable data for intracardiac physiologic parameters that could be used to permit the patient and attending physician to modify the patient's course of treatment and/or medications.

Accordingly, there is a need for interatrial shunt systems and methods that provide a an interatrial shunt having demonstrated beneficial flow characteristics and long-term patency, and which includes one or more sensors that provide actionable data for intracardiac physiologic parameters, and which enable a patient and attending physician to modify the patient's course of treatment and/or medications.

SUMMARY OF THE INVENTION

The present invention describes apparatus and methods for making and using improved interatrial shunts that incorporate sensors to improve treatment and outcomes for patients with cardiovascular and cardiopulmonary disorders, specifically HF and PAH. More specifically, interatrial shunts having incorporated physiologic sensors are provided for monitoring and treating cardiovascular syndromes, including heart failure and pulmonary hypertension. In accordance with the principles of the present invention, the one or more sensors are affixed to the shunt to measure a physiologic parameter within the interatrial shunt, either directly affixed to or within a lumenal surface of the shunt or mounted on a support structure disposed in a spaced relation to the shunt lumen, wherein the one or more sensors are disposed at locations subject to little or no pannus formation or cardiac wall motion artifact.

As discussed in this disclosure, sensors suitable for use with implantable interatrial shunts illustratively measure pressure, blood flow or blood velocity. It is to be understood by those with ordinary skill in the art that in the presented embodiments, the term sensor is used in its most generic sense as a device for measuring any suitable type of environmental phenomena, including detecting events or changes in that environment. More specifically, implantable sensors suitable for use in the shunts of the present invention are those that are indicative of key physiological parameters and/or permit the determination specific therapeutic actions, including without limitation flow, velocity, acceleration, pH, oxygen content or saturation, or chemical species concentrations such a B-type natriuretic peptide.

Interatrial shunts especially well-suited for use in constructing devices in accordance with the present invention are described in U.S. Pat. Nos. 9,707,382 B2, 9,980,815 B2 and 10,639,459 B2 to Nitzan et al., U.S. Pat. Nos. 10,076,403 B1 and 10,251,740 B2 and U.S. Patent Application Publication Nos. US 2019/008628 A1 and US 2019/0262118 A1 to Eigler et al., and U.S. Patent Application Publication No. US 2019/0110911 A1 to Nae et al., the entireties of each of which are all hereby incorporated by reference herein. These shunts, by way of having a suitable combination of design geometry and biomaterial properties including having encapsulated surfaces, overcome many the drawbacks of previously known shunts. Specifically, they: 1. Reduce susceptibility of a shunt to narrow or close due to neoendocardial tissue ingrowth, referred to as pannus, during the post-implantation healing period; 2. Reduce the potential and consequences of paradoxical thromboembolization from the right to the left atrium; 3. Facilitate the ability to non-surgically remove an embolized or fully healed implanted shunt from the body; 4. Improve shunt effective orifice size relative to true orifice size; and 5. Reduce the shunt septal footprint to reduce interference with septal wall motion, minimize shunt impingement on the septum and adjacent cardiac structures, simplify and improve shunt deployment success and allow adjacent septal access for procedures that require entering the left atrium via the transseptal route.

In view of the foregoing drawbacks of previously known interatrial shunts, a shunt having a sensor constructed in accordance with the principles of the present invention provides a more durable configuration that maintains luminal patency for extended periods of time. The inventive shunt enables monitoring of atrial pressures, and flow velocities, thereby enabling the physician to adjust the patient's medication regime, or in some embodiments the flow characteristics of the shunt, to redistribute interatrial blood volumes and adjust pressure imbalances, while reducing a risk of paradoxical embolism. The implantable sensors are provided to monitor, detect and diagnose cardiovascular and cardiopulmonary conditions. The sensor data may be communicated continuously or episodically to an external patient display device via RF telemetry or inductive coupling, and used as a guide for changing or adjusting medication therapy, adding indicated device therapies, or performing procedures to alter the physiological characteristics of the shunt. Data communicated from the implantable sensors also may be relayed in an encrypted format to the patient's physician via telephone or a suitable wide area network, such as the Internet.

For the indications of treating HF and PAH, the anticipated outcomes of use of the inventive shunts include enhanced safety, improved implantation procedure success, long term device performance and clinical efficacy, with resulting improvements in symptoms, exercise capacity, quality of life, and reduction of episodes of clinical decompensation that result in hospitalization and death. Moreover, the inventive shunt will reduce the negative impact associated with using separately implanted shunts and sensors in proximity to the interatrial septum, which could obstruct access the left atrium for other therapeutic procedures such as mitral valve repair, left atrial appendage occlusion, and treatment of atrial fibrillation by pulmonary vein ablation.

In accordance with the principles of the present invention, the inventive shunts provide HF patients with reductions in left atrial pressure, relieve pulmonary congestion, and lower pulmonary artery pressure, among other benefits. The inventive devices are configured for implantation as a unit, or as part of a single procedure, across the atrial septum, and preferably through the fossa ovalis. Alternatively, the shunt portion of a device may be implanted first with an option to add or activate sensor components immediately thereafter or some unspecified later time when clinically indicated.

In particular, a shunt constructed in accordance with the principles of the present invention is designed to control LAP by transferring a portion of the blood normally flowing from the left atrium to the left ventricle and diverting it instead to the right atrium, thereby modestly reducing LV end-diastolic filling volume. When the LAP is elevated, the LV operates on a steeper portion of its diastolic compliance curve. Accordingly, even a modest reduction in LV end-diastolic volume can lead to a substantial fall in LV end-diastolic pressure. That reduction causes a commensurate reduction in upstream filling pressures including LAP, pulmonary venous pressure, and pulmonary artery pressure. The anticipated clinical result of these pressure reductions is expected to relieve or even prevent pulmonary congestive symptoms. At smaller interatrial gradients with less shunting, the effect on LV volume and filling pressures becomes progressively smaller until it is negligible. As interatrial shunting primarily affects LV filling and not afterload, beneficial effects on lowering end-diastolic pressure are expected, regardless of LV systolic function, for patients with heart failure associated with reduced ejection fraction (HFrEF) and patients with heart failure and preserved ejection fraction (HFpEF).

In accordance with one aspect of the invention, the shunt portion characteristics are optimized to overcome the drawbacks and limitations of previously known orifice-plate mesh type shunt. Accordingly, the shunt portion of the inventive device employs a shunt described in the above-incorporated Nitzan et al., Eigler et al, and Nae et al., patents and published application. Further in accordance with the present invention, one or more sensors are attached to the shunt, either directly or via a support structure, so that the sensors do not substantially detract from the shunt operation, interfere with the deliverability of the shunt, and do not impede access via the shunt to the left ventricle for subsequent interventional procedures.

The present invention provides shunts that incorporate sensors to measure one or more of LAP, RAP, blood flow or blood flow velocity through the shunt orifice or other intracardiac parameters. Sensor anchoring, housing, deployment procedures and method of use are provided that perform seamlessly with associated shunts to minimize interruption of shunt flow, maintain the smallest achievable dimensions and septal footprint, harmonize with current best shunt deployment techniques, take advantage of the secure anchoring systems, use shunt design geometry and biomaterials to reduce waveform artifacts and extrinsic sensor drift, and make best use of the sensor data to manipulate medications in the setting of a shunt. Unlike current stand-alone intracardiac sensors, preferred embodiments of the invention also enable measurement of shunt flow characteristics, important physiological parameters that can guide therapy.

Subjects with a variety of heart pathologies may be treated with, and may benefit from, the inventive shunt. For example, in subjects with HF, improved control of LAP and LVEDP may provide a variety of benefits, including but not limited to: decreasing pulmonary congestion; decreasing pulmonary artery pressure; increasing LVEF; increasing fractional shortening; and decreasing LV internal diameter in systole. Other heart pathologies that may be beneficially treated include large myocardial infarctions with or without accompanying acute HF, which may be treated by deploying the device during or shortly following the myocardial infarction to reduce detrimental myocardial remodeling and the development of intractable HF. Patients with acute viral myocarditis may be similarly helped. The inventive shunts also may reduce the need for, or assist weening from, extracorporeal membrane oxygenation (ECMO) devices or the need for emergency ventricular assist devices of cardiac transplantation. Patients having mitral valve repair with a MitraClip or other similar therapy may benefit by placing an inventive shunt at the site of transseptal crossing to further help manage residual HF. Similar benefit may exist for patients undergoing pulmonary vein ablation for atrial fibrillation. A shunt constructed in accordance with the principles of the invention also may be used to manage residual HF due to left-sided cardiac dysfunction, which may help maintain sinus rhythm as well. Patients with PAH, whether idiopathic or from associated causes, may benefit from the dual effects of a right to left shunt unloading the RV, and sensor guided adjustment of medications that affect RV preload and afterload.

In accordance with another aspect of the invention, an alternative interatrial shunt for treating heart failure (HF) or pulmonary arterial hypertension (PAH) by shunting blood to relieve high pressure and monitoring at least one atrial physiologic parameter is provided. The interatrial shunt may include an anchor having a first flared region, a second flared region, and a neck region disposed between the first flared region and the second flared region, and a biocompatible covering disposed on the anchor to form a lumen that extends from the first flared region to the second flared region. In addition, the interatrial shunt may include a sensor having a housing, a sensing surface, and circuitry disposed within the housing for generating data indicative of the at least one atrial physiologic parameter and for communicating the data. The sensor may be pivotally coupled to the first flared region, e.g., via a torsion spring, such that the sensor may transition between a delivery configuration and a deployed configuration where the sensing surface is in fluid communication with the lumen. The biocompatible covering may include an opening sized and shaped to expose the sensing surface of the sensor when the sensor is in the deployed configuration, such that the sensing surface is in fluid communication with the lumen.

The anchor may include a plurality of longitudinal struts interconnected by a plurality of circumferential struts, and may transition between a collapsed delivery state and an expanded deployed state. In the deployed configuration, the sensor may be positioned in between a pair of adjacent longitudinal struts of the plurality of longitudinal struts, and a pair of adjacent circumferential struts of the plurality of circumferential struts, such that the sensing surface of the sensor is unobstructed by the plurality of longitudinal and circumferential struts when the sensor is in the deployed configuration. The torsion spring may be coupled to an outermost circumferential strut of the first flared region such that the torsion spring may pivot the sensor about the outermost circumferential strut. For example, a first end of the torsion spring may be coupled to the housing of the sensor and a second end of the torsion spring may be coupled to a longitudinal strut of the first flared region, such that a portion of the torsion spring between the first and second ends wraps around the outermost circumferential strut. Moreover, the torsion spring may be constructed to bias the sensor towards the deployed configuration. Accordingly, during delivery of the interatrial shunt within a delivery sheath, the sensor remains in the delivery configured via an inner wall of the delivery sheath, such that upon exposure from the delivery sheath, the sensor transitions to the deployed configuration. In the delivery configuration, the sensor may extend axially away from the anchor.

The sensing surface of the sensor may include a flexible sensing diaphragm. In addition, the sensor may include a ferrite core overwound by a telemetry coil disposed within the housing. The sensor further may include an MEMS sensor disposed within the housing. For example, the MEMS sensor may selected from a list consisting of a Wurth, TDK, or Fraunhoffer sensor. Alternatively or additionally, the sensor may include a strain gauge disposed within the housing. The data generated by the sensor may be indicative of a left atrial pressure, a right atrial pressure or a velocity of blood flow through the lumen. In some embodiments, an inlet of the first flared end region may be in a first plane, and an outlet of the second flared end region may be in a second plane, such that the first plane intersects the second plane in the expanded deployed state.

In accordance with yet another aspect of the invention, a system for treating heart failure (HF) or pulmonary arterial hypertension (PAH) by monitoring at least one atrial physiologic parameter and displaying information indicative of the at least one atrial physiologic parameter on a patient display device is provided. The system may include the alternative interatrial shunt described above having the sensor pivotally coupled to the first flared region of the anchor of the shunt, e.g., via a torsion spring, as well as a computer readable medium having instructions that, when executed by a processor of the patient display device, cause the processor to receive the data from the sensor and process the data for viewing on the patient display device. The system further may include a delivery sheath sized and shaped to receive the anchor in a collapsed delivery state and the sensor in the delivery configuration. The sensor may be biased toward the deployed configuration, such that upon exposure from the delivery sheath, the sensor transitions to the deployed configuration.

BRIEF DESCRIPTION OF THE DRAWINGS

Further features of the invention will become apparent from the detailed description, the claims, and the drawings, which are intended for illustration only and are not intended to limit the scope of the disclosure.

FIGS. 18A and 18B are graphs showing computational flow dynamics pressure fields of a shunt constructed in accordance with the principles of the present invention, which

FIGS. 24A and 24B are, respectively, an end view and a side view of an intra-atrial shunt formed from a wire braid covered with a biocompatible covering, having a sensor affixed within the flow lumen of the shunt, while

DETAILED DESCRIPTION OF THE INVENTION

Interatrial shunts are provided for redistributing interatrial blood volumes and reducing left atrial pressure that incorporate one or more physiologic sensors, which may be advantageous in treating subjects suffering from HF or other disorders associated with elevated left atrial pressure. A preferred embodiment of the inventive shunt includes an anchor, which may have an hourglass or "diabolo" shaped stent or frame, and a conduit, formed by encapsulating the frame in a synthetic biocompatible material. The shunt is configured to be lodged securely within a passage formed in the atrial septum, preferably the fossa ovalis, and provides one-way blood flow from the left atrium to the right atrium, when blood pressure in the left atrium exceeds that on the right and reversal of blood flow from the right atrium to the left atrium, when blood pressure in the right atrium exceeds that in the left. In accordance with the present invention, the one or more physiologic sensors are disposed on one or more support struts coupled to the anchor or are affixed to the biocompatible material.

Figure 1A:
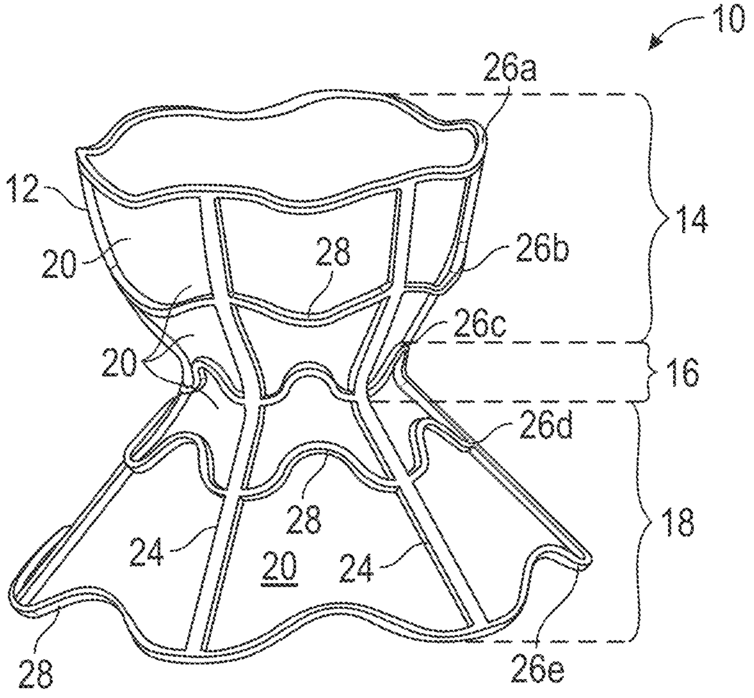
FIGS. 1A to 1C are, respectively, perspective, end and side views of a preferred embodiment of shunt structure suitable for use in a device constructed in accordance with the principles of the present invention.
Figure 1B:
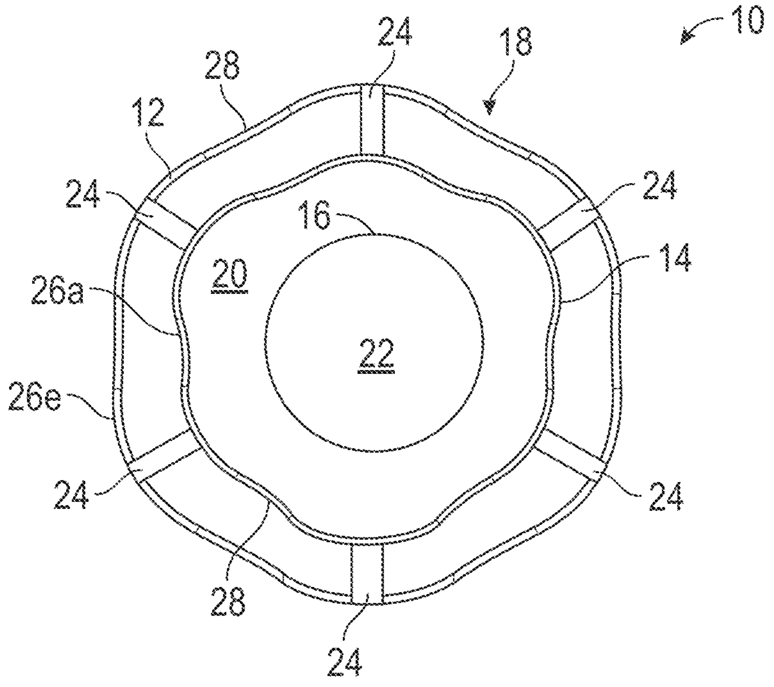
Figure 1C:
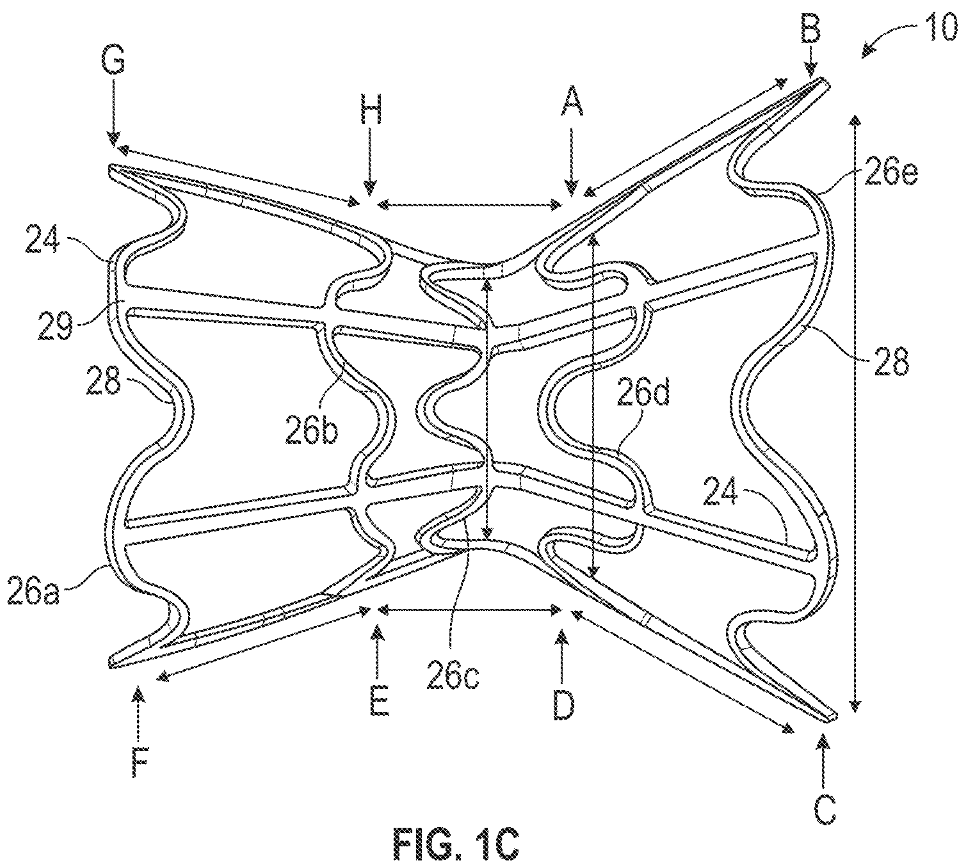

Referring now to FIGS. 1A to 1C, an illustrative embodiment of shunt 10, which may be configured such as described in any of the commonly assigned patents and applications incorporated by reference herein, is described. Shunt 10 generally comprises anchor 12 having three regions: flared or funnel-shaped end region 14, flared or funnel-shaped end region 18, and neck region 16 disposed between end regions 14 and 18. Neck region 16 is configured to lodge in an aperture, such as a puncture, formed in the atrial septum, preferably in the fossa ovalis. Flared end regions 14 and 18 are configured to partially engage and protrude beyond the right and left sides, respectively, of the atrial septum when implanted. Shunt 10 further comprises a conduit, illustratively formed by encapsulating anchor 12 with biocompatible material 20 that covers all or substantially all of anchor 12 to form a conduit defining a lumen or interior passageway 22.

Flared region 14 is configured to be disposed in the right atrium, while flared region 18 is configured to be disposed in the left atrium. In one embodiment, anchor 12 includes longitudinal struts 24 interconnected by circumferential struts 26*a*-26*e*. Longitudinal struts 24 may inhibit or prevent foreshortening of anchor 12 during expansion, while the sinusoidal or serpentine bends in circumferential struts 26*a*-26*e* permit the anchor to transition between a radially collapsed substantially cylindrical delivery state to an expanded, flared, deployed state as illustrated in FIGS. 1A to 1C. As depicted in the figures, a conduit is formed by biocompatible material 20 that encapsulates the entirety of neck 16, flared end region 18, and flared end region 14. Biocompatible material 20 preferably is affixed to anchor 12 using a suitable biocompatible adhesive or by sandwiching the anchor between inner and outer layers of biocompatible material using sintering techniques.

In a preferred embodiment, anchor 12 comprises a self-expanding material, such as a superelastic alloy, and circumferential struts 26*a*-26*e* are treated to expand a predetermined amount when deployed, so that together with encapsulation 20, lumen 22 has a contour that permits substantially laminar flow between flared end section 18 (in the left atrium) and flared end section 14 (in the right atrium). The sinusoidal or serpentine bends 28 are such that all circumferential struts are in phase with circumferential strut 26*a*. This arrangement provides a shunt that requires less force to be applied to flared end region 18 to crimp to a radially collapsed shape, such a retracting it into a constraining tube, e.g., an introducer sheath, used for shunt delivery. Alternatively, the sinusoidal or serpentine bends 28 of the circumferential struts on flared end region 14 preferably are 180 degrees out of phase with the sinusoidal or serpentine bends 28 in neck region 16 and flared end region 18, so that the sinusoidal or serpentine bends do not extend beyond the ends of longitudinal struts 24 in either the collapsed delivery state or deployed state.

As described in the above-incorporated patents and published applications, anchor 12 may comprise a biocompatible metal framework or laser-cut solid metallic tube made from nitinol, titanium alloy, cobalt chromium alloy, MP35N, 316 stainless steel, L605, Phynox/Elgiloy, platinum chromium or other biocompatible metal such as are known to persons with ordinary skill in the art. While a preferred embodiment employs a superelastic self-expanding alloy, anchor 12 alternatively another preferred embodiment may comprise plastically deformable material, e.g., balloon expandable, or may be a shape memory alloy that responds to temperature changes to transition between contracted delivery and expanded deployed states. As will be recognized by those of skill in the art, certain alloys, such as nickel-titanium alloys, may exhibit superelastic or shape memory properties depending upon the manufacturing processing technique, and either set of properties may advantageously be employed in an anchor for use in a shunt constructed in accordance with the principles of the present invention.

In one preferred embodiment, the anchor is made from nitinol with an austenitic finish temperature $A_f$ that is well below body temperature, ideally in the range of 5 to 20 degrees C., so that the nitinol is in a superelastic austenitic phase at body temperature. Furthermore, the anchor may have an adjustable diameter in neck region 16, as described in co-pending, commonly assigned U.S. patent application Ser. No. 16/875,652 entitled "Devices with dimensions that can be reduced and increased in vivo, and methods of making and using the same," which is hereby incorporated by reference herein in its entirety. By differential heat treatment, a region of the anchor centered on neck region 16, that may also be extended a distance into adjacent portions of flared regions 14 and 18, has an austenitic finish temperature $A_f$ that is above body temperature, for example in the range of 45 to 60 degrees C. At body temperature, the mid portion of the anchor will be predominantly or essentially in a martensitic phase having shape memory, that is, mechanically deformable to a larger diameter such as by balloon expansion, but returnable to its original shape by the application of transient heating to a temperature above $A_f$, either by flushing with warmed liquid such as saline solution or heating by other means such as RF induction. Flared end regions 14 and 18 have a lower $A_f$, in the range of 5-20 degrees C. and are thus in a predominantly or essentially austenitic phase and remain superelastic at body temperature.

The surface finish applied to the material of the anchor may be selected to control the distance, thickness, composition and/or growth pattern of pannus formation and thrombus formation, e.g., the external surfaces of anchor 12 may be electro-polished. The anchor may be coated with a biocompatible polymer or biological molecule such as heparin or other suitable coating that inhibits or prevents pannus tissue or thrombus formation.

In accordance with the principles of the present invention, the radial dimensions, axial lengths contours of neck region 16 and flared end regions 14 and 18 preferably are selected to provide laminar flow through the interior of the shunt, to reduce the formation of eddy currents when implanted, and thus inhibit thrombus formation; to inhibit pannus formation that could obstruct the neck region; to promote tissue ingrowth around the exterior of the neck region, sufficient to secure the shunt against migration; to provide a desired rate of blood flow between the left and right atria at physiological pressure differentials; and to inhibit or prevent retrograde paradoxical embolization.

Biocompatible material 20, when applied to the anchor, forms the conduit and preferably is resistant to transmural and translational ingrowth of pannus material having a tissue thickness greater than 0.6 mm accept around the exterior of the neck region, where the shunt contacts interatrial septum at the location of crossing the septum with the shunt following transseptal delivery. On the external surface of the neck region and extending into the contiguous flared regions, pannus tissue thickness may be greater than 0.6 mm.

Experimental ePTFE vascular grafts having a 60-micron internodal distance were observed to develop rapid, transmural infiltration with proliferating smooth muscle cells and granulation tissue, whereas ePTFE grafts with a 30-micron internodal distance were observed to develop only a slow growing, thin sheet of endothelium that advanced only a few millimeters into the graft lumen from the adjacent artery, as described in Clowes et al., "Mechanisms of arterial graft healing: Rapid transmural capillary ingrowth provides a source of intimal endothelium and smooth muscle in porous PTFE prostheses," Am. J. Pathology 1986; 123; 220-230, the entire contents of which are incorporated by reference herein. Porous polyester fabric coverings employed on some atrial septal defect ("ASD") occlusion devices would be poor choices for use in the shunt of the present invention, because such materials become completely enmeshed with penetrating fibrotic tissue. It is expected, and has been demonstrated in a normal ovine animal model that when shunt 10 comprises anchor 12 made of or including, for example, electropolished nitinol, and biocompatible material 20 is or includes an inert polymer, e.g. ePTFE, having an internodal distance of 30 microns or less, or (non-expanded) PTFE, pannus may grow to a thickness no greater than about 0.6 mm after extending translationally a distance of 3 mm from the site of contact with the Foramen Ovalis (FO) tissue. In such cases, the interior lumen of the conduit is expected not to narrow beyond a total of 1.2 mm from its original diameter at the neck. For the purposes of this disclosure, the term "luminal narrowing" shall be defined as a loss of minimal shunt lumen diameter of greater than 25% and the term "luminal obstruction" is defined as total blockage (100% loss of lumen diameter) of the lumen to the flow of blood. As used in this application, terms such as "about," "approximately," and "substantially" when used in conjunction with dimensions are intended to mean within ±20% of the stated value unless otherwise stated.

In yet another preferred embodiment, it has been demonstrated that in a normal ovine animal model that when shunt 10 comprises anchor 12 made of or including, for example, electropolished nitinol, and biocompatible material 20 is or includes an inert polymer, e.g. ePTFE, that the proliferating smooth muscle cells and granulation tissue at the neck region infiltrate into the internodal spaces of the polymer but do not chemically bind to the polymer. The shunt therefore may be held in place by mechanical interference of the proliferating tissue, thus making it resistant to embolization. Nevertheless, the attachment of tissue to biocompatible material 20 can be overcome with adequate retraction force, such as provided by a vascular Amplatz single loop snare placed around the neck region of the shunt device, which may be used to pull the shunt into a suitably sized introducer sheath. In this manner, shunts such as those described in FIGS. 1A-1C and 2 may remain removable even after they have been implanted for periods up to or exceeding 6 months. When removed in this way, the residual proliferative tissue may form a ring that inhibits or prevents tearing of the septum, leaving a residual approximately circular hole in the interatrial septum that closely approximates the outer diameter of the shunt device in the neck region.

In the preferred embodiment depicted in FIGS. 1A to 1C, anchor 12 has an hourglass shape formed of or including a superelastic metal, e.g., nitinol, or any other suitable material known in the art. Circumferential struts 26*a*-26*e* and longitudinal struts 24 preferably have a unitary construction, that is, entire anchor 12 is laser cut from a tube of superelastic metal.

Biocompatible material 20 may comprise, for example, a sheet of a polymer such as expanded polytetrafluoroethylene (ePTFE), polytetrafluoroethylene (PTFE) silicone, polycarbonate, urethane, DACRON (polyethylene terephthalate), Ultra High Molecular Weight Polyethylene (UHMWPE), or polyurethane. The biocompatible material also, or alternatively, may be or include a metal, ceramic, carbon nanotube array or any other suitable biocompatible material. For example, biocompatible material 20 may comprise ePTFE with an up to 30-micron internodal distance and may be applied as inner and outer layers that are sintered together to form a unitary conduit. Alternatively, biocompatible material 20 may be applied to the inner lumen and the outside of the anchor using electrospinning techniques. Other methods of encapsulation and other suitable polymers that inhibit or prevent transmural ingrowth of pannus tissue may be used, as will be understood by one of ordinary skill in the art. Bare metal regions of anchor 12, and any other regions of the anchor, optionally may be electropolished or otherwise treated to inhibit thrombus formation using known methods.

Neck region 16 of shunt 10 preferably is configured for implantation through the fossa ovalis of the atrial septum, and in some embodiments more preferably near or at the central portion of the fossa ovalis. As known to those of ordinary skill in the art, the fossa ovalis is a thinned portion of the atrial septum formed during fetal development of the heart, which appears as an indent in the right side of the atrial septum and is surrounded by a thicker portion of the atrial septum. While the atrial septum itself may be several millimeters thick and muscular, the fossa ovalis may be only approximately 1 mm thick and is formed primarily of fibrous tissue. In rare cases, the fossa ovalis may be up to 10 mm thick.

In some embodiments of the present invention, shunt 10 may be asymmetrically shaped to take advantage of the natural features of the atrial septum near the fossa ovalis, and to provide suitable flow characteristics, as described in co-pending, commonly assigned U.S. patent application Ser. No. 16/408,419 entitled "Asymmetric shunt for redistributing atrial blood volume," which is hereby incorporated by reference herein in its entirety. For example, in a preferred embodiment, the anchor comprises an hourglass or diabolo shape where the LA entry funnel resembles a conical-shaped nozzle and the RA exit funnel is "bell" shaped, with the wide mouth lumen of the bell at the RA exit port in the RA. The narrow entrance to the bell-shaped exit funnel connected to the orifice of the neck region may be configured to approximate the curved surface of a parabola. This type of convergent-divergent nozzle resembles the shape of a classical de Laval nozzle used in rocket engines. Left to right flow is largely governed by the smooth convergence of streamlines in the entry cone and the divergence of streamlines exiting the bell. Such a nozzle configuration is very efficient in the forward flow direction having a discharge coefficient resembling a classic Venturi tube, e.g., approximately 0.94-0.98.

Referring now to FIG. 1C, points B and C are located on the leftmost circumferential strut 26*e*, which defines the LA entry port. Points A and D are located on circumferential strut 26*d* along the LA entry funnel toward the neck from strut 26*e*. Points H and E are located on circumferential strut 26*b* along the RA exit funnel, and points G and F are located on circumferential strut 26*a*, which defines the RA exit port. In preferred embodiments, the diameter of lumen 22 in the neck region of the shunt orifice ranges from 5 to 6.5 mm. The portion of the shunt crossing the FO, bounded by points ADEH may be 3 mm in axial length but may be extended up to 10 mm in patients with a thicker FO. The diagonal length between points AB, CD, EF, and/or GH is preferably ≥3 mm so that pannus cannot grow translationally inward from the ends of the shunt and thus obstruct neck region 16. In addition, the horizontal component length between points AB, CD, EF, and/or GH, i.e. the distance the shunt protrudes into the left or right atrium, is preferably <15 mm, to avoid interference with existing cardiac structures when implanted.

Still referring to FIG. 1C as described above, and in accordance with another aspect of the invention, it has been determined that providing a length of segments EF and GH generally greater than 3 mm is expected to ensure that the end region that extends into the right atrium is disposed generally out of the flow path of blood returning from the inferior vena cava, the most likely source of entrained emboli that could cause paradoxical embolization. Truncated funnel cones bounded by ABCD and/or EFGH may have volumes ≤2 ml.

Other embodiments of the inventive shunt may include anchors with different combinations and configurations of circumferential ring and axial strut elements. Specifically, such embodiments may have more or less longitudinal struts 24 and more or less circumferential struts 26*a*-26*e* then depicted in FIGS. 1A-1C. These configurations may yield other shunt lumen geometries. In another embodiment, anchor 12 may be made of a self-expanding polymer. Alternatively, the anchor need not be self-expanding, and may be made from a plastically deformable biocompatible metal such as 316 L stainless steel, cobalt chromium alloys, or any other such suitable biocompatible material known to those of ordinary skill in the art. Such a deformable shunt anchor may be delivered by an expanding member, such as a balloon, that is configured to achieve the desired luminal geometry. The deformable anchor may be designed to expand prismatically or at certain localized sites where ductile hinges are configured for more selected expansion as taught by U.S. Pat. No. 6,242,762 to Shanley, the entire contents of which are incorporated by reference herein.

Figure 2:
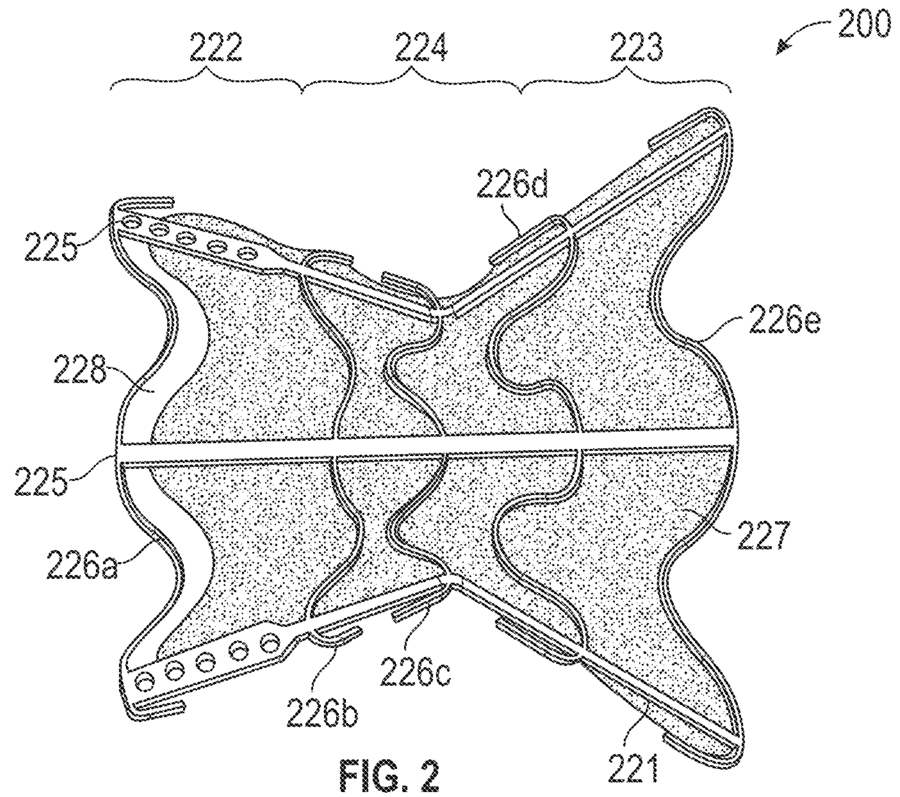
FIG. 2 is a side view of an alternative embodiment of a shunt suitable for use in the present invention having a cutout in its polymeric encapsulation to facilitate engagement with a delivery system.

Referring now to FIG. 2, an alternative embodiment of a shunt suitable for use in constructing a device of the present invention is described. Shunt 200 includes anchor 221, and is similar in construction to that described for the embodiment of FIGS. 1A-1C, having flared end regions 222 and 223 and neck region 224. When implanted in a patient's interatrial septum, flared end region 222 is disposed in the patient's right atrium, while flared end region 223 is disposed in the patient's left atrium, with neck region 224 situated in a passage formed in the interatrial septum. Anchor 221 includes longitudinal struts 225 and circumferential struts 226*a*-226*e* and is encapsulated by biocompatible material 227. Anchor 221 may comprise a self-expanding or plastically deformable material as described herein above. Shunt 220 of FIG. 2 differs from the embodiment of FIGS. 1A-1C in that biocompatible material 227, for example ePTFE, includes cutout 228 adjacent to circumferential strut 226*a*. Cutout 228 may extend proximally from circumferential strut 226*a* for a distance of 0.5 mm to 2 mm, and preferably about 1 mm, to permit circumferential strut 226*e* to be releasably engaged with a delivery system during deployment, for example, hooks, as described in U.S. Patent Application Publication No. 2014/0350565 to Yacoby et al., the entire contents of which are incorporated by reference herein.

Still referring to FIG. 2, biocompatible material 227 may be trimmed manually or mechanically from circumferential strut 226*a* to create cutout 228 or by laser cutting. In this manner, shunt 220 may be positioned and repositioned in a passage formed in the interatrial septum until the clinician is satisfied with the device placement, before being released. In a preferred embodiment, the conduit formed by biocompatible material 227 extends a distance of at least 3 mm beyond neck region 224 into flared end region 222, to ensure that pannus cannot grow translationally along luminal wall far enough to partially occlude the flow area of neck region 224. Additionally, flared end region 222 extends a distance of at least 3 mm into the right atrium when implanted in the interatrial septum to ensure that the entry of flared end region 224 is generally not aligned with flow paths generated by blood entering the right atrium from the inferior vena cava, thereby reducing the risk that emboli carried from the lower extremities into the right atrium will cause paradoxical embolism by passing through shunt 220.

In accordance with the principles of the present invention, all of the shunt designs described in the commonly assigned patents and applications incorporated herein may be designed to be deployed across the fossa ovalis and may be modified to accept a sensor located on or coupled to the shunt. The inventive shunts may be delivered as described in U.S. Pat. Nos. 9,713,696 B2, 10,478,594 B2 and U.S. Patent Application Publication No. US2020/0078558A1, all to Yacoby et al., the entire contents of each of which are incorporated by reference herein.

Sensors suitable for use in the inventive shunts include, for example, the leaded HeartPOD, the leadless V-LAP and the leadless CardioMEMs pressure sensors, which have established track records of satisfactory performance in chronically implanted cardiovascular applications. As a class, these sensors are characterized as having rigid encapsulated hermetic housings with elongated multi-millimeter dimensional form factors. In this disclosure, this group of devices is referred to as Large Format Pressure Sensors (LFPS). These devices may include circuitry such as sensor gauges formed of or including piezoresistive or variable capacitors, with or without an onboard application specific integrated circuit processor, and circuitry (such as an antenna) for transmitting measurements outside the body in a manner such as exemplified elsewhere herein. Hermetic housings may include, or may be fabricated from, titanium, titanium alloys or other suitable biocompatible metals, or alternatively, when appropriate, non-electromagnetic shielding housings may be or include a ceramic, such as zirconia, a glass such as fused silica, or other materials known well to those of ordinary skill in the art of implantable sensor materials.

The advantages of leaded LFPS designs are that the RF antenna for external power and data readout can be relatively large (approximately 20 mm in diameter in the case of HeartPOD) and surgically placed close to the skin (typically <5 cm deep). This makes possible the use of low-power communication devices (e.g. a PAM) that can be a battery powered handheld computer. In another embodiment, a mobile smart phone can be RF coupled with a leaded implant for powering, data transmission, storage, and local processing for dose-by-dose physician directed patient self-management (e.g. DynamicRx). A leaded implant also can easily be coupled to a cardiac rhythm management device such as a pacemaker or an implantable defibrillator. Potentially, an electrode on the sensor housing or anchoring system may be used to sense the intracardiac electrogram (IEGM) and to pace the interatrial septum, obviating the need for a separate right atrial lead. One example leaded pressure sensor that may be used in the present shunts is an IntraSense Calibrated sensor, commercially available from Silicon Microstructures, Inc. (Milpitas, CA).

The lead of a leaded implant may include an indifferent electrode sufficiently distant from a sensing electrode for bi-polar pacing. The timing of electrical events of the cardiac cycle can be used particularly with the LAP waveform for diagnostic purposes. For example, those with ordinary skill in the art such as a cardiologist would understand that the P-wave of the IEGM just proceeds the a-wave of the LAP tracing. The presence of P-waves with an absence of a-waves is diagnostic of a rare disorder seen in heart failure patient known as atrial electromechanical dissociation. Numerous conditions are diagnosable by combination of intracardiac pressure and IEGM and are described by U.S. Pat. No. 6,970,742 B2 to Mann et al., the entire contents of which are hereby incorporated by reference herein. Another advantage of a leaded sensor is that if the sensor should embolize from its optimal location on the interatrial septum, either at the time of implantation or sometime later, the sensor is tethered by the lead, making it relatively straight forward to reposition or to retrieve and remove it from the body.

Some disadvantages of a leaded LFPS are that the proximal lead and the communications antenna coil are best placed in a subcutaneous or submuscular surgical pocket located near the shoulder like a pacemaker. This may be achieved, for example, performing transseptal catheterization from a subclavian or axillary vein, which is more difficult than from the standard location for venous access in the right femoral vein. Alternatively, the lead can be placed from the site of transfemoral access, and then transferred to a superior venous access site as described in U.S. Patent Application Publication No. US2011/0022057 A1 to Eigler et al, the entire contents of which are hereby incorporated by reference herein. Both approaches proved clinically acceptable with the leaded HeartPOD system. Another disadvantage of a leaded LFPS is an increased possibility of device infection related to a greater volume of indwelling hardware and the creation of a subcutaneous surgical pocket. Typically, the infection rate for pacemakers that require device removal is about 1% per year.

The advantages and disadvantages of leadless LFPS designs are generally the reciprocal of the leaded LFPS as described above. Leadless sensors are less susceptible to device infection precisely because there is no subcutaneous pocket to get infected or a lead to track the infection to the circulation. A leadless LFPS can be placed more easily from transfemoral venous transseptal access without the need to reposition the lead to a superior venous access location. To minimize the risk of embolization, a leadless sensor must be tethered on its proximal side and released from the tether only after secure transseptal placement is confirmed. Even so, embolization during the insertion procedure or thereafter is possible, and the sensor can become lodged on the mitral or aortic valves or embolize into the systemic circulation and may require surgical removal. Leadless LFPS modules are generally longer and stiffer due to the extra volume that may be required to house an RF coupling antenna. In addition, as the antenna is relatively small and perpendicular to the long-axis of the sensor module, and is disposed substantially deeper under the skin (typically a minimum of 9-13 cm when disposed in the left atrium), RF powering may require a larger external coil and greater electromagnetic flux for the same sensor and implanted processor power requirements. In addition, the V-LAP leadless sensor includes an internal inductor coil wound around a small diameter ferrite, making demonstration of MRI compatibility more challenging.

Several important recent developments in implantable sensor technology may reduce form factor dimensions and power requirements. Improved sensors that implement these features are referred to in this disclosure as Small Format Pressure Sensors (SFPS). In addition to the piezoresistive and capacitive type pressure sensors described above, recent advances in technology and novel materials based have made possible the development of micro and potentially nanoscale pressure sensors for implantable medical indications, as described for example in Chang Y, et al., "State-of-the-art and recent developments in micro/nanoscale pressure sensors for smart wearable devices and health monitoring systems," Nanotechnology and Precision Engineering 2020; 3:43-52, https://doi.org/10.1016/j.npe.2019.12.006. One class of examples are resonant devices where pressure-induced stresses change their natural frequencies. Compared with conventional sensors, resonant devices may offer higher accuracy and sensitivity, as they are more immune to environmental noise. Surface acoustic wave resonators (SAWs), Lamb wave resonators (LWRs) and film bulk acoustic wave resonators (FBARs) also are known to those skilled in the art and described, for example, in the following references, the entire contents of each of which are incorporated by reference herein: Wang W N, et al., "Tire pressure monitoring system and wireless passive surface acoustic wave sensor," Appl Mech Mater 2014, 536-537:333-7; Mu X, et al., "Dual mode acoustic wave sensor for precise pressure reading," Appl Phys Lett 2014, 105(11), 113507; Della Lucia F, et al., "Design, fabrication and characterization of SAW pressure sensors for offshore oil and gas exploration," Sensors and Actuators A: Phys 2015, 222:322-8; Kropelnicki P, et al., "CMOS-compatible ruggedized high temperature Lamb wave pressure sensor," J Micromech Microeng 2013, 23(8), 085018; Anderas E, et al., "Tilted c-axis thin-film bulk wave resonant pressure sensors with improved sensitivity," IEEE Sensors J 2012, 12(8):2653-4; Nagaraju M, et al., "A 400 μW differential FBAR sensor interface IC with digital readout," 2015 joint conference of the IEEE international frequency control symposium and the European frequency and time forum, FCS 2015—proceedings, Denver, Colorado, 2015, p. 218-21; Zhang M, et al., "A film bulk acoustic resonator-based high-performance pressure sensor integrated with temperature control system," J Micromech Microeng 2017, 27(4), 045004; Galipeau D W, et al., "Surface acoustic wave microsensors and applications," Smart Mater Struct 1997, 6(6):658-67; Scholl G, et al., "Surface acoustic wave devices for sensor applications," Phys Status Solidi Appl Res 2001, 185(1):47-58; and Yantchev V, et al, "Thin film lamb wave resonators in frequency control and sensing applications: a review," J Micromech Microeng 2013, 23(4), 043001.

In another example, described in Chen L Y, et al., "Continuous wireless pressure monitoring and mapping with ultra-small passive sensors for health monitoring and critical care," Nature Communication 2014, 5:5028, the entire contents of which are incorporated by reference herein, the authors developed proof of concept for a 1×1×0.1 mm implantable pressure sensor comprising an LC oscillator fabricated with standard lithographic techniques on a polyimide-coated silicon wafer with incorporated PDMS flexible substrates and a copper printed antenna. That article states that the sensor could be implanted within the cranium of rodents to chronically measure intracranial pressure. Other advances in 2D nanomaterials including graphene, MXene, carbon nanotubes and metal nanowires can be made into flexible piezoresistive and capacitive pressure sensors that are stable and ultrasensitive. Breakthroughs in material science have also made self-powered pressure sensors possible, harvesting mechanical energy directly from the environment such as from the beating heart. SFPS devices have not yet demonstrated long-term accuracy and durability in the environmental milieu required for chronic implantable sensors that may support diagnosis and guide therapy of cardiovascular and cardiopulmonary conditions. Nonetheless, the development of sufficiently robust hermetic biocompatible packaging with practical wireless transmission of data and external power schemes should enable reliable small format, flexible implantable sensors to become available, either for pressure or other physiological parameter measurement, that can be incorporated into and made consistent with the inventive shunt of this disclosure.

Figure 3:
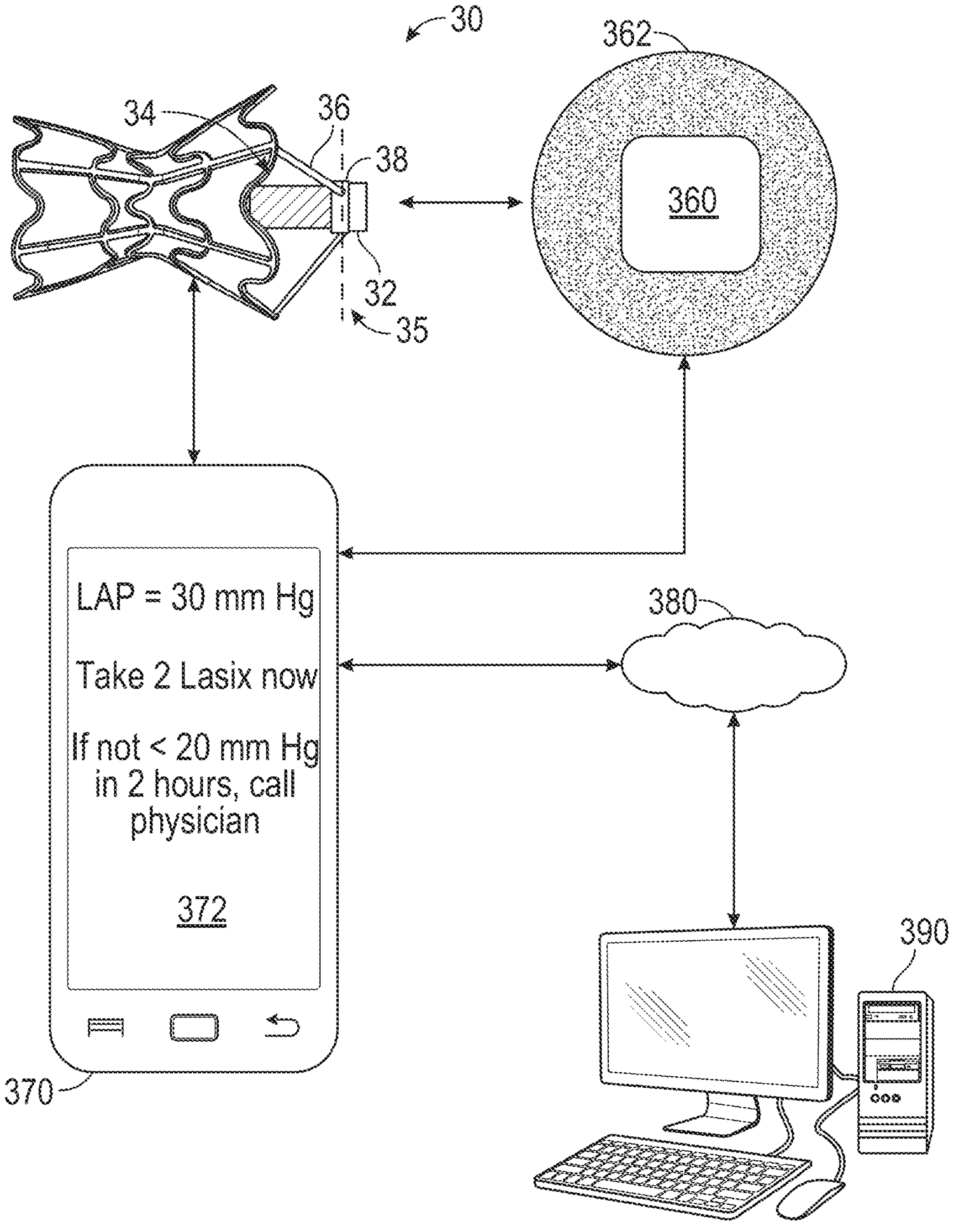
FIG. 3 is a schematic view of a system of the present invention for monitoring and treating patients afflicted with cardiovascular disease, such as HF and PAH, including a shunt having a wireless sensor that communicates with a patient display device and/or the patient's physician.

Referring now to FIG. 3, an exemplary embodiment of a system constructed in accordance with the principles of the present invention, including an inventive shunt for measuring a physiological parameter in the left atrium in patients with HF, is described. The shunt 30 illustratively includes a Nitzan type hourglass or diabolo shaped nitinol anchor like those described in FIGS. 1A-1C and 2, wherein the anchor may be fully or partially encapsulated with a biomaterial like those described with respect to FIGS. 1A-1C and 2. It will be appreciated that other shunts with other sensor configurations, such as exemplified herein, suitably may be used in place of shunt 30 illustrated in FIG. 3.

In FIG. 3, shunt 30 includes leadless sensor 34, having dimensions and characteristics consistent with the LFPSs described herein above, coupled to the shunt frame via support structure 35 including support struts 36 and collar 38. Alternatively, the sensor or sensors could be of the SFPS type, described above. Sensor 34 may include circuitry for measuring mechanical parameters including pressure, force, flow, velocity, acceleration, wall shear stress, temperature, and the like, or electrical properties exemplified as IEGM, resistance, impedance, current, inductance, capacitance, or chemical properties including, pH, osmolarity, chemical species identification, molecular concentrations, reaction rates, or any other desirable physiological parameters for which acceptable sensors have been developed. Illustratively, the circuitry may generate data indicative of a left atrial pressure (e.g., in the examples illustrated in FIG. 3 or such as described with reference to FIGS. 4A through 10 or FIG. 16A), a right atrial pressure (e.g., in the examples described with reference to FIGS. 12A through 15A), or a velocity of blood flow through the lumen. Moreover, the sensor may include circuitry for measuring multiple characteristics or may include a plurality of sensors, each including circuitry for measuring a respective characteristic and contained in a unitary package with the other sensors. Alternatively, multiple independent sensors may be mounted on the biocompatible material encapsulating the anchor of shunt 30.

Leadless sensor module 34 preferably includes an appropriately shaped (e.g., substantially cylindrical), hermetically sealed housing with a sensing diaphragm or surface that is facing towards and located within the LA chamber. In an alternative embodiment, the sensing surface of sensor 32 may be disposed facing towards the orifice of the shunt. In yet another embodiment, the sensor 34 may have an approximately rectangular solid shape, and may be disposed on any one or more of longitudinal and/or circumferential struts of shunt 30 in a manner such as described with reference to FIGS. 26A-26B, 28, 29, 30, 31A-31E, and 32A-32D. It is to be understood that the 3-dimensional geometric shape of the sensor is not limited in overall size and dimensions, so long as it does not sufficiently impede shunt flow or substantially reduce the clinical effectiveness of the shunt.

Leadless sensor module 34 may include circuitry to communicate data from leadless sensor module 34 directly to patient display device 370, illustratively a conventional smartphone programmed with a suitable application program and touchscreen display 372. Alternatively, leadless sensor module 34 may include circuitry to communicate indirectly with patient display device 370 via optional patient module 360. Whether optional patient module 360 is used may depend upon the communication mode employed by leadless sensor module 34.

In one embodiment, leadless sensor module 34 includes an RF transceiver circuit configured to exchange physiologic data and programming instructions directly with patient display device 370. In this manner, a patient may directly view a graph of a selected physiologic parameter, such as RAP or LAP, provided in real time by sensor module 34 for display in window 372 of patient display device 370. Patient display device 370 also may include programming that detects an abnormal situation, e.g., elevated LAP (illustratively, above 30 mmHg), and alerts the patient to take immediate action, e.g., "Take 2 Lasix now" and to call the physician if the pressure does not sufficiently reduce within a designated timeframe (illustratively, to below 20 mmHg within 2 hours).

The alert displayed by patient display device 370 also may instruct the patient to call for medical assistance if the abnormal situation does not resolve within a specified period. As depicted in FIG. 3, patient display device 370 also may upload data received from the sensor module 34 to physician's computer system 390 using either a telephone network or a wide area wireless network, e.g., using a WiFi network and access points to transmit data via Internet 380. It is to be understood that any such communication of patient data over a WAN should preferably first be encrypted to maintain patient privacy. Patient display device 370 also may be programmed to transmit an alert directly to the patient's physician or a suitable monitoring service to prompt the physician to provide additional guidance on subsequent treatment steps. In this case, communication between the physician and patient also may be bidirectional, using either text messaging or telephone or VOIP call from the physician to patient.

Optionally, the system for communicating data from leadless sensor module 34 to patient display module 370 and/or physician's computer 390 may employ patient module 360. Patient module 360 may comprise a compact electronics package (circuitry) configured for bidirectional data communications with leadless sensor module 34 that is mounted on adhesive patch 362. Patient module 360 may include, for example, an inductive coil, application specific electronics package, battery and RF transceiver. The electronics package may be programmed to transmit power and instructions to leadless sensor module 34 via the inductive coil and/or the RF transceiver. The electronics package of patient module 360 also may be programmed to download physiologic data stored on, or generated in real time by, leadless sensor module 34 and transmit that data for processing and display in window 372 of patient display device 370. Adhesive patch 362, including patient module 360, may be applied to a patient's chest or upper torso to maintain proximity to, and ensure uninterrupted transfer from, leadless sensor module 34. More specifically, use of patient module 360 may reduce the risk that a distance between patient display device 370 and leadless sensor module 34 will exceed a predetermined distance at which such intercommunication is compromised. Advantageously, patient module 360 may include a rechargeable battery that can be used to recharge or power the electronics in leadless sensor module, provides a more predictable power supply than a conventional smartphone battery in patient display device 370.

In an alternative embodiment described below with respect to FIGS. 6A and 6B, the sensor module may include a lead. In such an embodiment, instead of optional patient module 360 as described above, the sensor may be directly connected via the lead to an implantable module that is configured to communicate to an external device, such as patient display module 370. In that case, the implantable module may communicate directly with patient display device 370, which otherwise may programmed to display messages to the patient and/or communicate physiologic data and alerts to the physician as described in FIG. 3.

In one preferred embodiment of the embodiment of FIG. 3, support structure 35 preferably locates sensor 34 substantially coaxially with the longitudinal axis of shunt 30, such that sensing surface 32 of sensor is spaced apart from the shunt orifice. In this manner, the measured parameter is indicative of the parameter within the left atrial cavity and less affected by an increase flow velocity characteristics in the region of the shunt orifice. In a preferred embodiment, support struts 36 are integrally formed with the anchor structure of shunt 30, and extend from alternate longitudinal struts, terminating in collar 38 that accepts sensor module 34. Support struts 36 and collar 38 may be of a unitary construction, for example, laser cut, heat set, and electropolished from a single piece of superelastic nitinol tubing. Alternatively, the struts and/or collar may be welded or attached to the anchor of shunt 30 by other means. Support struts 36 alternatively may be formed from a suitable biocompatible polymeric composition. Sensor 34 and support structure 35 preferably are configured such that they can be crimped down and constrained within a loading cartridge or delivery introducer sheath for transvascular delivery, and then be expanded to their final configuration during the delivery process.

The sensing surface 32 of sensor 34 preferably is positioned so that during post-implantation healing, the distance for reactive translational tissue growth to extend from any point of shunt contact with cardiac structures, and grow over the support structure to reach the sensing surface, exceeds a total linear distance of 2.5 mm. From prior experiments conducted by the inventors, this distance should limit tissue growth over the sensing surface to $<300$ μm. Alternatively, support struts 36 may contact collar 38 at an angle that is $<\pm 45$ degrees from orthogonal with respect to the axis of the sensing surface and contact the collar at a minimum distance of 2.5 mm from the sensing surface. This will effectively mechanically isolate the sensing surface from reactive tissue growth and reduce bridging of tissue to the sensing surface. Further, such an arrangement will minimize transmission of changes in chamber wall tension due to cardiac contraction or relaxation to the sensing surface. Consequently, sensing surface movements will accurately reflect the left atrial pressure waveform and not be substantively artifactually degraded or rendered otherwise uncorrectable to be of diagnostic utility.

In an alternative embodiment, the body of the sensor module may extend proximally into or through the neck portion of the shunt lumen. Wireless LFPSs tend to be elongated structures so as to house RF coils of various configurations. The CardioMEMs sensor has a rectangular solid form factor and is approximately 15 mm long×3.4 mm wide by 2 mm thick. The V-LAP sensor is cylindrical, and is about 14 mm long with a diameter of 2.5 mm. To minimize protrusion of the distal end into the left atrium, these or similar form factor LFPS can be mounted so that their proximal portions extend into the shunt lumen, including the shunt neck and even into the right atrial portion of the shunt. To maintain similar flow characteristics, the cross-sectional area of the shunt neck should be enlarged by approximately the cross-sectional area of the sensor. For example, for a sensor with form factor like a V-LAP, that would extend through the neck region, to have the a shunt pressure/flow relationship similar to a standalone hourglass shunt with an internal minimal diameter of 5 mm, may entail enlarging the neck to approximately 5.6 mm in diameter. Similarly, the neck may be enlarged to 5.8 mm if a sensor with a form factor like a CardioMEMs were placed through it. These dimensions are first order approximations and may be suitably modified based on the results of pressure/flow testing or computational flow dynamic analysis based on actual shunt/sensor geometry.

Figure 4A:
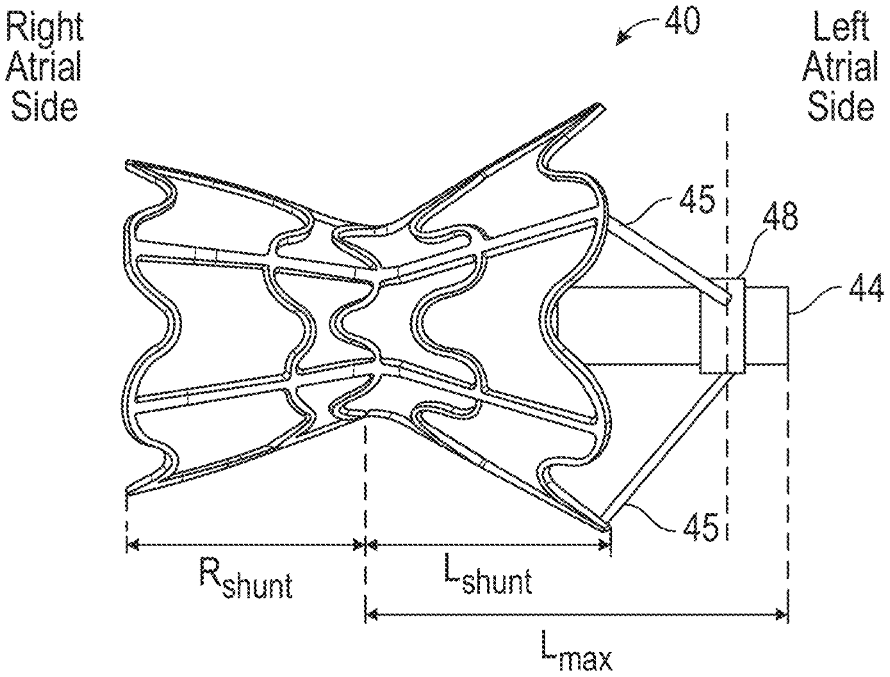
FIGS. 4A and 4B are, respectively, side and end views of a shunt constructed in accordance with the principles of the present invention having a coaxial wireless LAP sensor.
Figure 4B:
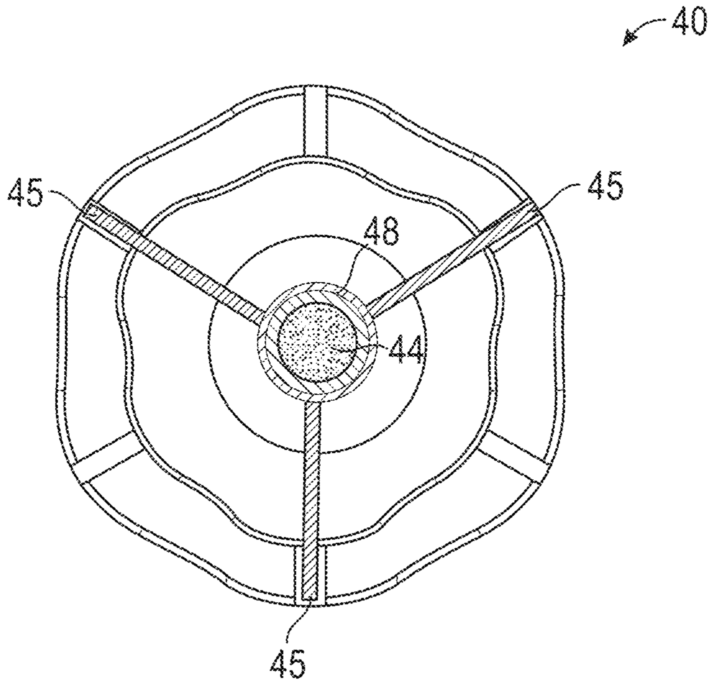

With respect to FIGS. 4A and 4B, further aspects of the inventive shunt of FIG. 3 are described. FIG. 4B shows that the sensor support structure illustratively includes three support struts 45 equally spaced around the circumference of the anchor frame 40 that adjoin the sensor collar 48. The extent to which the sensor 44 protrudes into the left atrial cavity is generally limited by the size of the LV cavity, which averages about 55 mm in diameter in patients with HF. The axial dimension of left sided protrusion, from the center of the shunt neck to the left end of the sensor, is labeled as $L_{max}$, as indicated in FIG. 4A. This dimension should be short enough so there is no contact between the shunt and vital structures of the left atrium or adjacent structures, such as the mitral valve, pulmonary veins, left atrial appendage, left atrial wall, etc., which could cause trauma or thrombus formation. In one embodiment, for the chamber diameter measured from the mid of the fossa ovalis to the ostium of the left atrial appendage, $L_{max}$ is limited not to exceed 50% of that distance. Thus, for a small diameter left atrium, such as found in patients with PAH, e.g., for a diameter of 20 mm, $L_{max}$ should not exceed 10 mm.

Figure 5A:
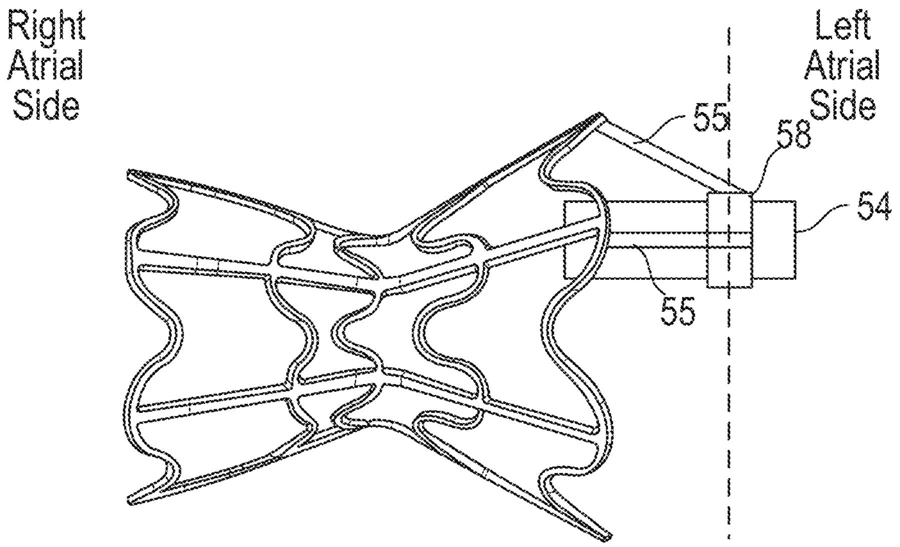
FIGS. 5A and 5B are, respectively, side and end views of an alternative embodiment of the inventive shunt having a non-coaxial wireless LAP sensor.
Figure 5B:
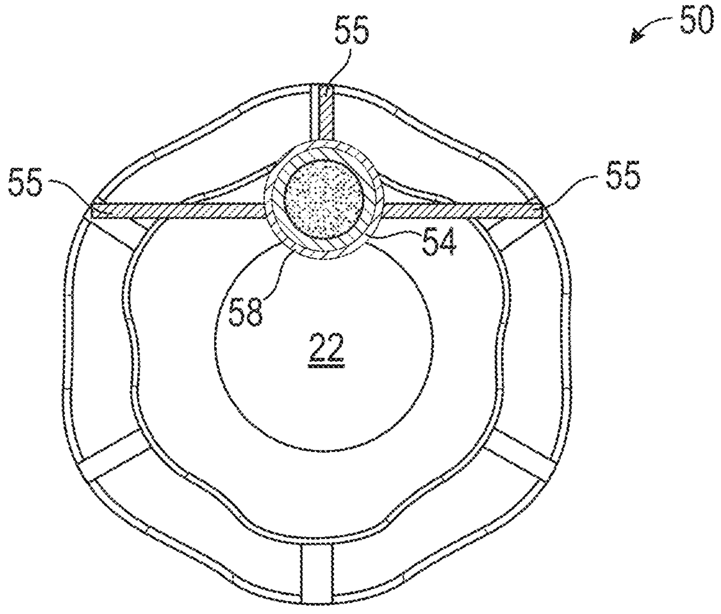

With respect to FIGS. 5A and 5B, an alternative embodiment is described, in which the sensor 54 is mounted substantially non-coaxial with the long axis of the shunt 50. The sensor may be of the LFPS or SFPS types, or non-pressure sensors, as described above. The long axis of the sensor 54 may extend parallel with the long axis of the shunt 50, but it need not necessarily be so arranged. The sensor 54 may be affixed to the shunt with a support structure including support struts 55 and collar 58 similarly as described for FIGS. 4A-4B, but supporting the sensor off-center from the lumen 22 of shunt 50. One advantage of the embodiment of FIGS. 5A-5B is that if future access to the left atrium is needed for large bore catheters, such catheters may be advanced through the shunt unimpeded by the sensor.

In examples such as described with reference to FIGS. 4A-4B and 5A-5B, as well as other examples provided herein, the shunt anchor may of the type described in the above-incorporated U.S. patent application Ser. No. 16/875,652 entitled "Devices with dimensions that can be reduced and increased in vivo, and methods of making and using the same." As such, the neck region of the anchor may have shape-memory characteristics with an $A_f$ higher than body temperature, and may be deformable by a balloon or other suitable means of dilatation, so that it may be made larger to accommodate crossing of even larger diameter catheters for left atrial access. In that case, the anchor may be heated above $A_f$ so that the shunt neck undergoes thermal transition and thereby resumes its prior size or configuration. Likewise, the support struts (e.g., struts 45 or 55) affixing the sensor to the shunt anchor frame may be of a similar shape-memory material with a similar transition temperature $A_f$. A balloon or other source of a dilating force may be used deform the support structure, further pushing the sensor more out of the way and allowing broader left atrial access. Upon transient heating above $A_f$, the sensor and its support structure return to their pre-deformed configuration.

Figure 6A:
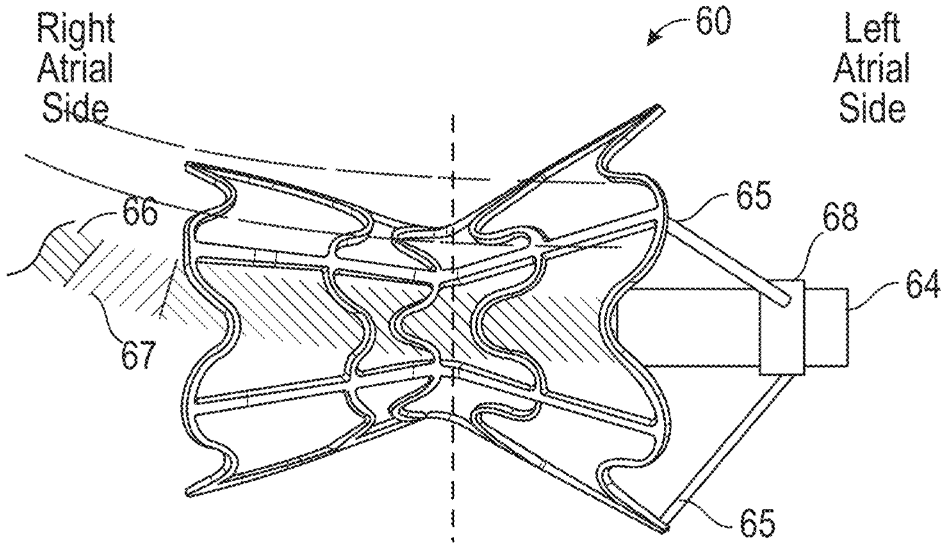
FIGS. 6A and 6B are, respectively, side and end views of a further alternative embodiment of a shunt having a coaxial LAP sensor with an electronic coaxial lead.
Figure 6B:
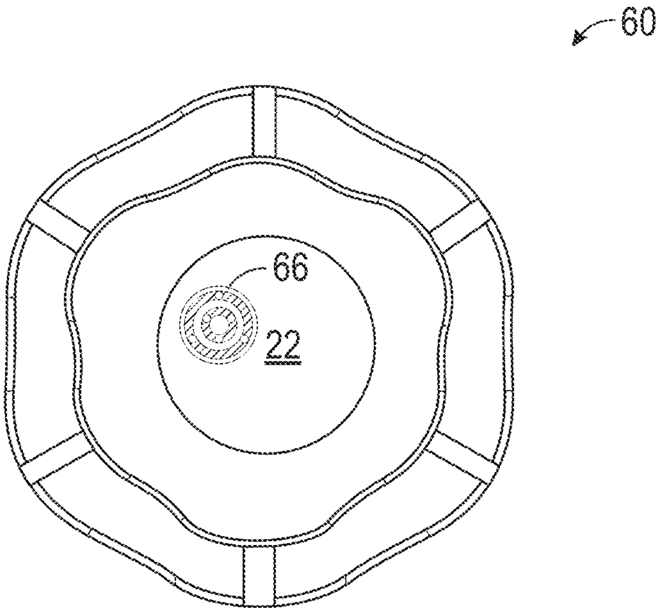

In FIGS. 6A and 6B, an embodiment with an encapsulated shunt anchor 60 and sensor support structure with struts 65 and collar 68 similar to that of FIGS. 4A-4B is described. The sensor depicted in this embodiment is a leaded LFPS type, wherein the lead 66 extends from the proximal side of the sensor module 64 to a venous access site near the left or right shoulder (not shown). The lead 66 may be or include a conventional pacing type lead design with an inner stylet lumen, 3-filer coiled inner and outer conductors and intervening and outer insulation made of silicone or other suitable polymeric material. The lead typically can range in size from 5 Fr to 8 Fr (1.7 to 2.7 mm diameter). The conductors may be coils or braided wire, depending on size and number of conductor requirements. Alternatively, the lead 66 may have a plurality of separately insulated conductors. A strain-relief portion may be employed to connect the sensor module 64 to the outer insulation. As in the embodiment of FIGS. 4A-4B, the shunt lumen 22 may be adjusted according to the size of the lead 66 to achieve the desired pressure/flow relationship.

Still referring to FIGS. 6A-6B, the lead 66 additionally may include an indifferent sensing electrode 67 to measure the IEGM for the vector between an electrode on the sensor module 64 and the indifferent electrode 67. The lead/sensor geometry may be selected so that lead contact with the shunt neck or other shunt structures is sufficiently low or is minimized, thereby to inhibit or prevent abrasion of the outer lead insulation and reduce the risk of possible wear fracture of conductors. The lead 66 may include a proximal connector such as an IS-1 or IS-4 connector, and the lead may be connected to a standalone antenna coil/capacitor or may be connected to an implanted pacemaker or defibrillator generator. In one embodiment, the shunt 60 may be placed after traditional transfemoral transseptal catheterization, with the lead subsequently transferred to a site of superior venous access as described above. Alternatively, transseptal catheterization and shunt/lead placement may be performed directly from a site of superior venous access, such as a subclavian, axillary or jugular vein.

Figure 7A:
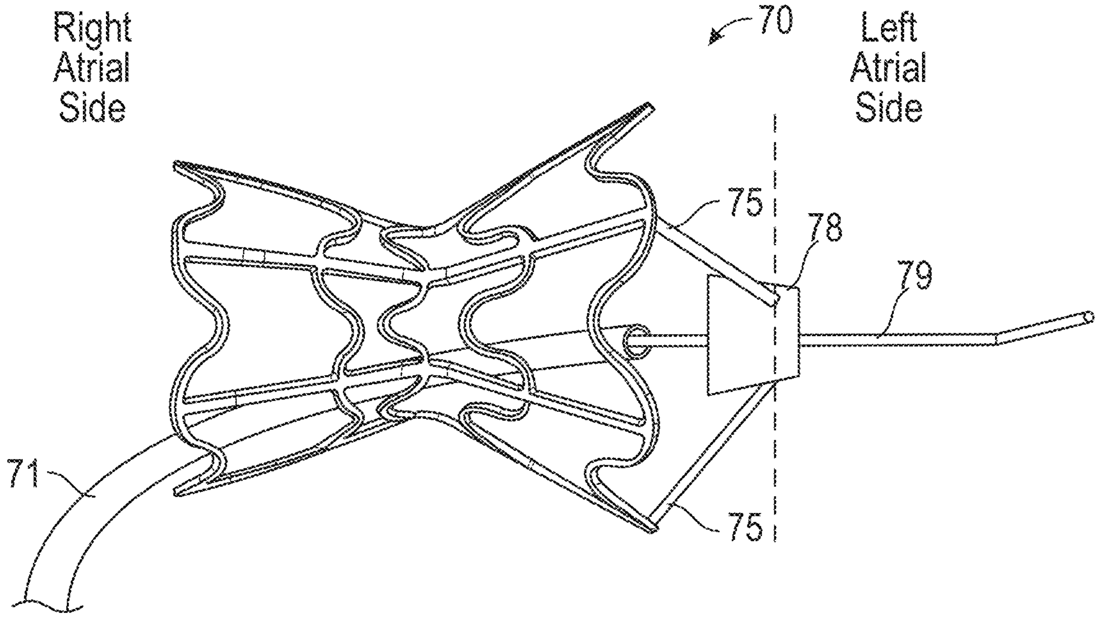
FIGS. 7A to 7F are, respectively, side and end views of another embodiment of an inventive shunt having a replaceable sensor.
Figure 7B:
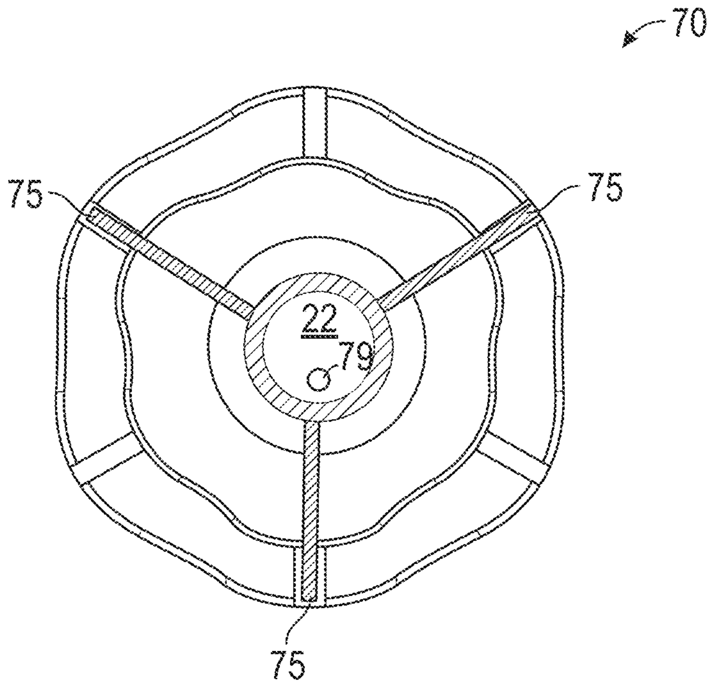
Figure 7C:
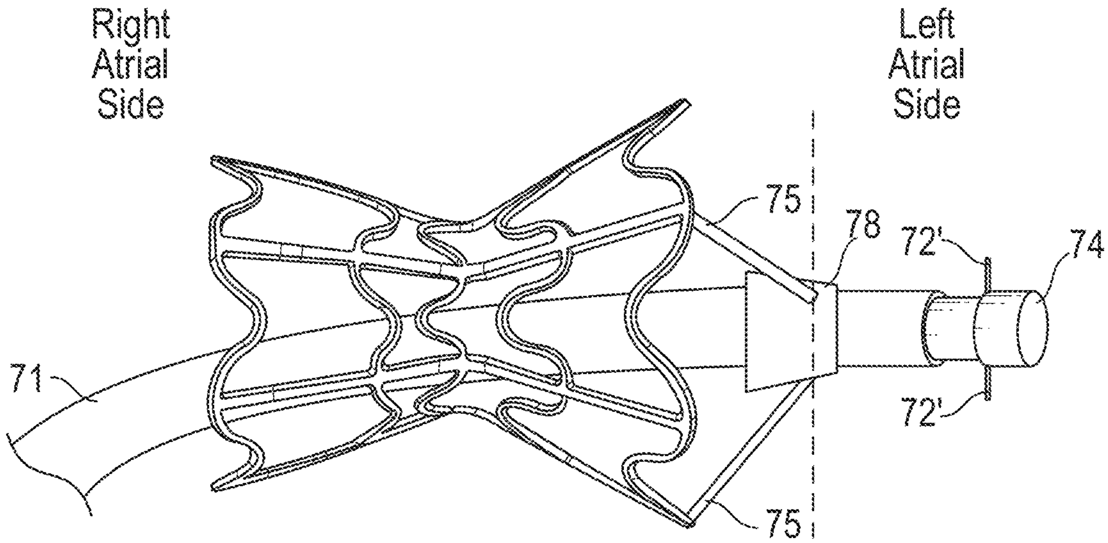
Figure 7D:
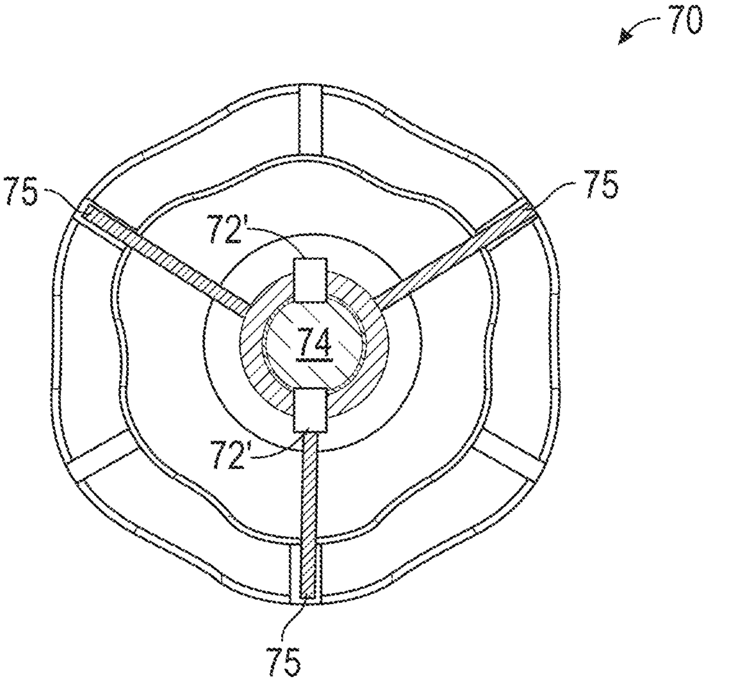
Figure 7E:
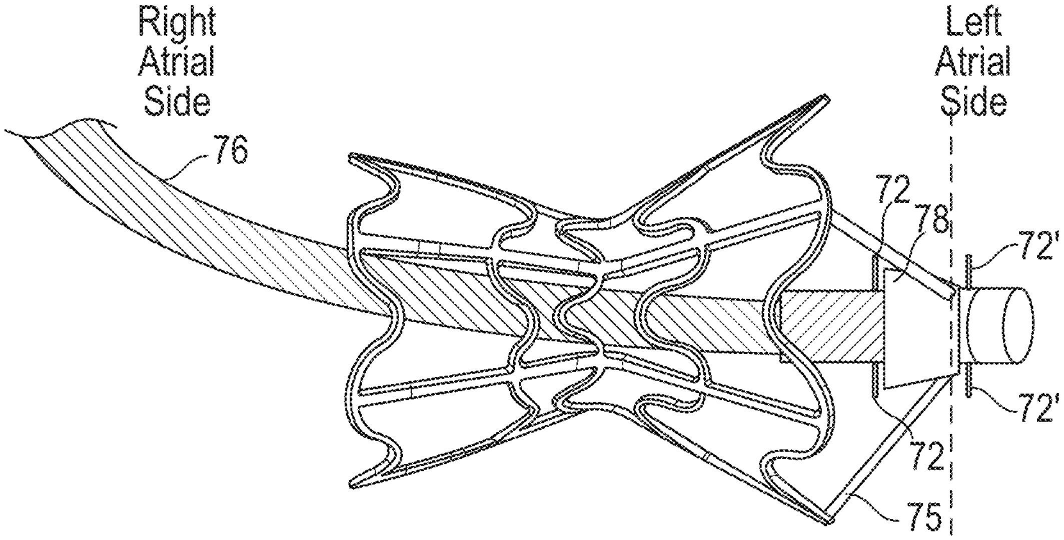
Figure 7F:
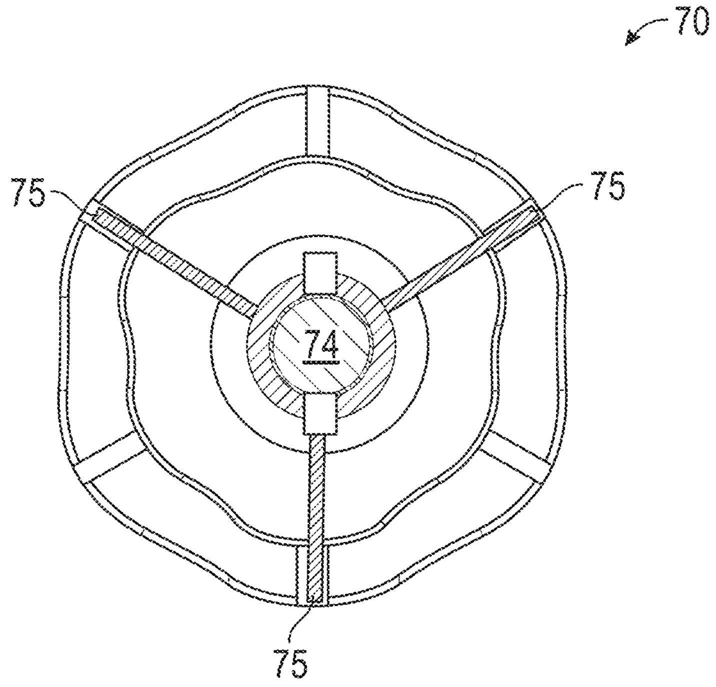

Referring now to FIGS. 7A to 7F, a further embodiment of an inventive shunt 70 having a leaded LFPS sensor 74 is described. In this embodiment, the shunt 70 including only a sensor support structure with struts 75 and 78, but no leaded sensor, is first positioned across the fossa ovalis in a manner such as illustrated in FIGS. 7A-7B. With a guidewire 79 extending through the sensor fixation collar 78, a sensor delivery introducer sheath 71 is then positioned across the collar in a manner such as shown in FIGS. 7C-7D. The sensor module 74 preferably includes one or more proximal and one or more distal superelastic retention tabs 72 that fold substantially flat when constrained within sensor delivery sheath 71. In one nonlimiting embodiment, there are two or more (e.g., 3) proximal retention tabs 72 and two or more (e.g., 3) distal retention tabs 72'. The distal tabs 72' secure the shunt in place as the distal tabs are exposed and the sheath 71 and sensor 74 are retracted proximally to register the distal tabs 72' against the fixation collar 78. As the sheath 71 is further retracted proximally, the proximal tabs 72 are deployed proximal to the collar in a manner such as illustrated in FIGS. 7E-7F. Following deployment, the lead 76 may be transferred to a site of superior venous access in a manner such as described with respect to FIG. 6.

In another embodiment, the lead 76 may be prepositioned within the sensor fixation collar 78 and deployed in a manner such as described for FIGS. 6A-6B. The advantage of this two-part structure is that the sensor 74 can be easily removed and replaced later should it become infected or inoperative. To do so, the proximal portion of the lead 76 may be surgically freed up and a locking stylet (not specifically illustrated) may be placed on the lead. A mechanical or excimer laser lead removal apparatus may be used to detach adherent portions of the lead from venous structures. A sheath (not specifically illustrated) may be advanced over the lead to just proximal of the collar to provide added support. The lead and sensor then can be retracted into the sheath, removed, and replaced, if desired, with a new leaded sensor 74.

In the foregoing embodiments such as described with reference to FIGS. 3-7F, the sensor may be affixed to the shunt by a support structure including one or more support struts and a collar. In alternative embodiments, the sensor may be disposed between layers of biocompatible encapsulation, such as ePTFE, wherein the layers are adhered to the shunt anchor frame by heat- or pressure-mediated sintering or welding processes, or encapsulation is accomplished by electrospinning of nanofibers of biomaterials. As described above, the biocompatible material may be or include a polymer, such as expanded polytetrafluoroethylene (ePTFE), PTFE polyurethane, Dacron (polyethylene terephthalate), silicone, polycarbonate, urethane, Ultra High Molecular Weight Polyethylene (UHMWPE) or carbon fiber. Alternatively, or additionally, the biocompatible material may be or include a metal, ceramic, carbon nanotube array or any other suitable biocompatible material. Furthermore, the sensor may be adhered to the shunt by adhesive bonding such as with epoxy, or the sensor may maintain its location by a friction or interference fit with other structural members, or hybrid combinations of the foregoing. This listing of fixation methods is intended to be illustrative and not exhaustive. Other means of sensor fixation to shunts will be apparent to those with ordinary skill in the art and are to be understood as incorporated within the scope of this disclosure.

Other embodiments of the inventive shunt may employ shunt designs such as shown in FIGS. 10 to 15 of commonly assigned U.S. Pat. No. 10,251,740, which is hereby incorporated by reference herein, which may incorporate a LFPS type sensor with an elongated cylindrical profile. In such embodiments, hybrid fixation mechanisms may be employed, for example, wherein the sensor is affixed by both a support structure 45, 48 in a manner such as described with reference to FIGS. 4A-4B and by incorporation between a biocompatible bilayer of encapsulant. Alternatively, a sensor may be affixed to a shunt purely by adhesion and interference fit with the encapsulant. As a further alternative, an inventive shunt may include an injection molded silicone rubber that forms a single-piece self-expanding shunt, in which the sensor is embedded. Other nonlimiting examples of structures and methods for coupling a sensor to a shunt are provided elsewhere herein.

Figure 8A:
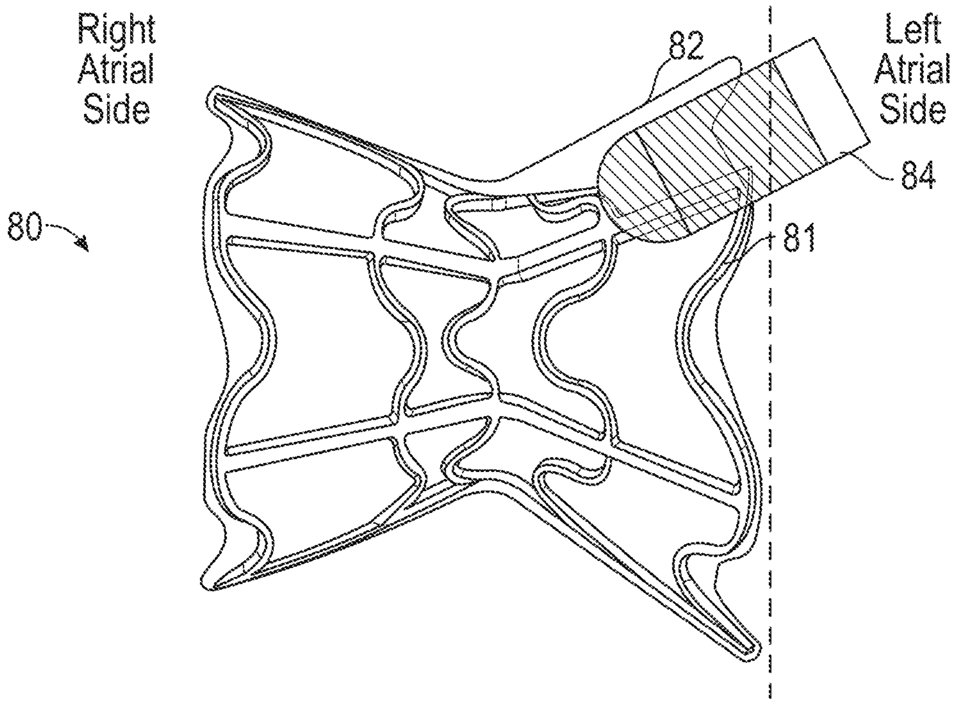
FIGS. 8A-8B, 9A-9B and 10A-10B are, respectively, side and end views of three embodiments of an inventive shunt, depicting alternative configurations for incorporating a sensor between multiple layers of the shunt covering.
Figure 8B:
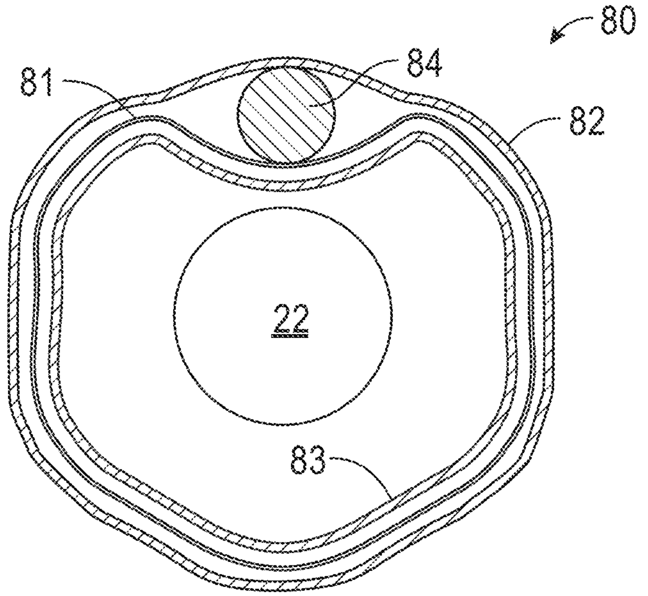
Figure 9A:
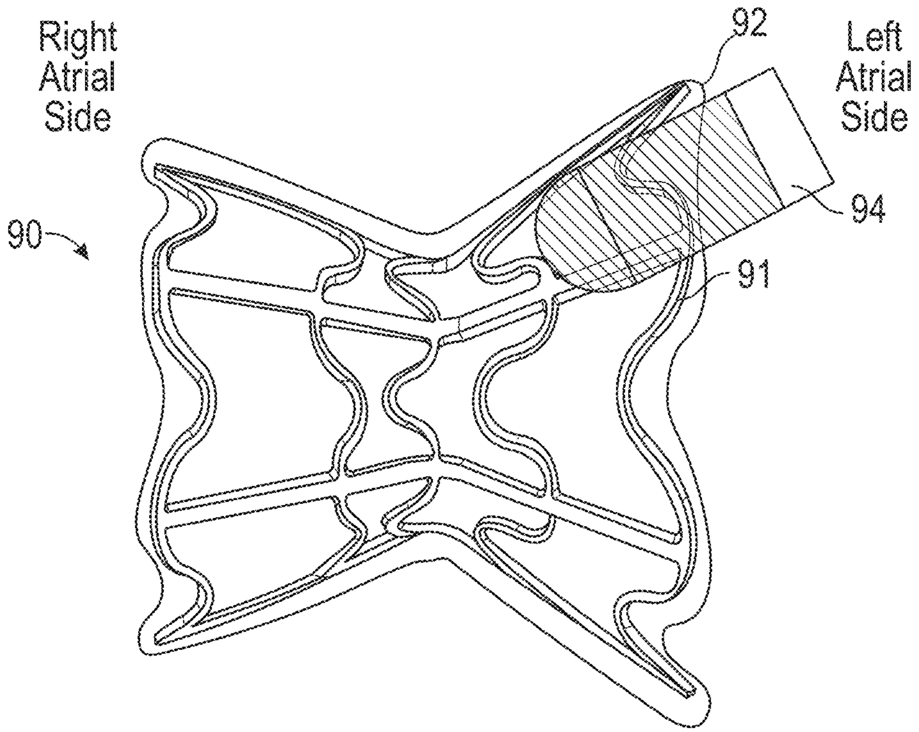
Figure 9B:
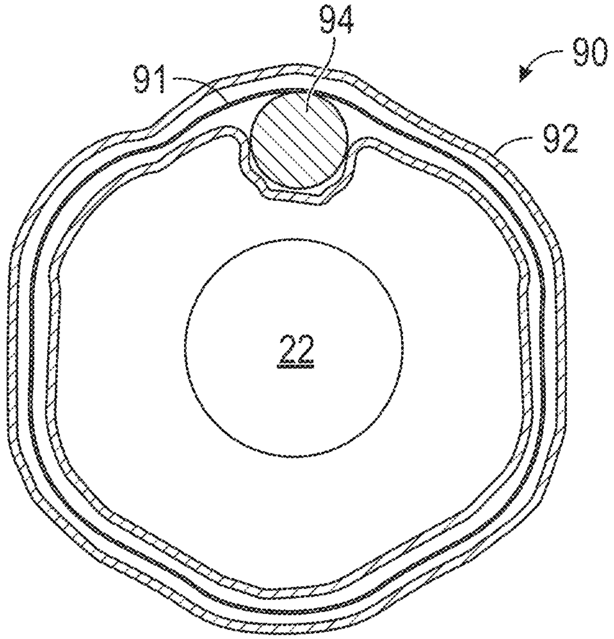
Figure 10A:
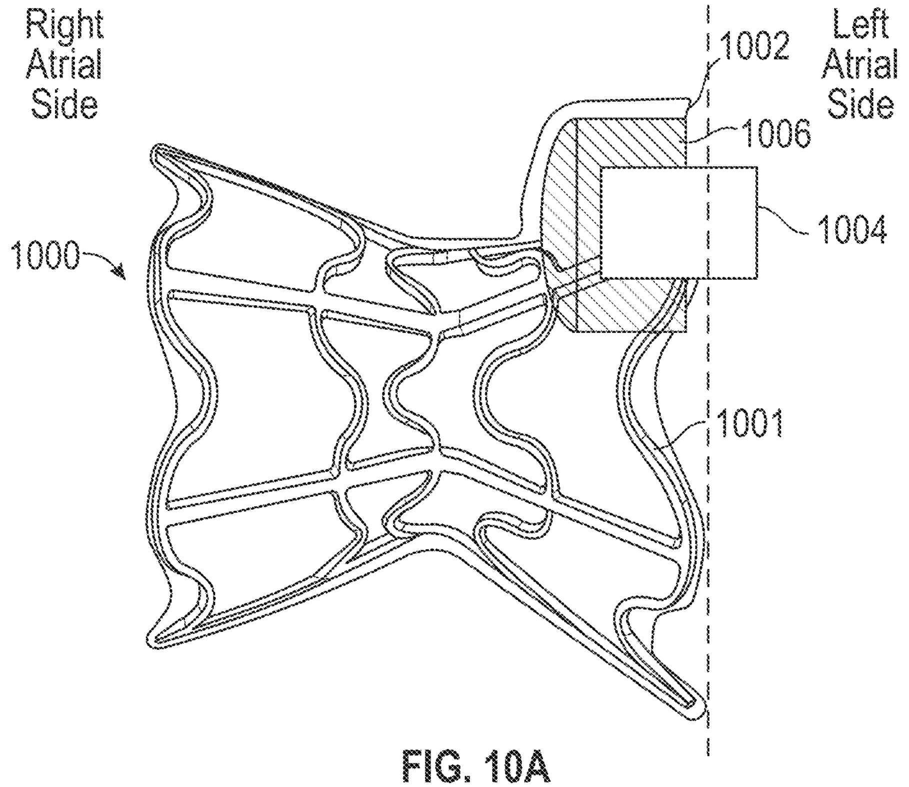
Figure 10B:
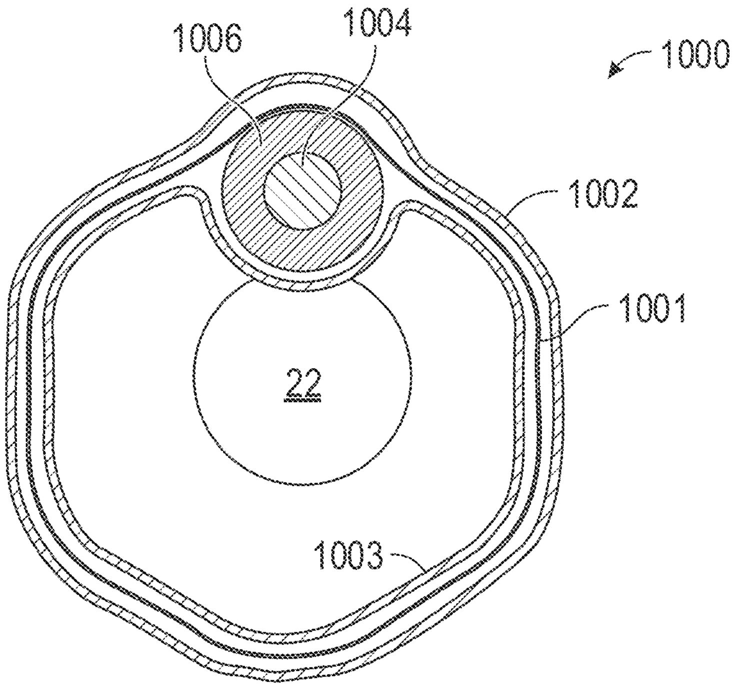

Referring now to FIGS. 8A through 10B, additional variants of the inventive shunt are described. In the embodiment of FIGS. 8A and 8B, shunt 80 is depicted in which the sensor 84 is affixed between the shunt frame 81 and an outer layer 82 of biocompatible material. An inner layer 83 of biocompatible material may be provided inside of the shunt frame 81. The shunt frame 81 may be deformed inward toward the lumen 22 to accommodate the sensor 84 and maintain an axially symmetric outer profile of the shunt, and the left atrial entry cone may be asymmetrically deformed inwardly in the region of the sensor. In FIGS. 9A and 9B, another embodiment is depicted in which the sensor 94 is affixed between the shunt frame 91 and an inner layer of biocompatible material 93. An outer layer 92 of biocompatible material may be provided outside of the shunt frame 91. In this embodiment, the shunt frame 91 is not deformed, but instead substantially maintains the axial symmetry of its outer profile, while the left atrial entry cone is asymmetrically deformed inwardly in the region of the sensor 94. In FIGS. 10A and 10B, another shunt embodiment 1000 is shown, in which the outer profile of the shunt frame 1001 is deformed to accommodate a sensor 1004 with a relatively large diameter RF coil 1006 to improve wireless power reception and telemetry. The sensor 1004 may be affixed between the shunt frame 1001 and an inner layer 1003 of biocompatible material. An outer layer 1002 of biocompatible material may be provided outside of the shunt frame 1001. The left atrial entry cone is asymmetrically deformed inwardly in the region of the sensor 1004, and both the inner and outer profiles of the shunt 1000 are asymmetrically deformed. Nonetheless, the shunt still can be crimped to fit inside a loading tube and a delivery introducer sheath.

Figure 11:
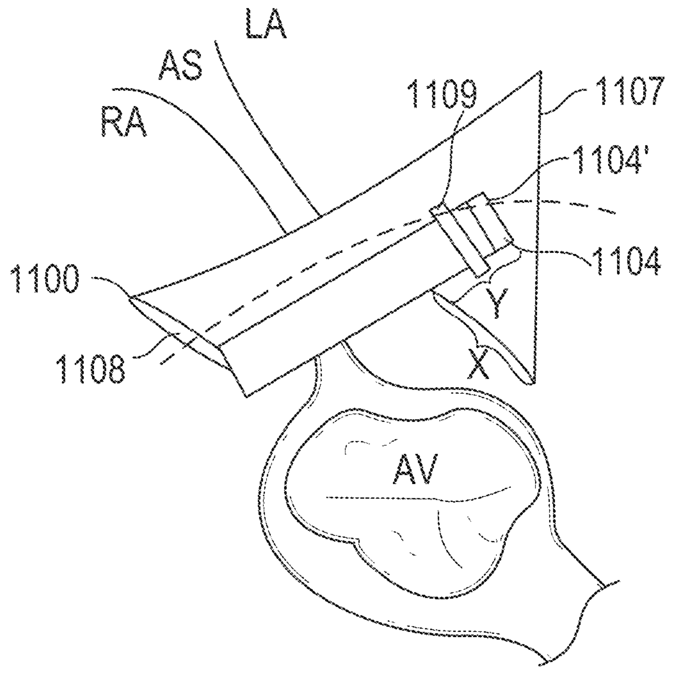
FIG. 11 illustrates an asymmetric shunt constructed in accordance with the principles of the present invention having an LAP sensor.

FIG. 11 shows an embodiment of an inventive shunt 1100 in which a sensor 1104 is affixed within an axially asymmetric shunt in a manner such as generally described in FIG. 8 of the above-incorporated U.S. Patent Application Publication No. US 2019/0262118 A1. The shunt 1100 in this embodiment incorporates a leadless LFPS 1104 with a form factor like that of the V-LAP system. In a preferred embodiment, the internal anchor framework may be adjusted to render the location of the LFPS 1104 internal to the frame near the LA entry, 1107 but external to the frame in the region of the neck and right atrial exit cone 1108. In this embodiment, the sensor 1104 may be encapsulated completely, or partly, with a biocompatible covering, such as ePTFE.

Still referring to FIG. 11, and in keeping with the principles of this disclosure, the minimum distance X along the inner curvature of the left atrial shunt cone 1107 to reach its juncture with the sensor body 1104, plus the minimum distance Y from said juncture to the sensing surface 1104' of sensor 1104, is at least 2.5 mm. Maintaining such distances helps assure that issue overgrowth on the sensing surface is unlikely to exceed a thickness of 300 μm and thus reduces or minimizes LAP waveform artifacts. In another embodiment, the dimensions X and Y, and the angle between X and Y are selected such that any tissue overgrowth of the sensing surface 1104' that is contiguous with any cardiac tissue is sufficiently mechanically isolated that artifacts in the sensed LAP waveform related to changes in cardiac wall tension will be insubstantial. In still another embodiment, a ring or other collar-like member 1109 may be disposed around the sensor body proximal to the sensing surface 1104' of the sensor 1104 to provide further mechanical isolation from artifacts due to changes in cardiac wall tension.

Figure 12A:
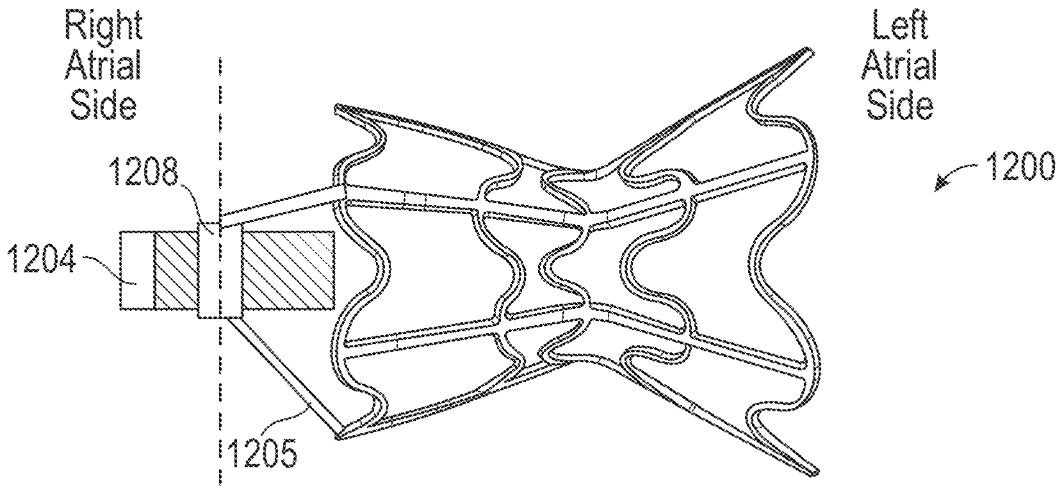
FIGS. 12A-12B, 13A-13B and 14A-14B are, respectively, side and end views of three inventive shunts having a coaxial wireless RAP sensor.
Figure 12B:
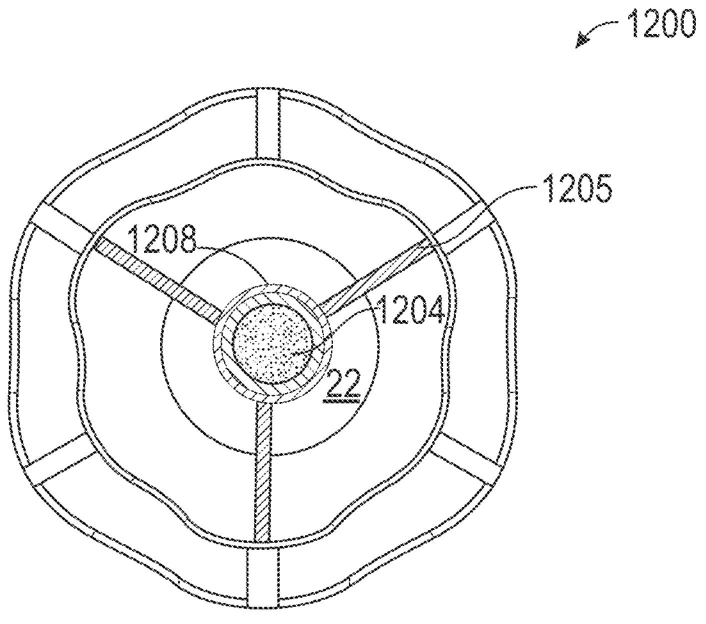

Turning now to FIGS. 12A and 12B, an inventive shunt 1200 is described that is equipped with a substantially coaxially oriented leadless LFPS sensor 1204 affixed to the shunt frame by a support structure including struts 1205 and collar 1208 similar to that described with respect to for FIGS. 4A-4B. In this embodiment, the support structure extends from the right atrial cone of the shunt 1200 so that the LFPS 1204 can measure RAP. This shunt design may be particularly beneficial for patients with PAH, who have enlarged right atria and suffer predominantly from right sided HF. It further will be apparent that such a sensor fixation method, with struts 1205 occupying the RA inlet, may be constructed to impede passage of embolic material through the shunt from one atrium to the other atrium.

Figure 13A:
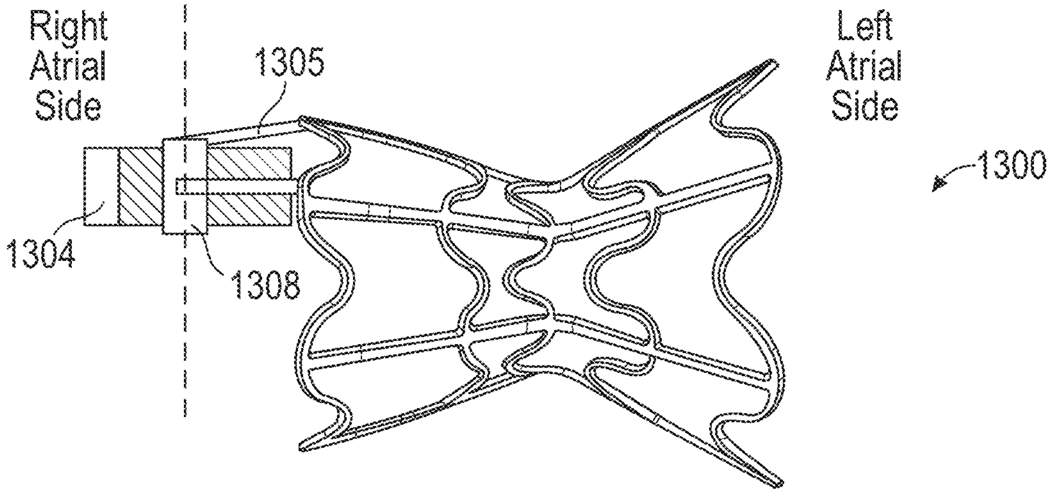
Figure 13B:
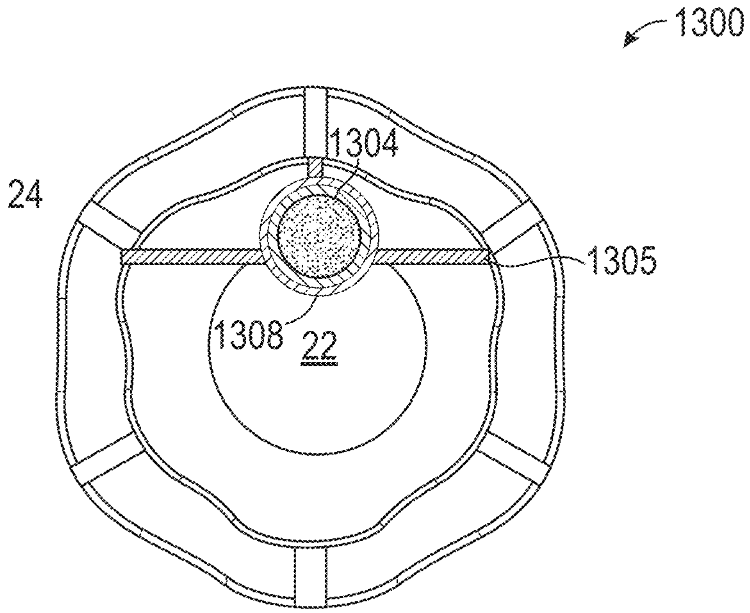

FIGS. 13A and 13B depict an additional embodiment of a shunt 1300, in which a substantially non-coaxial leadless LFPS sensor 1304 is affixed to the shunt anchor frame by a support structure including struts 1305 and collar 1308 off-center to lumen 22 in a manner similar to that of FIGS. 5A-5B, except extending from the right atrial cone of the shunt to measure RAP. This shunt design also may be particularly beneficial for patients with PAH, who have enlarged right atria and suffer predominantly from right sided HF. This arrangement also improves the ability later to pass through the shunt into the LA.

Figure 14A:
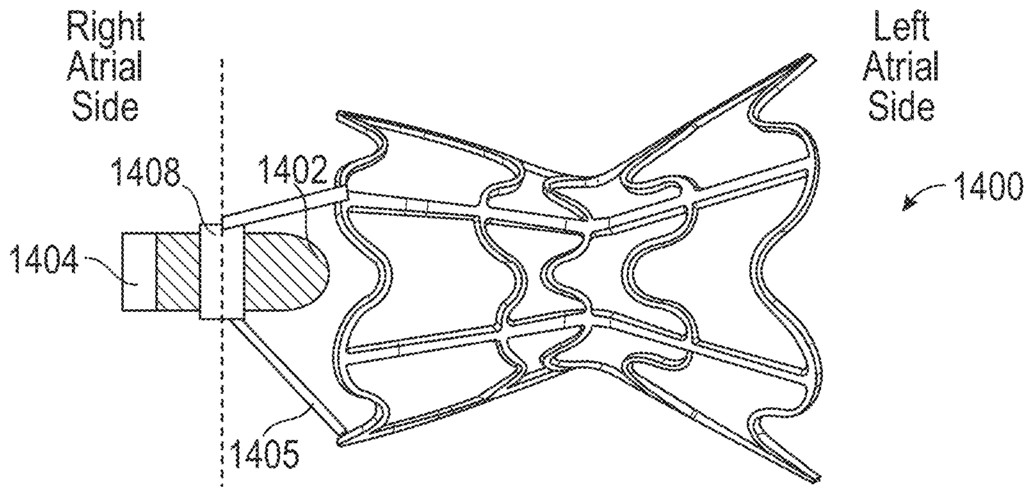
Figure 14B:
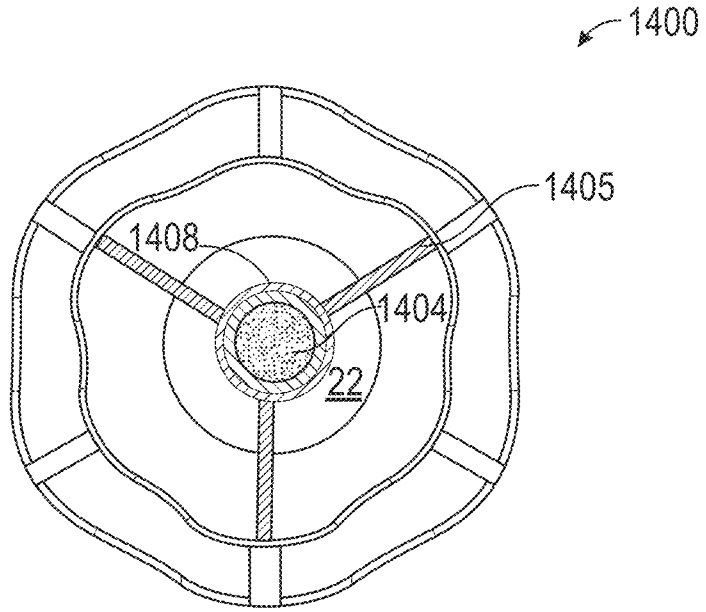

In FIGS. 14A and 14B, another embodiment 1400 of the inventive shunt is described, in which the end 1402 of the sensor 1404 opposite the sensing surface 1401 has a streamlined profile. As will be recognized by one of ordinary skill in the art, modifying a sensor body to streamline features on any surface exposed to blood flow may be beneficial for optimizing pressure/flow relationships and reducing turbulence and high shear forces that may activate platelets or otherwise potentiate thrombus formation.

Figure 15A:
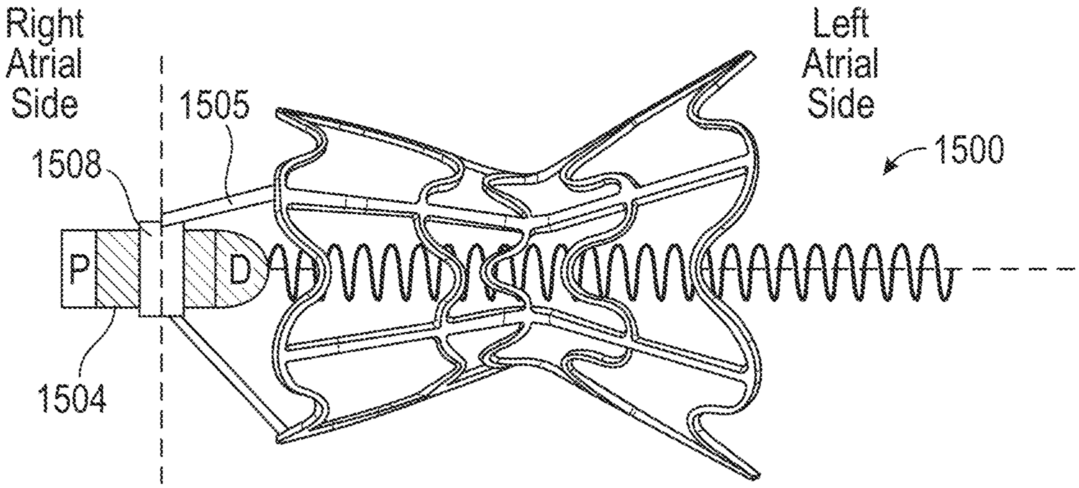
FIGS. 15A to 15D, are, respectively, side view of an invention shunt having a sensor that measures two physiological parameters; a graph of the computational flow dynamic profile of velocity through the shunt; a graph of the continuous wave Doppler flow velocity through a shunt with calculated velocity and pressure gradients; and a tracing of an RA pressure waveform.

Referring now FIGS. 15A to 15D, apparatus and methods are described that may be useful in treating HF, PAH, and other cardiovascular and cardiopulmonary disorders. In FIG. 15A, an exemplary shunt 1500 comprises any of the shunt configurations provided herein and includes a leadless LFPS 1504 disposed on the RA side of the shunt in a manner such as described with respect to FIGS. 12A-12B, 13A-13B, and 14A-14B, e.g., via struts 1505 and collar 1508. In one preferred embodiment, the sensor 1504 is a dual sensor with circuitry to measure at least two different physiological parameters. In the illustrated example, pressure sensing surface P is disposed near the proximal end of the sensor module and Doppler piezo acoustic transducer D, is positioned near the distal end of the sensor module. Sensor D measures the velocity profile along the longitudinal axis of the shunt, while sensor P measures RAP. In one preferred embodiment, D measures a continuous wave Doppler time-varying signal. Alternatively, sensor D may measure a time varying velocity signal along the longitudinal axis of the shunt in a volume at a specified distance from the transducer, using pulsed Doppler techniques. In yet another embodiment, sensor D may be capable of using either a continuous wave or a pulsed Doppler signal.

Figure 15B:
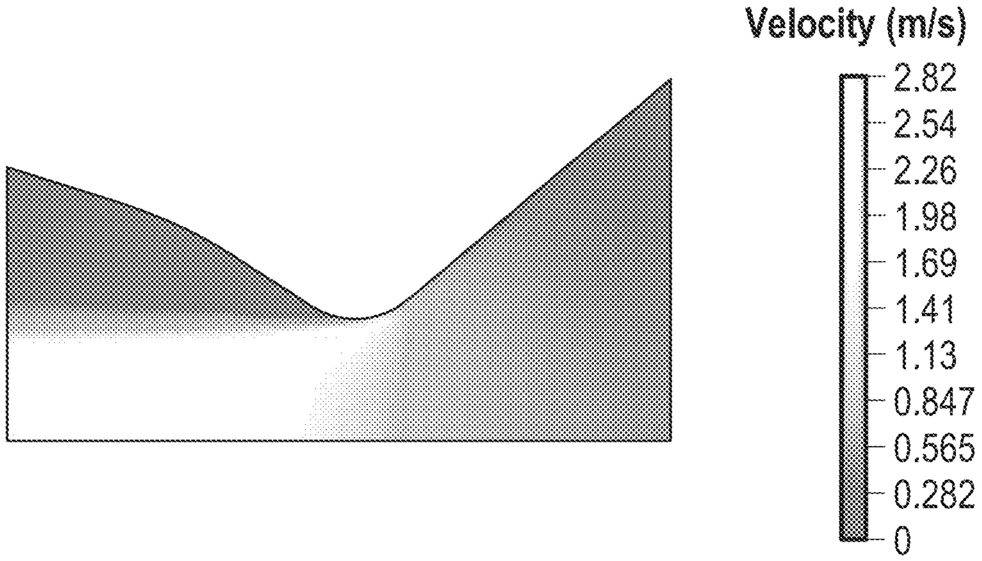

FIG. 15B depicts an example of the velocity profile through one half of the longitudinal lumen of the V-Wave Ventura® Interatrial Shunt under static pressure/flow conditions when the LAP is 38 mmHg, the RAP is 8 mmHg and the interatrial pressure gradient is 30 mmHg. It will be appreciated from the figure that the peak velocity is broadly localized to the central portion of the jet exiting the neck throat orifice of the shunt and extending beyond the outlet of the RA cone.

Figure 15C:
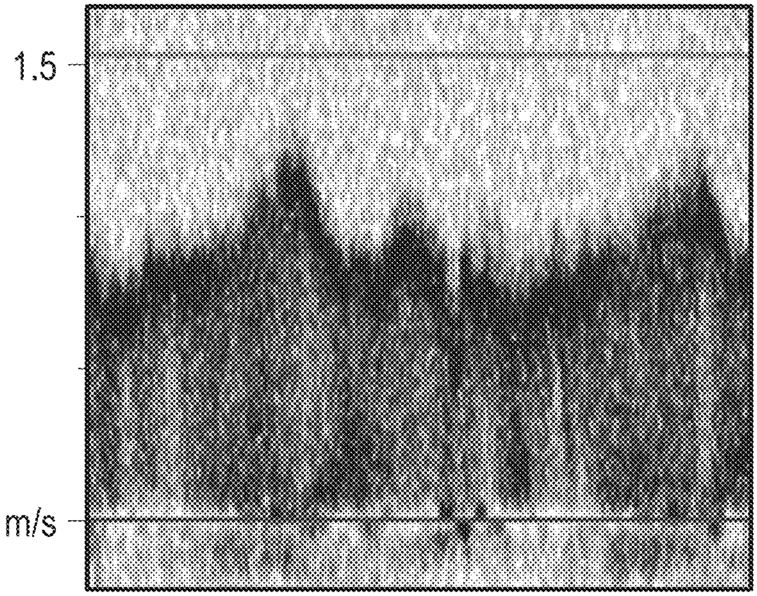

FIG. 15C is an example of a continuous wave Doppler time-varying signal obtained in an animal from an intracardiac echocardiographic probe located in the RA that is aimed through the central lumen of a V-Wave Ventura® Interatrial Shunt. The image shows continuous LA to RA shunting with a peak velocity V. of 1.19 M/s and a mean velocity $V_{mean}$ over multiple cardiac cycles of about 0.90 M/sec. It will be appreciated by one of ordinary skill in the art of echo/Doppler imaging that the pressure gradient across the shunt may be closely estimated by the formula $\Delta P=4V^2$. Values for peak and mean pressure gradient for this example are shown in the table adjoining the image in FIG. 15C.

Figure 15D:
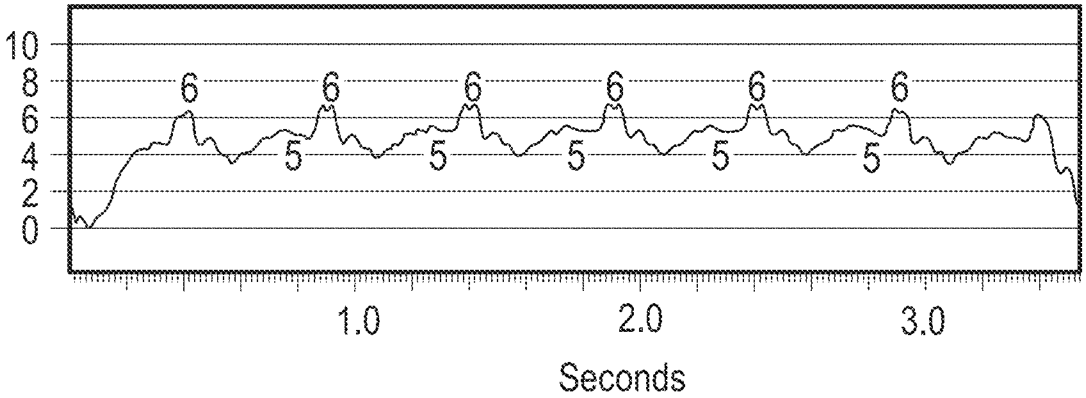

FIG. 15D is an example of a RAP pressure trace over multiple cardiac cycles taken with a catheter showing a mean RAP of about 5 mmHg. It is representative of the type of signal waveform obtainable by the LFPS shown in FIG. 15A. It is apparent that with the dual sensor configuration of FIG. 15A, located entirely near the RA end of the shunt, the instantaneous or mean pressure in each atrium can be measured simultaneously. RAP is measured directly by the LFPS and LAP is estimated by the sum RAP+|ΔP|. It will be appreciated that this shunt design may be used to guide therapy in patients with HF and the like, with predominantly left to right shunt flow, or alternatively in PAH and the like with predominantly right to left shunt flow. One advantage of the configuration shown in FIG. 15A is that LAP can be measured without the need for an additional sensor located on the left atrial side of the shunt. This may be particularly advantageous in PAH where the LA tends to be small relative to the dimensions of the RA.

Figure 16A:
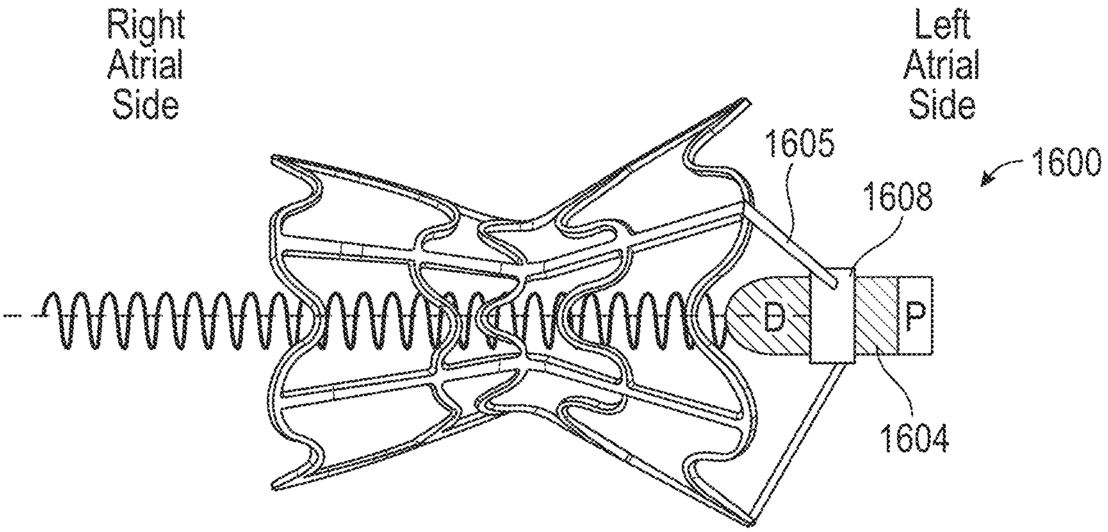
FIGS. 16A to 16C, are, respectively, a side view of an alternative embodiment of an inventive shunt arranged to measure two physiological parameters; a schematic representation of a color flow Doppler 2D echocardiographic image of flow from LA to RA through the shunt; and a graph of continuous wave Doppler flow velocity through a shunt with calculated of velocity and pressure gradient.
Figure 16B:
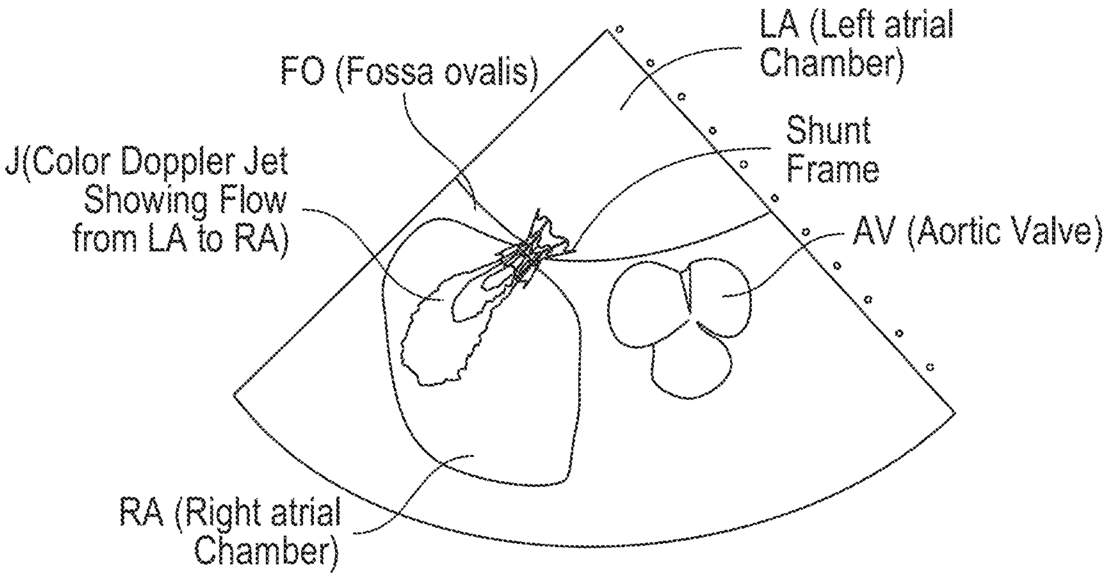
Figure 16C:
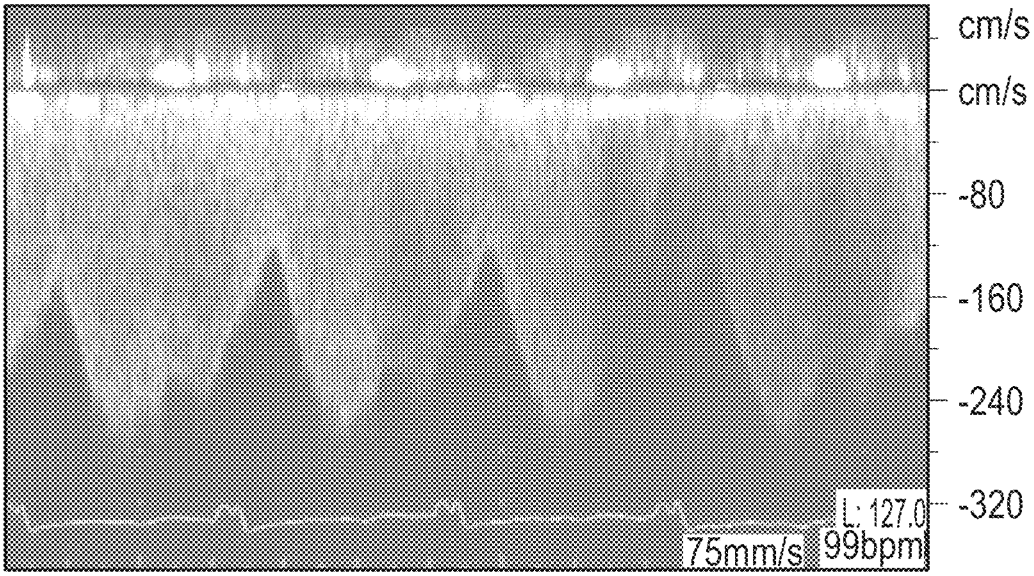

FIGS. 16A to 16C illustrate another exemplary embodiment having features analogous to FIGS. 15A to 15D. In this embodiment, however, the dual function sensor 1604 is reversed and placed on the LA side of the shunt 1600 using struts 1605 and collar 1608, such that pressure-sensing surface P is oriented toward the mid LA cavity and piezo acoustic Doppler transducer D is oriented along the longitudinal axis through the shunt. The image in FIG. 16B is a short axis transesophageal echocardiogram (TEE) color Doppler view of a V-Wave Ventura® Interatrial shunt positioned across the fossa ovalis of a patient with HF. The image shows a prominent left to right atrial high velocity jet exiting the shunt into the RA. FIG. 16C is a corresponding continuous Doppler waveform over multiple cardiac cycles, showing a peak velocity through the shunt from LA to RA of 2.5 M/s and a mean velocity of 1.7 M/s, corresponding the peak ΔP of 25 mmHg and a mean ΔP of 12 mmHg, respectively. RA pressure can be calculated as RA=LAP−|ΔP|. This embodiment 1600 of the inventive shunt may be used to guide therapy in therapy in patients with HF and the like, with predominantly left to right shunt flow, or alternatively in PAH and the like, with predominantly right to left shunt flow. In one preferred embodiment, the configuration may be most advantageous where LAP guided therapy is most relevant, such as in HF. The shunt 1600 of FIG. 16A also may be advantageous where the LA cavity is enlarged as in HF and the like.

Figure 17A:
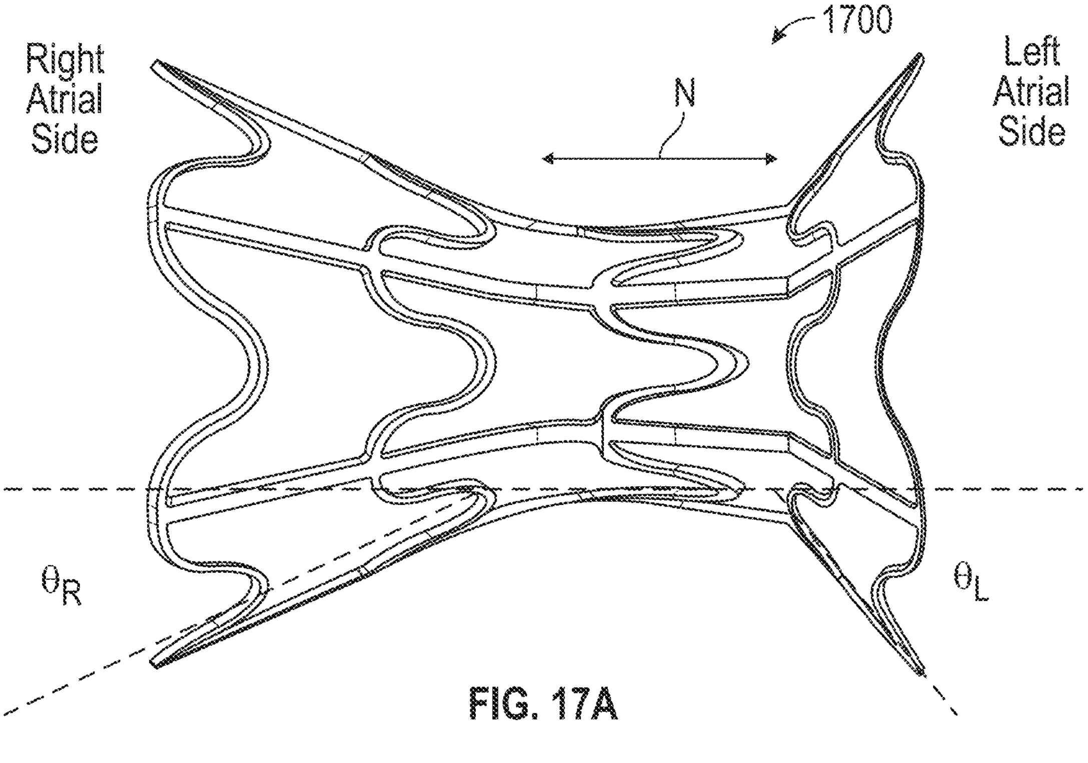
FIGS. 17A to 17C are, respectively, an illustration of the geometrical features of the shunt portion of an inventive shunt, a schematic depicting location and mode of operation of a sensor for measuring flow, and a schematic depicting inclusion of a pacing lead.
Figure 17B:
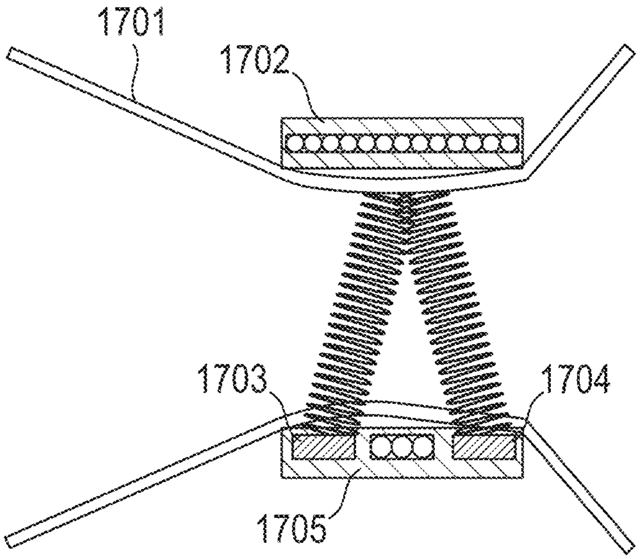
Figure 17C:
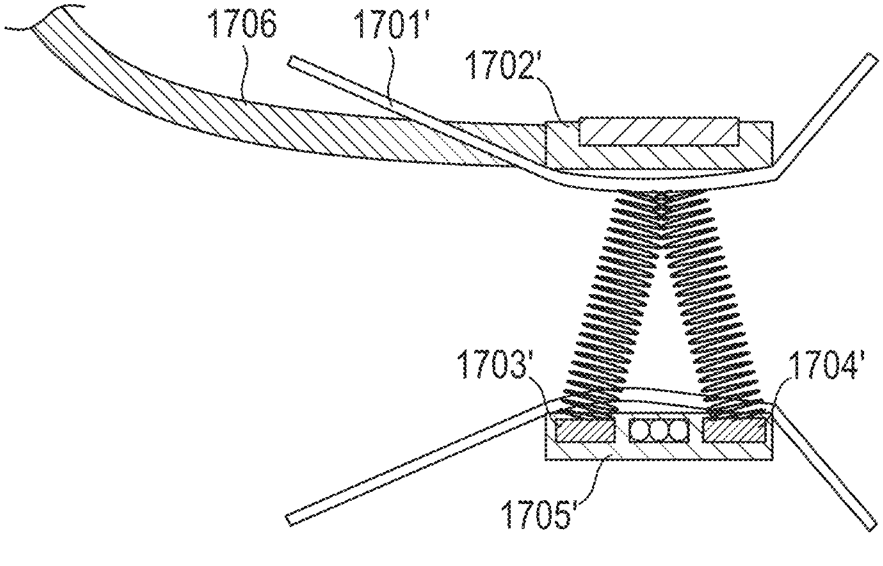

Referring now to FIGS. 17A to 17C, additional preferred embodiments of inventive shunt are described. FIG. 17A shows a shunt 1700 similar to that of FIGS. 1A-1C, wherein various features may be optimized for different anatomy. For example, the rake angle of the left atrial cone $\theta_L$ may be increased so that for the same base diameter of the LA cone, there is less protrusion into the LA cavity. This feature may be advantageous in treating RV failure in PAH and the like, where the LA is small and underfilled. Neck length N may be extended to accommodate thicker fossa ovalis. Although a thicker fossa ovalis may be more common in PAH, lipomatous infiltration of the interatrial septum may increase fossa ovalis minimal thickness to as much as 10 mm in the absence of other disease processes. Further, the rake angle of the RA cone $\theta_R$ may be decreased for the same diameter of the RA cone base, providing more protrusion into the RA. More protrusion of the RA cone may be advantageous in PAH and the like, where the RA is enlarged and the fossa ovalis is bowed toward the LA due to RAP>LAP, such that the fossa from the RA perspective appears as distinct depression or crater. In this situation, it may be more advantageous for the RA cone to be longer, so that it protrudes into the RA beyond the level of the limbus surrounding the fossa ovalis. This extension of the inlet cone in the setting of right to left shunting may reduce the risk of entrainment of thromboemboli into the left atrium, thus reducing the risk of stroke. Any combination of the above features may be utilized to create an interatrial shunt optimized for specific anatomical or physiological conditions.

FIG. 17B depicts use of an anatomically optimized shunt 1701 having a leadless transit time flow probe 1702 surrounding the neck region of the shunt. In the embodiment, the flow probe has dual piezo acoustic transducers, such that a first transducer 1703 transmits a pulse that that is reflected by the neck region of the shunt 1700, and received by the second transducer 1704. The next pulse is transmitted from the second transducer 1704, reflected by the neck region of the shunt 1700, and received by the first transducer 1703. The difference in transit time between transmission and reception in each direction is indicative of the direction and velocity of blood flow. The transducers may be arranged at different locations on the opposite sides of the neck (not shown), or the pattern of sound transmission and reflection may be "V-shaped" (as shown in FIG. 17B), or even "W-shaped" (not shown) as is well known to those of ordinary skill in the art of transit time flowmeters. In another embodiment, the transducers 1703, 1704, controlling electronics and an RF coil for external power reception and telemetry are housed in in a hermetic cylindrical collar 1705 having acoustic windows for the transducers. The collar 1705 may be slipped over the constrained shunt portion (neck) and may be affixed to the shunt 1700 by a variety of described above.

The embodiment 1701' depicted in FIG. 17C is like that of FIG. 17B and includes first and second transducers 1703', 1704', except that the flow sensor 1702' is leaded. In one embodiment, the lead 1706 transverses the wall of the RA cone, creating a more coaxial system that may be of benefit for constraining the shunt in a loading tube or introducer sheath prior to deployment. In another embodiment, the lead and internal electronics (circuitry) may be optimized so that the lead may be connected to a pacemaker generator. A pacing electrode or pacing electrodes may be placed externally on the collar for atrial pacing and/or IEGM sensing from the location of the fossa ovalis. Alternatively, the lead may contain a more proximal indifferent electrode (not shown) for bipolar pacing and/or IEGM sensing.

Figure 18A:
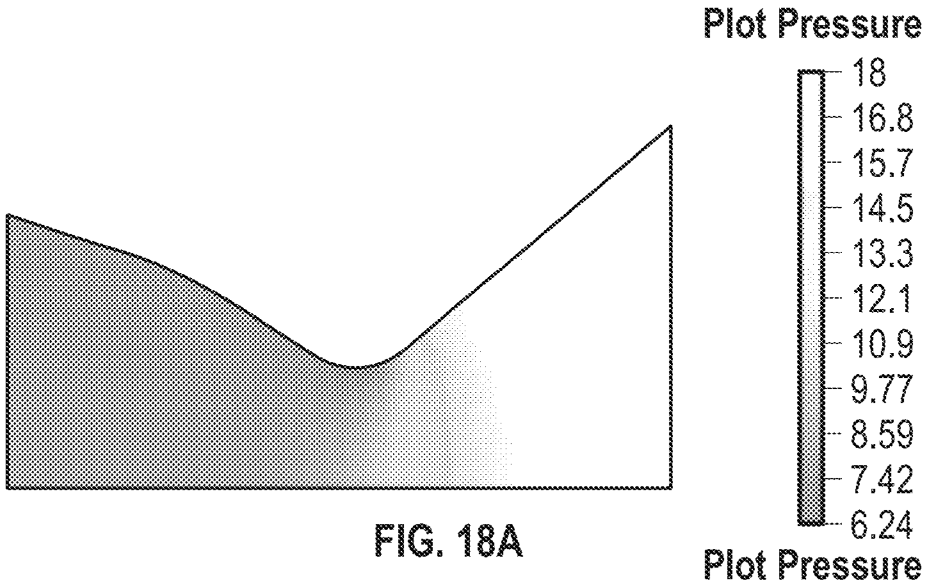
Figure 18B:
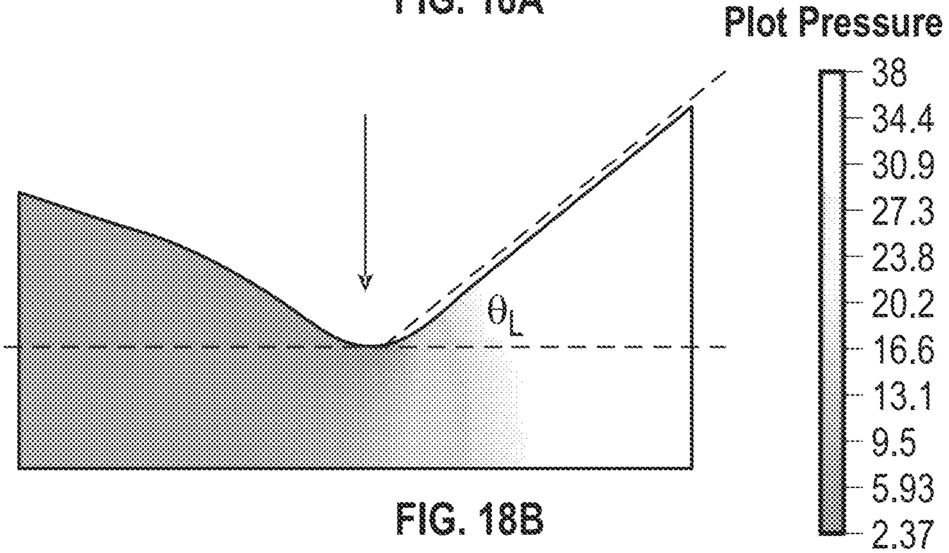

FIGS. 18A and 18B are illustrations of computational flow dynamics analyses of gauge pressure fields across half models of the V-Wave Ventura® Interatrial Shunt corresponding to two sets of boundary conditions. FIG. 18A simulates average or typical observed conditions in HF wherein a fixed gauge pressure of 18 mmHg is applied on the LA side (inlet) and 8 mmHg is applied on the RA side (outlet). Thus, ΔP=10 mmHg. FIG. 18B illustrates extreme conditions corresponding to decompensated HF, wherein a fixed gauge pressure of 38 mmHg is applied on the LA side (inlet) and there is no change in RA side (outlet) pressure, which remains constant at 8 mmHg. In this case, ΔP=30 mmHg. In both scenarios, the pressure in the distal half of the LA cone is essentially the same as LAP due to minimal acceleration of flow in that location. In addition, in both graphs, the pressure is lowest in the region of the shunt neck throat orifice; being substantially lower than in the RA. This is consistent with the Venturi effect of classical fluid dynamics, whereby a fluid gains kinetic energy when there is a reduction in pressure (potential energy), in accordance with Bernoulli's principle of conservation of energy.

With the increasing pressure gradient ΔP, the pressure at the neck falls dramatically from 6.24 to 2.37 mmHg. If the encapsulated shunt body has substantially impermeable walls and is elastically deformable, and has an adequate frequency response, the transition from a lower to a high ΔP, as shown in FIG. 18B, may be measured by assessing changes in the shunt's geometry. One example of changing geometry is an inward displacement of the shunt neck (arrow), while another example is a bending moment measurable as an increase of the rake angle $\theta_L$ of the LA cone. If these conditions are met, the shunt itself may be used as a force gauge, not unlike a pressure sensitive diaphragm. Sensor types that measure linear or angular displacement are well known and may be coupled directly to the force collector, in this case to the shunt.

Figure 18C:
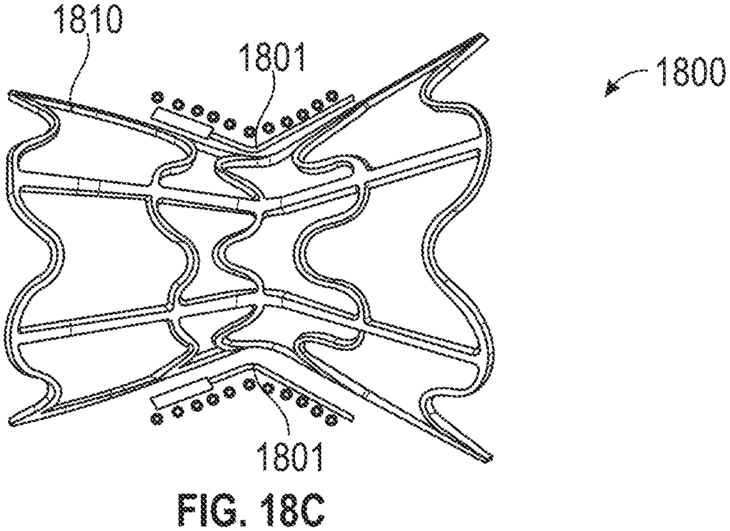
FIG. 18C shows an inventive shunt including strain gauge sensors.

Referring now to FIG. 18C, an embodiment 1800 having one or more flexible hermetic strain gauges in the form of SFPS sensors, is described. In FIG. 18C, the sensing elements 1801 may be arranged to measure the bending moment of the shunt frame 1810 near and at multiple positions around the circumference of the shunt neck. The sensor include circuitry such as piezoresistive strain gauges, accompanying application specific processing circuitry and an external inductor coil for remote RF power reception and telemetry. The electronics may be potted with a flexible polymeric material that inhibits or prevents ingress of moisture to the delicate electronics in an implanted environment. It will be apparent to one of ordinary skill in the art of implantable sensors that other suitable arrangements of components may be used to create a sensor that will measure displacement within the shunt itself.

Figure 19A:
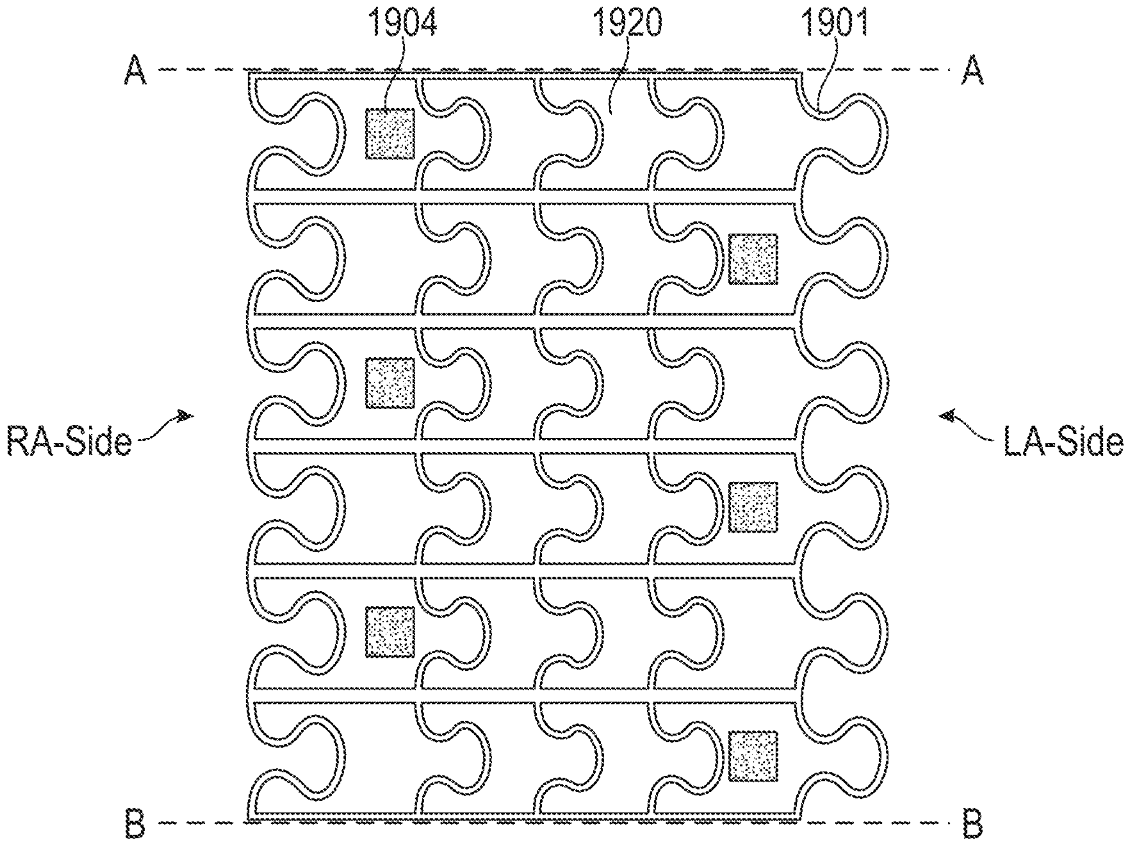
FIGS. 19A and 19B are, respectively, a plan view of an inventive shunt cut longitudinally and unrolled to a flat configuration and an end view of a shunt having a plurality of circumferentially spaced apart sensors.
Figure 19B:
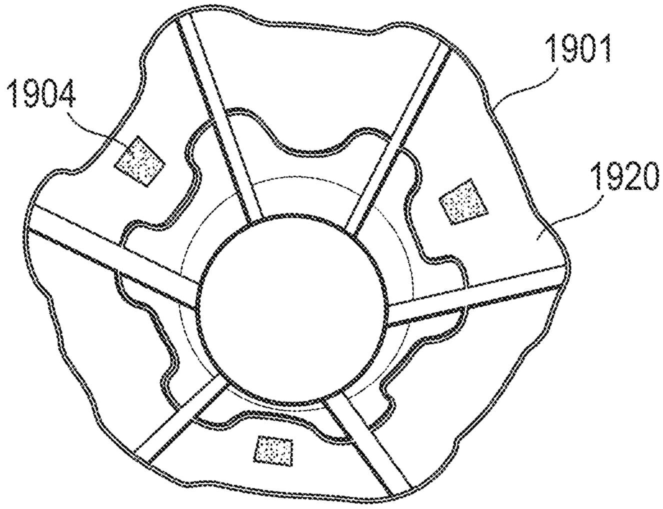

FIGS. 19A and 19B depict exemplary embodiments that employ SFPS technology. More specifically, FIG. 19A shows a shunt anchor frame 1901 as described elsewhere herein, wherein the anchor is cut longitudinally and unrolled into a flat plan view for simplicity of understanding. A plurality of 1×1×0.1 mm SFPS sensors 1904 are disposed on the biocompatible material 1920 that encapsulates the shunt anchor frame on both the RA and LA sides of the shunt. FIG. 19B depicts example locations for a plurality of SFPS 1904 with respect to the luminal aspect of the RA cone of the V-Wave Ventura® Interatrial Shunt. In one embodiment, the sensors may be adhered directly to the luminal surface of the ePTFE encapsulation 1920. Alternatively, the sensors 1904 may be disposed between the bilayers of ePTFE that are sintered together to sandwich the shunt anchor frame. Additionally, or alternatively, the minimum distance from each sensor 1904 to the respective atrial cone edge that may contact a cardiac structure may be about 2.5 mm in some examples. The pressure sensors 1904 preferably are located on the lumen wall at positions between the extreme left atrial or right atrial cone bases and the neck region of the shunt.

From FIGS. 15B and 18A and 18B, it is apparent that the regions of blood in proximity to the shunt lumen walls, other than at the shunt neck, may have relatively low velocity flows and pressures indicative of the cardiac chamber in immediate proximity to the respective pressure sensors. In one embodiment, a plurality of sensors are provided on each side of the shunt, all of which sensors may be or include pressure sensors. For example, if LC type SFPS sensors are used, each sensor could have a different fundamental resonant frequency and be activated in sequence by an appropriately multiplexed RF signal or read out simultaneously. For example, a change in pressure may change the resonant frequency from a zero-point frequency. If each of the sensors has a different zero-point frequency, and these frequencies are spaced far enough apart, the sensors may be read out all at once without multiplexing and the spectrum may cover the frequencies of all of the sensors which may be distinguished from one another. Alternatively, the sensors may be multiplexed, e.g., read out one at a time. The sampling rate to faithfully reproduce a cardiac pressure signal is approximately twice the 10th harmonic of the fundamental frequency of the heart rate. Most HF patients have a HR or fundamental frequency between 0.8 and 1.3 Hz. Even with a tachycardic HR of 2 Hz, a sampling rate of 40 Hz would be adequate. A device capable of frequency switching and sampling pressure of at least 240 Hz would be adequate to multiplex up to 6 pressure sensors. Being able to adequately reproduce the $20^{th}$ harmonic also would allow faithful calculation of dP/dt. For 6 sensors that are multiplexed this may utilize sampling at 480 Hz, well within the sampling capabilities for a practical RF carrier frequency of 100 kHz or greater.

Having a plurality of LAP sensors as described herein also may be beneficial for reducing noise by enabling signal averaging. Further, if a sensor were to fail or develop artifacts due to tissue overgrowth or mechanical connection due to chamber wall tension, information from that sensor could be ignored and the redundant sensors would permit continued access to vital pressure data. In another embodiment, individual sensors that respectively measure one of a plurality of physiological parameters or biochemical parameters could be employed, for example a shunt having multiple sensor types (e.g. pressure, oximetry, pH, acceleration, etc.).

With respect to FIGS. 20A-20C, 21A-21C, and 22, illustrative examples are described showing how implanted pressure sensors, e.g., LFPS or SFPS pressure sensors, may be used to guide drug and device therapies in HF patients.

Figure 20A:
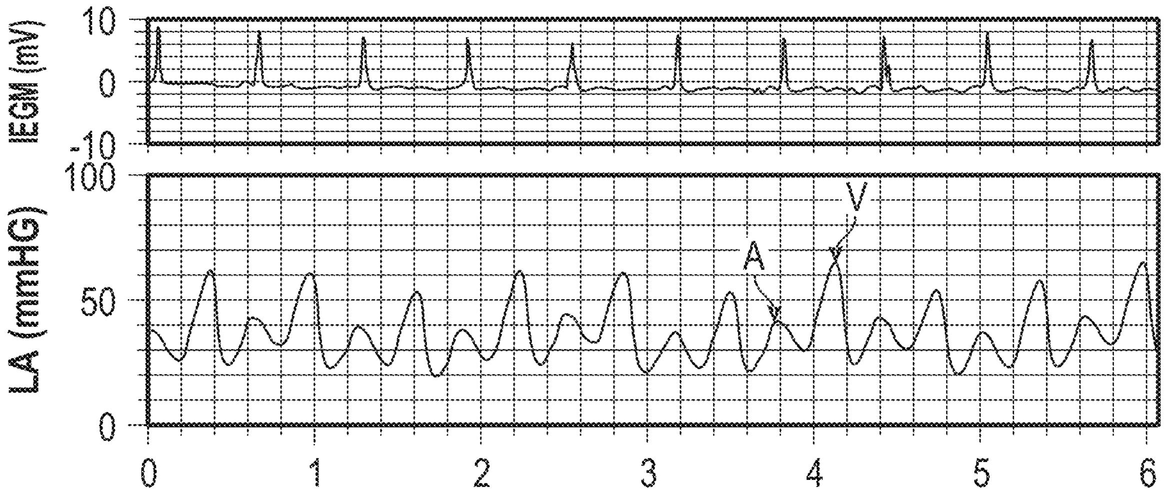
FIGS. 20A to 20C are, respectively, exemplary IEGM and pressure waveforms generated by an implanted LAP sensor showing LAP trends and response to changes in medical therapy in a patient with heart failure.
Figure 20B:
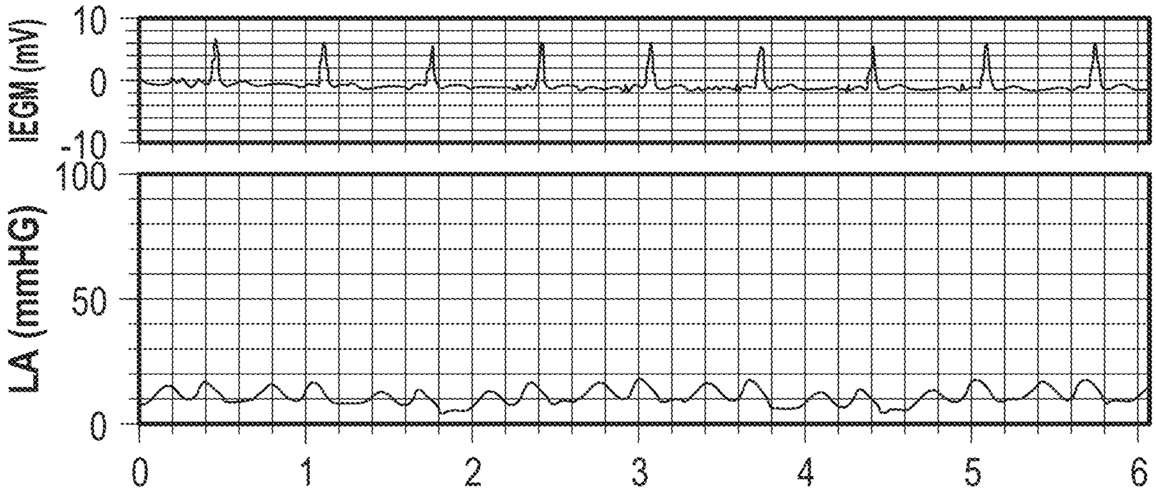
Figure 20C:
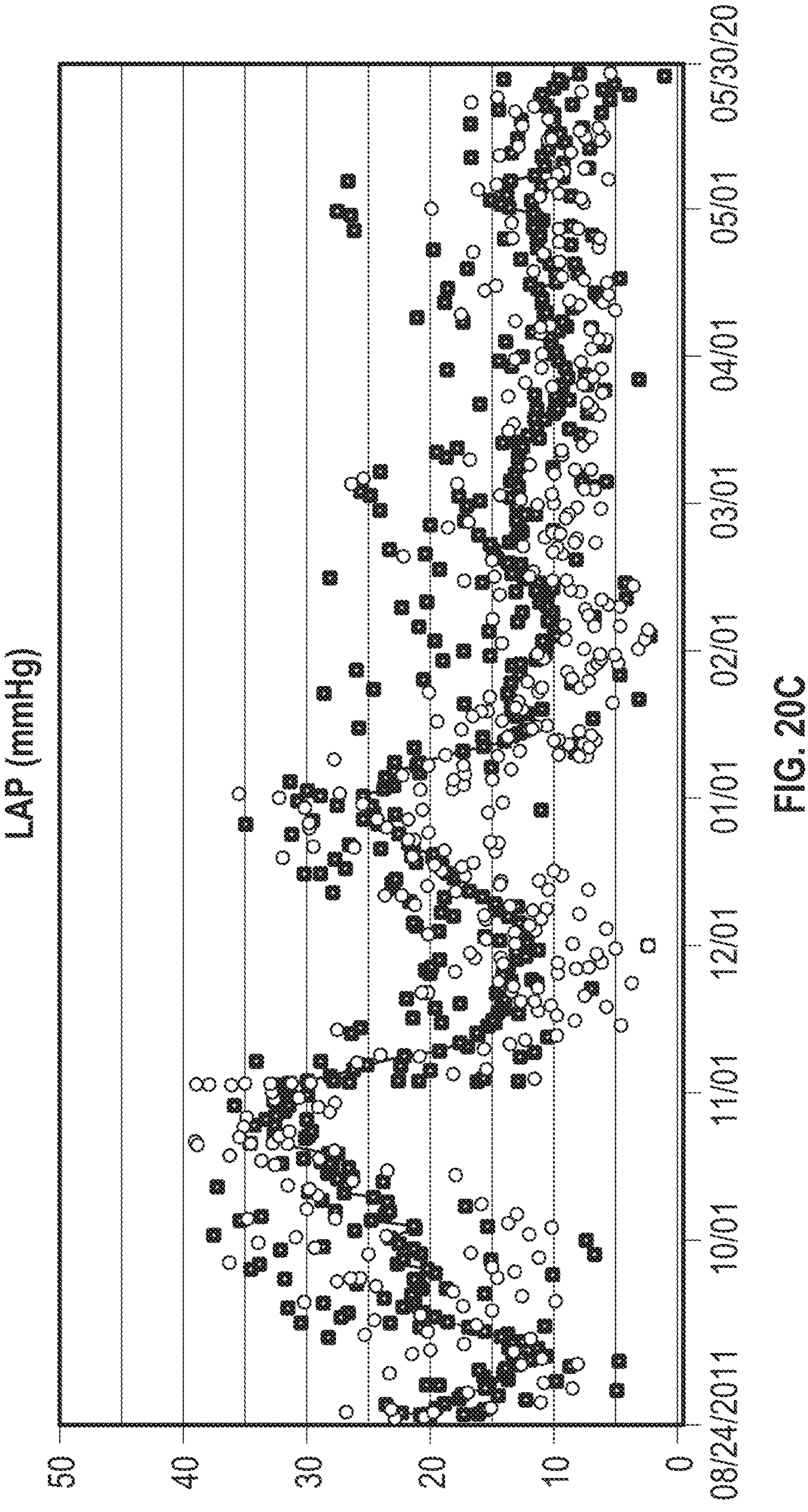

FIGS. 20A to 20C depict data from a patient with idiopathic cardiomyopathy with an LVEF of 25%, who was previously hospitalized with ADHF and then implanted with a leaded LAP sensor. FIG. 20A is a LAP waveform trace corresponding to an episode when the patient was short of breath. Mean LAP was substantially elevated at 36 mmHg with V-waves of 60 mmHg. FIG. 20B is a waveform trace taken sometime later, and shows a normal mean LAP of 11 mmHg. FIG. 20C is a temporal trend plot of diurnal LAP measurements (open circles=morning, closed circles=evening) and the 7-day moving average. During the first 4 months of monitoring, there were two episodes of acute decompensated HF. Physician directed patient self-management was initiated with serial up-titration of ACE inhibitor and beta-blocker drugs. Diuretics and long acting nitrates where adjusted according to the just measured LAP using the DynamicRx algorithm described above. During the last 8 months of the plot, LAP was largely normalized, averaging 10-12 mmHg and the patient was asymptomatic.

Figure 21A:
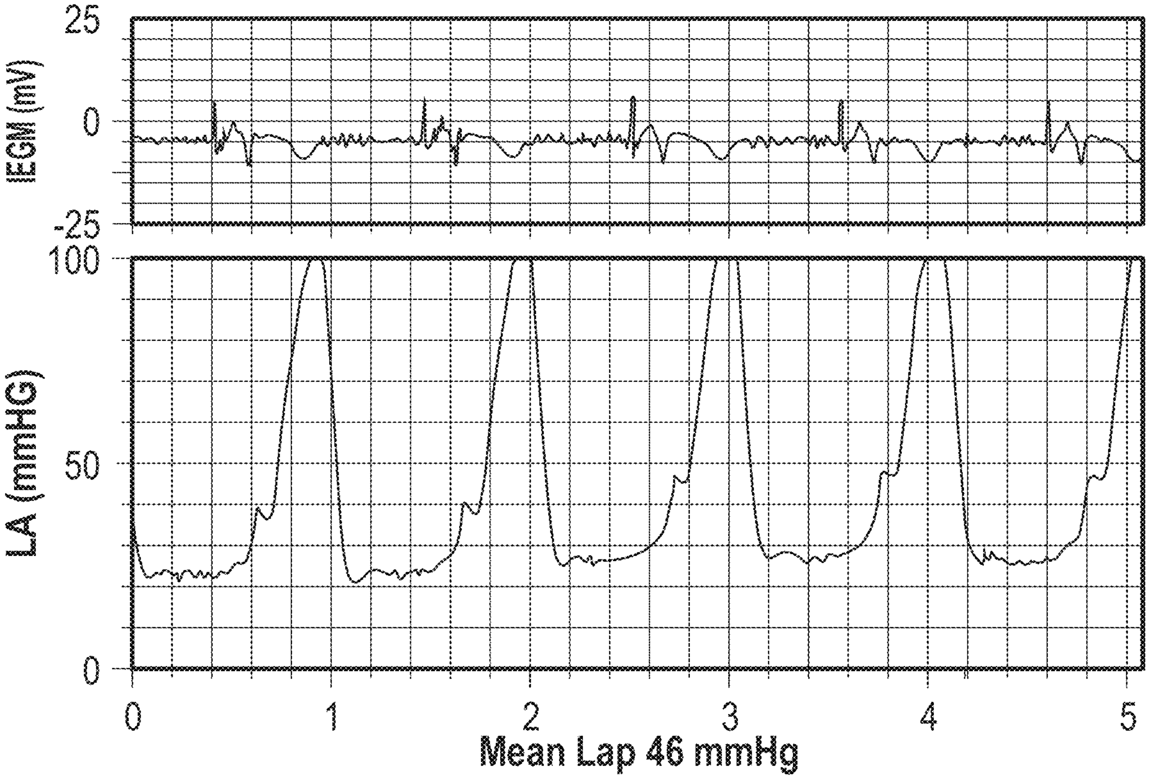
FIGS. 21A to 21C are, respectively, exemplary IEGM and pressure waveforms generated by an implanted LAP sensor, showing LAP trends, and response to a structural heart disease intervention and changes in medical therapy in a patient with heart failure.
Figure 21B:
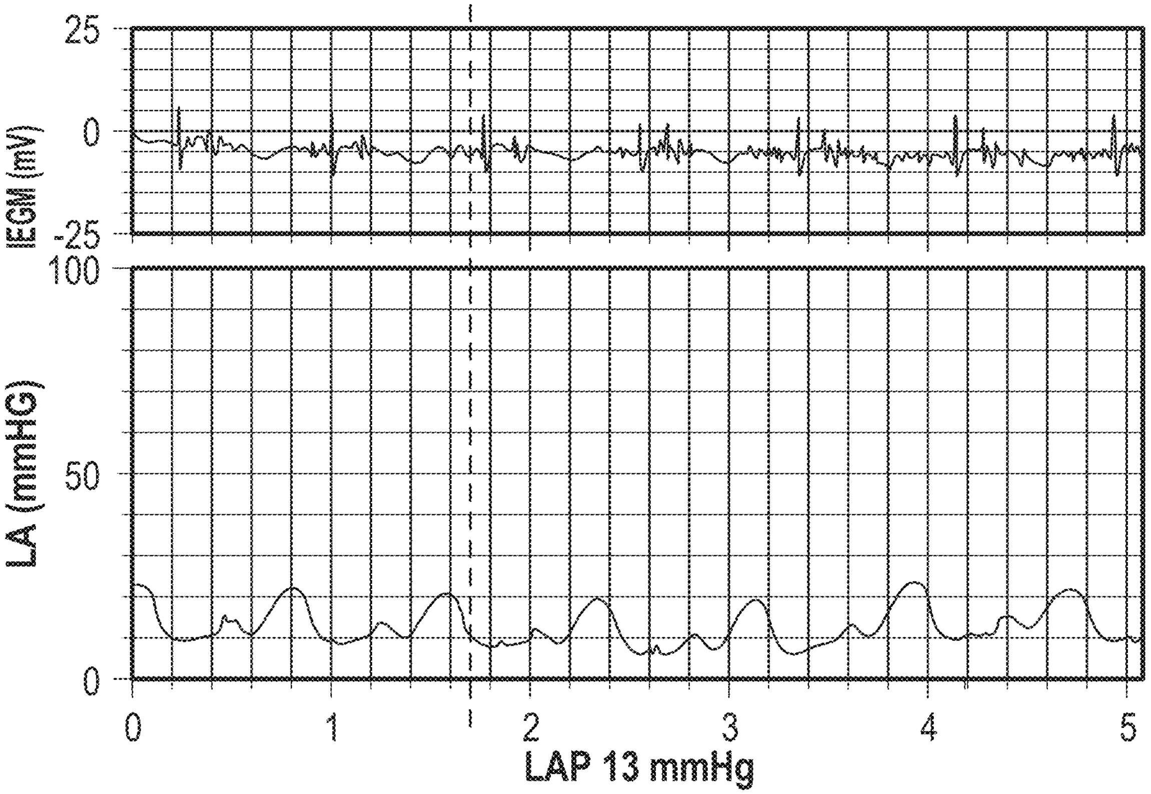
Figure 21C:
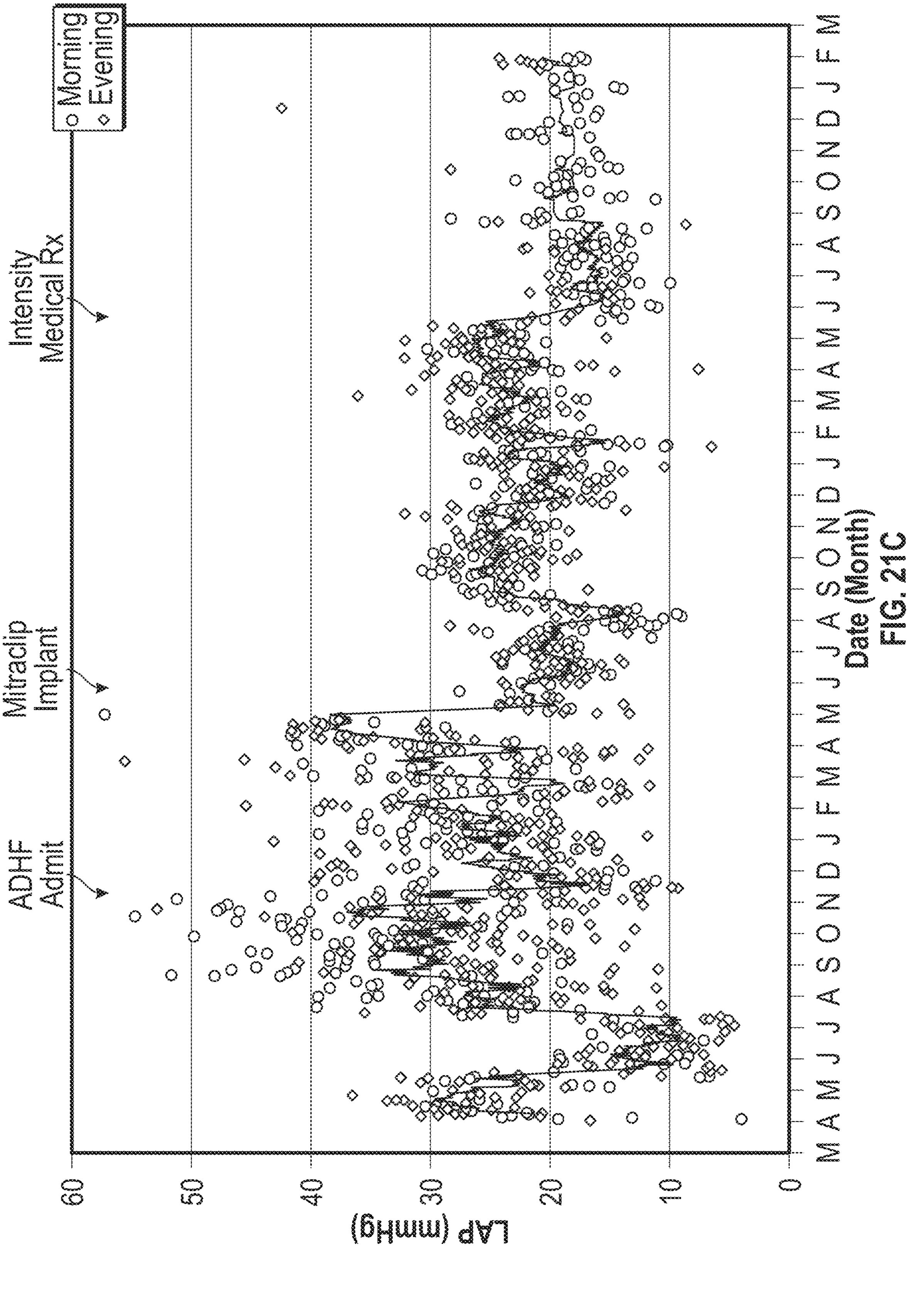

FIGS. 21A to 21C are LAP waveforms traces and a trend plot from an elderly patient with HFrEF who had experienced four prior hospitalizations for ADHF. During the first year after sensor implantation, the patient continued to have brief episodes of severely elevated LAP readings associated with giant v-waves (FIG. 21A). These episodes correlated with severe functional mitral valve regurgitation as observed with echocardiography. The patient underwent successful MitraClip implantation with the transseptal catheterization performed posterior to the location of the LAP pressure sensor on the fossa ovalis. The patient's symptoms improved with prevention of the most severe LAP excursions. Later intensification of drug therapy resulted in excellent control of LAP.

Figure 22:
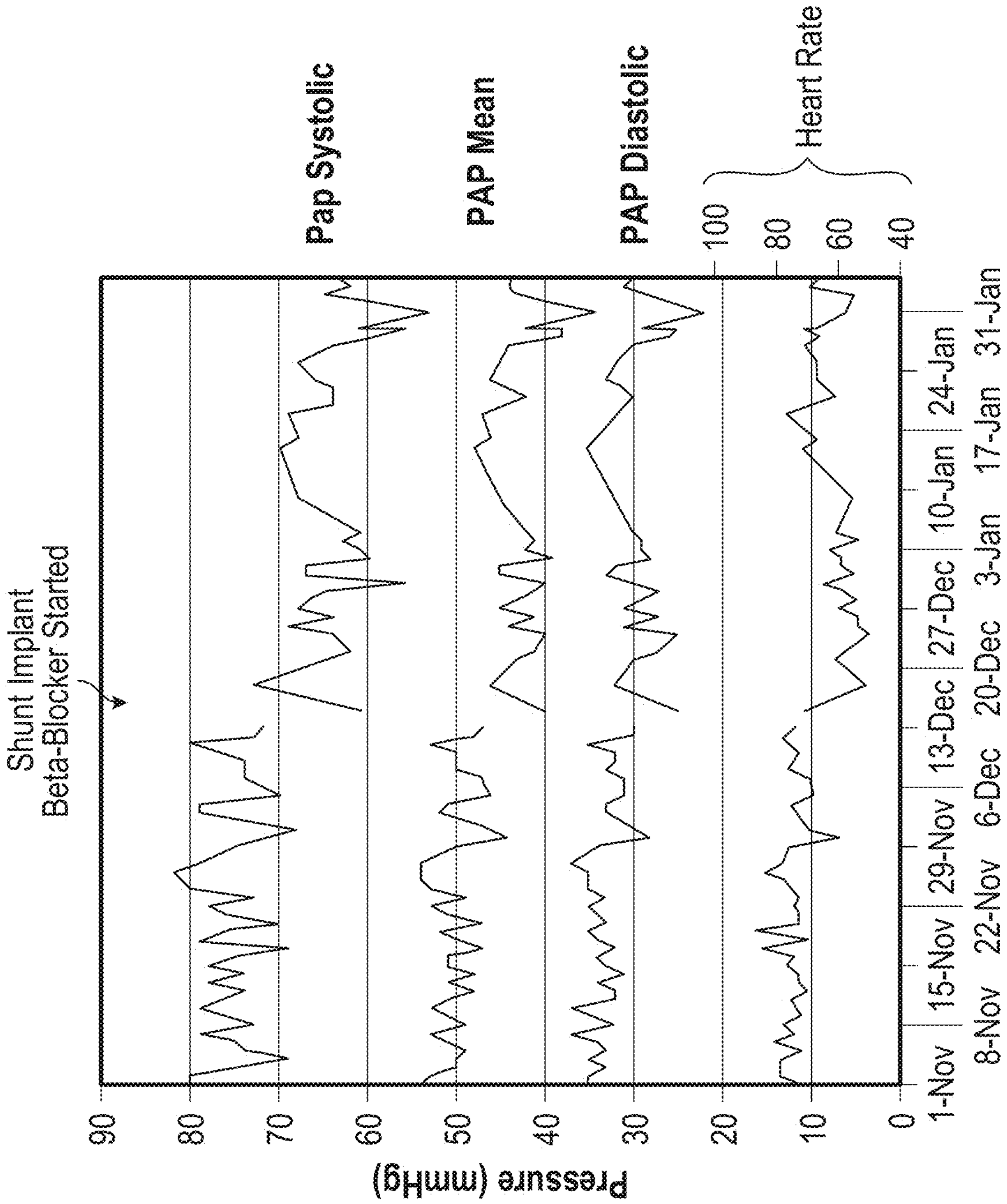
FIG. 22 is an exemplary graph of physiological parameter trend and response to implantation of an interatrial shunt and changes in medical therapy in a heart failure patient with an implanted pulmonary artery pressure sensor.

FIG. 22 shows a trend plot of pulmonary artery pressure and heart rate in a patient with HFpEF who was implanted with a CardioMEMS pressure sensor. The patient had NYHA class III symptoms with severe and sustained elevation of PA pressure. A V-Wave Ventura® Interatrial shunt was implanted, and heart rate lowered with beta-blockers to improve the efficiency of shunting decompression of the left heart. Those steps resulted in immediate and sustained reductions in PA pressures with an accompanying improvement in symptoms.

Figure 23:
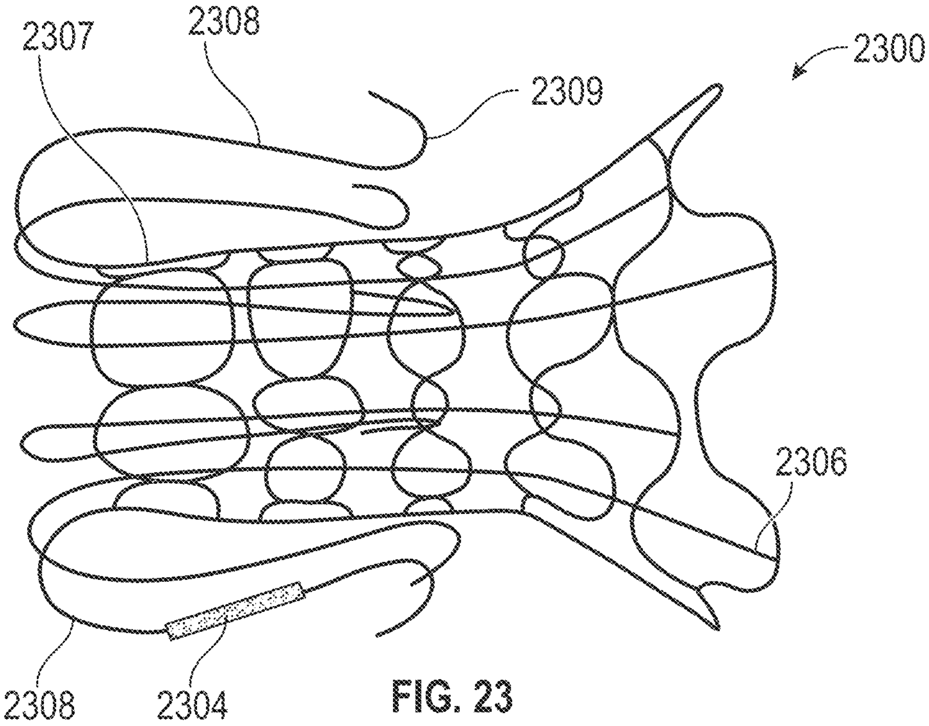
FIG. 23 is an embodiment of the inventive shunt in which an electrical component of the sensor is disposed on a retaining member of the shunt anchor.

FIG. 23 is an embodiment of the inventive shunt in which an electrical component of the sensor is disposed on a retaining member (leg) of the shunt anchor 2300. In FIG. 23, anchor frame 2301 similar to that depicted in FIG. 12 of commonly assigned U.S. Pat. No. 10,251,740 is described. More specifically, in FIG. 23, anchor 2300 suitable for use in an inventive shunt includes flared region 2306 configured for deployment in the left atrium and substantially cylindrical region 2307 that extends through the atrial septum and into the right atrium. Flexible struts 2308 bend distally, i.e., towards the septum when the anchor is released from its delivery sheath, and preferably include U-shaped inverted ends 2309 that contact, but do not penetrate, the right atrial wall in the fully deployed position, as depicted in FIG. 23. Preferably, anchor 2300, other than flexible struts 2308 includes a conduit formed by encapsulating the anchor with polymeric material that inhibits or prevents tissue ingrowth from obstructing the lumen of cylindrical region 2307, and may include or be made of a biocompatible shape memory alloy, as described for preceding embodiments. In the embodiment of FIG. 23, at least one of flexible struts 2308 includes sensor element 2304. Depending upon the height of flexible struts 2308 when deployed and whether the strut is likely to be overgrown by pannus, sensor element 2304 may include any suitable combination of one or more of the sensor itself or sensor circuitry, e.g., the sensor antenna and/or the sensor electronics package. In some examples, sensor element 2304 includes a temperature sensor, biochemical sensor, or other suitable sensor type.

Figure 24A:
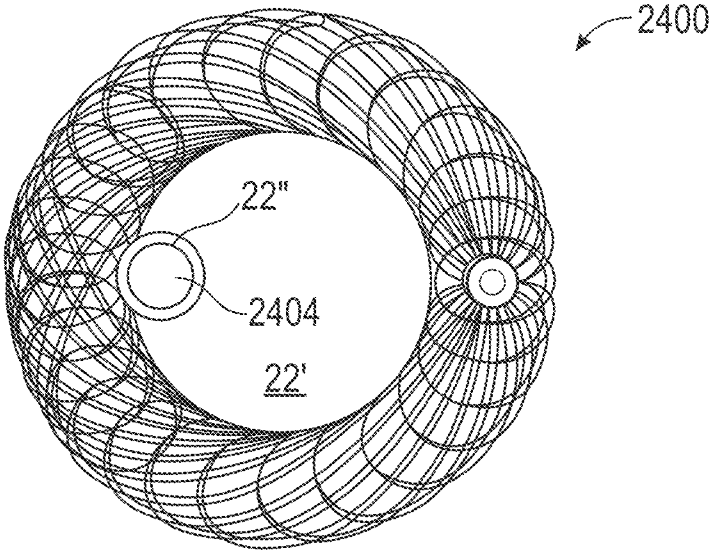
Figure 24B:
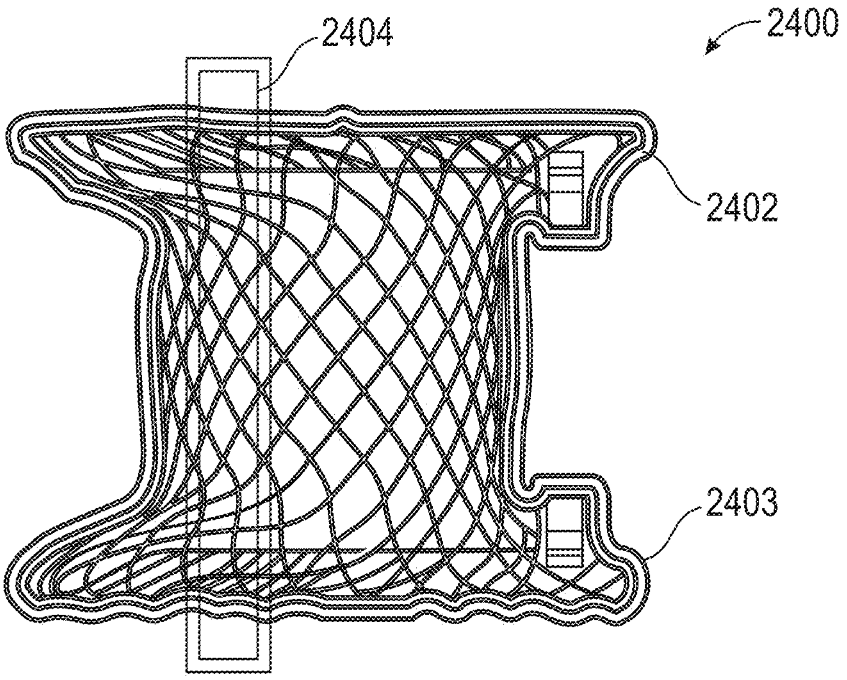
Figure 24C:
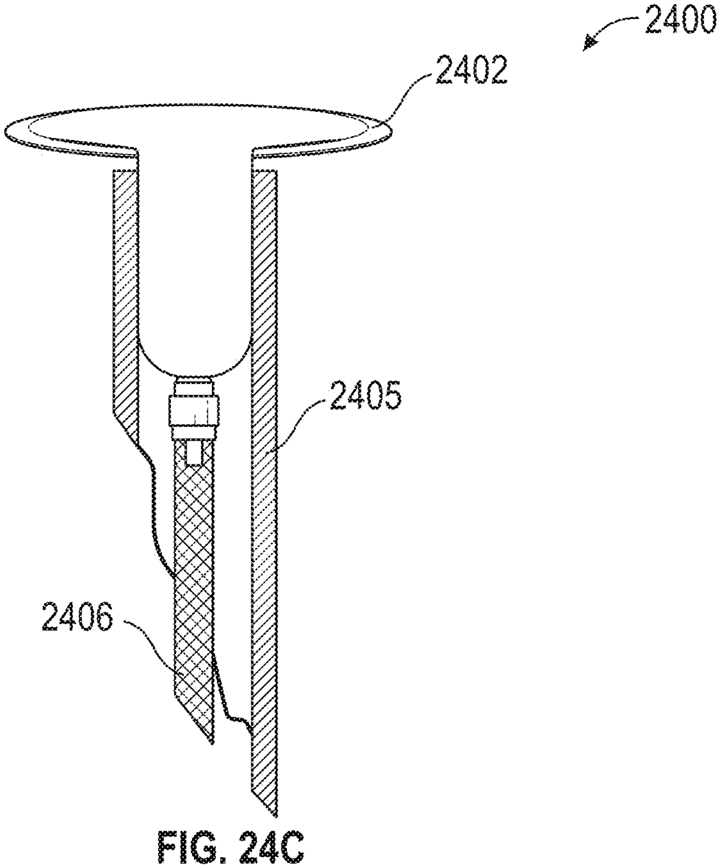
FIG. 24C depicts deploying the shunt of FIGS. 24A-24B in an atrial septum.

FIGS. 24A and 24B are, respectively, an end view and a side view of an intra-atrial shunt 2400 formed from a wire braid configured in a manner such as described in U.S. Pat. No. 6,468,303, the entire contents of which are incorporated by reference herein. Shunt 2400 may be covered with a biocompatible covering (not specifically illustrated), and may include a sensor 2404 affixed within the flow lumen 22' of the shunt. Sensor 2404 may be provided within a secondary lumen 22" that is located within lumen 22'. FIG. 24C depicts deploying the shunt of FIGS. 24A-24B in an atrial septum. For example, shunt 2400 (with some detail omitted for clarity) including sensor 2404 may be compressed within delivery sheath 2405, which may be extended across the atrial septum. Structure 2406 may be used to hold shunt 2400 in place while the sheath 2405 is retracted so that a first flange 2402 may self-expand into one of the atria. Sheath 2405 then may be further retracted so as to allow self-expansion of second flange 2403 into the other atrium in a manner so as to secure sensor 2404 across the atrial septum. Sensor 2404 may include circuitry configured so as to measure LAP, RAP, or both LAP and RAP. Note that although FIG. 24A may suggest that sensor 2404 has a substantially circular cross-section, sensor 2404 may have any suitable cross-sectional shape such as semi-circular, crescent moon shape, or otherwise, e.g., may have a cross-sectional shape that varies along the length of the sensor in a manner such as described in greater detail with reference to FIGS. 31A-31E and 32A-32D. Illustratively, sensor 2404 may have an at least partially annular cross section through which blood may flow, and the sensor may include circuitry for measuring the flow rate of blood therethrough. It will also be appreciated that although sensor 2404 may be positioned adjacent to the inner wall of lumen 22', shunt 2400 instead may include struts and a collar configured so as to support sensor 2404 concentrically and spaced apart from the inner wall of lumen 22'.

Figure 25A:
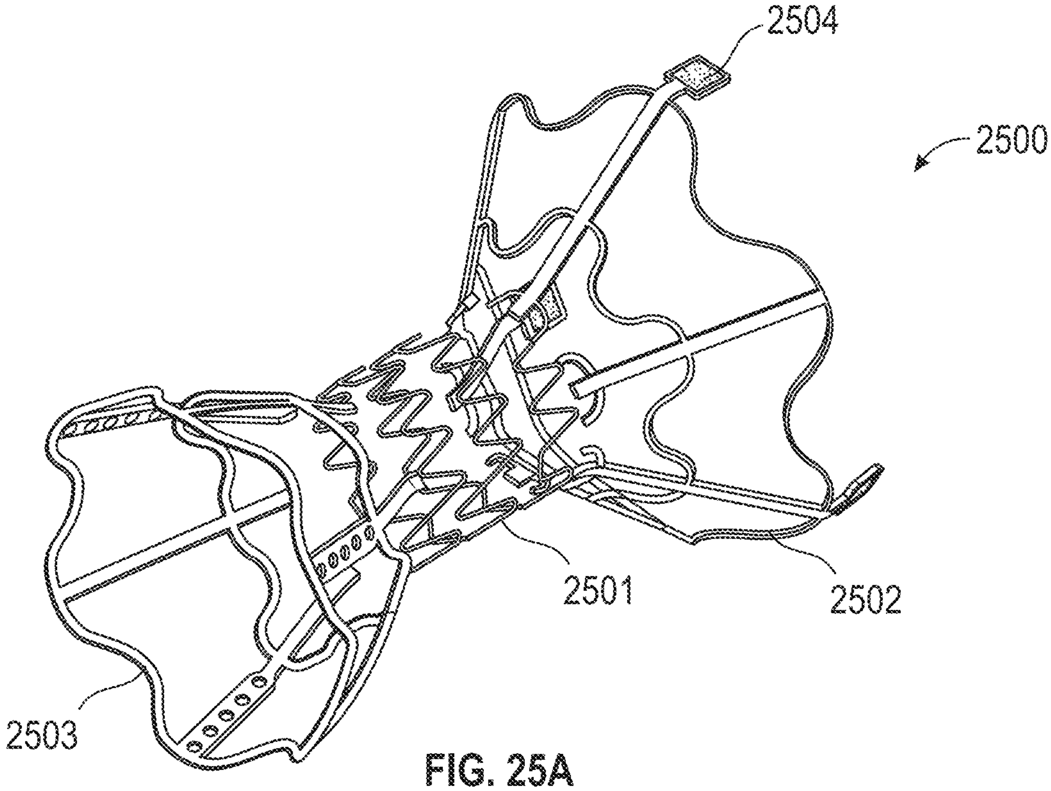
FIGS. 25A and 25B illustrate a further alternative embodiment of the inventive shunt in which the mid-region of the shunt anchor has a coil structure that serves as a circuit element of the sensor.
Figure 25B:
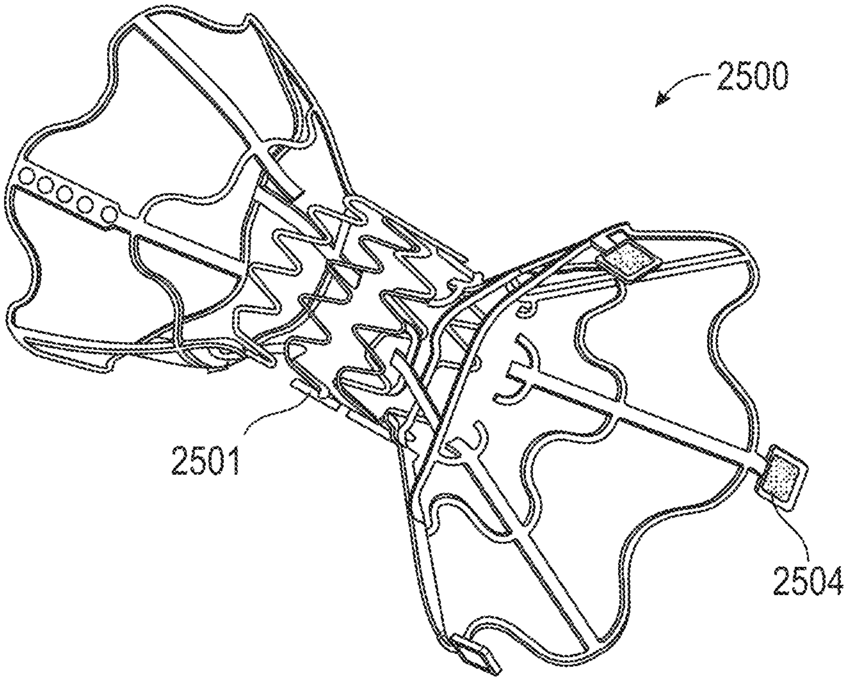

FIGS. 25A and 25B illustrate a further alternative embodiment of the inventive shunt in which the mid-region 2501 of the shunt anchor 2500 has a coil structure that serves as a circuit element of the sensor 2504. In this embodiment the frame neck 2501 (mid-region) may be laser cut in a geometry of a coil, and as such may form an inductor or telemetry coil in a manner similar to that described in Luo, "Selective and regulated RF heating of stent toward endohypothermia treatment of in-stent restenosis," Master's Thesis, University of British Columbia (Vancouver), 2014, the entire contents of which are incorporated by reference herein. The sensors 2504, e.g., capacitors, may be provided at the edges of the one or both of flanges 2502, 2503, and together with the neck 2501 (which may provide an inductor) may form an LC circuit which may be used as a passive resonant circuit. Illustratively, frame neck 2501 may form a multiple-turn coil that is fully encapsulated, may have an approximately 6 mm outer diameter, and may deployable through an 18 Fr or 24 Fr sheath. In some examples, frame neck 2501 may include or may be formed of a composite Nitinol/silver wire so as to have superelastic properties, and/or may be plated with platinum or silver so as to inhibit corrosion. In this regard, frame neck 2501 may not necessarily be integrally formed with flanges 2502 and 2503, and instead may be welded or otherwise coupled thereto.

Note that the inductance of a coil-shaped frame neck 2501 may be relatively small, and such inductance may change in responses to changes in the cross-sectional area and/or length of the coil, e.g., beat-to-beat or over time due to healing or remodeling. An active sensor using the aforementioned changes in inductance within this neck strut-ring coil may potentially measure flow through the shunt, because the pressure within the neck should drop with increasing flow due to the Venturi effect, thus reducing the cross-sectional area of the coil, and thus reducing its inductance. Because of the relatively high resonant frequency of an LC circuit using a capacitor of reasonable size, an active circuit for measuring the inductance and performing the telemetry may be provided.

Figure 26A:
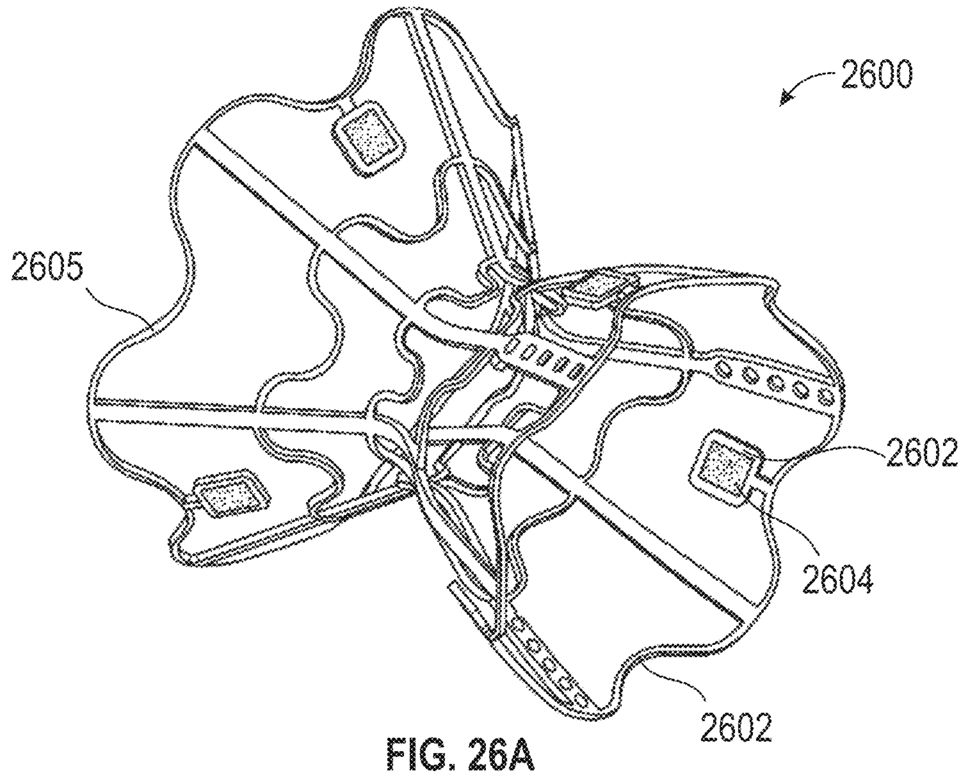
FIGS. 26A-26B illustrate an alternative embodiment of the shunt of FIGS. 19A and 19B, wherein the sensor is disposed in a laser cut frame element formed in the shunt anchor.
Figure 26B:
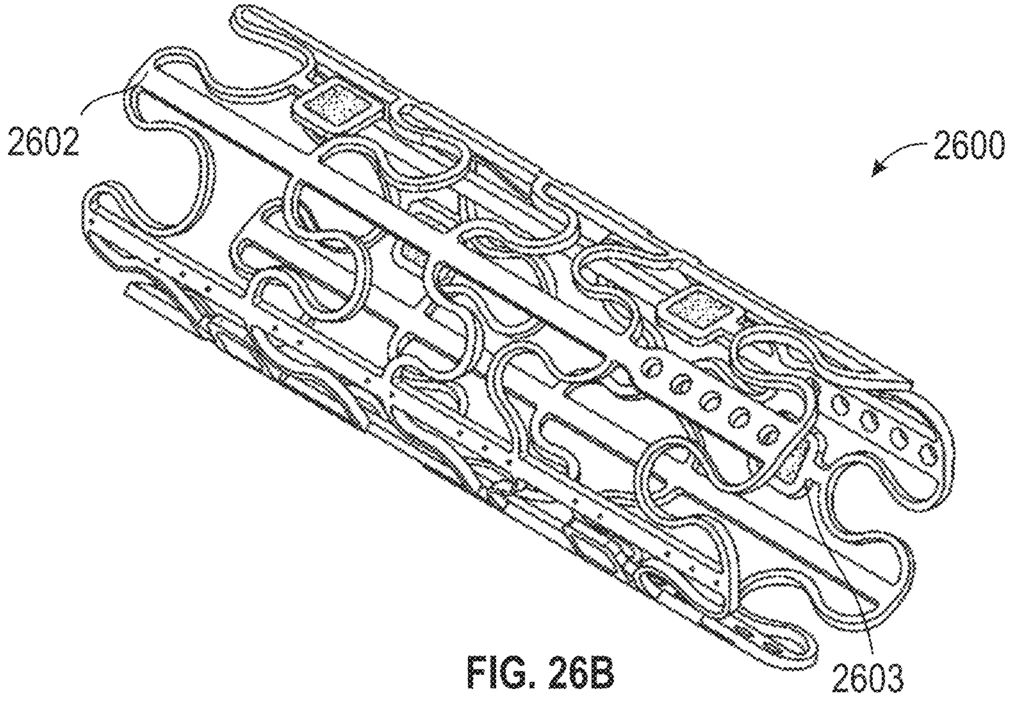

FIGS. 26A-26B illustrate an alternative embodiment of the shunt of FIGS. 19A and 19B, wherein the sensor is disposed in a laser cut frame element formed in the shunt anchor. Whereas in the embodiment of FIGS. 19A and 19B, multiple leadless sensors may be disposed on or within the biocompatible material that encapsulates the shunt anchor frame, in shunt 2600 of FIGS. 26A-26B, anchor frame 2602 includes one or more receptacles 2603 formed in circumferential struts 2605 each being configured to respectively accept and secure a sensor 2604. Multiple receptacles 2603 may be equally spaced around the circumference of the anchor frame 2602, and the receptacles may be located in either or both atria of the anchor frame and/or at the location of the shunt neck. Receptacles 2603 may be formed by any suitable process, including laser cutting during manufacture of the anchor frame or subsequent welding. Sensor 2604 may be affixed onto or into respective receptacles 2603 via any suitable process, e.g., using biocompatible adhesive or crimping. Alternatively, the sensors 2604 may be located in eyelets formed at one or both ends of the anchor frame, such as in eyelets 64 depicted in FIGS. 4 and 5 of commonly assigned U.S. Pat. No. 10,251,740. Advantageously, receptacles 2603 may be disposed within the length of the anchor frame, and thus may be less prone to potential bending during deployment of the shunt. For example, FIG. 26B illustrates shunt 2600 compressed into a delivery configuration in which receptacles 2603 generally follow the outer contour of the compressed shunt. Other example locations for receptacles are described with reference to FIGS. 28-30, as well as elsewhere herein.

Figure 27:
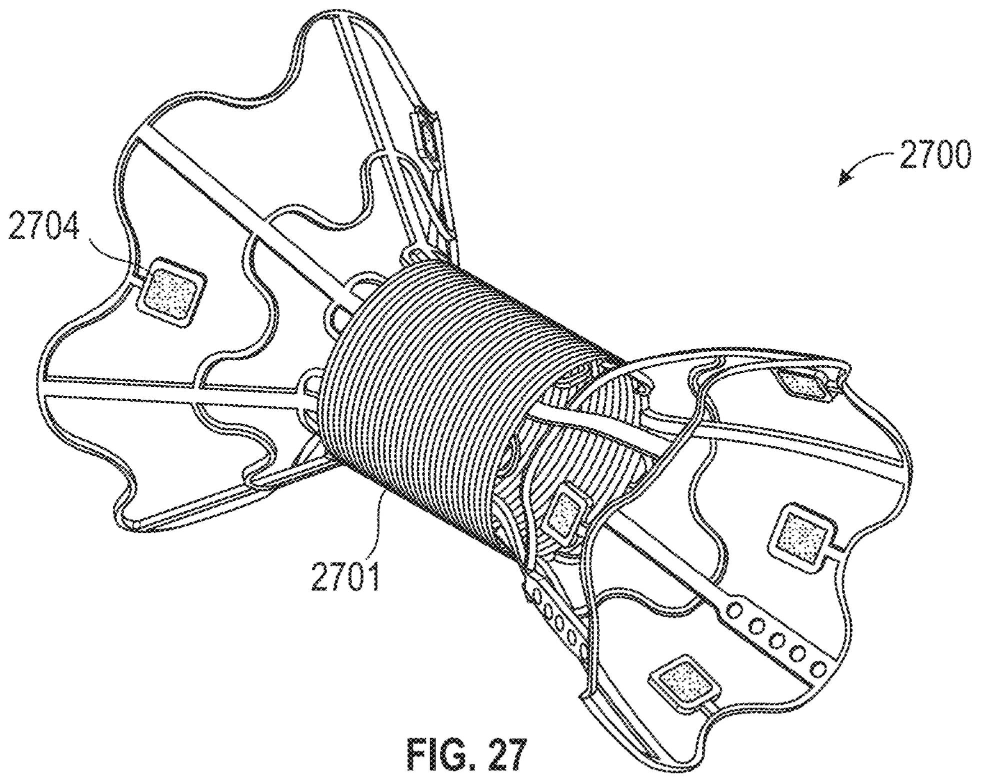
FIG. 27 illustrates a further alternative embodiment of the inventive shunt in which the mid-region of the shunt anchor has a coil structure that serves as a circuit element of the sensor.

FIG. 27 illustrates illustrate a further alternative embodiment of the inventive shunt in which the mid-region of the shunt anchor 2700 has a coil structure 2701 that may form a circuit element of the sensor(s) 2704 in a manner similar to that described with reference to FIGS. 25A-25B.

Figure 28:
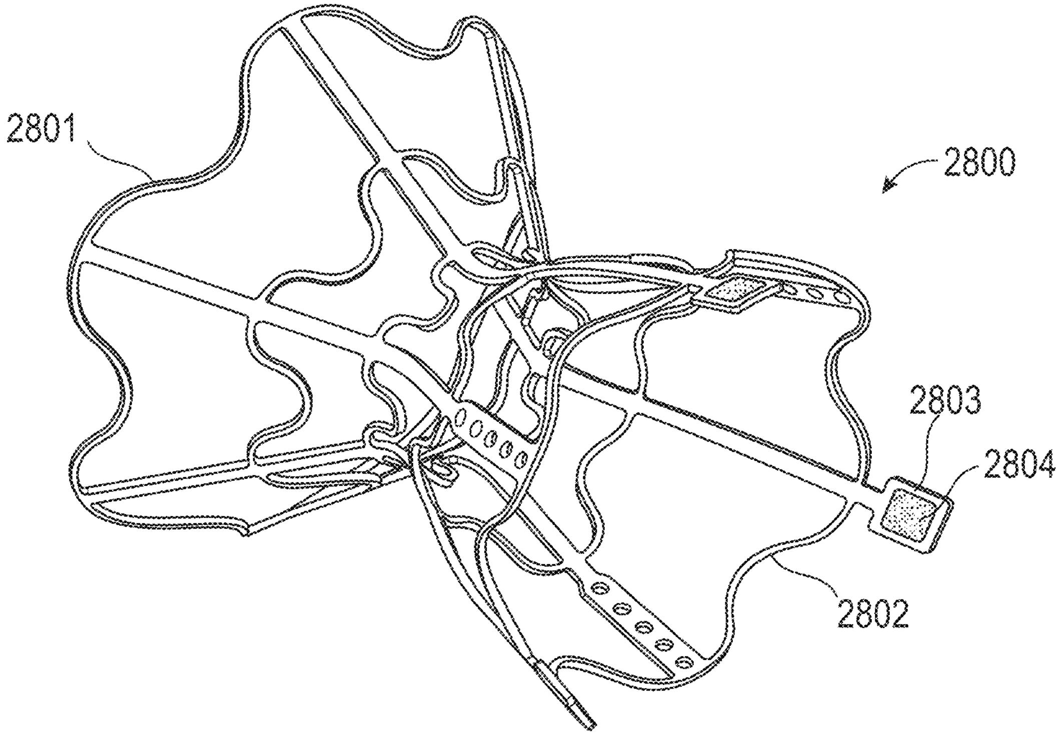
FIGS. 28-30 illustrate alternative embodiments of the inventive shunt in which sensors are located at various regions in the shunt anchor.
Figure 29:
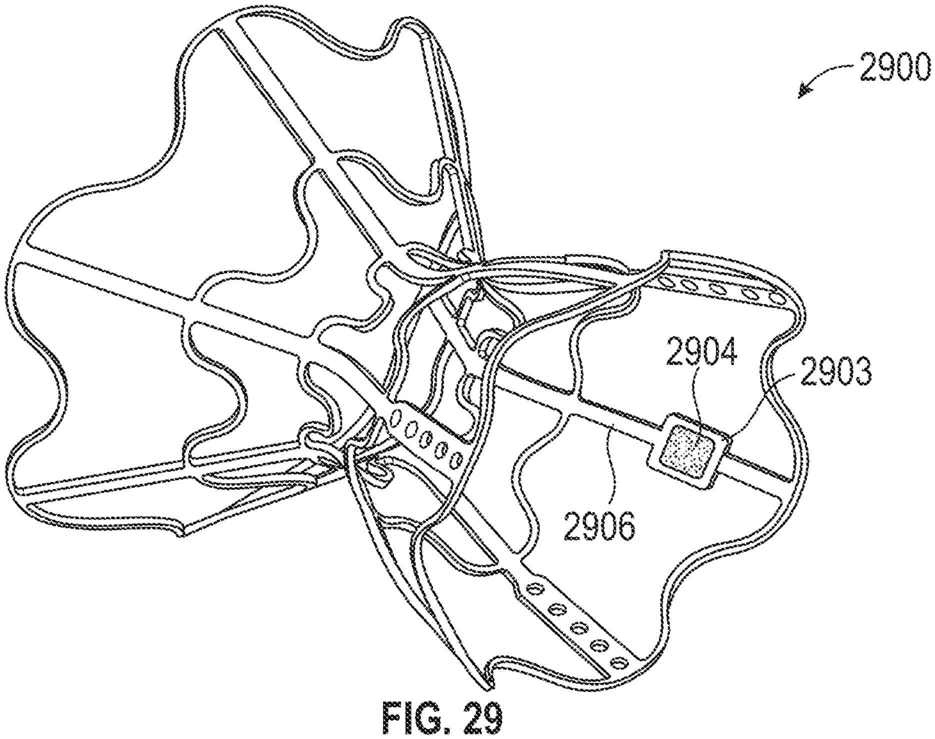
Figure 30:
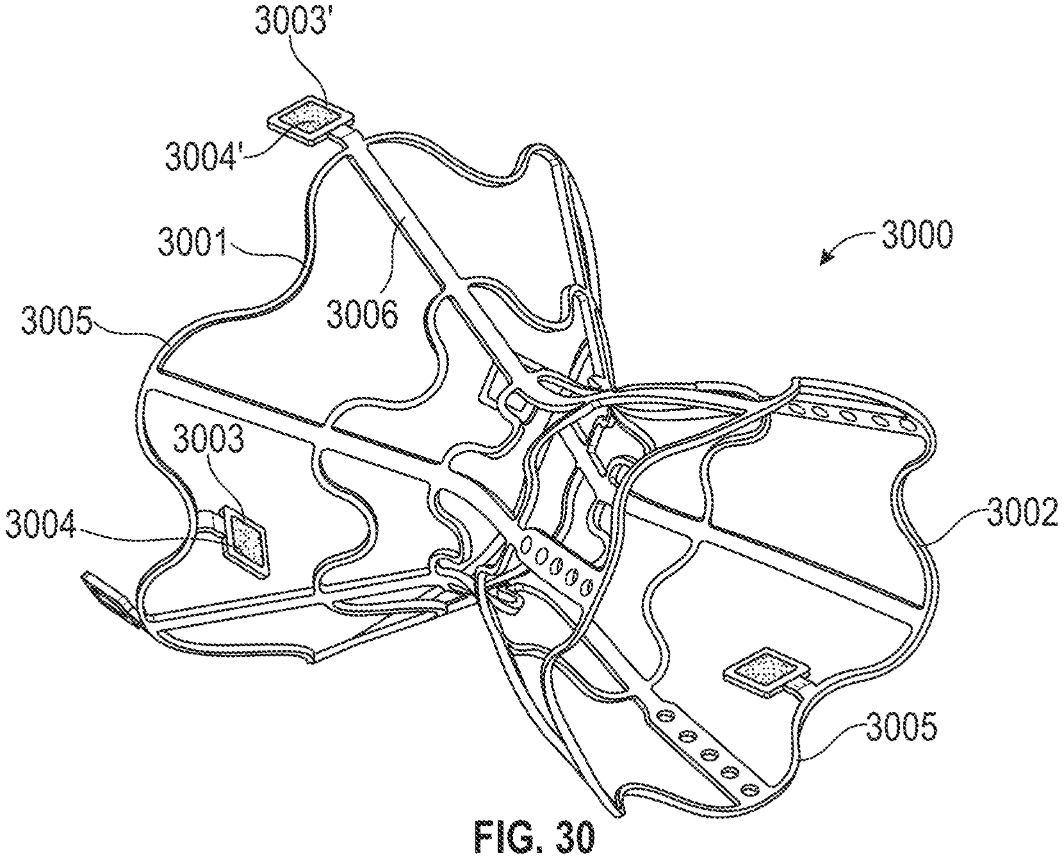

It will be appreciated that the shunts provided herein may include one or more sensors, each of which may be disposed at any suitable location of the shunt. For example, FIGS. 28-30 illustrate alternative embodiments of the inventive shunt in which sensors are located at various regions in the shunt anchor. For example, shunt anchor 2800 illustrated in FIG. 28 includes receptacles 2803 for sensors 2804 that are coupled to longitudinal struts 2806 and that extend beyond the periphery of flange 2802. As another example, shunt anchor 2900 illustrated in FIG. 29 includes receptacles 2903 for sensors 2904 that are coupled to longitudinal struts 2906 and are located within the length of the anchor frame in a manner similar to that described with reference to FIGS. 26A-26B. As yet another example, shunt anchor 3000 illustrated in FIG. 30 includes one or more receptacles 3003 for respective sensor(s) 3004 that are coupled to circumferential struts 3005, and one or more receptacles 3003' for respective sensor(s) 3004' that are coupled to longitudinal struts 3006. Any suitable ones of receptacles 3003, 3003' may be located within the length of the anchor frame (e.g., receptacles 3003 in the example shown in FIG. 30) and any suitable ones of receptacles 3003, 3003' may extend beyond the periphery of flange(s) 3001 and/or 3002.

Figure 31A:
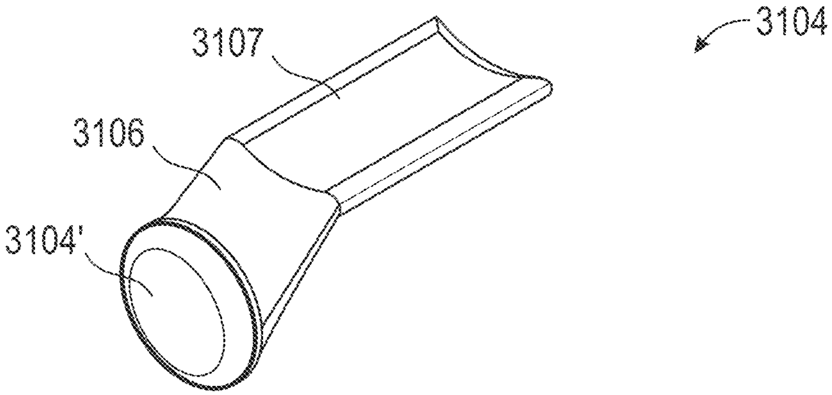
FIGS. 31A-31E illustrate an alternative embodiment of the inventive shunt in which the cross-sectional profile of the sensor varies.

As noted further above with reference to FIGS. 24A-24C, the sensor may have any suitable cross-sectional profile, and in some embodiments may have a cross-sectional profile that varies along the length of the sensor. For example, FIGS. 31A-31E illustrate an alternative embodiment of the inventive shunt 3100 in which the cross-sectional profile of the sensor varies. As illustrated in FIG. 31A, sensor 3104 may include a pressure sensor or other sensor type such as described elsewhere herein. Sensor 3104 may include sensor surface 3104', such as a pressure-sensing diaphragm, that may be substantially circular and may be configured to be disposed within or adjacent to either first flared end region 3102 or second flared end region 3103 so as to measure pressure within that region; concave section 3107 configured to be disposed within, and have a relatively low profile within, neck region 3101 of shunt frame 3110; and tapered section 3106 extending between the sensor surface and the concave section. In some embodiments, concave section 3107 may house circuitry of sensor 3104.

Figure 31B:
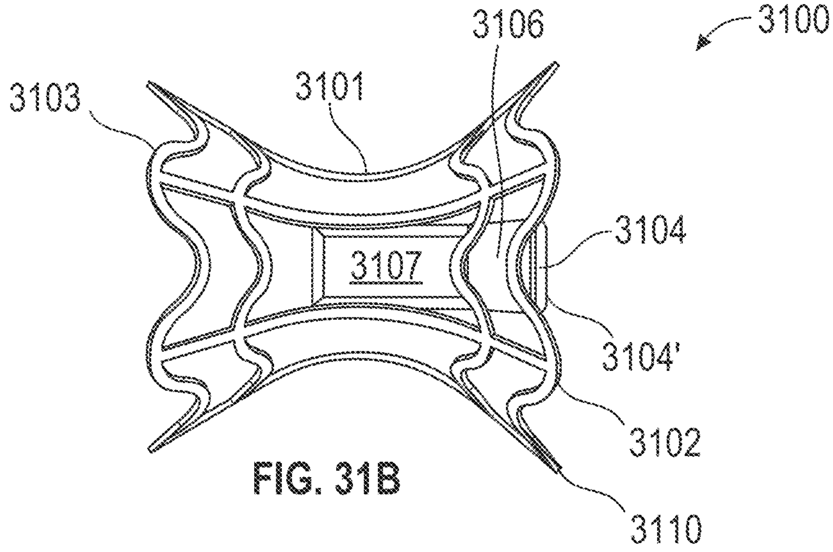
Figure 31C:
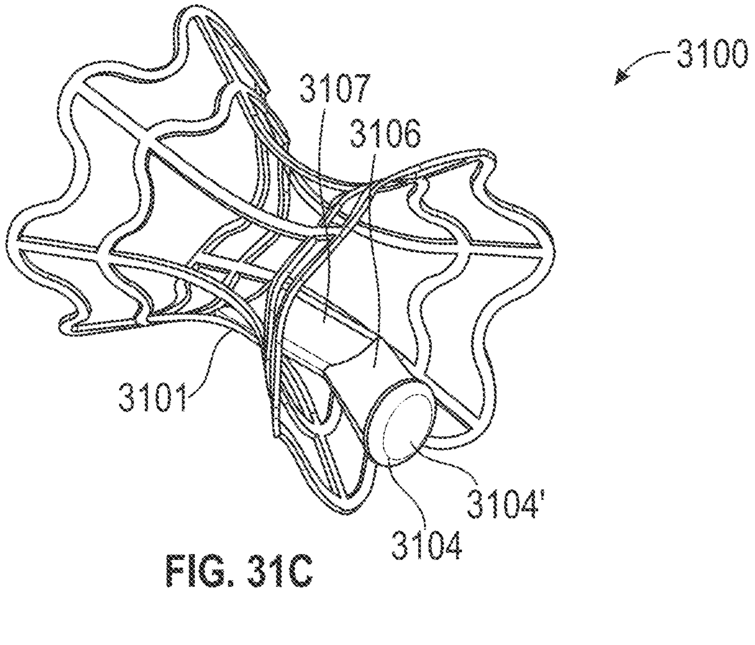
Figure 31D:
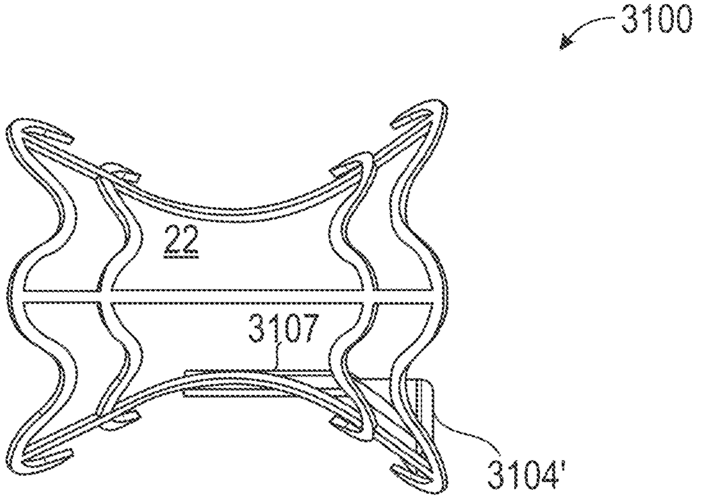
Figure 31E:
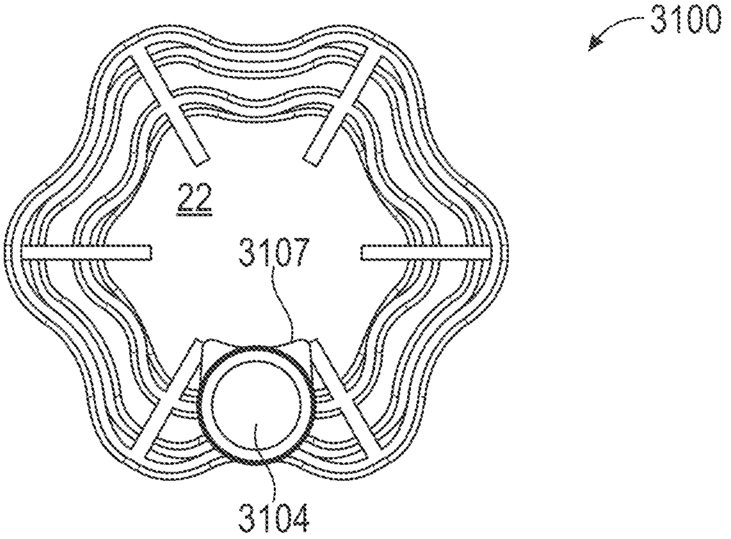

Sensor 3104 may be disposed at any suitable location within shunt 3100. For example, as illustrated in FIGS. 31B-31E, sensor 3104 may be disposed centrally along a first dimension of shunt frame 3110, and may be disposed off-centered along a second dimension of the shunt frame. Illustratively, sensor 3104 may be coupled to shunt frame 3110 along an interior surface of the shunt frame in such a manner as to reduce or minimize the extent to which sensor 3104 blocks blood from flowing through lumen 22. Concave section 3107 may have a similar profile as the interior of neck 3101 so as to reduce or minimize turbulence through lumen 22. As such, the circuitry of sensor 3104 may be disposed co-axially with the inner lumen 22 of shunt 3100. It will be appreciated that in embodiments such as illustrated in FIGS. 31A-31B, blood may flow along only a single side of concave section 3107 and tapered section 3106, the other sides of those sections being coupled to shunt frame 3110 in a manner so as to inhibit blood flow between those sections and the shunt frame.

Figure 32A:
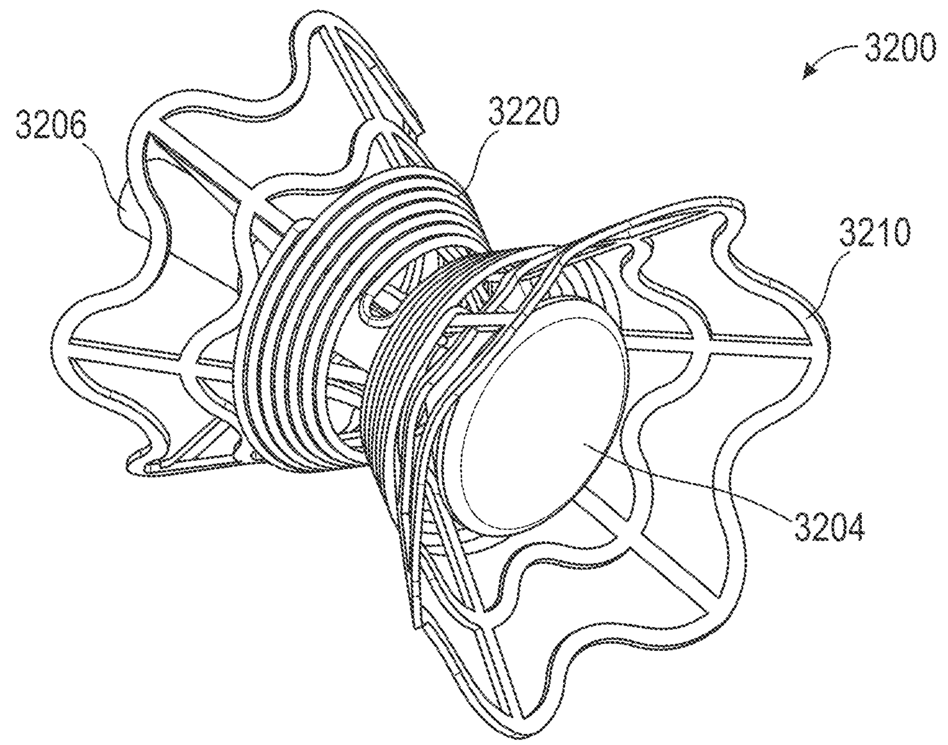
FIGS. 32A-32D illustrate another alternative embodiment of the inventive shunt in which the cross-sectional profile of the sensor varies and including a telemetry coil.
Figure 32B:
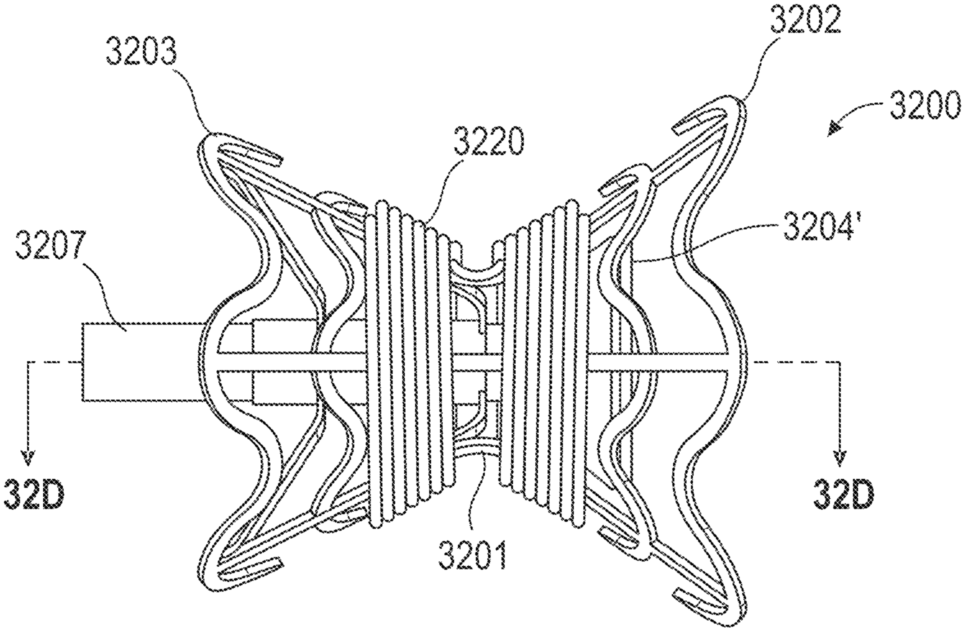
Figure 32C:
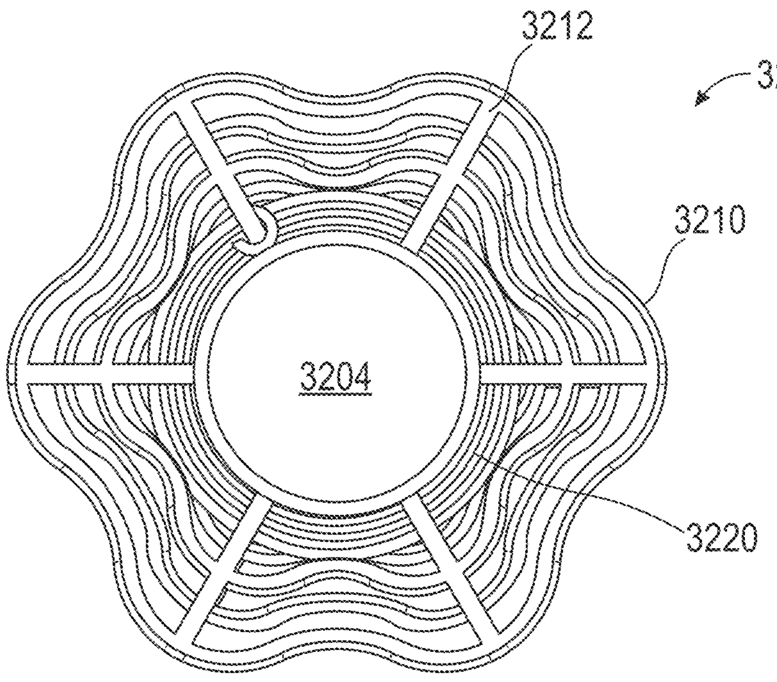
Figure 32D:
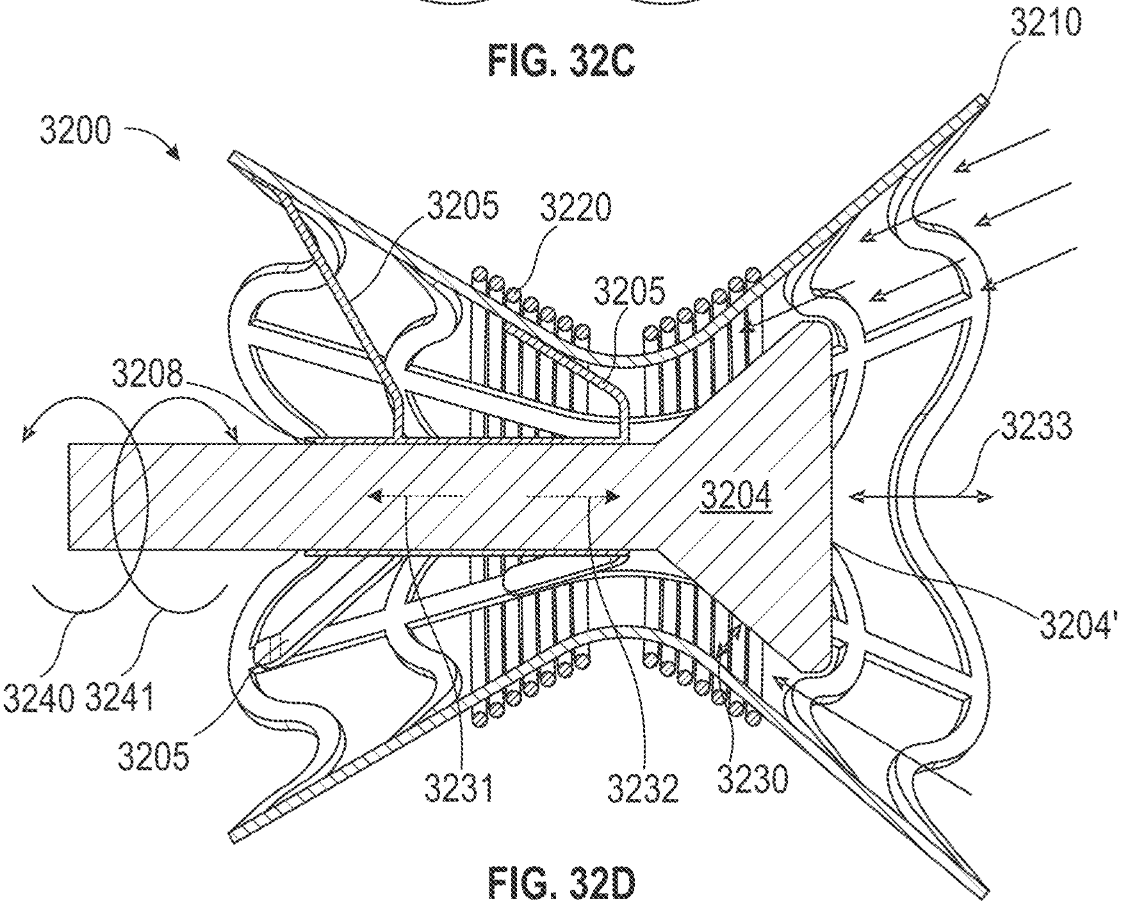

FIGS. 32A-32D illustrate another alternative embodiment of an inventive shunt 3200 in which the cross-sectional profile of the sensor varies and including a telemetry coil. As illustrated in FIG. 32A, sensor 3204 may include a pressure sensor or other sensor type such as described elsewhere herein. As perhaps best seen in FIG. 32D, sensor 3204 may include sensor surface 3204', such as a pressure-sensing diaphragm, that may be substantially circular and may be configured to be disposed within or adjacent to either first flared end region 3202 or second flared end region 3203 so as to measure pressure within that region; reduced diameter section 3207 configured to be disposed within, and have a relatively low profile within, neck region 3201 of shunt frame 3210 and optionally extending beyond the outer periphery of the shunt frame; and tapered section 3106 extending between the sensor surface and the concave section. In some embodiments, reduced diameter section 3207 may house circuitry of sensor 3204. Shunt 3200 further may include telemetry coil 3220.

Sensor 3204 may be disposed at any suitable location within shunt 3200. For example, as illustrated in FIGS. 32A-32D, sensor 3204 may be disposed centrally along one or more dimensions of shunt frame 3210. For example, sensor surface 3204' may be disposed substantially symmetrically within flared end region 3202 or within flared end region 3203. Illustratively, sensor 3204 may be coupled to shunt frame 3210 via collar 3208 into which sensor 3204 may be inserted, and struts 3205 coupling collar 3208 to longitudinal struts 3212 of shunt frame 3210. As such, blood may flow substantially symmetrically around and past sensor 3204 in a manner such as suggested by the unlabeled arrows in FIG. 32D, through annular gap 3230.

In some embodiments, the location of sensor 3204 within shunt frame 3210 may be adjustable in vivo or ex vivo so as to adjust the rate of blood flow through annular gap 3230. For example, collar 3208 and the outer surface of reduced diameter section 3207 each may be threaded and may engage with one another such that when sensor 3204 is rotated in a first direction such as suggested by arrow 3240 in FIG. 32D, the sensor moves laterally in a first direction such as suggested by arrow 3231 and reduces the size of gap 3230 causing a decrease in blood flow through the gap. Similarly, when sensor 3204 is rotated in a second direction such as suggested by arrow 3241 in FIG. 32D, the sensor moves laterally in a second direction such as suggested by arrow 3232 and increases the size of gap 3230 causing an increase in blood flow through the gap.

Figure 33A:
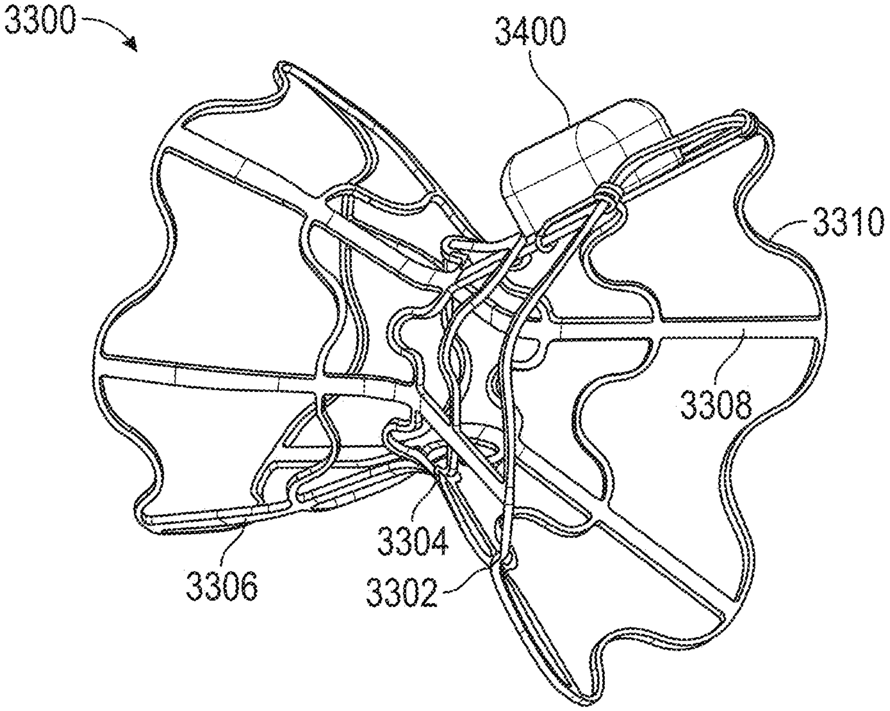
FIGS. 33A-33C illustrate alternative embodiments of the inventive shunt having a deployable sensor in a hermetically sealed housing.
Figure 33B:
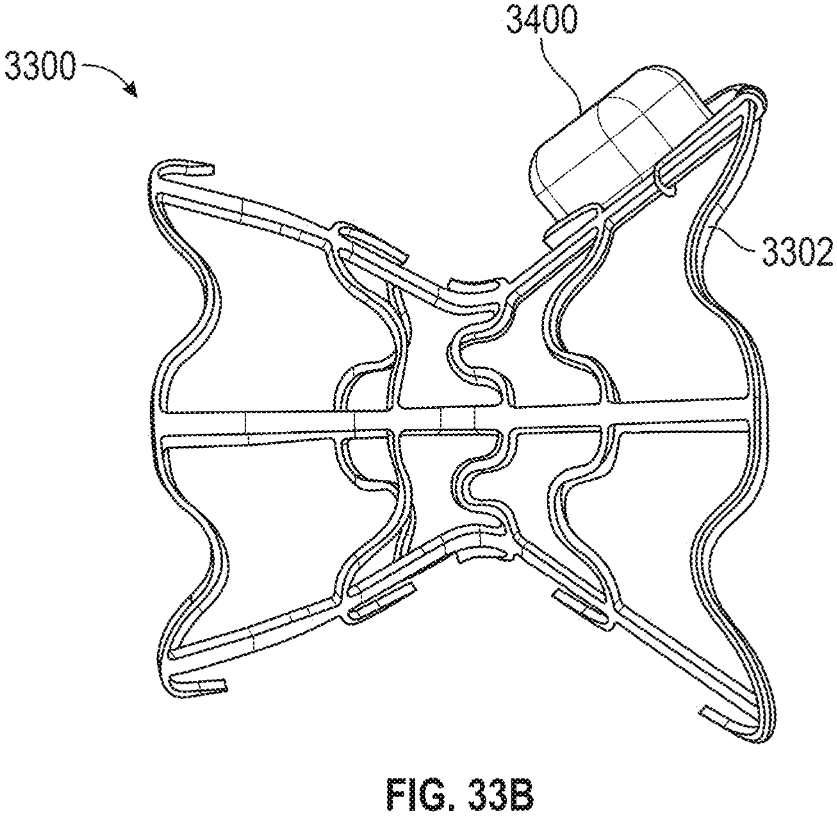
Figure 33C:
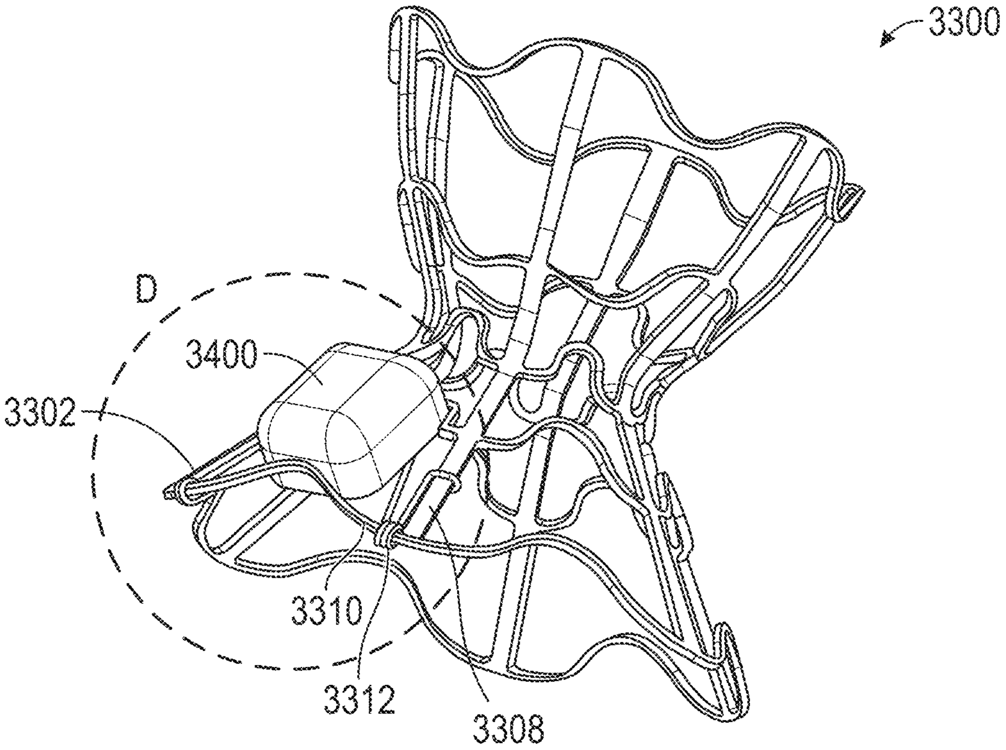

FIGS. 33A-33D illustrate yet another alternative embodiment of an inventive shunt 3300 in which the sensor may be deployable. As shown in FIGS. 33A-33C, shunt 3300 may include a Nitzan type hourglass or diabolo shaped nitinol anchor like those described in FIGS. 1A-1C and 2, wherein the anchor may be fully or partially encapsulated with a biocompatible material like those described with respect to FIGS. 1A-1C and 2. For example, the anchor may include first flared region 3302, second flared region 3306, and neck region 3304 disposed between first flared region 3302 and second flared region 3306. Moreover, the anchor may be formed by a plurality of longitudinal struts 3308 interconnected by a plurality of circumferential struts 3310.

Figure 33D:
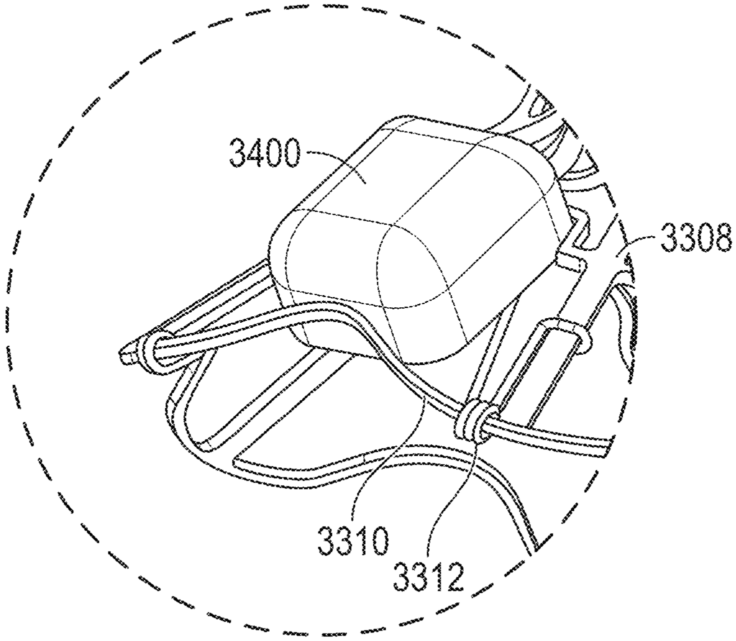
FIG. 33D is a close-up view of the sensor of FIG. 33C.

As shown in FIGS. 33A-33D, sensor 3400 may be pivotally coupled to an end of the anchor, e.g., at the end of first flared region 3400, such that sensor 3400 may pivot about the end of the anchor to transition between a delivery configuration and a deployed configuration (as shown in FIGS. 33A-33D), as described in further detail below. For example, as shown in FIG. 33D, which is a close-up view of encircled portion D of FIG. 33C, sensor 3400 may be coupled to the anchor via a support structure, e.g., torsion spring 3312. Torsion spring 3312 may be biased to a collapsed configuration to thereby bias sensor 3400 toward the deployed configuration, where the sensing surface of sensor 3400 is in fluid communication with the lumen of the anchor.

As shown in FIG. 33D, a first end of torsion spring 3312 may be fixed to longitudinal strut 3308 of the anchor, and a second end of torsion spring 3312 may be fixed to sensor 3400, such that a portion of torsion spring 3312 between the first and second ends wraps around the outermost circumferential strut 3310 of the anchor. In the collapsed configuration of which torsion spring 3312 is biased, the first and second ends of torsion spring 3312 are adjacent to each other, as shown in FIG. 33D. Accordingly, torsion spring 3312 causes sensor 3300 to transition between the delivery configuration and the deployed configuration by pivoting sensor 330 about the outermost circumferential strut 3310 of the anchor. Although FIG. 33D illustrates torsion spring 3312 wrapping two and a half times around circumferential strut 3310, as will be understood by a person having ordinary skill in the art, torsion spring 3312 may be wrapped around circumferential strut 3310 more or less times.

As shown in FIG. 33D, shunt 3300 may include two torsion springs, e.g., one on each side of sensor 3400, to thereby stabilize sensor 3400 as sensor 3400 transitions between the delivery configuration and the deployed configuration. Accordingly, each torsion spring may be coupled to adjacent longitudinal struts of the anchor, such that sensor 3400 is positioned in between two adjacent longitudinal struts of the anchor in the deployed configuration. This way, the sensing surface of sensor 3400 may be in fluid communication with the lumen of the anchor in the deployed configuration, without obstruction or interference by any longitudinal struts. Preferably, the anchor is not encapsulated with the biocompatible material where the sensing surface of sensor 3400 is in fluid communication with the lumen of the anchor. For example, an opening in the biocompatible material may be cutout. Additionally, the circumferential and/or longitudinal struts adjacent to sensor 3400 may be structured to be positioned around sensor 3400 when sensor 3400 is in its deployed configuration, such that sensor 3400 does not interact with any circumferential or longitudinal struts except via torsion spring 3312.

Like the sensors described herein, sensor 3400 may include circuitry for measuring mechanical parameters including pressure, force, flow, velocity, acceleration, wall shear stress, temperature, and the like, or electrical properties exemplified as IEGM, resistance, impedance, current, inductance, capacitance, or chemical properties including, pH, osmolarity, chemical species identification, molecular concentrations, reaction rates, or any other desirable physiological parameters for which acceptable sensors have been developed. For example, sensor 3400 may include an MEMS sensor, e.g., a Wurth, TDK, or Fraunhoffer sensor, disposed within the sensor housing. Additionally or alternatively, sensor 3400 may include a strain gauge. Although FIGS. 33A-33D illustrate shunt 3300 having a single sensor, as will be understood by a person ordinarily skilled in the art, shunt 3300 may have additional sensors, e.g., space around the end of first flared region 3302 and/or space around the end of second flared region 3306.

Referring now to FIGS. 34A-34G, sensor 3400 is described in further detail. As shown in FIGS. 34A-34G, sensor 3400 may include housing 3402, e.g., a ceramic sensor can, and sensing surface 3404, e.g., a titanium plate hermitically sealed to housing 3402, having sensing diaphragm 3406, e.g., a flexible and compressible pressure sensor diaphragm. Sensor housing 3402, and accordingly sensing surface 3404, may have an approximately rectangular shape with rounded corners. In some embodiments, sensor housing 3402 may be approximately 4 mm long, 3.5 mm wide, and 2.2 mm thick. Sensor housing 3420 has an internal cavity sized and shaped to store internal components of sensor 3400.

Figure 34A:
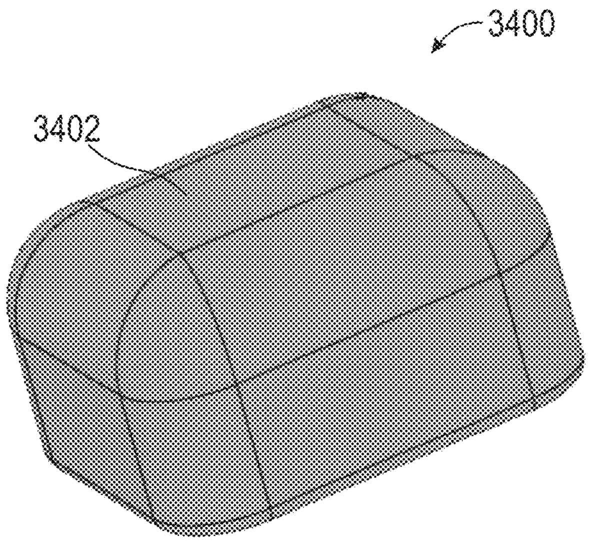
FIGS. 34A-34E illustrate various views of the sensor of FIGS. 33A-33D.
Figure 34B:
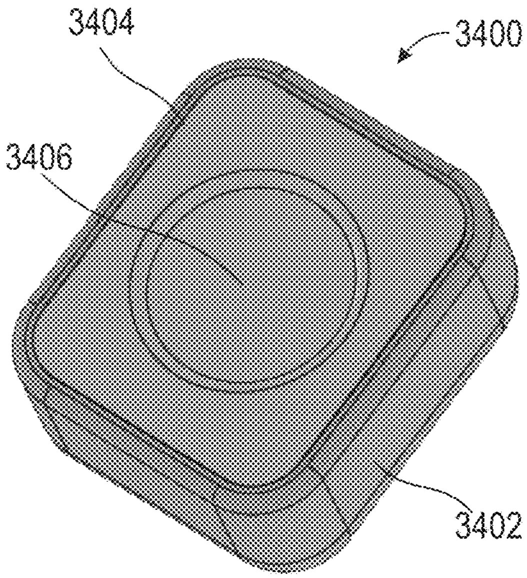
Figure 34C:
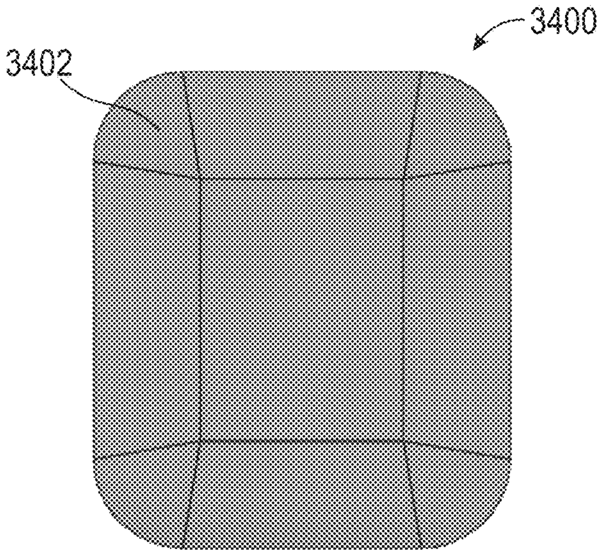
Figure 34D:
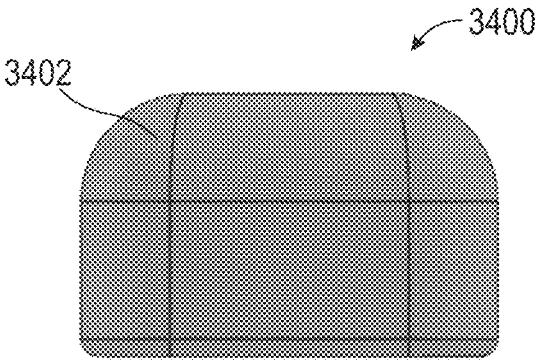
Figure 34E:
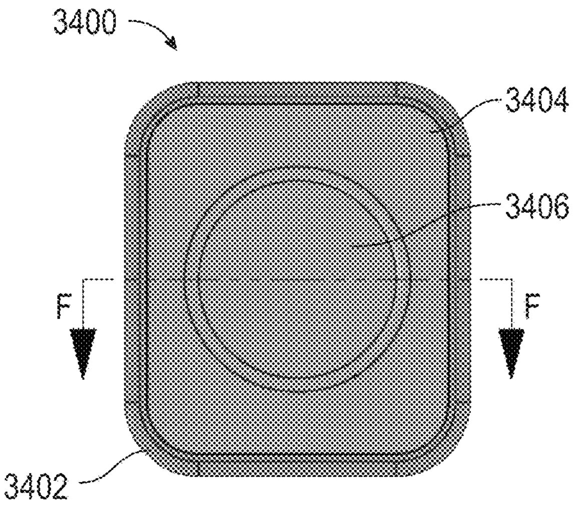
Figure 34F:
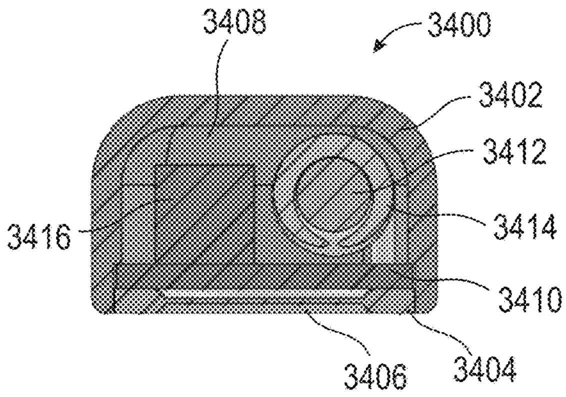
FIG. 34F illustrates a cross-sectional view of the sensor of FIG. 34E.
Figure 34G:
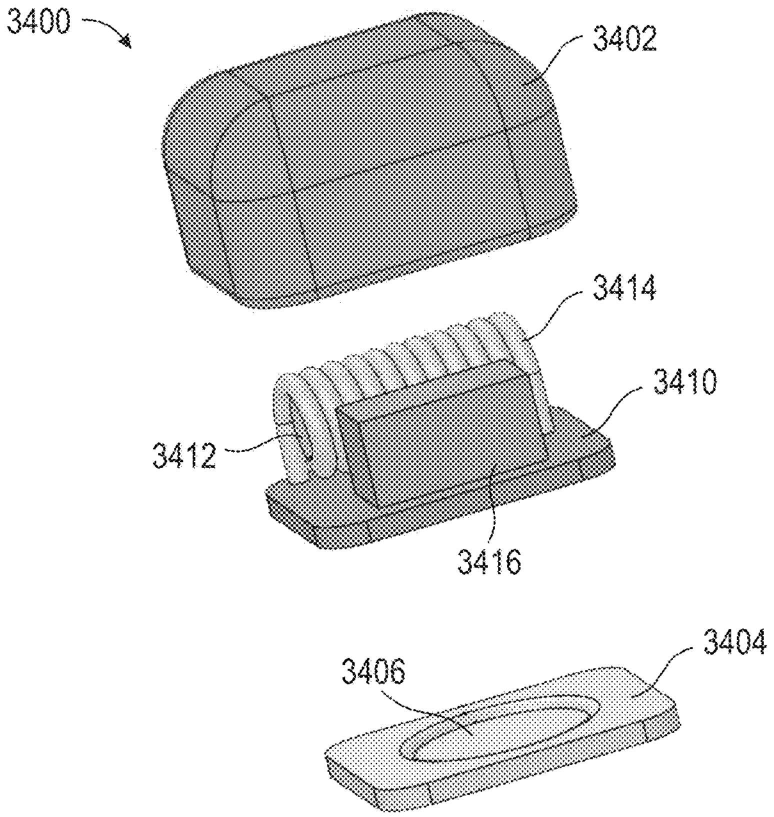
FIG. 34G is an exploded view of the sensor of FIGS. 34A-34F.

FIG. 34F is a cross-sectional view of sensor 3400 along line F-F of FIG. 34E, and FIG. 34G is an exploded view of sensor 3400. As shown in FIGS. 34F and 34G, the internal components may include sensor electronic components housing 3416 for housing sensor electronic components, e.g., electronic circuitry, and ferrite core 3412 overwound by telemetry coil 3414, e.g., a copper wire coil, all disposed on plate 3410. In some embodiments, ferrite core 3412 may have an approximately 0.7 mm diameter and a 2.5 mm length, and telemetry coil 3414 may have a 0.025 mm diameter. Accordingly, placing at least ferrite core 3412 and telemetry coil 3414 within housing 3402 minimizes the gas volume within housing 3402 to thereby maximize the interior pressure change for a given diaphragm displacement of sensing diaphragm 3406. Plate 3410 may have the same shape as sensing surface 3404, and may be positioned adjacent to sensing surface 3404 within sensor housing 3402, such that sensing diaphragm 3406 changes the volume between sensing surface 3404 and plate 3410 responsive to pressure changes across shunt 3300. It is to be understood that the 3-dimensional geometric shape of sensor 3400 is not limited in overall size and dimensions, so long as it does not sufficiently impede shunt flow or substantially reduce the clinical effectiveness of the shunt.

Illustratively, the circuitry may generate data indicative of a left atrial pressure (e.g., in the examples illustrated in FIG. 3 or such as described with reference to FIGS. 4A through 10 or FIG. 16A), a right atrial pressure (e.g., in the examples described with reference to FIGS. 12A through 15A), or a velocity of blood flow through the lumen. Moreover, sensor 3300 may include circuitry for measuring multiple characteristics or may include a plurality of sensors, each including circuitry for measuring a respective characteristic and contained in a unitary housing with the other sensors. Alternatively, multiple independent sensors may be pivotally coupled to the anchor of shunt 3300. The circuitry further may communicate with the patient display device described herein, to thereby transmit data therebetween. For example, sensor 3300 may include an RF transceiver circuit configured to exchange physiologic data and programming instructions directly with the patient display device.

Figure 35A:
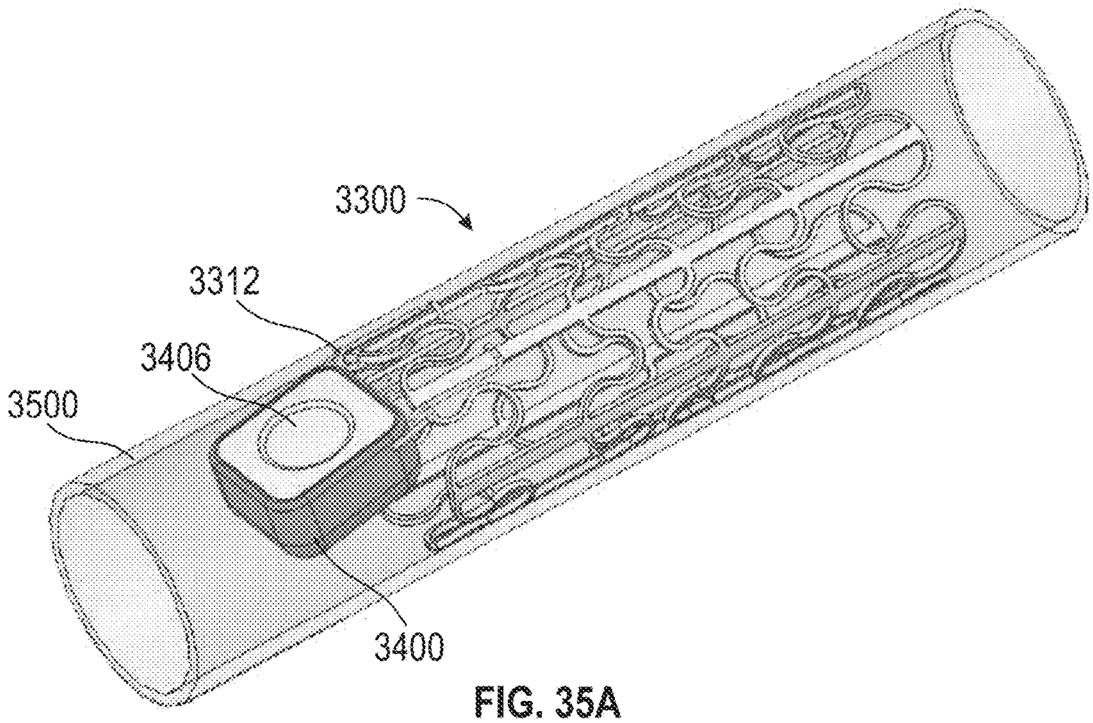
FIGS. 35A-35C illustrate the inventive shunt of FIGS. 33A-33C in a collapsed delivery state.
Figure 35B:
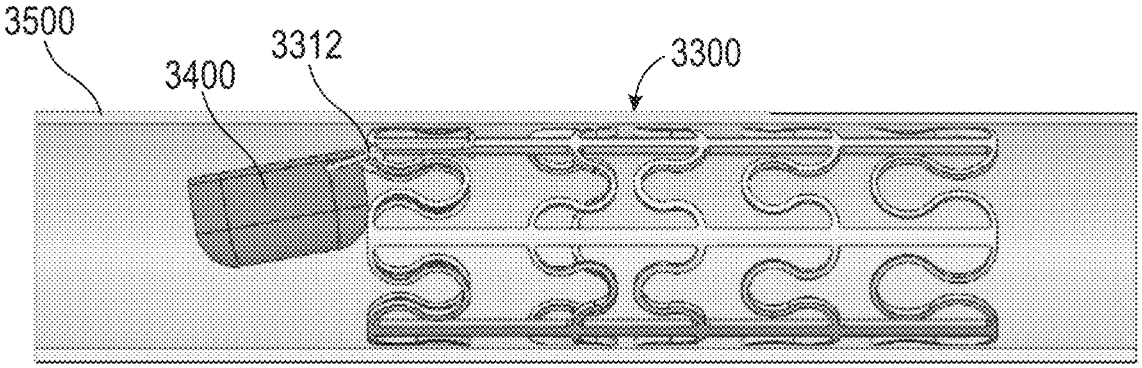
Figure 35C:
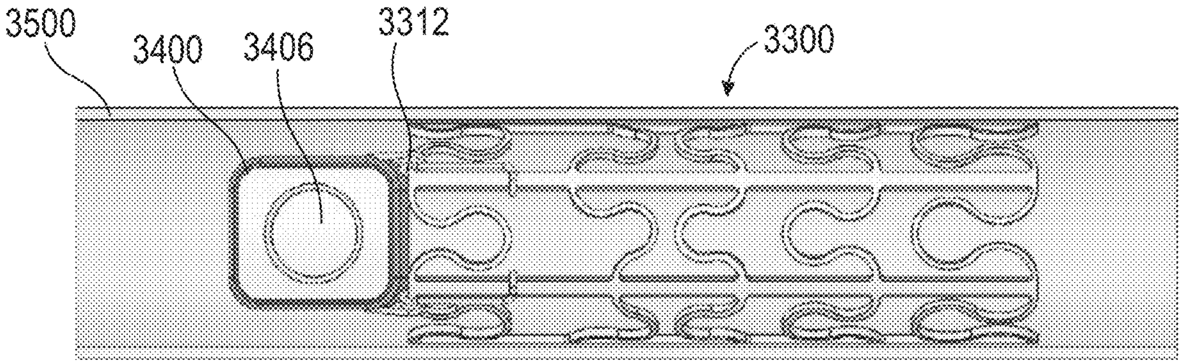

FIGS. 35A-35C illustrate shunt 3300 in the delivery configuration where the anchor is in a collapsed delivery state, and sensor 3400 is in its delivery configuration. As shown in FIGS. 35A-35C, sensor 3400 may be folded back such that it pivots about the outermost circumferential strut of the anchor via torsion spring 3312, and is substantially in line with and extends axially from the collapsed anchor, thereby providing a minimal profile of shunt 3300 for delivery via delivery sheath 3500. As described above, torsion spring 3312 is biased toward its collapsed state, such that sensor 3400 is biased toward the delivery configuration. Accordingly, the inner wall of delivery sheath 3500 maintains sensor 3400 in its delivery configuration when shunt 3300 is in its collapsed delivery state within delivery sheath 3500. Upon exposure from delivery sheath 3500, the anchor may self-expand to its expanded deployed state, and sensor 3400 transitions to its deployed configuration via torsion spring 3312, as shown in FIGS. 33A-33C.

Figure 36:
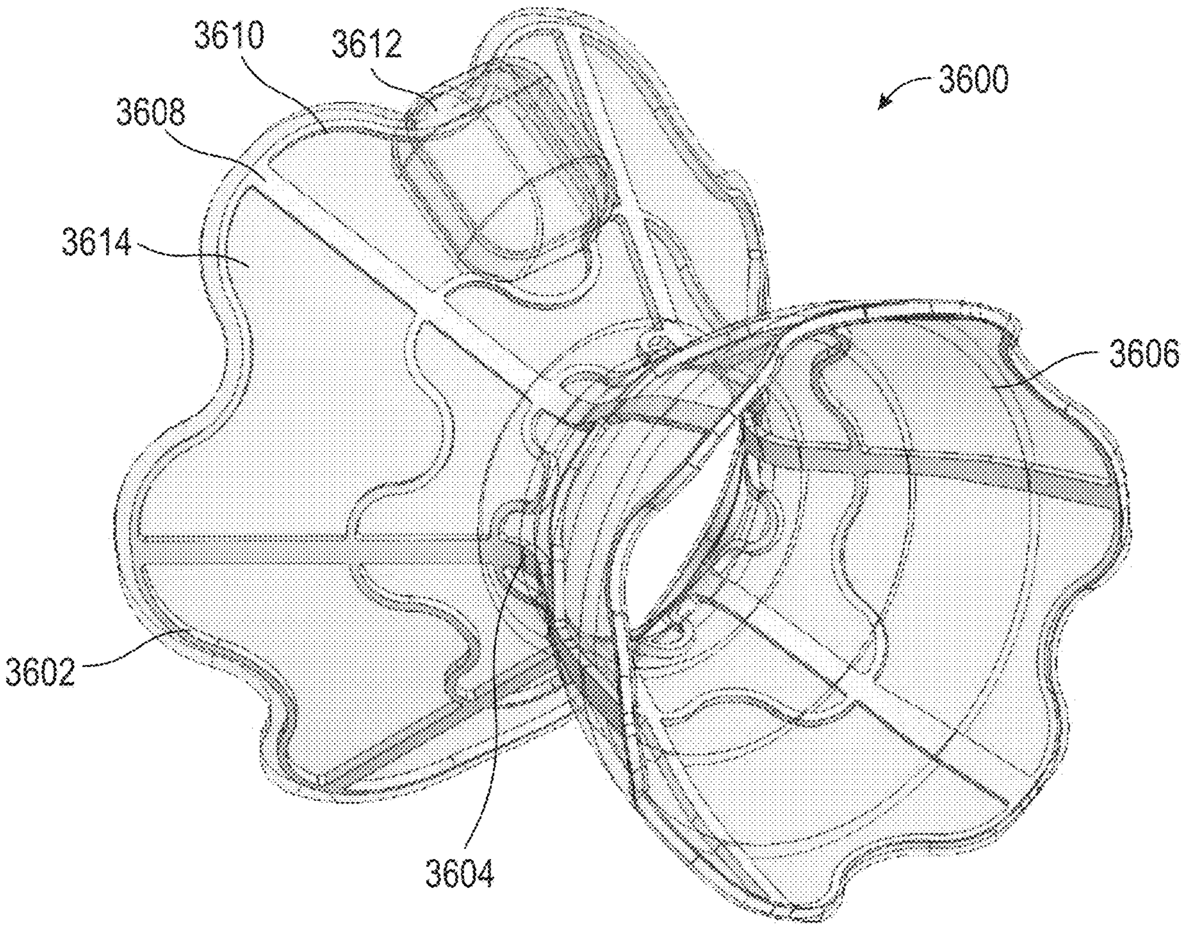
FIG. 36 illustrates an alternative embodiment of the inventive shunt in which the sensor is encapsulated in a biocompatible covering.

FIG. 36 illustrates an alternative embodiment of the shunt of FIGS. 33A-33D in which sensor 3612 of shunt 3600 is encapsulated with biocompatible material 3614. For example, a pocket may be formed within biocompatible material 3614 to accommodate sensor 3612. However, the sensing surface of sensor 3612 may not be covered with biocompatible material 3614, such that the sensing surface may be in fluid communication with the lumen of the anchor of shunt 3600. Like the anchor of shunt 3300, the anchor of shunt 3600 may include first flared region 3602, second flared region 3606, and neck region 3604 disposed between first flared region 3602 and second flared region 3606, and may be formed by a plurality of longitudinal struts 3608 interconnected by a plurality of circumferential struts 3610. As shown in FIG. 36, sensor 3612 may be positioned between adjacent longitudinal struts 3608 and adjacent circumferential struts 3610, such that the sensing surface of sensor 3612 is not obstructed by any longitudinal struts or circumferential struts.

Shunt 3600 need not include a torsion spring for pivotally coupling sensor 3612 to first flared region 3602 such that sensor 3612 is fixed in place relative to the anchor. For example, sensor 3612 may be fixed to the anchor via one or more support structures. Alternatively, biocompatible material 3614 may encapsulate at least a portion of the sensing surface of sensor 3612, e.g., around the peripheral edges of the sensing surface, while not obstructing the sensing diaphragm of the sensing surface so as to not interfere with the sensing capabilities of sensor 3612.

Additionally, it will be appreciated that when multiple receptacles are provided for sensors, such receptacles may be, but need not necessarily be, approximately equally spaced around the circumference of the anchor frame. Additionally, or alternatively, the receptacles may be located in either or both atria of the anchor frame and/or at the location of the shunt neck.

The receptacles may be formed by any suitable process, including laser cutting during manufacture of the anchor frame or subsequent welding to the anchor frame. Additionally, or alternatively, one or more sensors may be placed between two layers of biocompatible material (e.g., ePTFE) at the neck, left atrial side, or right atrial side of the shunt. Illustratively, the sensor may be placed inside of a "pocket" created beforehand by two layers of the biocompatible material and then may be sealed using any suitable combination of heat, biocompatible adhesive, and/or a suitable suture. Alternatively, the sensor may be positioned on one layer of the biocompatible material and the other layer of biocompatible material folded back on it.

In various configurations provided herein, the connection between the sensor and the shunt substantially may not increase crimp strains in the shunt frame. For example, encapsulated sensors may be configured so as to be relatively easily folded or compressed together with the shunt frame into a delivery configuration, substantially without causing plastic deformations to the structure, and also may have a fail-safe release mechanism when deployed. Sensor encapsulation (e.g., using Parylene or similar) may provide relatively long-term durability to temperature changes, for example to ensure that the sensor remains functional even if temporarily exposed to relatively high heat (e.g., saline heated to above 45 degrees Celsius).

Although certain mechanisms and methods of delivering the present shunts are described herein and in the incorporated references, it will be appreciated that any suitable mechanism and method may be used, such as a screw-on delivery cable as previously used to deliver Amplatzer shunt designs, a hookless design, a clamp around the sensor body, and the like.

The foregoing real-world patient demonstrates the clinical feasibility and potential synergies achievable by combining interatrial shunts, which rapidly and automatically rebalance pathological cardiac pressures, with implantable sensors that assess key physiological parameters an yield actionable data for guiding therapeutic decisions.

Accordingly, some examples herein provide a system for treating heart failure (HF) or pulmonary arterial hypertension (PAH) by monitoring at least one atrial physiologic parameter and displaying information indicative of the at least one atrial physiologic parameter on a patient display device. The system may include an interatrial shunt comprising: (i) an anchor having a first flared region, a neck region and a second flared region, the neck region disposed between the first flared region and the second flared region, and (ii) a biocompatible covering disposed on the anchor to form a lumen that extends from the first flared region to the second flared region. The system further may include a sensor comprising circuitry for generating data indicative of the at least one atrial physiologic parameter, and a support structure for coupling the sensor to the interatrial shunt. The support structure may locate the sensor relative to the lumen to monitor the at least one physiologic parameter and at which location post-implantation tissue growth does not exceed 300 microns. The system may include a computer readable medium storing programming to be executed by a processor of the patient display device, the programming including instructions to receive the data from the sensor and process the data for viewing on the patient display device. Nonlimiting examples of such a system are described with reference to FIG. 3, and nonlimiting examples of interatrial shunts and sensors for use in such a system are described with reference to FIGS. 1-2, 4A-4B, 5A-5B, 6A-6B, 7A-7F, 8A-8B, 9A-9B, 10A-10B, 11, 12A-12B, 13A-13B, 14A-14B, 15A, 16A, 17A-17C, 18C, 19A-19B, 23, 24A-24C, 25A-25B, 26A-26B, 27, 28, 29, 30, 31A-31E, 32A-32D, 33A-33D, 34A-34G, 35A-35C, and 36.

Some examples herein provide an interatrial shunt for treating heart failure (HF) or pulmonary arterial hypertension (PAH) by shunting blood to relieve high pressure and monitoring at least one atrial physiologic parameter. The shunt may include an anchor having a first flared region, a neck region and a second flared region, the neck region disposed between the first flared region and the second flared region. In some embodiments, an inlet of the first flared end region may be in a first plane, and an outlet of the second flared end region may be in a second plane, such that the first plane intersects the second plane in the expanded deployed state, as described in U.S. 2019/0262118 to Eigler, the entire contents of which are incorporated by reference herein. Moreover, the shunt may include a biocompatible covering disposed on the anchor to form a lumen that extends from the first flared region to the second flared region. The shunt may include a sensor comprising circuitry for generating data indicative of the at least one atrial physiologic parameter. The sensor may be disposed relative to the lumen such that post-implantation tissue growth does not exceed 300 microns. Nonlimiting examples of interatrial shunts and sensors are described with reference to FIGS. 1-2, 4A-4B, 5A-5B, 6A-6B, 7A-7F, 8A-8B, 9A-9B, 10A-10B, 11, 12A-12B, 13A-13B, 14A-14B, 15A, 16A, 17A-17C, 18C, 19A-19B, 23, 24A-24C, 25A-25B, 26A-26B, 27, 28, 29, 30, 31A-31E, 32A-32D, 33A-33D, 34A-34G, 35A-35C, and 36.

It is to be appreciated that certain features of the invention, which are, for clarity, described in the context of separate embodiments, also may be provided in combination in a single embodiment. Conversely, various features of the invention, which for brevity are described in the context of a single embodiment, also may be provided separately or in any suitable subcombination. While various illustrative embodiments of the invention are described above, it will be apparent to one with ordinary skill in the art that various changes and modifications may be made herein without departing from the invention. Therefore, the full scope of the invention must be ascertained by reference to the appended claims, along with the full scope of equivalents to which those claims are legally entitled.

In the foregoing disclosure, embodiments have been described with reference to specific example implementations thereof. It will be evident that various modifications may be made thereto without departing from the broader spirit and scope of the disclosure as set forth in the following claims.

What is claimed is:

1. An interatrial shunt for treating heart failure (HF) or pulmonary arterial hypertension (PAH) by shunting blood to relieve high pressure and monitoring at least one atrial physiologic parameter, the interatrial shunt comprising:

- a valveless anchor having a first flared region, a second flared region, and a neck region disposed between the first flared region and the second flared region;
- a biocompatible covering disposed on the valveless anchor to form a lumen that extends from the first flared region to the second flared region; and
- a sensor comprising a housing, a sensing surface, and circuitry disposed within the housing for generating data indicative of the at least one atrial physiologic parameter and for communicating the data, the sensor being pivotally coupled to the first flared region and configured to pivot about the valveless anchor to transition between a delivery configuration and a deployed configuration where the sensing surface is disposed within the lumen.

2. The interatrial shunt of claim 1, wherein the valveless anchor comprises a plurality of longitudinal struts interconnected by a plurality of circumferential struts.

3. The interatrial shunt of claim 2, wherein, in the deployed configuration, the sensor is positioned in between a pair of adjacent longitudinal struts of the plurality of longitudinal struts, and a pair of adjacent circumferential struts of the plurality of circumferential struts, such that the sensing surface of the sensor is unobstructed by the plurality of longitudinal and circumferential struts.

4. The interatrial shunt of claim 1, wherein the valveless anchor is configured to transition between a collapsed delivery state and an expanded deployed state.

5. The interatrial shunt of claim 4, wherein an inlet of the first flared end region is in a first plane, and an outlet of the second flared end region is in a second plane, such that the first plane intersects the second plane in the expanded deployed state.

6. The interatrial shunt of claim 1, wherein, in the delivery configuration, the sensor extends axially away from the valveless anchor.

7. The interatrial shunt of claim 1, wherein the sensor is pivotally coupled to the first flared region via a torsion spring.

8. The interatrial shunt of claim 7, wherein the torsion spring is configured to bias the sensor towards the deployed configuration.

9. The interatrial shunt of claim 8, wherein, during delivery of the interatrial shunt within a delivery sheath, the sensor is configured to remain in the delivery configured via an inner wall of the delivery sheath, such that upon exposure from the delivery sheath, the sensor transitions to the deployed configuration.

10. The interatrial shunt of claim 7, wherein the torsion spring is coupled to an outermost circumferential strut of the first flared region such that the torsion spring is configured to pivot the sensor about the outermost circumferential strut.

11. The interatrial shunt of claim 10, wherein a first end of the torsion spring is coupled to the housing of the sensor and a second end of the torsion spring is coupled to a longitudinal strut of the first flared region, such that a portion of the torsion spring between the first and second ends wraps around the outermost circumferential strut.

12. The interatrial shunt of claim 1, wherein the sensing surface comprises a flexible sensing diaphragm.

13. The interatrial shunt of claim 1, wherein the sensor comprises a ferrite core overwound by a telemetry coil disposed within the housing.

14. The interatrial shunt of claim 1, wherein the sensor comprises an MEMS sensor disposed within the housing.

15. The interatrial shunt of claim 14, wherein the MEMS sensor is selected from a list consisting of a Wurth, TDK, or Fraunhoffer sensor.

16. The interatrial shunt of claim 1, wherein the sensor comprises a strain gauge disposed within the housing.

17. The interatrial shunt of claim 1, wherein the data generated by the sensor is indicative of a left atrial pressure, a right atrial pressure or a velocity of blood flow through the lumen.

18. The interatrial shunt of claim 1, wherein the biocompatible covering comprises an opening sized and shaped to expose the sensing surface of the sensor when the sensor is in the deployed configuration, such that the sensing surface is in fluid communication with the lumen.

19. A system for treating heart failure (HF) or pulmonary arterial hypertension (PAH) by monitoring at least one atrial physiologic parameter and displaying information indicative of the at least one atrial physiologic parameter on a patient display device, the system comprising:

an interatrial shunt comprising:

a valveless anchor having a first flared region, a second flared region, and a neck region disposed between the first flared region and the second flared region; and a biocompatible covering disposed on the valveless anchor to form a lumen that extends from the first flared region to the second flared region;

a sensor comprising a housing, a sensing surface, and circuitry disposed within the housing for generating data indicative of the at least one atrial physiologic parameter, the sensor being pivotally coupled to the first flared region and configured to pivot about the valveless anchor to transition between a delivery configuration and a deployed configuration where the sensing surface is disposed within the lumen; and a non-transitory computer readable medium having instructions that, when executed by a processor of the patient display device, cause the processor to receive the data from the sensor and process the data for viewing on the patient display device.

20. The system of claim 19, wherein the sensor is pivotally coupled to the first flared region via a torsion spring.

21. The system of claim 19, further comprising a delivery sheath configured to receive the valveless anchor in a collapsed delivery state and the sensor in the delivery configuration.

22. The system of claim 21, wherein the sensor is biased toward the deployed configuration, such that upon exposure from the delivery sheath, the sensor transitions to the deployed configuration.

* * * * *